US012350312B2

(12) United States Patent
Riddell et al.

(10) Patent No.: US 12,350,312 B2
(45) Date of Patent: Jul. 8, 2025

(54) METHODS FOR IMPROVING ADOPTIVE CELL THERAPY

(71) Applicant: FRED HUTCHINSON CANCER CENTER, Seattle, WA (US)

(72) Inventors: Stanley R. Riddell, Sammamish, WA (US); Shivani Srivastava, Seattle, WA (US)

(73) Assignee: FRED HUTCHINSON CANCER CENTER, Seattle, WA (US)

( * ) Notice: Subject to any disclaimer, the term of this patent is extended or adjusted under 35 U.S.C. 154(b) by 721 days.

(21) Appl. No.: 16/645,092

(22) PCT Filed: Sep. 6, 2018

(86) PCT No.: PCT/US2018/049812
§ 371 (c)(1),
(2) Date: Mar. 6, 2020

(87) PCT Pub. No.: WO2019/051135
PCT Pub. Date: Mar. 14, 2019

(65) Prior Publication Data
US 2021/0106618 A1     Apr. 15, 2021

Related U.S. Application Data

(60) Provisional application No. 62/555,034, filed on Sep. 6, 2017.

(51) Int. Cl.
| | |
|---|---|
| *A61K 38/17* | (2006.01) |
| *A61K 31/282* | (2006.01) |
| *A61K 31/675* | (2006.01) |
| *A61K 39/00* | (2006.01) |
| *A61K 39/395* | (2006.01) |
| *A61K 40/11* | (2025.01) |
| *A61K 40/31* | (2025.01) |
| *A61K 40/42* | (2025.01) |
| *A61K 45/06* | (2006.01) |
| *A61P 35/00* | (2006.01) |
| *A61P 35/02* | (2006.01) |
| *C07K 14/705* | (2006.01) |
| *C07K 14/725* | (2006.01) |
| *C07K 16/28* | (2006.01) |
| *C12N 5/0783* | (2010.01) |

(52) U.S. Cl.
CPC ........ *A61K 38/1774* (2013.01); *A61K 31/282* (2013.01); *A61K 31/675* (2013.01); *A61K 38/177* (2013.01); *A61K 39/3955* (2013.01); *A61K 40/11* (2025.01); *A61K 40/31* (2025.01); *A61K 40/421* (2025.01); *A61K 45/06* (2013.01); *A61P 35/00* (2018.01); *A61P 35/02* (2018.01); *C07K 14/7051* (2013.01); *C07K 14/70521* (2013.01); *C07K 14/70578* (2013.01); *C07K 16/2803* (2013.01); *C12N 5/0636* (2013.01); *A61K 2039/505* (2013.01); *A61K 2039/545* (2013.01); *A61K 2239/38* (2023.05); *A61K 2239/48* (2023.05); *A61K 2239/49* (2023.05); *A61K 2239/55* (2023.05); *C07K 2317/622* (2013.01); *C07K 2317/76* (2013.01); *C07K 2319/02* (2013.01); *C07K 2319/03* (2013.01); *C07K 2319/30* (2013.01); *C07K 2319/33* (2013.01)

(58) Field of Classification Search
CPC .... A61K 35/17; A61K 31/282; A61K 31/675; A61K 38/177; A61K 38/1774; A61K 39/3955; A61K 45/06; A61K 2039/505; A61K 2039/5156; A61K 2039/5158; A61K 2039/545; A61K 2300/00; A61K 39/0011; A61P 35/00; A61P 35/02; C07K 14/7051; C07K 14/70521; C07K 14/70578; C07K 16/2803; C07K 2317/622; C07K 2317/76; C07K 2319/02; C07K 2319/03; C07K 2319/30; C07K 2319/33; C12N 5/0636; C12N 2510/00; A01K 2217/052; A01K 2217/054; A01K 2227/105; A01K 2267/0331; A01K 67/0276; Y02A 50/30
See application file for complete search history.

(56) References Cited

U.S. PATENT DOCUMENTS

| | | | |
|---|---|---|---|
| 5,283,173 | A | 2/1994 | Fields et al. |
| 5,420,032 | A | 5/1995 | Marshall et al. |
| 5,468,614 | A | 11/1995 | Fields et al. |
| 6,410,319 | B1 | 6/2002 | Raubitschek et al. |

(Continued)

FOREIGN PATENT DOCUMENTS

| | | |
|---|---|---|
| WO | WO 2011053750 A2 | 5/2011 |
| WO | WO 2012075158 A1 | 6/2012 |

(Continued)

OTHER PUBLICATIONS

Pfirschke et. al. (Immunity 44:343-354. (2016)) (Year: 2016).*

(Continued)

*Primary Examiner* — Meera Natarajan
*Assistant Examiner* — Francesca Edgingtongiordano
(74) *Attorney, Agent, or Firm* — Seed IP Law Group LLP

(57) ABSTRACT

The present disclosure provides reagents and methods for treating disease using modified immune cells (e.g., T cell comprising CAR or TCR) in combination with an agent associated with induction of immunogenic cell death (ICD) and optionally further in combination with an agent that specifically binds to and/or inhibits an immune suppression component and/or an agonist of an immune stimulatory molecule.

47 Claims, 63 Drawing Sheets
Specification includes a Sequence Listing.

(56) References Cited

U.S. PATENT DOCUMENTS

| | | | |
|---|---|---|---|
| 6,833,252 | B1 | 12/2004 | Dujon et al. |
| 7,446,191 | B2 | 11/2008 | Jensen |
| 7,514,537 | B2 | 4/2009 | Jensen |
| 8,119,772 | B2 | 2/2012 | Yang et al. |
| 8,697,359 | B1 | 4/2014 | Zhang |
| 8,822,647 | B2 | 9/2014 | Jensen |
| 9,217,040 | B2 | 12/2015 | Kipps et al. |
| 9,316,646 | B2 | 4/2016 | Rader et al. |
| 9,574,000 | B2 | 2/2017 | Langermann et al. |
| 10,780,118 | B2 * | 9/2020 | Jensen ............... A61P 35/02 |
| 2004/0002092 | A1 | 1/2004 | Arnould et al. |
| 2004/0087025 | A1 | 5/2004 | June et al. |
| 2006/0078552 | A1 | 4/2006 | Arnould et al. |
| 2006/0153826 | A1 | 7/2006 | Arnould et al. |
| 2006/0206949 | A1 | 9/2006 | Arnould et al. |
| 2007/0117128 | A1 | 5/2007 | Smith et al. |
| 2010/0065818 | A1 | 3/2010 | Kim et al. |
| 2011/0189141 | A1 | 8/2011 | Kieback et al. |
| 2011/0243972 | A1 | 10/2011 | Jaffee |
| 2011/0301073 | A1 | 12/2011 | Gregory et al. |
| 2012/0058051 | A1 | 3/2012 | Rader et al. |
| 2013/0251642 | A1 | 9/2013 | Rader et al. |
| 2014/0068797 | A1 | 3/2014 | Doudna et al. |
| 2014/0186843 | A1 | 7/2014 | Zhang et al. |
| 2015/0232569 | A1 | 8/2015 | Kipps et al. |
| 2020/0283729 | A1 | 9/2020 | Loew et al. |
| 2021/0145882 | A1 | 5/2021 | Maloney et al. |

FOREIGN PATENT DOCUMENTS

| | | | | |
|---|---|---|---|---|
| WO | WO 2012076066 | A1 | 6/2012 | |
| WO | WO 2013025779 | A1 | 2/2013 | |
| WO | WO 2014031687 | A1 | 2/2014 | |
| WO | WO 2015071474 | A2 | 5/2015 | |
| WO | 2016016344 | A1 | 2/2016 | |
| WO | WO 2016040724 | A1 | 3/2016 | |
| WO | WO 2016054638 | A1 | 4/2016 | |
| WO | WO 2016134333 | A1 | 8/2016 | |
| WO | 2016164731 | A2 | 11/2016 | |
| WO | WO 2017021526 | A1 | 2/2017 | |
| WO | WO-2017112741 | A1 * | 6/2017 | ......... A61K 39/0011 |
| WO | WO 2017214207 | A2 | 12/2017 | |
| WO | WO-2018013918 | A2 * | 1/2018 | ........... A61K 31/519 |

OTHER PUBLICATIONS

Turtle et. al. Sci Transl Med. 8(355):1-24. (2016)) (Year: 2016).*
Pfirschke et al., "Immunogenic Chemotherapy Sensitizes Tumors to Checkpoint Blockade Therapy," *Immunity* 44:343-354, Feb. 16, 2016.
Ajina et al., "Prospects for combined use of oncolytic viruses and CAR T-cells," *Journal for ImmunoTherapy of cancer* 5(90), 2017. (27 pages).
Cherkassky et al., "Human CAR T cells with cell-intrinsic PD-1 checkpoint blockage resist tumor-mediated inhibition," *The Journal of Clinical Investigation* 126(8):3130-3144, Aug. 2016.
Chong et al., "Chimeric Antigen Receptor Modified T Cells Directed Against CD19 (CTL019) in Patients with Poor Prognosis, Relapsed or Refractory CD19+ Follicular Lymphoma: Prolonged Remissions Relative to Antecedent Therapy," *Blood* 128(22), 2016. (6 pages).
Ghobadi et al., "Chimeric antigen receptor T cell therapy for non-Hodgkin lymphoma," *Current Research in Translation Medicine* 66:43-49, 2018.
John et al., "Anti-PD-1 Antibody Therapy Potently Enhances the Eradication of Established Tumors by Gene-Modified T cells," *Clinical Therapy: Preclinical* 19(20):5636-5646, Oct. 15, 2013.
Locke et al., "Phase 1 Results of Zuma-1: A Multicenter Study of KTE-C19 Anti-CD19 CAR T Cell Therapy in Refractory Aggressive Lymphoma," *Molecular Therapy* 25(1):285-295, Jan. 2017.
Lu et al., "Treatment of Patients With Metastatic Cancer Using a Major Histocompatibility Complex Class II-Restricted T-cell Receptor Targeting the Cancer Germline Antigen MAGE-A3," *Journal of Clinical Oncology* 35(29):3322-3329, Oct. 10, 2017.
Tian et al., "Anti-CD138 chimeric antigen receptor-modified T cell therapy for multiple myeloma with extensive extramedullary involvement," *Annals of Hematology* 96:1407-1410, Jun. 2, 2017.
Xu et al., "Combination therapy: a feasibility strategy for CAR-T cell therapy in the treatment of solid tumors (Review)," *Oncology Letters* 16:2063-2070, 2018.
Altschul et al., "Gapped BLAST and PSI-BLAST: a new generation of protein database search programs," *Nucleic Acids Research* 25(17):3389-3402, 1997.
Argast et al., "I-*Ppo* I and I-*Cre* I Homing Site Sequence Degeneracy Determined by Random Mutagenesis and Sequential in Vitro Enrichment," *J. Mol. Biol.* 280:345-353, 1998.
Ashworth et al., "Computational redesign of endonuclease DNA binding and cleavage specificity," *Nature* 441(7093):656-659, Jun. 1, 2006.
Belfort et al., "Homing endonucleases: keeping the house in order," *Nucleic Acids Research* 25(17):3379-3388, 1997.
Bentzen et al., "BK channel activators and their therapeutic perspectives," *Frontiers in Physiology* 5:389, Oct. 2014. (12 pages).
Boozari et al., "Antitumoural immunity by virus-mediated immunogenic apoptosis inhibits metastatic growth of hepatocellular carcinoma," *Gut* 59(10):1416-1426, Jul. 30, 2010.
Bouquet et al., "TGFβ1 Inhibition Increases the Radiosensitivity of Breast Cancer Cells *In Vitro* and Promotes Tumor Control by Radiation *In Vivo*," *Clin Cancer Res.* 17(21):6754-6765, Nov. 1, 2011.
Bowerman et al., "Engineering the Binding Properties of the T Cell Receptor: Peptide:MHC Ternary Complex that Governs T Cell Activity," *Mol Immunol.* 46(15):3000-3008, Sep. 2009.
Bramante et al., "Oncolytic virotherapy for treatment of breast cancer, including triple-negative breast cancer," *Oncoimmunology* 5(2):e1078057, 2016. (8 pages).
Brentjens et al., "CD19-targeted T cells rapidly induce molecular remissions in adults with chemotherapy-refractory acute lymphoblastic leukemia," *Sci Transl Med.* 5(177):177ra38, Mar. 20, 2013. (19 pages).
Brentjens et al., "Genetically Targeted T Cells Eradicate Systemic Acute Lymphoblastic Leukemia Xenografts," *Clin Cancer Res* 13(18):5426-5435, Sep. 15, 2007.
Chevalier et al., "Design, Activity, and Structure of a Highly Specific Artificial Endonuclease," *Molecular Cell* 10:895-905, Oct. 2002.
Choi et al., "Pre-clinical Specificity and Safety of UC-961, a First-in-Class Monoclonal Antibody Targeting ROR1," *Clinical Lymphoma, Myeloma, & Leukemia* 15(S1):S167-169, 2015.
Chothia et al., "The outline structure of the T-cell αβ receptor," *The EMBO Journal* 7(12):3745-3755, 1988.
Clements et al., "All that glitters is not gold: the need to consider desirable and undesirable immune aspects of oncolytic virus therapy," *Oncoimmunology* 5(1):e1057674, Jan. 2016. (3 pages).
Coiffier et al., "Chop Chemotherapy Plus Rituximab Compared With Chop Alone in Elderly Patients With Diffuse Large-B-Cell Lymphoma," *N Engl J Med* 346(4):235-242, Jan. 24, 2002.
Cole et al., "CD8: Adhesion Molecule, Co-Receptor and Immuno-Modulator," *Cellular & Molecular Immunology* 1(2):81-88, Apr. 2004.
Dangaj et al., "Novel Recombinant Human B7-H4 Antibodies Overcome Tumoral Immune Escape to Potentiate T-Cell Antitumor Responses," *Cancer Res* 73(15):4820-4829, Aug. 1, 2013.
Desjarlais et al., "Use of a zinc-finger consensus sequence framework and specificity rules to design specific DNA binding proteins," *Proc. Natl. Acad. Sci.* USA 90:2256-2260, Mar. 1993.
Dewan et al., "Fractionated but not single dose radiotherapy induces an immune-mediated abscopal effect when combined with anti-CTLA-4 antibody," *Clin Cancer Res.* 15(17):5379-5388, Sep. 1, 2009.
Dossett et al., "Adoptive Immunotherapy of Disseminated Leukemia With TCR-transduced, CD8+ T Cells Expressing a Known Endogenous TCR," *Molecular Therapy* 17(4):742-749, Apr. 2009.

(56) References Cited

OTHER PUBLICATIONS

Draghiciu et al., "From Tumor Immunosuppression to Eradication: Targeting Homing and Activity of Immune Effector Cells to Tumors," *Clinical and Developmental Immunology* 2011:439053, 2011. (15 pages).
Dujon et al., "Mobile introns: definition of terms and recommened nomenclature," *Gene* 82:115-118, 1989.
Emeagi et al., "Proinflammatory Characteristics of SMAC/DIABLO-Induced Cell Death in Antitumor Therapy," *Cancer Res* 72(6):1-11, Mar. 15, 2012.
Engels et al., "Retroviral Vectors for High-Level Transgene Expression in T Lymphocytes," *Human Gene Therapy* 14:1155-1168, Aug. 10, 2003.
Epinat et al., "A novel engineered meganuclease induces homologous recombination in yeast and mammalian cells," *Nucleic Acids Research* 31(11):2952-2962, 2003.
Floros et al., "Anticancer Cytokines: Biology and Clinical Effects of IFN-$\alpha$2, IL-2, IL-15, IL-21, and IL-12," *Semin Oncol.* 42(4):539-548, Aug. 2015.
Frecha et al., "Advances in the Field of Lentivector-based Transduction of T and B Lymphocytes for Gene Therapy," *Molecular Therapy* 18(10):1748-1757, Oct. 2010.
Fucikova et al., "High hydrostatic pressure induces immunogenic cell death in human tumor cells," *Int. J. Cancer* 135:1165-1177, 2014.
Fucikova et al., "Human Tumor Cells Killed by Anthracyclines Induce a Tumor-Specific Immune Response," *Cancer Res* 71(14):4821-4833, 2011.
Galluzi et al., "Immunogenic cell death in cancer and infectious disease," *Nature Reviews Immunology* 17:97-111, Feb. 2017.
Galluzzi et al., "Classification of current anticancer immunotherapies," *Oncotarget* 5(24):12472-12508, Dec. 2014.
Gao et al., "Molecular interactions of coreceptor CD8 and MCH class I: the molecular basis for functional coordination with the T-cell receptor," *Immunology Today* 21(12):630-636, Dec. 2000.
Garg et al., "A novel pathway combining calreticulin exposure and ATP secretion in immunogenic cancer cell death," *The EMBO Journal* 31:1062-1079, 2012.
Garg et al., "Dendritic cell vaccines based on immunogenic cell death elicit danger signals and T cell-driven rejection of high-grade glioma," *Science Translational Medicine* 8(328):328ra27, Mar. 2, 2016. (16 pages).
Garg et al., "Resistance to anticancer vaccination effect is controlled by a cancer cell-autonomous phenotype that disrupts immunogenic phagocytic removal," *Oncotarget* 6(29):26841-26860, Jul. 23, 2015.
Garg et al., "ROS-induced autophagy in cancer cells assists in evasion from determinants of immunogenic cell death," *Autophagy* 9(9):1292-1307, Jun. 19, 2013.
Garg et al., "Trial watch: Immunogenic cell death induction by anticancer chemotherapeutics," *Oncoimmunology* 6(12):e1386829, 2017. (18 pages).
Geurts et al., "Gene Transfer into Genomes of Human Cells by the Sleeping Beauty Transposon System," *Molecular Therapy* 8(1):108-117, Jul. 2003.
Gimble et al., "Substrate Recognition and Induced DNA Distortion by the PI-SceI Endonuclease, an Enzyme Generated by Protein Splicing," *J. Mol. Biol.* 263: 163-180, 1996.
Golden et al., "Radiation fosters dose-dependent and chemotherapy-induced immunogenic cell death," *Oncoimmunology* 3:e28518, Apr. 2014. (12 pages).
Green et al., "Mitichondria and Apoptosis," *Science* 281:1309-1312, Aug. 28, 1998.
Guest et al., "The Role of Extracellular Spacer Regions in the Optimal Design of Chimeric Immune Receptors," *J Immunother* 28:203-211, 2005.
Harris et al., "Adoptive T Cell Therapies: a Comparison of T Cell Receptors and Chimeric Antigen Receptors," *Trends in Pharmacological Sciences* 37(3):220-230, Mar. 2016.

Haso et al., "Anti-CD22-chimeric antigen receptors targeting B-cell precursor acute lymphoblastic leukemia," *Blood* 121(7):1165-1174, 2013.
Hemminki et al., "A century of oncolysis evolves into oncolytic immunotherapy," *Oncoimmunology* 5(2):e1074377, 2016. (3 pages).
Henkart et al., "Cytotoxic T-Lymphocytes" in *Fundamental Immunology*, Paul (ed.) (2003 Lippincott Williams & Wilkins, Philadelphia, PA pp. 1127-1150.
Hoa et al., "Nuclear Targeting of IGF-1 Receptor in Orbital Fibroblasts from Graves' Disease: Apparent Role of ADAM17," *PLoS One* 7(4):e34173, Apr. 10, 2012. (9 pages).
Jackson et al., "The Differential Effects of Mutant *p53* Alleles on Advanced Murine Lung Cancer," *Cancer Res* 65(22):10280-10288, 2005.
James et al., "Antigen sensitivity of CD22-specific chimeric T cell receptors is modulated by target epitope distance from the cell membrane," *J Immunol.* 180(10):7028-7038, May 15, 2008.
Janeway et al., Immunobiology: The Immune System in Health and Disease, 3rd Ed., Current Biology Publications, pp. 3:1-3:11, 1997.
Jasin, "Genetic manipulation of genomes with rare-cutting endonucleases," *Trends in Genetics* 12(6):224-228, Jun. 1996.
Jinek et al., "A programmable dual RNA-guided DNA endonuclease in adaptive bacterial immunity," *Science* 337(6096):816-821, Aug. 17, 2012.
Jolly, D J. 1999. Emerging Viral Vectors. pp 209-240 in Friedmann T. ed. The Development of Human Gene Therapy. New York: Cold Spring Harbor Lab).
Jores et al., "Resolution of hypervariable regions in T-cell receptor $\beta$ chains by a modified Wu-Kabat index of amino acid diversity," *Proc. Natl. Acad. Sci. USA* 87:9138-9142, Dec. 1990.
Kabat, et al., "Sequences of Proteins of Immunological Interest," US Dept. Health and Human Services, Public Health Service National Institutes of Health, 1991, 5th ed.)).
Kalos et al., "T Cells with Chimeric Antigen Receptors Have Potent Antitumor Effects and Can Establish Memory in Patients with Advanced Leukemia," *Sci Transl Med* 3(95):95ra73, Aug. 10, 2011. (21 pages).
Kim et al., "High Cleavage Efficiency of a 2A Peptide Derived from Porcine Teschovirus-1 in Human Cell Lines, Zebrafish and Mice," *PLoS ONE* 6(4):e18556, Apr. 29, 2011. (8 pages).
Kisselev et al., "Proteasome Inhibitors: An Expanding Army Attacking a Unique Target," *Chem Biol.* 19(1):99-115, Jan. 27, 2012.
Kochenderfer et al., "Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor," *Journal of Clinical Oncology* 33(6):540-549, Feb. 20, 2015.
Krisky et al., "Development of herpes simplex virus replication-defective multigene vectors for combination gene therapy applications," *Gene Therapy* 5:1517-1530, 1998.
Kroemer et al., "Immunogenic Cell Death in Cancer Therapy," *Annual Review of Immunology* 31:51-72, Nov. 2012.
Kuball et al., "Facilitating matched pairing and expression of TCR chains introduced into human T cells," *Blood* 109(6):2331-2338, Mar. 15, 2007.
Larsson et al., "Local co-administration of gene-silencing RNA and drugs in cancer therapy: State-of-the-art and therapeutic potential," *Cancer Treat Rev.* 55:128-135, Apr. 2017.
Lee et al., "T cells expressing CD19 chimeric antigen receptors for acute lymphoblastic leukaemia in children and young adults: a phase 1 dose-escalation trial," *The Lancet* 385:517-528, Feb. 7, 2015.
Leen et al., "Improving T Cell Therapy for Cancer," *Annu. Rev. Immunol.* 25:243-265, 2007.
Lefranc et al., "IMGT unique numbering for immunoglobulin and T cell receptor variable domains and Ig superfamily V-like domains," *Developmental and Comparative Immunology* 27:55-77, 2003.
Liu et al., "Selective inhibition of IDO1 effectively regulates mediators of antitumor immunity," *Blood* 115(17):3520-3530, Apr. 29, 2010.
Mautino et al., "Abstract 491: NLG919, a novel indoleamine-2,3-dioxygenase (IDO)-pathway inhibitor drug candidate for cancer

(56) References Cited

OTHER PUBLICATIONS therapy," in *Proceedings: AACR 104th Annual Meeting 2013*, American Association for Cancer Research, Washington, DC, Apr. 6-10, 2013. (4 pages).

Menger et al., "Cardiac Glycosides Exert Anticancer Effects by Inducing Immunogenic Cell Death," *Science Translational Medicine* 4(143):143ra99, Jul. 18, 2012. (10 pages).

Mátés et al., "Molecular evolution of a novel hyperactive *Sleeping Beauty* transposase enables robust stable gene transfer in vertebrates," *Nature Genetics, Advance Online Publication*, May 3, 2009. (33 pages).

Nguyen et al., "Identification of a murine CD28 dileucine motif that suppresses single-chain chimeric T-cell receptor expression and function," *Blood* 102(13):4320-4325, Dec. 15, 2003.

Patel et al., "Impact of chimeric immune receptor extracellular protein domains on T cell function," *Gene Therapy* 6:412-419, 1999.

Perler et al., "Protein splicing elements: inteins and exteins—a definition of terms and recommended nomenclature," *Nucleic Acids Research* 22(7):1125-1127, 1994.

Porter et al., "Chimeric antigen receptor T cells persist and induce sustained remissions in relapsed refractory chronic lymphocytic leukemia," *Science Translational Medicine* 7(303):303ra139, Sep. 2, 2015.

Porteus et al., "Gene targeting using zinc finger nucleases," *Nature Biotechnology* 23(8):967-973, Aug. 2005.

Pâques et al., "Meganucleases and DNA Double-Strand Break-Induced Recombination: Perspectives for Gene Therapy," *Current Gene Therapy* 7(1):49-66, 2007.

Ren et al., "Multiplex genome editing to generate universal CAR T cells resistant to PD1 inhibition," *Clin Cancer Res* 23(9):2255-2266, May 1, 2017.

Sadelain et al., "The basic principles of chimeric antigen receptor (CAR) design," *Cancer Discov.* 3(4):388-398, Apr. 2013.

Sambrook et al., *Molecular Cloning: a Laboratory Manual* 2d ed. (Cold Spring Harbor Laboratory, 1989.

Savoldo et al., "CD28 costimulation improves expansion and persistence of chimeric antigen receptor-modified T cells in lymphoma patients," *J Clin Invest.* 121(5):1822-1826, May 2011.

Sazinsky et al., "Aglycosylated immunoglobulin G1 variants productively engage activating Fc receptors," *Proc Natl Acad Sci USA* 105(51):20167-20172, Dec. 23, 2008.

Scatchard, "The Attractions of Proteins for Small Molecules and Ions," *Annals of the New York Academy of Sciences* 51(4):660-672, May 31, 1949.

Schmitt et al., "T Cell Receptor Gene Therapy for Cancer," *Human Gene Therapy* 20:1240-1248, Nov. 2009.

Scholten et al., "Codon modification of T cell receptors allows enhanced functional expression in transgenic human T cells," *Clinical Immunology* 119:135-145, 2006.

Shekarian et al., "Pattern recognition receptors: immune targets to enhance cancer immunotherapy," *Annals of Oncology* 28:1756-1766, 2017.

Srivastava et al., "Immunogenic chemotherapy enhances recruitment of CAR-T cells to lung tumors and improves anti-tumor efficacy when combined with checkpoint blockade," *Cancer Cell.* 39(2):193-208.e10, Feb. 8, 2021.

Stone et al., "A novel T cell receptor single-chain signaling complex mediates antigen-specific T cell activity and tumor control," *Cancer Immunol. Immunother.* 63(11):1163-1176, Nov. 2014.

Sussman et al., "Isolation and Characterization of New Homing Endonuclease Specificites at Individual Target Site Positions," *J. Mol. Biol.* 342:31-41, 2004.

Terentis et al., "The Selenazal Drug Ebselen Potently Inhibits Indoleamine 2,3-Dioxygenase by Targeting Enzyme Cysteine Residues," *Biochemistry* 49(3):591-600, 2010.

Tesniere et al., "Immunogenic death of colon cancer cells treated with oxaliplatin," *Oncogene* 29:482-491, Nov. 2, 2009.

Tesniere et al., "Molecular characteristics of immunogenic cancer cell death," *Cell Death and Differentiation* 15:3-12, 2008.

Till et al., "Adoptive immunotherapy for indolent non-Hodgkin lymphoma and mantle cell lymphoma using genetically modified autologous CD20-specific T cells," *Blood* 112(6):2261-2271, Sep. 15, 2008.

Till et al., "CD20-specific adoptive immunotherapy for lymphoma using a chimeric antigen receptor with both CD28 and 4-1BB domains: pilot clinical trial results," *Blood* 119(17):3940-3950 (2012).

Torikai et al., "A foundation for universal T-cell based immunotherapy: T cells engineered to express a CD19-specific chimeric-antigen-receptor and eliminate expression of endogenous TCR," *Blood* 119(24):5697-5705, Jun. 14, 2012.

Torikai et al., "Genetic editing of HLA expression in hematopoietic stem cells to broaden their human application," *Nature Scientific Reports* 6:21757, Feb. 23, 2016. (11 pages).

Torikai et al., "Toward eliminating HLA class I expression to generate universal cells from allogeneic donors," *Blood* 122(8):1341-1349, Aug. 22, 2013.

UniProt, "CD4_HUMAN," sequence ID No. P01730, download date Feb. 15, 2023. (16 pages).

UniProt, "CD8A_HUMAN," sequence ID No. P01732, download date Feb. 15, 2023. (9 pages).

UniProt, "CD8B_HUMAN," sequence ID No. P10966, download date Feb. 15, 2023. (7 pages).

Vanpoiulle-Box et al., "DNA exonuclease Trex1 regulates radiotherapy-induced tumour immunogenicity," *Nature Communications* 8:15618, Jun. 9, 2017. (15 pages).

Veinalde et al., "Oncolytic measles virus encoding interleukin-12 mediates potent antitumor effects through T cell activation," *Oncoimmunology* 6(4):e1285992, 2017. (11 pages).

Verhoeyen et al., Methods in Molecular Biology, Methods and Protocols vol. 506, Humana Press, 2009, Chapter 8, "Lentiviral Vector Gene Transfer into Human T Cells," pp. 97-114.

Walchli et al., "A Practical Approach to T-Cell Receptor Cloning and Expression," *PLoS One* 6(11):e27930, Nov. 2011. (11 pages).

Walseng et al., "A TCR-based Chimeric Antigen Receptor," *Nature Scientific Reports* 7:10713, Sep. 6, 2017. (10 pages).

Wang et al., "A transgene-encoded cell surface polypeptide for selection, in vivo tracking, and ablation of engineered cells," *Blood* 118(5):1255-1263, Aug. 4, 2011.

Wang et al., "Optimizing Adoptive Polyclonal T Cell Immunotherapy of Lymphomas, Using a Chimeric T Cell Receptor Possessing CD28 and CD137 Costimulatory Domains," *Human Gene Therapy* 18:712-725, Aug. 2007.

Wennerberg et al., "Barriers to Radiation-Induced *In Situ* Tumor Vaccination," *Frontiers in Immunology* 8:229, Mar. 13, 2017. (11 pages).

Wilson, "Analyzing Biomolecular Interactions," *Science* 295:2103-2105, Mar. 15, 2002.

Wolfe et al., "Analysis of Zinc Fingers Optimized via Phage Display: Evaluating the Utility of a Recognition Code," *J. Mol. Biol.* 285:1917-1934 (1999).

Wolff et al., "Monoclonal Antibody Homodimers: Enhanced Antitumor Activity in Nude Mice," *Cancer Research* 53:2560-2565, Jun. 1, 1993.

Woller et al., "Oncolytic viruses as anticancer vaccines," *Frontiers in Oncology* 4:188, Jul. 21, 2014. (13 pages).

Xie et al., "sgRNAcas9: a Software Package for Designing CRISPR sgRNA and Evaluating Potential Off-Target Cleavage Sites," *PLoS ONE* 9(6):e100448, Jun. 23, 2014.

Yang et al., "Therapeutic Potential and Challenges of Targeting Receptor Tyrosine Kinase ROR1 with Monoclonal Antibodies in B-Cell Malignancies," *PLoS ONE* 6(6):e21018, Jun. 15, 2011. (15 pages).

Zhao et al., "Primary Human Lymphocytes Transduced with NY-ESO-1 Antigen-Specific TCR Genes Recognize and Kill Diverse Human Tumor Cell Lines," *J Immunol* 174:4415-4423, 2005.

"Autologous RORIR-CAR-T Cells for Chronic Lymphocytic Leukemia (CLL)," ClinicalTrials.gov Identifier: NCT02194374, Jul. 18, 2014 (10 pages).

"Genetically Modified T-Cell Therapy in Treating Patients With Advanced ROR1+ Malignancies," ClinicalTrials.gov Identifier: NCT02706392, Mar. 11, 2016 (15 pages).

(56) References Cited

OTHER PUBLICATIONS

"Genetically Modified T-Cell Therapy in Treating Patients With Advanced ROR1+ Malignancies," ClinicalTrials.gov Identifier: NCT02706392, Version 7, Mar. 15, 2017 (7 pages).

Berger et al., "Safety of Targeting ROR1 in Primates with Chimeric Antigen Receptor-Modified T Cells," *Cancer Immunology Research* 3(2):206-216, Feb. 2015. (11 pages).

Du et al., "Medium Dose Intermittent Cyclophosphamide Induces Immunogenic Cell Death and Cancer Cell Autonomous Type I Interferon Production in Glioma Models," *Cancer Lett* 470:170-180, Feb. 1, 2020. (28 pages).

Hudecek et al., "Naive CD4+T Cells Modified to Express a ROR1-Specific CAR Mediate Anti-Tumor Activity and Provide Superior Help to CD8+ROR1-CAR T Cells," *Blood*, Nov. 18, 2011 [Biosis, Biosciences Information Service, Nov. 1, 2011] (1 page).

Hudecek et al., "Receptor Affinity and Extracellular Domain Modifications Affect Tumor Recognition by ROR1-Specific Chimeric Antigen Receptor T Cells," *Clinical Cancer Research* 19(12), Jun. 15, 2013 [Published Online Apr. 25, 2013] (13 pages).

International Search Report and Written Opinion, mailed Jul. 26, 2019, for International Application No. PCT/US2019/027371 (13 pages).

Luznik et al., "Post-transplantation cyclophosphamide for tolerance induction in HLA-haploidentical BMT," *Semin Oncol* 39(6), Dec. 2012. (16 pages).

Nair et al., "A simple practice guide for dose conversion between animals and human," *Journal of Basic and Clinical Pharmacy* 7(2):27-31, Mar.-May 2016. (5 pages).

Shalapour et al., "Immunosuppressive plasma cells impede T-cell-dependent immunogenic chemotherapy," *Nature* 521:94-98, May 2015. (28 pages).

Specht et al., "Phase I study of immunotherapy for advanced ROR1+ malignancies with autologous ROR1-specific chimeric antigen receptor-modified (CAR)-T cells," *Journal of Clinical Oncology* 36(5), 2018 [Supplement 1] (1 page).

Davies et al., "Crosstown Traffic: Lymphodepleting Chemotherapy Drives Car T Cells," *Cancer Cell* 39:138-140, Feb. 8, 2021. (3 pages).

Ma et al., " Enhanced CAR-T cell activity against solid tumors by vaccine boosting through the chimeric receptor," *Science* 365(6449):162-168, Jul. 12, 2019 (HHS Public Access Author Manuscript, available in PMC Oct. 19, 2019). (15 pages).

Petroni et al., "Immunogenic therapies drive Car T cells toward superior efficacy," *Trends in Cancer* 7(3):179-181, Mar. 2021. (10 pages).

Reinhard et al., "An RNA vaccine drives expansion and efficacy of claudin-CAR-T cells against solid tumors," *Science* 367:446-453, Jan. 24, 2020. (8 pages).

Salter et al., "Comparative analysis of TCR and CAR signaling informs CAR designs with superior antigen sensitivity and in vivo function," *Sci. Signal.* 14:eabe2606, Aug. 24, 2021. (17 pages).

Srivastava et al., "Engineering CAR-T Cells: Design Concepts," *Trends Immunol* 36(8):494-502, Aug. 2015 (HHS Public Access Author Manuscript, available in PMC Aug. 1, 2016). (20 pages).

\* cited by examiner

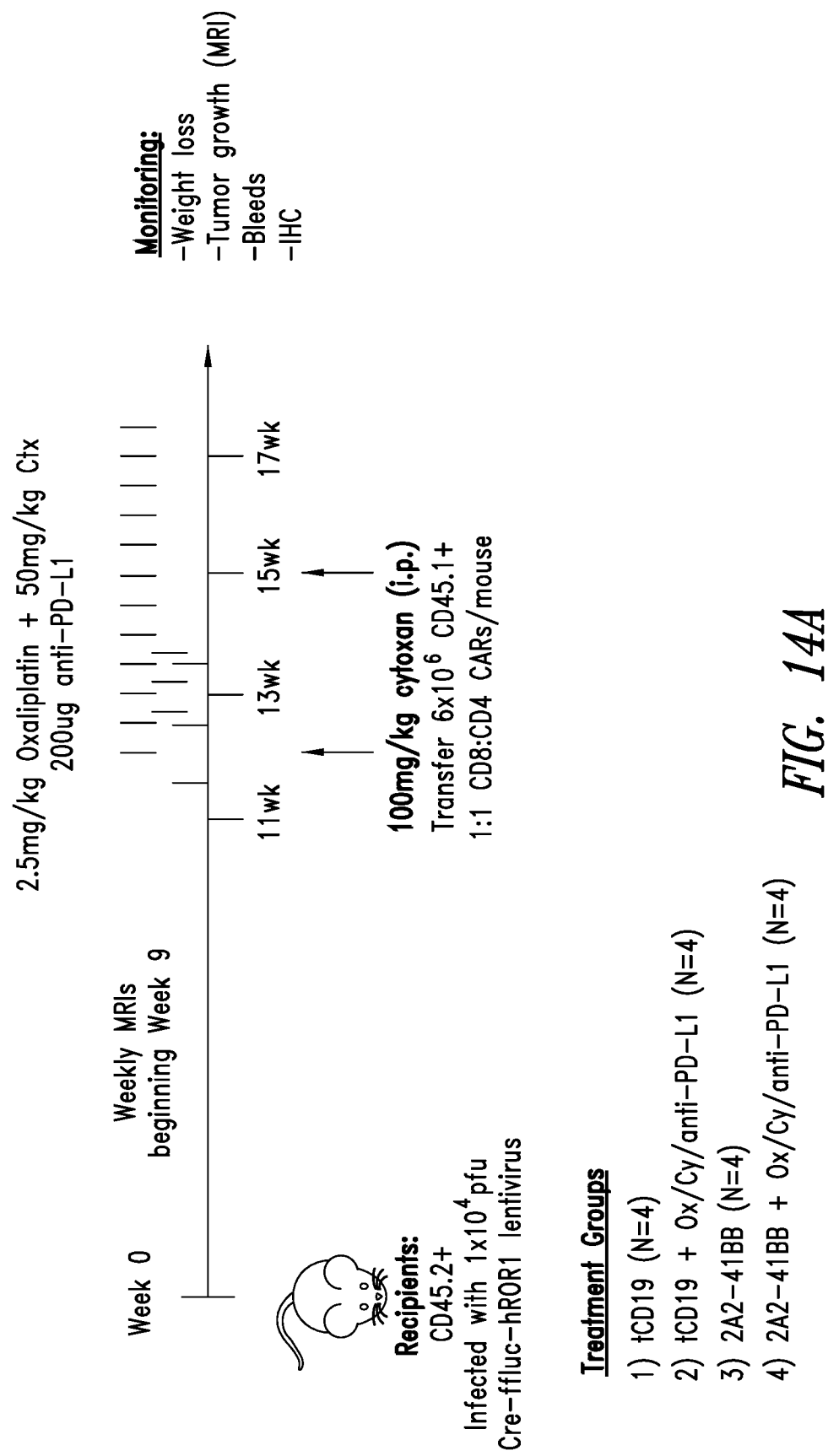

Control T cells

0/10 = 0% regressing

>50% CD3 Infiltration

<5% CD3 Infiltration

| Pathway Description | Count in Gene Set | False Discovery Rate |
|---|---|---|
| Cytokine-cytokine receptor interaction | 23 | 2.87e-13 |
| Chemokine signaling pathway | 12 | 3.01e-05 |
| Cell adhesion molecules (CAMs) | 10 | 0.000193 |

METHODS FOR IMPROVING ADOPTIVE CELL THERAPY

CROSS-REFERENCE TO RELATED APPLICATION(S)

This application claims the priority benefit of U.S. Patent Application No. 62/555,034, filed Sep. 6, 2017, which is incorporated herein by reference for all purposes as if fully set forth herein.

STATEMENT OF GOVERNMENT INTEREST

This invention was made with government support under CA114536 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_457USPC_SEQUENCE_LISTING.txt. The text file is 10.9 KB, was created on Mar. 5, 2020, and is being submitted electronically via EFS-Web.

BACKGROUND

Adoptive transfer of genetically modified T cells has emerged as a potent therapy for various malignancies. The most widely employed strategy has been infusion of patient-derived T cells expressing chimeric antigen receptors (CARs) targeting tumor associated antigens. This approach has numerous theoretical advantages, including the ability to target T cells to any cell surface antigen, circumvent loss of major histocompatibility complex as a tumor escape mechanism, and employ a single vector construct to treat any patient, regardless of human leukocyte antigen haplotype. For example, CAR clinical trials for B cell non-Hodgkin's lymphoma (NHL) have, to date, targeted CD19, CD20, or CD22 antigens that are expressed on malignant lymphoid cells as well as on normal B cells (Brentjens et al., *Sci Transl Med* 2013; 5(177):177ra38; Haso et al., *Blood* 2013; 121(7):1165-74; James et al., *J Immunol* 2008; 180(10):7028-38; Kalos et al., *Sci Transl Med* 2011; 3(95):95ra73; Kochenderfer et al., *J Clin Oncol* 2015; 33(6):540-9; Lee et al., *Lancet* 2015; 385(9967):517-28; Porter et al., *Sci Transl Med* 2015; 7(303):303ra139; Savoldo et al., *J Clin Invest* 2011; 121(5):1822-6; Till et al., *Blood* 2008; 112(6):2261-71; Till et al., *Blood* 2012; 119(17):3940-50; Coiffier et al., *N Engl J Med* 2002; 346(4):235-42). Further advances can be advantageous for improving adoptive cell therapies.

For example, the ability of transferred cells bearing CARs or TCRs specific for a particular antigen to target and attack antigen-bearing cells may be limited by the number of transferred cells that expand, activate, and home to a cancer site, such as a tumor. Further, the tumor microenvironment can elicit a number of tolerance or immunosuppression mechanisms that can reduce the activity of adoptive cell therapies (see, e.g., Draghiciu et al., *Clin. Dev. Immunol.* 439053 (2011). Accordingly, improved strategies are needed in adoptive cell therapies. The presently disclosed embodiments address these needs and provide other related advantages.

DETAILED DESCRIPTION

Figure 1:
FIG. 1 shows a scheme for adapting the KP mouse model of non-small cell lung cancer (NSCLC) to study anti-ROR1 CAR T cell therapy.
Figure 1:
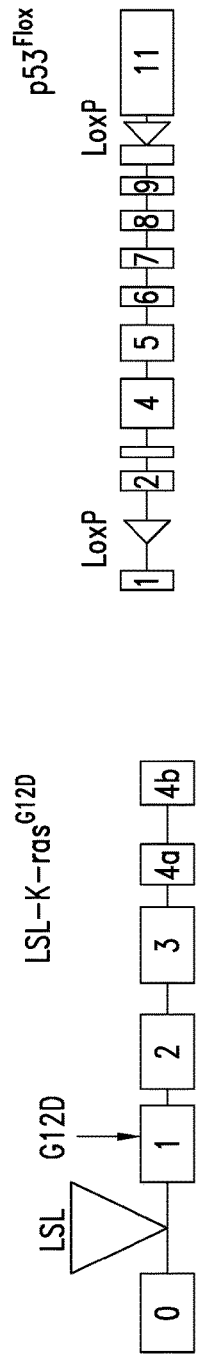
Figure 1:
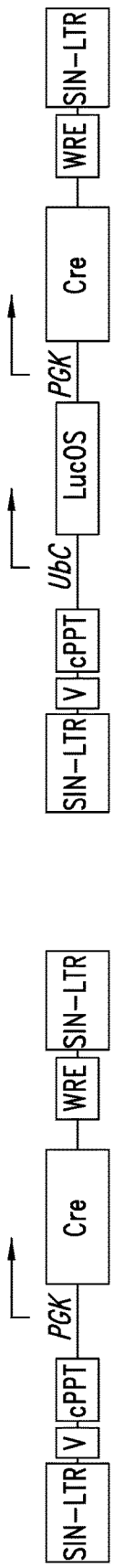

The present disclosure provides reagents and methods for treating disease using modified immune cells (e.g., T cells comprising a CAR or a TCR) in combination with an agent associated with induction of immunogenic cell death (ICD) and optionally further in combination with an agent that specifically binds to and/or inhibits an immune suppression component.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is, in some aspects, to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, is to be understood to include any integer within the recited range, unless otherwise indicated. As used herein, the term "about" in some aspects means ±20% of the indicated range, value, or structure, unless otherwise indicated. It should be understood that the terms "a" and "an" as used herein in some aspects refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

"Optional" or "optionally" in some aspects means that the subsequently described element, component, event, or circumstance may or may not occur, and that the description includes instances in which the element, component, event, or circumstance occurs and instances in which they do not.

In addition, it should be understood that the individual constructs, or groups of constructs, derived from the various combinations of the structures and subunits described herein, are disclosed by the present application to the same extent as if each construct or group of constructs was set forth individually. Thus, selection of particular structures or particular subunits is within the scope of the present disclosure.

The term "consisting essentially of" is not equivalent to "comprising" and in some aspects refers to the specified materials or steps of a claim, or to those that do not materially affect the basic characteristics of a claimed subject matter. For example, a protein domain, region, or module (e.g., a binding domain, hinge region, or linker) or a protein (which may have one or more domains, regions, or modules) "consists essentially of" a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, in some aspects, "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and 0-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that functions in a manner similar to a naturally occurring amino acid.

As used herein, in some aspects, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s).

A "conservative substitution" in some aspects refers to amino acid substitutions that do not significantly affect or alter binding characteristics of a particular protein. Generally, conservative substitutions are ones in which a substituted amino acid residue is replaced with an amino acid residue having a similar side chain. Conservative substitutions include a substitution found in one of the following groups: Group 1: Alanine (Ala or A), Glycine (Gly or G), Serine (Ser or S), Threonine (Thr or T); Group 2: Aspartic acid (Asp or D), Glutamic acid (Glu or Z); Group 3: Asparagine (Asn or N), Glutamine (Gln or Q); Group 4: Arginine (Arg or R), Lysine (Lys or K), Histidine (His or H); Group 5: Isoleucine (Ile or I), Leucine (Leu or L), Methionine (Met or M), Valine (Val or V); and Group 6: Phenylalanine (Phe or F), Tyrosine (Tyr or Y), Tryptophan (Trp or W). Additionally or alternatively, amino acids can be grouped into conservative substitution groups by similar function, chemical structure, or composition (e.g., acidic, basic, aliphatic, aromatic, or sulfur-containing). For example, an aliphatic grouping may include, for purposes of substitution, Gly, Ala, Val, Leu, and Ile. Other conservative substitutions groups include: sulfur-containing: Met and Cysteine (Cys or C); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information can be found in Creighton (1984) *Proteins*, W.H. Freeman and Company.

As used herein, in some aspects, "protein" or "polypeptide" refers to a polymer of amino acid residues. Proteins apply to naturally occurring amino acid polymers, as well as to amino acid polymers in which one or more amino acid residue is an artificial chemical mimetic of a corresponding naturally occurring amino acid and non-naturally occurring amino acid polymers.

As used herein, in some aspects, "fusion protein" refers to a protein that, in a single chain, has at least two distinct domains, wherein the domains are not naturally found together in a protein. A polynucleotide encoding a fusion protein may be constructed using PCR, recombinantly engineered, or the like, or such fusion proteins can be synthesized. A fusion protein may further contain other components, such as a tag, a linker, or a transduction marker. In certain embodiments, a fusion protein expressed or produced by a host cell (e.g., a T cell) locates to a cell surface, where the fusion protein is anchored to the cell membrane (e.g., via a transmembrane domain) and comprises an extracellular component (e.g., containing a binding domain) and an intracellular component (e.g., containing an effector domain, a co-stimulatory domain, or a combination thereof).

"Nucleic acid molecule" or "polynucleotide" in some aspects refers to a polymeric compound including covalently linked nucleotides, which can be made up of natural subunits (e.g., purine or pyrimidine bases) or non-natural subunits (e.g., morpholine ring). Purine bases include adenine, guanine, hypoxanthine, and xanthine, and pyrimidine bases include uracil, thymine, and cytosine. Nucleic acid molecules include polyribonucleic acid (RNA), polydeoxyribonucleic acid (DNA), which includes cDNA, genomic DNA, and synthetic DNA, either of which may be single- or double-stranded. If single-stranded, the nucleic acid molecule may be the coding strand or non-coding (anti-sense strand). A nucleic acid molecule encoding an amino acid sequence includes all nucleotide sequences that encode the same amino acid sequence. Some versions of the nucleotide sequences may also include intron(s) to the extent that the intron(s) would be removed through co- or post-transcriptional mechanisms. In other words, different nucleotide sequences may encode the same amino acid sequence as the result of the redundancy or degeneracy of the genetic code, or by splicing.

Variants of nucleic acid molecules of this disclosure are also contemplated. Variant nucleic acid molecules are in some aspects at least 70%, 75%, 80%, 85%, 90%, and preferably 95%, 96%, 97%, 98%, 99%, or 99.9% identical a nucleic acid molecule of a defined or reference polynucleotide as described herein, or that hybridize to a polynucleotide under stringent hybridization conditions of 0.015M sodium chloride, 0.0015M sodium citrate at about 65-68° C. or 0.015M sodium chloride, 0.0015M sodium citrate, and 50% formamide at about 42° C. Nucleic acid molecule variants retain the capacity to encode a binding protein or a binding domain thereof having a functionality described herein, such as specifically binding a target molecule.

"Percent sequence identity" in some aspects refers to a relationship between two or more sequences, as determined by comparing the sequences. Preferred methods to determine sequence identity are designed to give the best match between the sequences being compared. For example, the sequences are aligned for optimal comparison purposes (e.g., gaps can be introduced in one or both of a first and a second amino acid or nucleic acid sequence for optimal alignment). Further, non-homologous sequences may be disregarded for comparison purposes. The percent sequence identity referenced herein is calculated over the length of the reference sequence, unless indicated otherwise. Methods to determine sequence identity and similarity can be found in publicly available computer programs. Sequence alignments and percent identity calculations may be performed using a BLAST program (e.g., BLAST 2.0, BLASTP, BLASTN, or BLASTX). The mathematical algorithm used in the BLAST programs can be found in Altschul et al., *Nucleic Acids Res.* 25:3389-3402, 1997. Within the context of this disclosure, it will be understood that where sequence analysis software is used for analysis, the results of the analysis are based on the "default values" of the program referenced. "Default values" mean any set of values or parameters which originally load with the software when first initialized.

The term "isolated" in some aspects means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region ("leader and trailer") as well as intervening sequences (introns) between individual coding segments (exons).

A "functional variant" in some aspects refers to a polypeptide or polynucleotide that is structurally similar or substantially structurally similar to a parent or reference compound of this disclosure, but differs slightly in composition (e.g., one base, atom or functional group is different, added, or removed), such that the polypeptide or encoded polypeptide is capable of performing at least one function of the encoded parent polypeptide with at least 50% efficiency, preferably at least 55%, 60%, 70%, 75%, 80%, 85%, 90%, 95% or 100% level of activity of the parent polypeptide. In other words, a functional variant of a polypeptide or encoded polypeptide of this disclosure has "similar binding," "similar affinity" or "similar activity" when the functional variant displays no more than a 50% reduction in performance in a selected assay as compared to the parent or reference polypeptide, such as an assay for measuring binding affinity (e.g., Biacore® or tetramer staining measuring an equilibrium association constant ($K_a$) or an equilibrium dissociation constant ($K_d$)).

As used herein, in some aspects, a "functional portion" or "functional fragment" refers to a polypeptide or polynucleotide that comprises only a domain, portion or fragment of a parent or reference compound, and the polypeptide or encoded polypeptide retains at least 50% activity associated with the domain, portion or fragment of the parent or reference compound, preferably at least 55%, 60%, 70%, 75%, 80%, 85%, 90%, 95% or 100% level of activity of the parent polypeptide, or provides a biological benefit (e.g., effector function). A "functional portion" or "functional fragment" of a polypeptide or encoded polypeptide of this disclosure has "similar binding" or "similar activity" when the functional portion or fragment displays no more than a 50% reduction in performance in a selected assay as compared to the parent or reference polypeptide (preferably no more than 20% or 10%, or no more than a log difference as compared to the parent or reference with regard to affinity), such as an assay for measuring binding affinity or measuring effector function (e.g., cytokine release).

As used herein, in some aspects, "heterologous" or "non-endogenous" or "exogenous" refers to any gene, protein, compound, nucleic acid molecule, or activity that is not native to a host cell or a subject, or any gene, protein, compound, nucleic acid molecule, or activity native to a host cell or a subject that has been altered. Heterologous, non-endogenous, or exogenous includes genes, proteins, compounds, or nucleic acid molecules that have been mutated or otherwise altered such that the structure, activity, or both is different as between the native and altered genes, proteins, compounds, or nucleic acid molecules. In certain embodiments, heterologous, non-endogenous, or exogenous genes, proteins, or nucleic acid molecules (e.g., receptors, ligands, etc.) may not be endogenous to a host cell or a subject, but instead nucleic acids encoding such genes, proteins, or nucleic acid molecules may have been added to a host cell by conjugation, transformation, transfection, electroporation, or the like, wherein the added nucleic acid molecule may integrate into a host cell genome or can exist as extra-chromosomal genetic material (e.g., as a plasmid or other self-replicating vector). The term "homologous" or "homolog" refers to a gene, protein, compound, nucleic acid molecule, or activity found in or derived from a host cell, species, or strain. For example, a heterologous or exogenous polynucleotide or gene encoding a polypeptide may be homologous to a native polynucleotide or gene and encode a homologous polypeptide or activity, but the polynucleotide or polypeptide may have an altered structure, sequence, expression level, or any combination thereof. A non-endogenous polynucleotide or gene, as well as the encoded polypeptide or activity, may be from the same species, a different species, or a combination thereof.

As used herein, in some aspects, the term "endogenous" or "native" refers to a polynucleotide, gene, protein, compound, molecule, or activity that is normally present in a host cell or a subject.

The term "expression", as used herein, in some aspects, refers to the process by which a polypeptide is produced based on the encoding sequence of a nucleic acid molecule, such as a gene. The process may include transcription, post-transcriptional control, post-transcriptional modification, translation, post-translational control, post-translational modification, or any combination thereof. An expressed nucleic acid molecule is typically operably linked to an expression control sequence (e.g., a promoter).

The term "operably linked" in some aspects, refers to the association of two or more nucleic acid molecules on a single nucleic acid fragment so that the function of one is affected by the other. For example, a promoter is operably linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

As used herein, "expression vector" in some aspects, refers to a DNA construct containing a nucleic acid molecule that is operably linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself. In the present specification, "plasmid," "expression plasmid," "virus" and "vector" are often used interchangeably.

In some aspects, the term "introduced" in the context of inserting a nucleic acid molecule into a cell, means "transfection", or "transformation" or "transduction" and includes reference to the incorporation of a nucleic acid molecule into a eukaryotic or prokaryotic cell wherein the nucleic acid molecule may be incorporated into the genome of a cell (e.g., chromosome, plasmid, plastid, or mitochondrial DNA), converted into an autonomous replicon, or transiently expressed (e.g., transfected mRNA). As used herein, the term "engineered," "recombinant" or "non-natural" refers to an organism, microorganism, cell, nucleic acid molecule, or vector that includes at least one genetic alteration or has been modified by introduction of a heterologous or an exogenous nucleic acid molecule, wherein such alterations or modifications are introduced by genetic engineering (i.e., human intervention). Genetic alterations include, for example, modifications introducing expressible nucleic acid molecules encoding proteins, binding proteins or enzymes, or other nucleic acid molecule additions, deletions, substitutions or other functional disruption of a cell's genetic material. Additional modifications include, for example, non-coding regulatory regions in which the modifications alter expression of a polynucleotide, gene or operon.

In some embodiments, as described herein, more than one heterologous nucleic acid molecule can be introduced into a host cell as separate nucleic acid molecules, as a plurality of individually controlled genes, as a polycistronic nucleic acid molecule, as a single nucleic acid molecule encoding a binding protein, or any combination thereof. When two or more heterologous nucleic acid molecules are introduced into a host cell, it is understood that the two or more heterologous nucleic acid molecules can be introduced as a single nucleic acid molecule (e.g., on a single vector), on separate vectors, integrated into the host chromosome at a single site or multiple sites, or any combination thereof. The number of referenced heterologous nucleic acid molecules or protein activities refers to the number of encoding nucleic acid molecules or the number of protein activities, not the number of separate nucleic acid molecules introduced into a host cell.

The term "construct" in some aspects refers to any polynucleotide that contains a recombinant nucleic acid molecule. A construct may be present in a vector (e.g., a bacterial vector, a viral vector) or may be integrated into a genome. A "vector" is a nucleic acid molecule that is capable of transporting another nucleic acid molecule. Vectors may be, for example, plasmids, cosmids, viruses, a RNA vector or a linear or circular DNA or RNA molecule that may include chromosomal, non-chromosomal, semi-synthetic or synthetic nucleic acid molecules. Vectors of the present disclosure also include transposon systems (e.g., Sleeping Beauty, see, e.g, Geurts et al., *Mol. Ther.* 8:108, 2003: Mátés et al., *Nat. Genet.* 41:753 (2009)). Exemplary vectors are those capable of autonomous replication (episomal vector) or expression of nucleic acid molecules to which they are linked (expression vectors).

Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996). "Retroviruses" in some aspects are viruses having an RNA genome, which is reverse-transcribed into DNA using a reverse transcriptase enzyme, the reverse-transcribed DNA is then incorporated into the host cell genome. "Gammaretrovirus" refers to a genus of the retroviridae family. Examples of gammaretroviruses include mouse stem cell virus, murine leukemia virus, feline leukemia virus, feline sarcoma virus, and avian reticuloendotheliosis viruses.

"Lentiviral vector," as used herein, in some aspects, means HIV-based lentiviral vectors for gene delivery, which can be integrative or non-integrative, have relatively large packaging capacity, and can transduce a range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration into the DNA of infected cells. Additional vectors useful for practicing embodiments of the present disclosure are described herein.

As used herein, the term "host" in some aspects refers to a cell (e.g., T cell) or microorganism targeted for genetic modification with a heterologous nucleic acid molecule to produce a polypeptide of interest (e.g., a binding protein of the present disclosure). In certain embodiments, a host cell may optionally already possess or be modified to include other genetic modifications that confer desired properties related or unrelated to, e.g., biosynthesis of the heterologous protein (e.g., inclusion of a detectable marker; deleted, altered or truncated endogenous TCR; or increased co-stimulatory factor expression).

As used herein, a "hematopoietic progenitor cell" in some aspects is a cell that can be derived from hematopoietic stem cells or fetal tissue and is capable of further differentiation into mature cells types (e.g., immune system cells). Exemplary hematopoietic progenitor cells include those with a $CD24^{Lo}$ $Lin^-$ $CD117^+$ phenotype or those found in the thymus (referred to as progenitor thymocytes).

As used herein, an "immune system cell" or "immune cell" in some aspects means any cell of the immune system that originates from a hematopoietic stem cell in the bone marrow, which gives rise to two major lineages, a myeloid progenitor cell (which give rise to myeloid cells such as monocytes, macrophages, dendritic cells, megakaryocytes and granulocytes) and a lymphoid progenitor cell (which give rise to lymphoid cells such as T cells, B cells, natural killer (NK) cells, and NK-T cells). Exemplary immune system cells include a $CD4^+$ T cell, a $CD8^+$ T cell, a $CD4^-$ $CD8^-$ double negative T cell, a γδ T cell, a regulatory T cell, a stem cell memory T cell, a natural killer cell (e.g., a NK cell or a NK-T cell), and a dendritic cell. Macrophages and dendritic cells may be referred to as "antigen presenting cells" or "APCs," which are specialized cells that can activate T cells when a major histocompatibility complex (MEW) receptor on the surface of the APC complexed with a peptide interacts with a TCR on the surface of a T cell.

In any of the presently described embodiments, an immune cell of the present disclosure can be modified to comprise a heterologous polynucleotide, a chromosomal gene knockout or mutation, or a combination thereof.

A "T cell" or "T lymphocyte" is an immune system cell that matures in the thymus and produces T cell receptors (TCRs). T cells can exhibit phenotypes or markers associated with naïve T cells (e.g., not exposed to antigen; increased expression of CD62L, CCR7, CD28, CD3, CD127, and CD45RA, and decreased expression of CD45RO as compared to $T_{CM}$), memory T cells ($T_M$) (e.g., antigen-experienced and long-lived), and effector cells (antigen-experienced, cytotoxic). $T_M$ can be further divided into subsets exhibiting phenotypes or markers associated with of central memory T cells ($T_{CM}$, e.g., increased expression of CD62L, CCR7, CD28, CD127, CD45RO, and CD95, and decreased expression of CD54RA as compared to naïve T cells) and effector memory T cells ($T_{EM}$, e.g., decreased expression of CD62L, CCR7, CD28, CD45RA, and increased expression of CD127 as compared to naïve T cells or $T_{CM}$).

Effector T cells ($T_E$) can refer to antigen-experienced $CD8^+$ cytotoxic T lymphocytes that has decreased expression of CD62L, CCR7, CD28, and are positive for granzyme and perforin as compared to $T_{CM}$. Helper T cells ($T_H$) can include $CD4^+$ cells that influence the activity of other immune cells by releasing cytokines. $CD4^+$ T cells can activate and suppress an adaptive immune response, and which of those two functions is induced will depend on presence of other cells and signals. T cells can be collected using known techniques, and the various subpopulations or combinations thereof can be enriched or depleted by known techniques, such as by affinity binding to antibodies, flow cytometry, or immunomagnetic selection. Other exemplary T cells include regulatory T cells, such as $CD4^+$ $CD25^+$ ($Foxp3^+$) regulatory T cells and Treg17 cells, as well as Tr1, Th3, $CD8^+$ $CD28^-$, and Qa-1 restricted T cells.

"Cells of T cell lineage" in some aspects refer to cells that show at least one phenotypic characteristic of a T cell, or a precursor or progenitor thereof that distinguishes the cells from other lymphoid cells, and cells of the erythroid or myeloid lineages. Such phenotypic characteristics can include expression of one or more proteins specific for T cells (e.g., $CD3^+$, $CD4^+$, $CD8^+$), or a physiological, morphological, functional, or immunological feature specific for a T cell. For example, cells of the T cell lineage may be progenitor or precursor cells committed to the T cell lineage; $CD25^+$ immature and inactivated T cells; cells that have undergone CD4 or CD8 linage commitment; thymocyte progenitor cells that are $CD4^+$ $CD8^+$ double positive; single positive $CD4^+$ or $CD8^+$; TCRαβ or TCR γδ; or mature and functional or activated T cells.

"Major histocompatibility complex molecules" (MHC molecules) in some aspects refer to glycoproteins that deliver peptide antigens to a cell surface. MHC class I molecules are heterodimers consisting of a membrane spanning a chain (with three α domains) and a non-covalently associated β2 microglobulin. MHC class II molecules are composed of two transmembrane glycoproteins, a and (3, both of which span the membrane. Each chain has two domains. MHC class I molecules deliver peptides originating in the cytosol to the cell surface, where a peptide:MHC complex is recognized by $CD8^+$ T cells. MHC class II molecules deliver peptides originating in the vesicular system to the cell surface, where they are recognized by CD4+ T cells. An MHC molecule may be from various animal species, including human, mouse, rat, cat, dog, goat, horse, or other mammals.

"CD4" in some aspects refers to an immunoglobulin co-receptor glycoprotein that assists the TCR in communicating with antigen-presenting cells (see, Campbell & Reece, Biology 909 (Benjamin Cummings, Sixth Ed., 2002); UniProtKB P01730). CD4 is found on the surface of immune cells such as T helper cells, monocytes, macrophages, and dendritic cells, and includes four immunoglobulin domains (D1 to D4) that are expressed at the cell surface. During antigen presentation, CD4 is recruited, along with the TCR complex, to bind to different regions of the MHCII molecule (CD4 binds MHCII β2, while the TCR complex binds MHCII α1/β1). Without wishing to be bound by theory, the close proximity to the TCR complex in some contexts allows CD4-associated kinase molecules to phosphorylate the immunoreceptor tyrosine activation motifs (ITAMs) present on the cytoplasmic domains of CD3. This activity is thought to amplify the signal generated by the activated TCR in order to produce various types of T helper cells.

As used herein, the term "CD8 co-receptor" or "CD8" in some aspects means the cell surface glycoprotein CD8, either as an alpha-alpha homodimer or an alpha-beta heterodimer. The CD8 co-receptor assists in the function of cytotoxic T cells (CD8+) and functions through signaling via its cytoplasmic tyrosine phosphorylation pathway (Gao and Jakobsen, Immunol. Today 21:630-636, 2000; Cole and Gao, Cell. Mol. Immunol. 1:81-88, 2004). In humans, there are five (5) different CD8 beta chains (see UniProtKB identifier P10966) and a single CD8 alpha chain (see UniProtKB identifier P01732).

As used herein, "statistically significant" in some aspects can refer to a p value of 0.050 or less when calculated using the Students t-test and indicates that it is unlikely that a particular event or result being measured has arisen by chance.

Binding Proteins, Polynucleotides, and Modified Immune Cells

In certain aspects, the present disclosure provides binding proteins that specifically bind to an antigen expressed by or associated with a disease or disorder.

A "binding protein" refers herein to a protein or polypeptide that possesses the ability to specifically and non-covalently associate, unite, or combine with a target (e.g., a disease-associated antigen, such as a hyperproliferative disease-associated antigen or a cancer-associated antigen). Exemplary binding proteins include antibodies, T cell receptors (TCRs), chimeric antigen receptors (CARs), other receptors, ligands, or the like.

In certain embodiments, a binding protein of the present disclosure comprises a binding domain that specifically binds to an antigen expressed by or associated with a disease or disorder. A "binding domain" (also referred to as a "binding region" or "binding moiety"), as used herein, refers to a molecule or portion thereof (e.g., peptide, oligopeptide, polypeptide, protein (e.g., a binding protein)) that possesses the ability to specifically and non-covalently associate, unite, or combine with a target (e.g., a disease-associated antigen, such as a hyperproliferative disease-associated antigen or a cancer-associated antigen). A binding domain includes any naturally occurring, synthetic, semi-synthetic, or recombinantly produced binding partner for a biological molecule, a molecular complex (i.e., complex comprising two or more biological molecules), or other target of interest. Exemplary binding domains include single chain immunoglobulin variable regions (e.g., scTCR, scFv, Fab, TCR variable regions), receptor ectodomains, ligands (e.g., cytokines, chemokines), or synthetic polypeptides selected for their specific ability to bind to a biological molecule, a molecular complex or other target of interest.

"Antigen" or "Ag," as used herein, refers to an immunogenic molecule that provokes an immune response. An immune response may involve, for example, antibody production, production of and signaling by cytokines or chemokines, activation of specific immunologically-competent cells (e.g., T cells), migration of the cells to a site of antigen expression or presentation, or any combination thereof. An antigen (immunogenic molecule) may be, for example, a peptide, glycopeptide, polypeptide, glycopolypeptide, polynucleotide, polysaccharide, lipid, or the like. An antigen can be synthesized, produced recombinantly, or derived from a biological sample. Exemplary biological samples that can contain one or more antigens include tissue samples, tumor samples, cells, biological fluids, or combinations thereof. Antigens can be produced by cells that have been modified or genetically engineered to express an antigen.

The term "epitope" or "antigenic epitope" includes any molecule, structure, amino acid sequence or protein determinant that is recognized and specifically bound by a cognate binding molecule, such as an immunoglobulin, T cell receptor (TCR), chimeric antigen receptor, or other binding molecule, domain or protein. Epitopic determinants generally contain chemically active surface groupings of molecules, such as amino acids or sugar side chains, and can have specific three dimensional structural characteristics, as well as specific charge characteristics.

The terms "complementarity determining region," and "CDR," are synonymous with "hypervariable region" or "HVR," and are known in the art to refer to non-contiguous sequences of amino acids within TCR or antibody variable regions, which confer antigen specificity and/or binding affinity. In general, there are three CDRs in each variable region of an immunoglobulin binding protein; e.g., for antibodies, the $V_H$ and $V_L$ regions comprise six CDRs (CDRH1, CDRH2, CDRH3; CDRL1, CDRL2, CDRL3). In general, for TCRs (which comprise α and β chains), there are three CDRs in each alpha chain variable region (αCDR1, αCDR2, αCDR3) and three CDRs in each beta chain variable region (βCDR1, βCDR2, βCDR3). In the case of TCRs, CDR3 is thought to be the main CDR responsible for recognizing processed antigen, and CDR1 and CDR2 are thought to mainly interact with the MHC. As used herein, a "variant" of a CDR refers to a functional variant of a CDR sequence having up to 1-3 amino acid substitutions, deletions, or combinations thereof.

In any of the embodiments described herein, a binding protein can be or can comprise a T cell receptor or a chimeric antigen receptor. "T cell receptor" (TCR) refers to an immunoglobulin superfamily member (having a variable binding domain, a constant domain, a transmembrane region, and a short cytoplasmic tail; see, e.g., Janeway et al., *Immunobiology: The Immune System in Health and Disease,* 3rd Ed., Current Biology Publications, p. 4:33, 1997) capable of specifically binding to an antigen peptide bound to a MHC receptor. A TCR can be found on the surface of a cell or in soluble form and generally is comprised of a heterodimer having α and β chains (also known as TCRα and TCRβ, respectively), or γ and δ chains (also known as TCRγ and TCRδ, respectively). The extracellular portion of each TCR chain (e.g., α-chain, β-chain) contains two immunoglobulin domains: a variable domain (e.g., α-chain variable domain or $V_\alpha$, β-chain variable domain or $V_\beta$; typically amino acids 1 to 116 based on Kabat numbering (Kabat et al., "Sequences of Proteins of Immunological Interest, *US* Dept. Health and Human Services, Public Health Service National Institutes of Health, 1991, 5*th* ed.) at the N-terminal end; and one constant domain (e.g., α-chain constant domain or $C_\alpha$, typically amino acids 117 to 259 based on Kabat, β-chain constant domain or $C_\beta$, typically amino acids 117 to 295 based on Kabat) adjacent the cell membrane. Also, like immunoglobulins, the variable domains contain complementary determining regions (CDRs) separated by framework regions (FRs) (see, e.g., Jores et al., *Proc. Nat'l Acad. Sci. U.S.A.* 87:9138, 1990; Chothia et al., *EMBO J.* 7:3745, 1988; see also Lefranc et al., *Dev. Comp. Immunol.* 27:55, 2003). In certain embodiments, a TCR is found on the surface of T cells (or T lymphocytes) and associates with the CD3 complex. The source of a TCR as used in the present disclosure may be from various animal species, such as a human, mouse, rat, rabbit or other mammal. Methods for producing engineered TCRs are described in, for example, Bowerman et al., *Mol. Immunol.,* 46(15):3000 (2009), the techniques of which are herein incorporated by reference.

In certain embodiments, the antigen-binding fragment of the TCR comprises a single chain TCR (scTCR), which comprises both TCR Vα and Vβ domains, but only a single TCR constant domain (Cα or Cβ). In certain embodiments, the antigen-binding fragment of the TCR or chimeric antigen receptor (described herein) is chimeric (e.g., comprises amino acid residues or motifs from more than one donor or species), humanized (e.g., comprises residues from a non-human organism that are altered or substituted so as to reduce the risk of immunogenicity in a human), or human.

"Chimeric antigen receptor" (CAR) in some aspects refers to a binding protein of the present disclosure that is engineered to contain two or more naturally-occurring amino acid sequences linked together in a way that does not occur naturally or does not occur naturally in a host cell, which binding protein can function as a receptor when present on a surface of a cell. CARs of the present disclosure can include an extracellular portion comprising an antigen-binding domain (e.g., obtained or derived from an immunoglobulin or immunoglobulin-like molecule, such as a scFv derived from an antibody or TCR specific for a cancer antigen, or an antigen-binding domain derived or obtained from a killer immunoreceptor from an NK cell) linked to a transmembrane domain and one or more intracellular signaling domains (optionally containing co-stimulatory domain(s)) (see, e.g., Sadelain et al., *Cancer Discov.,* 3(4): 388 (2013); see also Harris and Kranz, *Trends Pharmacol. Sci.,* 37(3):220 (2016); and Stone et al., *Cancer Immunol. Immunother.,* 63(11):1163 (2014)). In certain embodiments, a binding protein comprises a CAR comprising an antigen-specific TCR binding domain (see, e.g., Walseng et al., *Scientific Reports* 7:10713, 2017; the TCR CAR constructs and methods of which are hereby incorporated by reference in their entirety).

Methods of making binding proteins, including CARs, are described, for example, in U.S. Pat. Nos. 6,410,319; 7,446, 191; U.S. Patent Publication No. 2010/065818; U.S. Pat. No. 8,822,647; PCT Publication No. WO 2014/031687; U.S. Pat. No. 7,514,537; and Brentjens et al., 2007, *Clin. Cancer Res.* 13:5426, the techniques of which are herein incorporated by reference.

As used herein, "specifically binds" or "specific for" in some aspects refers to an association or union of a binding protein (e.g., a T cell receptor or a chimeric antigen receptor) or a binding domain (or binding protein thereof) to a target molecule (e.g., an antigen that is associated with a disease, such as a hyperproliferative disease; e.g., a cancer) in a sample with an affinity or $K_A$ (i.e., an equilibrium association constant of a particular binding interaction with units of 1/M) equal to or greater than $10^5$ $M^{-1}$ (which equals the ratio of the on-rate $[k_{on}]$ to the off rate $[k_{off}]$ for this association reaction), while not significantly associating or uniting with any other molecules or components in the sample. Binding proteins or binding domains (or binding proteins thereof) may be classified as "high-affinity" binding proteins or binding domains (or binding proteins thereof) or as "low-affinity" binding proteins or binding domains (or binding proteins thereof). "High-affinity" binding proteins or binding domains refer to those binding proteins or binding domains having a $K_A$ of at least $10^7 M^{-1}$, at least $10^8 M^{-1}$, at least $10^9$ $M^1$, at least $10^{10}$ $M^{-1}$, at least $10^{11}$ $M^{-1}$, at least $10^{12}$ $M^{-1}$, or at least $10^{13}$ $M^{-1}$. "Low-affinity" binding proteins or binding domains refer to those binding proteins or binding domains having a $K_A$ of up to $10^7$ $M^{-1}$, up to $10^6$ $M^{-1}$, up to $10^5$ $M^{-1}$. Alternatively, affinity may be defined as an equilibrium dissociation constant ($K_D$) of a particular binding interaction with units of M (e.g., $10^{-5}$ M to $10^{-13}$ M or less).

In certain embodiments, a receptor or binding domain may have "enhanced affinity," which refers to selected or engineered receptors or binding domains with stronger binding to a target antigen than a wild type (or parent) binding domain. For example, enhanced affinity may be due to a $K_A$ (equilibrium association constant) for the target antigen that is higher than the wild type binding domain, due to a $K_D$ (equilibrium dissociation constant) for the target antigen that is less than that of the wild type binding domain, due to an off-rate ($k_{off}$) for the target antigen that is less than that of the wild type binding domain, or a combination thereof. In certain embodiments, binding proteins may be codon-optimized to enhance expression in a particular host cell, such as a T cell (Scholten et al., *Clin. Immunol.* 119:135, 2006).

A variety of assays are known for identifying binding domains of the present disclosure that specifically bind a particular target, as well as determining binding domain or binding protein affinities, such as Western blot, ELISA, analytical ultracentrifugation, spectroscopy and surface plasmon resonance (Biacore®) analysis (see, e.g., Scatchard et al., *Ann. N.Y. Acad. Sci.* 51:660, 1949; *Wilson, Science* 295:2103, 2002; Wolff et al., *Cancer Res.* 53:2560, 1993; and U.S. Pat. Nos. 5,283,173, 5,468,614, or the equivalent). Assays for assessing affinity or apparent affinity or relative affinity are also known. In certain examples, apparent affinity for a binding protein is measured by assessing binding to various concentrations of tetramers, for example, by flow cytometry using labeled tetramers. In some examples, apparent $K_D$ of a binding protein is measured using 2-fold dilutions of labeled tetramers at a range of concentrations, followed by determination of binding curves by non-linear regression, apparent $K_D$ being determined as the concentration of ligand that yielded half-maximal binding.

In some embodiments, the binding protein specifically binds to a tumor-associated antigen. In particular embodiments, the tumor-associated antigen is selected from ROR1, EGFR, EGFRvIII, EGP-2, EGP-40, GD2, GD3, HPV E6, HPV E7, Her2, L1-CAM, Lewis A, Lewis Y, MUC1, MUC16, PSCA, PSMA, CD19, CD20, CD22, CD56, CD23, CD24, CD30, CD33, CD37, CD44v7/8, CD38, CD56, CD123, CA125, c-MET, FcRH5, WT1, folate receptor α, VEGF-α, VEGFR1, VEGFR2, IL-13Ra2, IL-11Ra, MAGE-A1, MAGE-A3, MAGE-A4, SSX-2, PRAME, HA-1$^H$, PSA, ephrin A2, ephrin B2, an NKG2D, NY-ESO-1, TAG-72, mesothelin, NY-ESO, 5T4, BCMA, FAP, Carbonic anhydrase 9, ERBB2, BRAF$^{V600E}$, and CEA.

In some embodiments, the tumor-associated antigen is ROR1. In certain embodiments, the binding domain comprises HCDRs according to SEQ ID NOs: 6, 7, and 8, and LCDRs according to SEQ ID NOs:2, 3, and 4. In other embodiments, the binding domain comprises HCDRs according to SEQ ID NOs: 15, 16, and 17, and LCDRs according to SEQ ID NOs:11, 12, and 13

In some embodiments, the binding domain includes a heavy chain variable domain ($V_H$) comprising or consisting of an amino acid sequence having at least 80%, 85%, 90%, 91%, 92%, 93%, 94%, 95%, 96%, 97%, 98%, 99%, or 100% sequence identity the amino acid sequence set forth in SEQ ID NO:5, and a light chain variable domain heavy chain variable domain ($V_L$) comprising or consisting of an amino acid sequence having at least 80%, 85%, 90%, 91%, 92%, 93%, 94%, 95%, 96%, 97%, 98%, 99%, or 100% sequence identity to amino acid sequence set forth in SEQ ID NO:1. In other embodiments, the binding domain comprises a $V_H$ comprising or consisting of an amino acid sequence having at least 80%, 85%, 90%, 91%, 92%, 93%, 94%, 95%, 96%, 97%, 98%, 99%, or 100% sequence identity the amino acid sequence set forth in SEQ ID NO:14, and a $V_L$ comprising or consisting of an amino acid sequence having at least 80%, 85%, 90%, 91%, 92%, 93%, 94%, 95%, 96%, 97%, 98%, 99%, or 100% sequence identity the amino acid sequence set forth in SEQ ID NO:10. In particular embodiments, the binding protein comprises a binding domain derived from antibody 2A2, antibody R12, antibody R11, antibody UC-961, antibody D10, or antibody H10. Incorporated herein by reference are all the ROR1 antibodies and related protein and nucleic acid constructs and related sequences disclosed in WO 2014/031687, WO 2012/076066, US 2015/232569, US 2012/0058051; U.S. Pat. No. 9,316,646; US 2013/0251642; U.S. Pat. No. 9,217,040; Yang et al., PLoS One 6(6):e21018 (2011); and Choi et al., Clin. Lymphoma Myeloma Leu. (2015) 15(Suppl):S167-5169.

In some embodiments, the binding domain is or comprises a single chain variable fragment (scFv) comprising heavy chain and light chain variable regions connected by short linker peptide. In any of the embodiments of the instant disclosure, a linker can comprise or consist of the amino acid sequence set forth in any one of SEQ ID NOs:18-21.

Any scFv of the present disclosure may be engineered so that the C-terminal end of $V_L$ domain is linked by a short peptide sequence to the N-terminal end of the $V_H$ domain, or vice versa (i.e., (N)$V_L$(C)-linker-(N)$V_H$(C) or (N)$V_H$(C)-linker-(N)$V_L$(C). In certain embodiments, a binding domain of the present disclosure comprises a scFv comprising or consisting of the amino acid sequence set forth in SEQ ID NO:9. In certain embodiments, the binding protein comprises a transmembrane component disposed between an extracellular component comprising a binding domain and an intracellular component comprising an effector domain. As used herein, an "effector domain" is an intracellular portion or a signaling domain of a binding protein or receptor that can directly or indirectly promote a biological or physiological response in a cell when receiving an appropriate signal. In certain embodiments, an effector domain is from a protein or a signaling portion thereof, or from a protein complex, that receives a signal when bound, or when the protein or signaling portion thereof or protein complex binds directly to a target molecule and triggers a signal from the effector domain.

An effector domain may directly promote a cellular response when it contains one or more signaling domains or motifs, such as an Intracellular Tyrosine-based Activation Motif (ITAM), as found in costimulatory molecules. Without wishing to be bound by theory, in some contexts, the ITAMs can be important for T cell stimulation or activation following ligand (e.g., antigen) engagement by a T cell receptor or by a binding protein comprising a T cell effector domain. In certain embodiments, the intracellular component comprises an ITAM. Exemplary effector domains include those from CD27, CD28, 4-1BB (CD137), OX40 (CD134), CD3ε, CD3δ, CD3ζ, CD25, CD27, CD28, CD79A, CD79B, CARD11, DAP10, FcRα, FcRβ, FcRγ, Fyn, HVEM, ICOS, Lck, LAG3, LAT, LRP, NKG2D, NOTCH1, NOTCH2, NOTCH3, NOTCH4, Wnt, ROR2, Ryk, SLAMF1, Slp76, pTα, TCRα, TCRβ, TRIM, Zap70, PTCH2, or any combination thereof. In certain embodiments, an effector domain comprises a lymphocyte receptor signaling domain (e.g., CD3ζ).

In further embodiments, the intracellular component of the binding protein comprises a co-stimulatory domain or a signaling portion thereof selected from CD27, CD28, 4-1BB (CD137), OX40 (CD134), or a combination thereof. In certain embodiments, the intracellular component comprises a CD28 costimulatory domain or a signaling portion thereof (which may optionally include a LL→GG mutation at positions 186-187 of the native CD28 protein; see Nguyen et al., Blood 102:4320, 2003)), a 4-1BB costimulatory domain or a signaling portion thereof, or both.

In certain embodiments, an effector domain comprises CD3 or a functional portion thereof. An exemplary amino acid sequence from a human 4-1BB is provided in SEQ ID NO:24. In certain embodiments, a co-stimulatory domain comprises or consists of an amino acid sequence having at least 80%, 85%, 90%, 91%, 92%, 93%, 94%, 95%, 96%, 97%, 98%, 99%, or 100% sequence identity the amino acid sequence set forth in SEQ ID NO:24. In further embodiments, an effector domain comprises a portion or a signaling domain from CD27. In further embodiments, an effector domain comprises a portion or a signaling domain from CD28. In still further embodiments, an effector domain comprises a portion or a signaling domain from 4-1BB. An exemplary amino acid sequence from a human 4-1BB is provided in SEQ ID NO:23. In further embodiments, an effector domain comprises a portion or a signaling domain from OX40.

An extracellular component and an intracellular component of the present disclosure are connected by a transmembrane domain. A "transmembrane domain", as used herein, is a portion of a transmembrane protein that can insert into or span a cell membrane. Transmembrane domains have a three-dimensional structure that is thermodynamically stable in a cell membrane and generally range in length from about 15 amino acids to about 30 amino acids. The structure of a transmembrane domain may comprise an alpha helix, a beta barrel, a beta sheet, a beta helix, or any combination thereof. In certain embodiments, a transmembrane domain comprises or is derived from a known transmembrane protein (i.e., a CD4 transmembrane domain, a CD8 transmembrane domain, a CD27 transmembrane domain, a CD28 transmembrane domain, or any combination thereof). An exemplary amino acid sequence from a human CD28 is provided in SEQ ID NO:22. In particular embodiments, a transmembrane component of a binding protein is derived from CD28 and an intracellular component that comprises a CD3 signaling domain and optionally a co-stimulatory domain, such as a 4-1BB signaling domain. In certain embodiments, a transmembrane component of a binding protein comprises or consists of an amino acid sequence having at least 80%, 85%, 90%, 91%, 92%, 93%, 94%, 95%, 96%, 97%, 98%, 99%, or 100% sequence identity the amino acid sequence set forth in SEQ ID NO:22. In certain embodiments, a costimulatory domain comprises or consists of an amino acid sequence having at least 80%, 85%, 90%, 91%, 92%, 93%, 94%, 95%, 96%, 97%, 98%, 99%, or 100% sequence identity the amino acid sequence set forth in SEQ ID NO:23.

In particular embodiments, a binding protein of the instant disclosure comprises a scFv comprising or consisting of the amino acid sequence set forth in SEQ ID NO:9, a transmembrane component comprising or consisting of the amino acid sequence set forth in SEQ ID NO:22, and a costimulatory domain comprising or consisting of the amino acid sequence set forth in SEQ ID NO:23.

In certain embodiments, the extracellular component of the binding protein further comprises a linker disposed between the binding domain and the transmembrane domain. As used herein when referring to a component of a binding protein that connects the binding and transmembrane domains, a "linker" may be an amino acid sequence having from about two amino acids to about 500 amino acids, which can provide flexibility and room for conformational movement between two regions, domains, motifs, fragments, or modules connected by the linker. For example, a linker of the present disclosure can position the binding domain away from the surface of a host cell expressing the binding protein to enable proper contact between the host cell and a target cell, antigen binding, and activation (Patel et al., *Gene Therapy* 6: 412-419, 1999). Linker length may be varied to maximize antigen recognition based on the selected target molecule, selected binding epitope, or antigen binding domain seize and affinity (see, e.g., Guest et al., *J. Immunother.* 28:203-11, 2005; PCT Publication No. WO 2014/031687). Exemplary linkers include those having a glycine-serine amino acid chain having from one to about ten repeats of $Gly_xSer_y$, wherein x and y are each independently an integer from 0 to 10, provided that x and y are not both 0 (e.g., $(Gly_4Ser)_2$, $(Gly_3Ser)_2$, $Gly_2Ser$, or a combination thereof, such as $((Gly_3Ser)_2Gly_2Ser)$. In any of the embodiments of the instant disclosure, a linker can comprise or consist of the amino acid sequence set forth in any one of SEQ ID NOs:18-21.

Linkers of the present disclosure also include immunoglobulin constant regions (i.e., CH1, CH2, CH3, or CL, of any isotype) and portions thereof. In certain embodiments, the linker comprises a CH3 domain, a CH2 domain, or both. In certain embodiments, the linker comprises a CH2 domain and a CH3 domain. In further embodiments, the CH2 domain and the CH3 domain are each a same isotype. In particular embodiments, the CH2 domain and the CH3 domain are an IgG4 or IgG1 isotype. In other embodiments, the CH2 domain and the CH3 domain are each a different isotype. In specific embodiments, the CH2 comprises a N297Q mutation. Without wishing to be bound by theory, in some contexts, CH2 domains with N297Q mutation do not bind FcγR (see, e.g., Sazinsky et al., *PNAS* 105(51):20167 (2008)). In certain embodiments, the linker comprises a human immunoglobulin constant region or portion thereof.

In any of the embodiments described herein, a linker may comprise a hinge region or portion thereof. Hinge regions are flexible amino acid polymers of variable length and sequence (typically rich in proline and cysteine amino acids) and connect larger and less-flexible regions of immunoglobulin proteins. For example, hinge regions connect the heavy chain constant and variable regions of antibodies and connect the constant and transmembrane regions of TCRs.

In certain embodiments, one or more of an extracellular component, a binding domain, a linker, a transmembrane domain, an intracellular component (such as an effector domain, a costimulatory domain or both) of a binding protein comprises junction amino acids. "Junction amino acids" or "junction amino acid residues" refer to one or more (e.g., about 2-20) amino acid residues between two adjacent domains, motifs, regions, modules, or fragments of a protein, such as between a binding domain and an adjacent linker, between a transmembrane domain and an adjacent extracellular or intracellular domain, or on one or both ends of a linker that links two domains, motifs, regions, modules, or fragments (e.g., between a linker and an adjacent binding domain or between a linker and an adjacent hinge). Junction amino acids may result from the construct design of a binding protein (e.g., amino acid residues resulting from the use of a restriction enzyme site or self-cleaving peptide sequences during the construction of a polynucleotide encoding a binding protein). For example, a transmembrane domain of a binding protein may have one or more junction amino acids at the amino-terminal end, carboxy-terminal end, or both.

In some embodiments, a binding protein of the present disclosure may further comprise a protein tag (also called a peptide tag or tag peptide herein). Protein tags are unique peptide sequences that are affixed or genetically fused to, or are a part of, a protein of interest and can be recognized or bound by, for example, a heterologous or non-endogenous cognate binding molecule or a substrate (e.g., receptor, ligand, antibody, carbohydrate, or metal matrix). Protein tags are useful for detecting, identifying, isolating, tracking, purifying, enriching for, targeting, or biologically or chemically modifying tagged proteins of interest, particularly when a tagged protein is part of a heterogenous population of cells (e.g., a biological sample like peripheral blood). In the provided binding proteins, the ability of the tag(s) to be specifically bound by the cognate binding molecules is distinct from, or in addition to, the ability of the binding domain(s) to specifically bind the hyperproliferative disease-associated antigen. In certain embodiments, the protein tag is a Myc tag, His tag, Flag tag, Xpress tag, Avi tag, Calmodulin tag, Polyglutamate tag, HA tag, Nus tag, S tag, SBP tag, Softag, V5 tag, CBP, GST, MBP, GFP, Thioredoxin tag, Strep® Tag, or any combination thereof.

Methods useful for isolating and purifying recombinantly produced soluble binding proteins, by way of example, may include obtaining supernatants from suitable host cell/vector systems that secrete the recombinant soluble binding protein into culture media and then concentrating the media using a commercially available filter. Following concentration, the concentrate may be applied to a single suitable purification matrix or to a series of suitable matrices, such as an affinity matrix or an ion exchange resin. One or more reverse phase HPLC steps may be employed to further purify a recombinant polypeptide. These purification methods may also be employed when isolating an immunogen from its natural environment. Methods for large scale production of one or more of the isolated/recombinant soluble binding protein described herein include batch cell culture, which is monitored and controlled to maintain appropriate culture conditions. Purification of the soluble binding protein may be performed according to methods described herein and known in the art and that comport with laws and guidelines of domestic and foreign regulatory agencies.

Binding proteins as described herein may be functionally characterized according to any of a large number of art-accepted methodologies for assaying host cell (e.g., T cell)

activity, including determination of T cell binding, stimulation, activation or induction and also including determination of T cell responses that are antigen-specific. Examples include determination of T cell proliferation, T cell cytokine release, antigen-specific T cell stimulation, MHC restricted T cell stimulation, cytotoxic T lymphocyte (CTL) activity (e.g., by detecting $^{51}$Cr or Europium release from pre-loaded target cells), changes in T cell phenotypic marker expression, and other measures of T-cell functions. Procedures for performing these and similar assays are may be found, for example, in Lefkovits (Immunology Methods Manual: The Comprehensive Sourcebook of Techniques, 1998). See, also, *Current Protocols in Immunology*; Weir, *Handbook of Experimental Immunology*, Blackwell Scientific, Boston, MA (1986); Mishell and Shigii (eds.) *Selected Methods in Cellular Immunology*, Freeman Publishing, San Francisco, CA (1979); Green and Reed, *Science* 281:1309 (1998) and references cited therein.

Levels of cytokines may be determined according to methods described herein and practiced in the art, including for example, ELISA, ELISPOT, intracellular cytokine staining, and flow cytometry and combinations thereof (e.g., intracellular cytokine staining and flow cytometry). Immune cell proliferation and clonal expansion resulting from an antigen-specific elicitation or stimulation of an immune response may be determined by isolating lymphocytes, such as circulating lymphocytes in samples of peripheral blood cells or cells from lymph nodes, stimulating the cells with antigen, and measuring cytokine production, cell proliferation and/or cell viability, such as by incorporation of tritiated thymidine or non-radioactive assays, such as MTT assays and the like. The effect of an immunogen described herein on the balance between a Th1 immune response and a Th2 immune response may be examined, for example, by determining levels of Th1 cytokines, such as IFN-γ, IL-12, IL-2, and TNF-β, and Type 2 cytokines, such as IL-4, IL-5, IL-9, IL-10, and IL-13.

In another aspect, nucleic acid molecules or polynucleotides are provided that encode any one or more of the binding proteins described herein. A polynucleotide encoding a desired binding protein can be obtained or produced using recombinant methods known in the art using standard techniques, such as screening libraries from cells expressing a desired sequence or a portion thereof, by deriving a sequence from a vector known to include the same, or by isolating a sequence or a portion thereof directly from cells or tissues containing the same. Alternatively, a sequence of interest can be produced synthetically. Such nucleic acid molecules can be inserted into an appropriate vector (e.g., viral vector or non-viral plasmid vector) for introduction into a host cell of interest (e.g., an immune cell, such as a T cell).

In certain embodiments, a polynucleotide of the instant disclosure comprises a polynucleotide that encodes a binding protein and a polynucleotide that encodes a transduction marker (e.g., truncated human CD19 (huCD19t), a truncated human EGFR (huEGFRt; see Wang et al., *Blood* 118:1255 (2011)), a truncated human NGFR (e.g., huNGFRt), a truncated human CD34 (e.g., huCD34t), a GFP, and extracellular domain of human CD2, or the like). In certain embodiments, the encoded marker comprises EGFRt, CD19t, CD34t, or NGFRt. Markers can be used to identify or monitor expression of a heterologous polynucleotide by a host cell transduced with the same, or to detect cells expressing a binding protein of interest.

In any of the embodiments described herein, the binding protein-encoding polynucleotide can further comprise a polynucleotide that encodes a self-cleaving polypeptide, wherein the polynucleotide encoding the self-cleaving polypeptide is located between the polynucleotide encoding the binding protein and the polynucleotide encoding the marker. When the binding protein encoding polynucleotide is expressed by a host cell comprising the same, the binding protein and the marker are expressed as separate molecules at the host cell surface.

In certain embodiments, a self-cleaving polypeptide comprises a 2A peptide from porcine teschovirus-1 (P2A), *Thosea asigna* virus (T2A), equine rhinitis A virus (E2A), or foot-and-mouth disease virus (F2A)) or variant thereof. Further exemplary nucleic acid and amino acid sequences the 2A peptides are set forth in, for example, Kim et al. (*PLOS One* 6:e18556, 2011, which 2A nucleic acid and amino acid sequences are incorporated herein by reference in their entirety). In some embodiments, the binding protein-encoding polynucleotide is separated from the transduction-marker-encoding polynucleotide by a polynucleotide that encodes a self-cleaving polypeptide (e.g., P2A, F2A, T2A, E2A, and variants thereof, which are described in Kim et al. (*PLOS One* 6:e18556, 2011), the 2A peptides and amino acid and nucleic sequences thereof are incorporated herein by reference in their entirety).

In any of the embodiments described herein, a polynucleotide of the present disclosure may be codon-optimized for a host cell containing the polynucleotide (see, e.g, Scholten et al., *Clin. Immunol.* 119:135-145 (2006)).

In further aspects, expression constructs are provided, wherein the expression constructs comprise a polynucleotide of the present disclosure operably linked to an expression control sequence (e.g., a promoter). In certain embodiments, the expression construct is comprised in a vector. An exemplary vector may comprise a polynucleotide capable of transporting another polynucleotide to which it has been linked, or which is capable of replication in a host organism. Some examples of vectors include plasmids, viral vectors, cosmids, and others. Some vectors may be capable of autonomous replication in a host cell into which they are introduced (e.g. bacterial vectors having a bacterial origin of replication and episomal mammalian vectors), whereas other vectors may be integrated into the genome of a host cell or promote integration of the polynucleotide insert upon introduction into the host cell and thereby replicate along with the host genome (e.g., lentiviral vector, retroviral vector). Additionally, some vectors are capable of directing the expression of genes to which they are operatively linked (these vectors may be referred to as "expression vectors"). According to related embodiments, it is further understood that, if one or more agents (e.g., polynucleotides encoding fusion proteins as described herein) are co-administered to a subject, that each agent may reside in separate or the same vectors, and multiple vectors (each containing a different agent or the same agent) may be introduced to a cell or cell population or administered to a subject.

In certain embodiments, polynucleotides of the present disclosure may be operatively linked to certain elements of a vector. For example, polynucleotide sequences that are needed to effect the expression and processing of coding sequences to which they are ligated may be operatively linked. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest.

In certain embodiments, the vector comprises a plasmid vector or a viral vector (e.g., a vector selected from lentiviral vector or a γ-retroviral vector). In certain embodiments, the viral vector can be a gammaretrovirus, e.g., Moloney murine leukemia virus (MLV)-derived vectors. In other embodiments, the viral vector can be a more complex retrovirus-derived vector, e.g., a lentivirus-derived vector. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing CAR transgenes are known in the art and have been previous described, for example, in: U.S. Pat. No. 8,119,772; Walchli et al., *PLoS One* 6:327930, 2011; Zhao et al., *J. Immunol.* 174:4415, 2005; Engels et al., *Hum. Gene Ther.* 14:1155, 2003; Frecha et al., *Mol. Ther.* 18:1748, 2010; and Verhoeyen et al., *Methods Mol. Biol.* 506:97, 2009. Retroviral and lentiviral vector constructs and expression systems are also commercially available. Other viral vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., *Gene Ther.* 5:1517, 1998).

When a viral vector genome comprises a plurality of polynucleotides to be expressed in a host cell as separate transcripts, the viral vector may also comprise additional sequences between the two (or more) transcripts allowing for bicistronic or multicistronic expression. Examples of such sequences used in viral vectors include internal ribosome entry sites (IRES), furin cleavage sites, viral 2A peptide, or any combination thereof.

Other vectors used for gene therapy can also be used with the compositions and methods of this disclosure. Such vectors include those derived from baculoviruses and α-viruses. (Jolly, D J. 1999. *Emerging Viral Vectors*. pp 209-40 in Friedmann T. ed. The Development of Human Gene Therapy. New York: Cold Spring Harbor Lab), or plasmid vectors (such as sleeping beauty or other transposon vectors).

Construction of an expression vector that is used for genetically engineering and producing a binding protein of interest can be accomplished by using any suitable molecular biology engineering techniques known in the art. To obtain efficient transcription and translation, a polynucleotide in each recombinant expression construct includes at least one appropriate expression control sequence (also called a regulatory sequence), such as a leader sequence and particularly a promoter operably (i.e., operatively) linked to the nucleotide sequence encoding the immunogen.

In certain embodiments, polynucleotides of the present disclosure are used to transfect/transduce a host cell (e.g., a T cell) for use in adoptive transfer therapy (e.g., targeting a cancer antigen or targeting an adoptively transferred cell that expresses a tag peptide). Methods for transfecting/transducing T cells with desired nucleic acids have been described (e.g., U.S. Patent Application Pub. No. US 2004/0087025) as have adoptive transfer procedures using T cells of desired target-specificity (e.g., Schmitt et al., *Hum. Gen.* 20:1240, 2009; Dossett et al., *Mol. Ther.* 17:742, 2009; Till et al., *Blood* 112:2261, 2008; Wang et al., *Hum. Gene Ther.* 18:712, 2007; Kuball et al., *Blood* 109:2331, 2007; US 2011/0243972; US 2011/0189141; Leen et al., *Ann. Rev. Immunol.* 25:243, 2007), such that adaptation of these methodologies to the presently disclosed embodiments is contemplated, based on the teachings herein, including those directed to binding proteins of the present disclosure. Accordingly, in another aspect, host cells are provided that are modified to comprise a polynucleotide of the present disclosure and express the encoded binding protein, wherein the encoded binding protein locates to the cell surface of the host cell when expressed. In certain embodiments, the host cell is a hematopoietic progenitor cell or a human immune system cell. In further embodiments, the immune system cell is a $CD4^+$ T cell, a $CD8^+$ T cell, a $CD4^-$ $CD8^-$ double negative T cell, a stem cell memory T cell, a γδ T cell, a natural killer cell (e.g., NK cell or NK-T cell), a dendritic cell, or any combination thereof. In certain embodiments, the immune system cell is a $CD4^+$ T cell, a $CD8^+$ T cell, or both. In certain embodiments, the T cell is a naïve T cell, a central memory T cell, a stem cell memory T cell, an effector memory T cell, or any combination thereof. In embodiments, the modified immune cell may, or may not be, be resistant to the agent associated with induction of immunogenic cell death (ICD) (agents associated with induction of ICD are described further herein), or can be further manipulated or modified to be resistant to the agent associated with induction of ICD; see, e.g., PCT Publication No. WO 2011/053750, which drug-resistant cells and methods of making and using the same are incorporated herein by reference.

A host cell may include any individual cell or cell culture, which may receive a vector or the incorporation of nucleic acids or express proteins. The term also encompasses progeny of the host cell, whether genetically or phenotypically the same or different. Suitable host cells may depend on the vector and may include mammalian cells, animal cells, human cells, simian cells, insect cells, yeast cells, and bacterial cells. These cells may be induced to incorporate the vector or other material by use of a viral vector, transformation via calcium phosphate precipitation, DEAE-dextran, electroporation, microinjection, or other methods. See, for example, Sambrook et al., *Molecular Cloning: A Laboratory Manual* 2d ed. (Cold Spring Harbor Laboratory, 1989).

In any of the embodiments described herein, a host cell may be an immune cell that is modified to inhibit, reduce or eliminate expression of one or more endogenous genes that encode a polypeptide product selected from PD-1, LAG-3, CTLA4, TIM3, TIGIT, an HLA molecule, a TCR molecule, or any component or combination thereof.

Without wishing to be bound by theory, certain endogenously expressed immune cell proteins may inhibit or reduce the immune activity of a modified immune host cell (e.g., PD-1, LAG-3, CTLA4, TIGIT), or may compete with a binding protein of the present disclosure for expression by the host cell, or may interfere with the binding activity of a heterologously expressed binding protein of the present disclosure and interfere with the modified immune cell binding to a target cell or antigen. Further, endogenous proteins (e.g., endogenous host cell proteins, such as an HLA) expressed on a donor immune cell (e.g., a host cell comprising a polynucleotide encoding a binding protein) to be used in a cell transfer therapy may be recognized as foreign by an allogeneic recipient, which may result in elimination or suppression of the donor immune cell by the allogeneic recipient, or can render the administered donor cell to be immunogenic in an allogeneic recipient.

Accordingly, decreasing or eliminating expression or activity of such endogenous genes or proteins can improve the activity, function, expansion or persistence, or reduce the risk of immunogenicity of the administered host cells in an autologous or allogeneic recipient, and allows universal administration of the cells (e.g., to any recipient regardless of HLA type). In certain embodiments, a modified host immune cell is an allogeneic or an autologous cell. In certain embodiments, a modified host immune cell of this disclosure comprises a chromosomal gene knockout or introduction of a mutation, for example, using gene editing, of one or more of a gene that encodes PD-1, LAG-3, CTLA4, TIM3, TIGIT, an HLA component (e.g., a gene that encodes an α1 macroglobulin, an α2 macroglobulin, an α3 macroglobulin, a β1 microglobulin, or a β2 microglobulin), or a TCR component (e.g., a gene that encodes a TCR variable region or a TCR constant region) (see, e.g., Torikai et al., *Nature Sci. Rep.* 6:21757 (2016); Torikai et al., *Blood* 119(24):5697 (2012); and Torikai et al., *Blood* 122(8):1341 (2013); the gene-editing methods, techniques, compositions, and adoptive cell therapies of which are herein incorporated by reference in their entirety).

In some embodiments, the term "chromosomal gene knockout" refers to a genetic alteration in a host cell that prevents or inhibits production, by the host cell, of a functionally active endogenous polypeptide product. In some aspects, the modified host immune cell is modified to introduce a mutation, such as a deletion, insertion, substitution, missense mutation and/or nonsense mutation, at one or more of a gene that encodes PD-1, LAG-3, CTLA4, TIM3, TIGIT, an HLA component (e.g., a gene that encodes an α1 macroglobulin, an α2 macroglobulin, an α3 macroglobulin, a β1 microglobulin, or a β2 microglobulin), or a TCR component (e.g., a gene that encodes a TCR variable region or a TCR constant region). Alterations resulting in a chromosomal gene knockout or a mutation can include, for example, introduced nonsense mutations (including the formation of premature stop codons), missense mutations, gene deletion, and strand breaks. In some aspects, decreasing or eliminating expression or activity of such endogenous genes or proteins can be carried out by heterologous expression of inhibitory nucleic acid molecules that inhibit endogenous gene expression in the host cell. In some aspects, modifications can introduce nucleic acid sequences that are different from the endogenous nucleic acid sequence at the endogenous genes encoding such proteins, for example, by knock-in of a different sequence at the endogenous genes.

In certain embodiments, a chromosomal gene knock-out, gene knock-in or mutation is introduced by chromosomal editing of a host cell, e.g., using gene editing methods. Chromosomal editing or gene editing can be performed using, for example, endonucleases, such as targeted endonucleases. In some aspects, "endonuclease" refers to an enzyme capable of catalyzing cleavage of a phosphodiester bond within a polynucleotide chain. In certain embodiments, an endonuclease is capable of cleaving a targeted gene thereby inactivating or "knocking out" the targeted gene. An endonuclease may be a naturally occurring, recombinant, genetically modified, or fusion endonuclease. The nucleic acid strand breaks caused by the endonuclease are commonly repaired through the distinct mechanisms of homologous recombination or non-homologous end joining (NHEJ). During homologous recombination, a donor nucleic acid molecule may be used for a donor gene "knock-in", for target gene "knock-out", and optionally to inactivate a target gene through a donor gene knock in or target gene knock out event, and/or by introduction of particular mutations, such as a deletion, insertion, substitution, missense mutation and/or nonsense mutation, at the targeted gene. NHEJ is an error-prone repair process that often results in changes to the DNA sequence at the site of the cleavage, e.g., a substitution, deletion, or addition of at least one nucleotide. NHEJ may be used to "knock-out" a target gene. Examples of endonucleases, such as targeted endonucleases, include zinc finger nucleases, TALE-nucleases, CRISPR-Cas nucleases, meganucleases, and megaTALs.

In some embodiments, a "zinc finger nuclease" (ZFN) refers to a fusion protein comprising a zinc finger DNA-binding domain fused to a non-specific DNA cleavage domain, such as a Fok1 endonuclease. Each zinc finger motif of about 30 amino acids binds to about 3 base pairs of DNA, and amino acids at certain residues can be changed to alter triplet sequence specificity (see, e.g., Desjarlais et al., *Proc. Natl. Acad. Sci.* 90:2256-2260, 1993; Wolfe et al., *J. Mol. Biol.* 285:1917-1934, 1999). Multiple zinc finger motifs can be linked in tandem to create binding specificity to desired DNA sequences, such as regions having a length ranging from about 9 to about 18 base pairs. By way of background, ZFNs mediate genome editing by catalyzing the formation of a site-specific DNA double strand break (DSB) in the genome, and targeted integration of a transgene comprising flanking sequences homologous to the genome at the site of DSB is facilitated by homology directed repair. Alternatively, a DSB generated by a ZFN can result in knock out of target gene via repair by non-homologous end joining (NHEJ), which is an error-prone cellular repair pathway that results in the insertion or deletion of nucleotides at the cleavage site. In certain embodiments, a gene knockout comprises an insertion, a deletion, a mutation or a combination thereof, made using a ZFN molecule.

In some embodiments, a "transcription activator-like effector nuclease" (TALEN) refers to a fusion protein comprising a TALE DNA-binding domain and a DNA cleavage domain, such as a FokI endonuclease. A "TALE DNA binding domain" or "TALE" in some aspects is composed of one or more TALE repeat domains/units, each generally having a highly conserved 33-35 amino acid sequence with divergent 12th and 13th amino acids. The TALE repeat domains are involved in binding of the TALE to a target DNA sequence. The divergent amino acid residues, referred to as the Repeat Variable Diresidue (RVD), correlate with specific nucleotide recognition. The natural (canonical) code for DNA recognition of these TALEs has been determined such that an HD (histine-aspartic acid) sequence at positions 12 and 13 of the TALE leads to the TALE binding to cytosine (C), NG (asparagine-glycine) binds to a T nucleotide, NI (asparagine-isoleucine) to A, NN (asparagine-asparagine) binds to a G or A nucleotide, and NG (asparagine-glycine) binds to a T nucleotide. Non-canonical (atypical) RVDs are also known (see, e.g., U.S. Patent Publication No. US 2011/0301073, which atypical RVDs are incorporated by reference herein in their entirety). TALENs can be used to direct site-specific double-strand breaks (DSB) in the genome of T cells. Non-homologous end joining (NHEJ) ligates DNA from both sides of a double-strand break in which there is little or no sequence overlap for annealing, thereby introducing errors that knock out gene expression. Alternatively, homology directed repair can introduce a transgene at the site of DSB providing homologous flanking sequences are present in the transgene. In certain embodiments, a gene knockout comprises an insertion, a deletion, a mutation or a combination thereof, and made using a TALEN molecule.

In some embodiments, a "clustered regularly interspaced short palindromic repeats/Cas" (CRISPR/Cas) nuclease system refers to a system that employs a CRISPR RNA (crRNA)-guided Cas nuclease to recognize target sites within a genome (known as protospacers) via base-pairing complementarity and then to cleave the DNA if a short, conserved protospacer associated motif (PAM) immediately follows 3' of the complementary target sequence. CRISPR/Cas systems are classified into three types (i.e., type I, type II, and type III) based on the sequence and structure of the Cas nucleases. The crRNA-guided surveillance complexes in types I and III need multiple Cas subunits. Type II system, the most studied, comprises at least three components: an RNA-guided Cas9 nuclease, a crRNA, and a trans-acting crRNA (tracrRNA). The tracrRNA comprises a duplex forming region. A crRNA and a tracrRNA form a duplex that is capable of interacting with a Cas9 nuclease and guiding the Cas9/crRNA:tracrRNA complex to a specific site on the target DNA via Watson-Crick base-pairing between the spacer on the crRNA and the protospacer on the target DNA upstream from a PAM. Cas9 nuclease cleaves a double-stranded break within a region defined by the crRNA spacer. Repair by NHEJ results in insertions and/or deletions which disrupt expression of the targeted locus. Alternatively, a transgene with homologous flanking sequences can be introduced at the site of DSB via homology directed repair. The crRNA and tracrRNA can be engineered into a single guide RNA (sgRNA or gRNA) (see, e.g., Jinek et al., *Science* 337: 816-21, 2012). Further, the region of the guide RNA complementary to the target site can be altered or programed to target a desired sequence (Xie et al., *PLOS One* 9:e100448, 2014; U.S. Pat. Appl. Pub. No. US 2014/0068797, U.S. Pat. Appl. Pub. No. US 2014/0186843; U.S. Pat. No. 8,697,359, and PCT Publication No. WO 2015/071474; each of which is incorporated by reference). In certain embodiments, a gene knockout comprises an insertion, a deletion, a mutation or a combination thereof, and made using a CRISPR/Cas nuclease system.

Exemplary gRNA sequences and methods of using the same to knock out endogenous genes that encode immune cell proteins include those described in Ren et al. (*Clin. Cancer Res.* 23:2255-2266, (2017), the gRNAs, Cas9 DNAs, vectors, and gene knockout techniques of which are hereby incorporated by reference in their entirety.

In some embodiments, a "meganuclease," also referred to as a "homing endonuclease," refers to an endodeoxyribonuclease characterized by a large recognition site (double stranded DNA sequences of about 12 to about 40 base pairs). Meganucleases can be divided into five families based on sequence and structure motifs: LAGLIDADG, GIY-YIG, HNH, His-Cys box and PD-(D/E)XK. Exemplary meganucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII, whose recognition sequences are known (see, e.g., U.S. Pat. Nos. 5,420,032 and 6,833,252; Belfort et al., *Nucleic Acids Res.* 25:3379-3388, 1997; Dujon et al., *Gene* 82:115-118, 1989; Perler et al., *Nucleic Acids Res.* 22:1125-1127, 1994; Jasin, *Trends Genet.* 12:224-228, 1996; Gimble et al., *J. Mol. Biol.* 263:163-180, 1996; Argast et al., *J. Mol. Biol.* 280:345-353, 1998).

In certain embodiments, naturally occurring meganucleases may be used to promote site-specific genome modification of a target selected from PD-1, LAG3, TIM3, CTLA4, TIGIT, an HLA-encoding gene, or a TCR component-encoding gene. In other embodiments, an engineered meganuclease having a novel binding specificity for a target gene is used for site-specific genome modification (see, e.g., Porteus et al., *Nat. Biotechnol.* 23:967-73, 2005; Sussman et al., *J. Mol. Biol.* 342:31-41, 2004; Epinat et al., *Nucleic Acids Res.* 31:2952-62, 2003; Chevalier et al., *Molec. Cell* 10:895-905, 2002; Ashworth et al., *Nature* 441:656-659, 2006; Paques et al., *Curr. Gene Ther.* 7:49-66, 2007; U.S. Patent Publication Nos. US 2007/0117128; US 2006/0206949; US 2006/0153826; US 2006/0078552; and US 2004/0002092). In further embodiments, a chromosomal gene knockout is generated using a homing endonuclease that has been modified with modular DNA binding domains of TALENs to make a fusion protein known as a megaTAL. MegaTALs can be utilized to not only knock-out one or more target genes, but to also introduce (knock in) heterologous or exogenous polynucleotides when used in combination with an exogenous donor template encoding a polypeptide of interest.

In certain embodiments, the host cell (e.g., an immune cell) comprising a heterologous polynucleotide encoding a binding protein that specifically binds to a disease-associated antigen can be modified to inhibit, reduce or eliminate expression of one or more endogenous genes by introducing an inhibitory nucleic acid molecule into the cell. In some aspects, the inhibitory nucleic acid molecule encodes a target-specific inhibitor wherein the encoded target-specific inhibitor inhibits endogenous gene expression (e.g., of PD-1, TIM3, LAG3, CTLA4, TIGIT, an HLA component, or a TCR component, or any combination thereof) in the host immune cell.

The presence of the introduced chromosomal gene knockout or mutation can be confirmed directly by DNA sequencing of the host immune cell following use of the knockout procedure or agent. Chromosomal gene knockout, mutation, or inhibition of expression of the endogenous genes can also be inferred from the absence of gene expression (e.g., the absence of an mRNA or polypeptide product encoded by the gene) following the knockout, gene editing, introduction of a mutation, or inhibition of expression of the endogenous genes.

Agents Associated with Induction of Immunogenic Cell Death (ICD)

In other aspects, the present disclosure provides agents that are associated with induction of immunogenic cell death. "Immunogenic cell death" or "ICD," in some embodiments, refers to a form of regulated or programmed cell death that stimulates an immune response against dead-cell derived antigens, such as antigens from dead hyperproliferative (e.g., cancer) cells. ICD, in some aspects, is distinguished from non-immunogenic and tolerigenic cell death modalities on both functional and molecular bases.

From a functional standpoint, cells succumbing to ICD, in some contexts, may need to elicit (rather than suppress) a specific T cell-dependent protective immune response by the host (e.g., specific to an antigen expressed or released by the now-dead cell) in the absence of an adjuvant. An inducer of ICD can lead to increased efficacy against diseased cells (e.g., hyperproliferative cells) in an immunocompetent host, but reduced or no efficacy against the same cells in an immunocompromised host. Cells succumbing to ICD are able to vaccinate syngeneic immunocompetent hosts against a subsequent challenge with living diseased cells of the same type, and can result in local recruitment of T cells to the site(s) of disease. Also, chemotherapy that includes an agent associated with ICD induction in some contexts may need to exert anti-proliferative effects (i.e., in the context of a hyperproliferative disease) in vivo. See, e.g., Galluzzi and Kepp, *Annu. Rev. Immunol.* 31:51 (2012), and Garg et al.,

*Oncoimmunology* 6(12):e1386829 (2017), the ICD-inducing agents, markers, and assays of which are incorporated herein by reference.

In some embodiments, cells that succumb to ICD can be identified using any of a number of biophysical markers. Markers of ICD include, for example, secreted damage-associated molecular patterns (DAMPs), such as high mobility group box 1 (HMGB1) protein, secreted uric acid, cell surface-exposed ER chaperones such as calreticulin, extracellular ATP, extracellular nucleic acids, hyaluronan, secreted annexin, A1, secreted type I interferon, and secreted or cell-surface expressed heat shock proteins (such as HSP70 and HSP90). See, e.g., Garg et al., *Oncoimmunology* 6(12):e1386829 (2017). Indirect indicators of ICD include the transport of extracellular DNA into dendritic cells (DCs) via Toll-like Receptor 9 (TLR9), of extracellular RNA into DCs via Toll-like Receptor 3 (TLR3), increased expression of pentraxin-3 (which interacts with a synapse formed between DC cells and apoptotic bodies), proliferation and local recruitment of $CD8^+$ T cells or NK, and the release of inflammatory cytokines (e.g., IL-6, IL-8, IL-10, TNF-$\alpha$, MCP1, IL-1$\beta$, IL-15, and IFN-$\gamma$). See, e.g., Tesniere et al., *Cell Death and Differentiation* 15:3 (2008); see also Woller et al., *Front. Oncol.* 4:188 (2014). In some cases, "induction," as used herein, can mean directly or indirectly causing a result (e.g., ICD).

In some contexts, ICD can induce or increase expression of genes or molecules involved in immune cell recruitment or trafficking, such as chemokine ligands, e.g., CXCL9 or CXCL10, by cells in the tumor or the tumor microenvironment. In some aspects, such expression can attract immune cells, such as T cells, that express the receptors for such molecules, such as CXCR3. In some aspects, ICD or agents that are associated with induction of ICD can result in increased expression of genes or molecules, such one or more of: Ccl12; Ccl17; Ccl2; Ccl7; Ccl9; Ccr2; Ccr8; CD40; CD401g; Csf1; Csf3r; Cxcl10; Cxcr2; Eda2r; Fas; IL21r; IL2rb; IL17r; Tnfrsf25; Tnfsrf9; Tnfsf8; Xcl1; Gng7; CD226; CD80; CD8$\alpha$; Cldn2; H2-M2; Pdcd1Ig2; Sele; Selp; or any combination thereof.

In certain embodiments, agents that are associated with induction of ICD include a chemotherapeutic agent or an active metabolite thereof, an agent specific for a pattern recognition receptor (PRR), an oncolytic virus, an antibody that specifically binds to a disease-associated antigen, such as a hyperproliferative-disease-associated antigen (provided that the antigen is not the antigen bound by the binding protein), irradiation, and combinations thereof.

As used herein, the term "chemotherapeutic agent" (which may also be called a "chemotherapeutic" or a "chemotherapy" herein) refers to a chemical agent, drug, or other therapeutic modality that selectively targets diseased cells (e.g., hyperproliferating cells) for inhibition or death. Chemotherapeutic agents of the present disclosure encompass different structures, forms, and systems of delivery, and are to be understood in terms of their functionality for selectively inhibiting or killing diseased cells (e.g., hyperproliferating cells). Certain chemotherapeutic agents are associated with induction of ICD.

In certain embodiments, a chemotherapeutic agent associated with induction of ICD comprises an alkylating agent, such as a DNA alkylating agent. Without wishing to be bound by theory, alkylating agents in some contexts bind to negatively charged sites on DNA with high affinity and thereby disrupt normal functions (e.g., transcription and translation) of the DNA strand, and are in some aspects capable of inducing ICD. Alkylating agents of the present disclosure include, for example, temozolomide, nitrogen mustards (e.g., mechlorethamine; cyclophosphamide and analogs; melphalan; chlorambucil), ethylenimines and methylmelamines (e.g., hexamethylmelamine and thiotepa), alkyl sulfonates-busulfan, nitrosoureas (e.g., carmustine (BiCNU) and analogs; streptozocin), trazenes-dacarbazinine (DTIC), and combinations thereof. In certain embodiments, the alkylating agent is or comprises cyclophosphamide.

In some embodiments, a chemotherapeutic agent associated with induction of ICD comprises an anthracycline. Without wishing to be bound by theory, anthracyclines in some contexts can inhibit gene expression by binding to cellular DNA and have been shown to induce ICD in cancer cells. See, e.g., Fucikova et al. *Cancer Res* 71:4821 (2011). In embodiments, an anthracycline comprises daunorubicin, doxorubicin, epiribucin, idarubicin, mitoxantrone and derivatives thereof (e.g., pixantrone), sabarubicin, valrubicin, or any combination thereof. In certain embodiments, the alkylating agent is or comprises doxorubicin, idarubicin or mitoxantrone.

In further embodiments, a chemotherapeutic agent associated with induction of ICD comprises an antimetabolite. In some embodiments, an exemplary antimetabolite is or comprises gemcitabine, 5-fluorouracil, foxuridine, cytarabine, capecitabine, methotrexate, 6-mercaptopurine, 6-thioguanine, cladribine, fludarabine, pentostatin, a folate antagonist, or any combination thereof.

In certain embodiments, a chemotherapeutic agent associated with induction of ICD comprises a caspase activator. Exemplary caspase activators of this disclosure include second mitochondria-derived activator of caspase (SMAC, "proSMAC"=full-length; "tSMAC"=processed) and mimetics, and combinations thereof. See, e.g., Umeagi et al., *Microenvironment and Immunology* (2012). In some embodiments, a caspase inhibitor (e.g., SMAC) can be delivered to a diseased cell (e.g., hyperproliferating cell) using a vector as described herein, including a viral (e.g., lentiviral) vector).

In some embodiments, a chemotherapeutic agent associated with induction of ICD comprises a microtubule inhibitor. Without wishing to be bound by theory, microtubule inhibitors in some contexts can inhibit mitosis, cell motion, and intracellular organelle transport. Exemplary microtubule inhibitors of this disclosure include taxanes, such as paclitaxel and analogs thereof (see, e.g., Golden et al., *OncoImmunol.* 3 (2014)), docetaxel, vinca alkaloids (e.g., vincristine, vinblastine, leurosine, vindesine, vinolrebine), nocodazole, epothilones, colchicine, navelbine, or any combination thereof.

In certain embodiments, a chemotherapeutic agent associated with induction of ICD comprises a proteasome inhibitor. Without wishing to be bound by theory, proteasome inhibitors inhibit proteolytic action in cells, thereby accumulating toxic levels of proteins and preventing degradation of pro-apoptotic factors. In some embodiments, a proteasome inhibitor comprises bortezomib, cafilzomib, ixazomib, marizomib, oprozomib, CEP-18770, MLN-9708, ONX-0912, or any combination thereof. See, e.g., Kisselev et al., *Chem. Biol.* 19(1):99-115 (2013). In particular embodiments, a proteasome inhibitor of the present disclosure is or comprises bortezimib. In further embodiments, a proteasome inhibitor of the present disclosure comprises a viral vector (e.g., hTert-Ad) comprising bortezimib with mitomycin C and (see, e.g., Boozari et al., *Gut* 59:1416 (2010)).

In certain embodiments, a chemotherapeutic agent associated with induction of ICD comprises a BK channel agonist. BK ("Big Potassium" or "Big K") channels transport potassium through cell membranes. Without wishing to be bound by theory, agonists of BK channels allow potassium ions to passively enter the cell, thereby disrupting the intracellular ionic balance and inducing ICD. See, e.g., Hoa et al., *PLoS One* 7:831732 (2012). Exemplary BK channel agonists of the present disclosure include phloretin, pimaric acid, arachidonic acid, metabolites of cytochrome P450, epoxygenase, lipoxygenase, omega-3 docosahexaenoic acid, 17β-estradiol, xenoestrogens including Tamoxifen, anti-epileptics such as zonisamide and chlorzoxazone, phosphodiesterase III inhibitors such as cilotazol, Human β-defensin 2, DHS-I, benzimidazolones including NS004 and NS1619, Cym04, NS11021, NS19504, BMS204352, thioureas, tetrahydroquinolines such as compound 36 and compound Z, terpenes, benzofuroindoles, and Andolast, or any combination thereof. See, e.g., Bentzen et al., *Front. Physiol.* 5:389 (2014), which BK channel agonists are incorporated by reference herein.

In certain embodiments, a chemotherapeutic agent associated with induction of ICD comprises a cardiac glycoside (CG) with a non-ICD inducer. Cardiac glycosides are a class of organic compounds that increase the output force of the heart and decrease its rate of contractions. Cardiac glycosides in some contexts can act on the contractile force of the cardiac muscle and exert toxic effects resulting in induction of CRT exposure, ATP release, and HMGB1 release. When combined with non-ICD-inducing agents such as cisplatin, mitomycin C, or epotoside (i.e., administered simultaneously, concurrently, or sequentially), cardiac glycosides stimulate ICD. See, e.g., Menger et al., *Sci. Transl. Med.* 4:143ra99 (2012).

In certain embodiments, a chemotherapeutic agent associated with induction of ICD comprises an ER stressor with a platinum-based antineoplastic drug ("platin"). ER stressors, as defined herein, encompass any composition or molecule that induces or results in an accumulation of unfolded or misfolded proteins in the lumen of the endoplasmic reticulum. Prolonged accumulation of such proteins can lead to apoptosis. Exemplary ER stressors of this disclosure include thapsigargin. Without wishing to be bound by theory, thapsigargin can block calcium influx into the ER, which inhibits autophagy of lysosomes, causing stress to the cell. Combining an ER stressor with a platin (e.g., cisplatin, oxaliplatin, carboplatin, nedaplatin, phenantrhiplatin, picoplatin, satraplatin, triplatin tetranitrate) may induce ICD. See, e.g., Tesniere et al., *Oncogene* 29:482 (2010). In some embodiments, the platin comprises cisplatin. In some embodiments, the platin is or comprises oxaliplatin. In some embodiments, the ER stressor comprises thapsigargin.

In certain embodiments, a chemotherapeutic agent associated with induction of ICD is or comprises oxaliplatin (or an active metabolite or derivative thereof).

In certain embodiments, a chemotherapeutic agent associated with induction of ICD is or comprises bleomycin.

In particular embodiments, a chemotherapeutic agent associated with induction of ICD comprises cyclophosphamide, oxaliplatin, doxorubicin, idarubicin, mitoxantrone, bleomycin, or bortezomib, or any combination thereof.

It will be appreciated that any combination of two or more chemotherapeutic agents associated with induction of ICD may be used in practicing methods according to the present disclosure. Additional chemotherapeutic agents are described herein and may also be employed in practicing the presently disclosed methods.

Other agents associated with induction of immunogenic cell death are described in, for example, Galluzzi and Klepp, *Ann. Rev. Immunol.* 31:51 (2012) and Garg et al., *Oncoimmunology* 6(12):e1386829 (2017) (and the references cited therein), which agents, combinations of agents, and methods are herein incorporated by reference.

In certain embodiments, an agent associated with induction of ICD is or comprises an agent that can target a pattern-recognition receptor (PRR). In general, pattern recognition receptors are organized into five families: Toll-like receptors (TLRs); RIG-I-like receptors (RLRs); nucleotide-binding oligomerization domain (NOD)-like receptors (NLRs); C-type lectin receptors (CLRs); and DNA sensors. PRRs detect pathogen-associated molecular patterns (PAMPs), including, for example: lipopolysaccharide (LPS); lipoproteins; flagellin; nucleic acids from bacteria, virus, fungi, and parasites; and damage-associated molecular patterns (DAMPs) that are secreted or released upon apoptosis, necrosis, or cellular stress. Recognition by PRRs stimulates expression of pro-inflammatory genes and immune cell activation. Exemplary agents capable of targeting a PRR are described in Shekarian et al., *Annals of Oncology* 28(8):1756 (2017), and include: lipopolysaccharides (LPS); bacterial membrane components; flagellins and derivatives and variants thereof; R848; surface glycoproteins; CpG-containing oligonucleotides (e.g., PF-3512676; Agatolimod), optionally in combination with MPL (AS15); MIW815 (ADU-S100); MK-454; BO-112; Amplivant; PolyICLC (optionally in combination with Resiquimod and/or LPS); Rintatolimod and derivatives thereof; Hilontol and derivatives thereof; GSK1572932; G100; CBLB502; Imiquimod and derivatives thereof; MEDI9197; Motolimod and derivatives thereof; CMP-001; MGN1703; SD-101; 1018 ISS; and a nucleic acid (e.g. DNA or RNA from a virus, bacteria, fungi, or a parasite, which includes double- and single-stranded RNA, microbial DNA with unmethylated CpG, or the like).

In certain embodiments, an agent associated with induction of ICD is or comprises an oncolytic virus. Oncolytic viruses are viruses that preferentially target and kill cancer cells. Exemplary oncolytic viruses include adenovirus, reovirus, measles virus, Herpes Simplex Virus (CMV), Newcastle disease virus, vaccinia virus, Semliki Forest Virus; Echo-7y Virus; paprapoxvirus; and senecavirus, which viruses may be attenuated or non-attenuated, and naturally occurring mutants and modified variants thereof, such as H101 (Oncorine, Shanghai Sunway Biotech), Onyx-15, and T-VEC. Oncolytic immunotherapies comprising viruses that may be used in the presently disclosed methods include those described in Veinalde et al., *Oncoimmunology* 6:e1285992 (2017); Hemminki and Hemminki, *Oncoimmunology* 5:e1074377 (2016); Clements et al., *Oncolimmunology* 5:e1057674 (2016), and Bramante et al., *Oncoimmunology* 5:e1078057 (2016), which immunotherapies and oncolytic ciruses are incorporated herein by reference.

In certain embodiments, an agent associated with induction of ICD is or comprises an antibody that specifically binds to a disease-associated antigen. In some embodiments, the disease-associated antigen is a different antigen to the one bound by the binding protein. Binding by an antibody to a disease-associated antigen can elicit ICD by, for example, antibody-dependent cellular cytotoxicity, complement-dependent cytotoxicity (CDC), or by another mechanism. Exemplary monoclonal antibodies useful in cancer therapies are known in the art and include, for example, monoclonal antibodies described in Galluzzi et al., *Oncotarget* 5(24): 12472-12508, 2014.

Other modalities can induce ICD and may be employed in the presently disclosed methods. In certain embodiments, an agent associated with induction of ICD is or comprises radiation therapy. Radiation therapy includes, for example, X-ray therapies, such as gamma-irradiation, and radiopharmaceutical therapies. Radiation therapies that trigger ICD include those disclosed in Vanpoiulle-Box et al., *Nat. Communi.* 8:15618 (2017); Dewan et al., *Clin. Cancer Res.* 15:5379 (2009); Bouquet et al., *Clin. Cancer Res.* 17:6754 (2011); and Wennerberg et al., *Front. Immunol.* 8:229 (2017), which radiation therapies and treatment regimens are incorporated herein in their entireties.

Photodynamic therapies (PDTs) can also induce ICD. Exemplary PDTs include those described by Garg et al. (*Sci. Transl. Med.* 8:328ra27 (2016); *Oncotarget* 6:26841 (2015); *EMBOI* 31:1062 (2012); *Autophagy* 9:1292 (2013)), which PDTs are incorporated herein in their entireties.

High hydrostatic pressure has been shown to induce ICD in tumor cell lines and primary tumor cells in vitro (see, e.g. Fucikova et al., *Tumor Immunology* 135(5):2014; Galluzi et al., *Nat. Rev. Immunol.* 17:97 (2017); and Garg et al., *Front. Immunol.* 6:588 (2015); the hydrostatic pressure techniques of these references are incorporated herein in their entireties). In certain embodiments, a method comprises inducing ICD in a cell using hydrostatic pressure and introducing the cell in which ICD was induced to a subject according to the present disclosure, or in vivo to a modified immune cell of the present disclosure, or both.

Immunomodulatory Agents

In certain aspects, a combination therapy comprises a modified immune cell of the present disclosure and an agent that is associated with induction of ICD (e.g., together, or in a sequence, or administering one to a subject who has previously received the other) with an immunomodulatory agent (e.g., an agent that specifically binds to and/or is an inhibitor of an immune suppression component, or an agonist of a stimulatory immune checkpoint molecule, as described herein), to enhance a response, such as an antitumor response by the immune system to, and ultimately treat, ameliorate, or reduce, a disease or disorder, e.g., tumor or associated cancer. In some embodiments, the immune response comprises an antitumor response and the disease or disorder comprises a hyperproliferative disease (e.g., a cancer) that is associated with the tumor.

As used herein, the term "immune suppression component" or "immunosuppression component" in some aspects refers to one or more cells, proteins, molecules, compounds or complexes providing inhibitory signals to assist in controlling or suppressing an immune response. For example, immune suppression components include those molecules that partially or totally block immune stimulation; decrease, prevent or delay immune activation; or increase, activate, or up regulate immune suppression. Exemplary immunosuppression component targets are described in further detail herein and include PD-1, PD-L1, CTLA4, B7-H3, B7-H4, CD244/2B4, HVEM, BTLA, CD160, TIM3, GALS, KIR, PVR1G (CD112R), PVRL2, adenosine, A2aR, immunosuppressive cytokines (e.g., IL-10, IL-4, IL-1RA, IL-35), IDO, arginase, VISTA, TIGIT, LAIR1, CEACAM-1, CEACAM-3, CEACAM-5, Treg cells, or any combination thereof.

An agent that specifically binds to and/or is an inhibitor of an immune suppression component may be a compound, an antibody, an antibody fragment or fusion polypeptide (e.g., Fc fusion, such as CTLA4-Fc or LAG3-Fc), an antisense oligonucleotide, a ribozyme or RNAi molecule, an aptamer, or a low molecular weight organic molecule. In any of the embodiments disclosed herein, a combination comprises one or more agent that specifically binds to and/or is an inhibitor of any one of the following immune suppression components, singly or in any combination. In any of the embodiments disclosed herein, a method may comprise administering a modified immune cell and an ICD-induction associated agent with one or more inhibitor of any one of the following immune suppression components, singly or in any combination.

In certain embodiments, a combination therapy comprises a PD-1 inhibitor, for example a PD-1-specific antibody or binding fragment thereof, such as pidilizumab, nivolumab (Keytruda, formerly MDX-1106), pembrolizumab (Opdivo, formerly MK-3475), MEDI0680 (formerly AMP-514), AMP-224, BMS-936558, or any combination thereof. In further embodiments, a modified immune cell of the present disclosure and an agent that is associated with induction of ICD are used in combination with a PD-L1 specific antibody or binding fragment thereof, such as BMS-936559, durvalumab (MEDI4736), atezolizumab (RG7446), avelumab (MSB0010718C), MPDL3280A, or any combination thereof.

In certain embodiments, a combination therapy comprises a LAG3 inhibitor, such as LAG525, IMP321, IMP701, 9H12, BMS-986016, or any combination thereof.

In certain embodiments, a combination therapy comprises an inhibitor of CTLA4. In particular embodiments, the modified immune cell is used in combination with a CTLA4 specific antibody or binding fragment thereof, such as ipilimumab, tremelimumab, a CTLA4-Ig fusion protein (e.g., abatacept, belatacept), or any combination thereof.

In certain embodiments, a combination therapy comprises a B7-H3 specific antibody or binding fragment thereof, such as enoblituzumab (MGA271), 376.96, or both. A B7-H4 antibody binding fragment may be a scFv or fusion protein thereof, as described in, for example, Dangaj et al., *Cancer Res.* 73:4820, 2013, as well as those described in U.S. Pat. No. 9,574,000 and PCT Patent Publication Nos. WO/201640724A1 and WO 2013/025779A1.

In certain embodiments, a combination therapy comprises an inhibitor of CD244. In certain embodiments, a combination therapy comprises an inhibitor of BLTA, HVEM, CD160, or any combination thereof. Anti CD-160 antibodies are described in, for example, PCT Publication No. WO 2010/084158. In certain embodiments, a combination therapy comprises an inhibitor of TIM3. In certain embodiments, a combination therapy comprises an inhibitor of Ga19. In certain embodiments, a combination therapy comprises an inhibitor of adenosine signaling, such as a decoy adenosine receptor. In certain embodiments, a combination therapy comprises an inhibitor of A2aR. In certain embodiments, a combination therapy comprises an inhibitor of KIR, such as lirilumab (BMS-986015). In certain embodiments, a combination therapy comprises an inhibitor of an inhibitory cytokine (typically, a cytokine other than TGFβ) or Treg development or activity. In certain embodiments, a combination therapy comprises an IDO inhibitor, such as levo-1-methyl tryptophan, epacadostat (INCB024360; Liu et al., *Blood* 115:3520-30, 2010), ebselen (Terentis et al., *Biochem.* 49:591-600, 2010), indoximod, NLG919 (Mautino et al., American Association for Cancer Research 104th Annual Meeting 2013; Apr. 6-10, 2013), 1-methyl-tryptophan (1-MT)-tira-pazamine, or any combination thereof.

In certain embodiments, a combination therapy comprises an arginase inhibitor, such as N(omega)-Nitro-L-arginine methyl ester (L-NAME), N-omega-hydroxy-nor-1-arginine (nor-NOHA), L-NOHA, 2(S)-amino-6-boronohexanoic acid (ABH), S-(2-boronoethyl)-L-cysteine (BEC), or any combination thereof.

In certain embodiments, a combination therapy comprises an inhibitor of VISTA, such as CA-170 (Curis, Lexington, Mass.). In certain embodiments, a combination therapy comprises an inhibitor of TIGIT such as, for example, COM902 (Compugen, Toronto, Ontario Canada), an inhibitor of CD155, such as, for example, COM701 (Compugen), or both. In certain embodiments, a combination therapy comprises an inhibitor of PVRIG, PVRL2, or both. Anti-PVRIG antibodies are described in, for example, PCT Publication No. WO 2016/134333. Anti-PVRL2 antibodies are described in, for example, PCT Publication No. WO 2017/021526. In certain embodiments, a combination therapy comprises a LAIR1 inhibitor. In certain embodiments, a combination therapy comprises an inhibitor of CEACAM-1, CEACAM-3, CEACAM-5, or any combination thereof.

In certain embodiments, a modified immune cell of the present disclosure and an agent that is associated with induction of ICD (e.g., together, or in a sequence, or administering one to a subject who has previously received the other) are used in combination with an agent that increases the activity (i.e., is an agonist) of a stimulatory immune checkpoint molecule. For example, a modified immune cell of the present disclosure and an agent that is associated with induction of ICD can be used in combination with a CD137 (4-1BB) agonist (such as, for example, urelumab), a CD134 (OX-40) agonist (such as, for example, MEDI6469, MEDI6383, or MEDI0562), lenalidomide, pomalidomide, a CD27 agonist (such as, for example, CDX-1127), a CD28 agonist (such as, for example, TGN1412, CD80, or CD86), a CD40 agonist (such as, for example, CP-870,893, rhuCD40L, or SGN-40), a CD122 agonist (such as, for example, IL-2) an agonist of GITR (such as, for example, humanized monoclonal antibodies described in PCT Patent Publication No. WO 2016/054638), an agonist of ICOS (CD278) (such as, for example, GSK3359609, mAb 88.2, JTX-2011, Icos 145-1, Icos 314-8, or any combination thereof). In any of the embodiments disclosed herein, a method may comprise administering a modified immune cell of the present disclosure and an agent that is associated with induction of ICD with one or more agonist of a stimulatory immune checkpoint molecule, including any of the foregoing, singly or in any sequence or combination.

In any of the embodiments disclosed herein, a combination therapy comprises an agent that increases the activity (i.e., is an agonist) of a stimulatory immune checkpoint molecule. In certain embodiments, a modified human immune cell and an agent associated with induction of ICD are used, e.g., administered, in combination with an agent that increases the activity (i.e., is an agonist) of a stimulatory immune checkpoint molecule. For example, a modified immune cell and an ICD-induction-associated agent can be used in combination with a CD137 (4-1BB) agonist (such as, for example, urelumab), a CD134 (OX-40) agonist (such as, for example, MEDI6469, MEDI6383, or MEDI0562), lenalidomide, pomalidomide, a CD27 agonist (such as, for example, CDX-1127), a CD28 agonist (such as, for example, TGN1412, CD80, or CD86), a CD40 agonist (such as, for example, CP-870,893, rhuCD40L, or SGN-40), a CD122 agonist (such as, for example, IL-2), an agonist of GITR (such as, for example, humanized monoclonal antibodies described in PCT Patent Publication No. WO 2016/054638), or an agonist of ICOS (CD278) (such as, for example, GSK3359609, mAb 88.2, JTX-2011, Icos 145-1, or Icos 314-8), or any combination thereof. In any of the embodiments disclosed herein, a method may comprise administering a modified immune cell, e.g., human immune cell, and an ICD-induction-associated agent with one or more agonist of a stimulatory immune checkpoint molecule, including any of the foregoing, singly or in any combination.

Any of the agents described herein may be administered to a subject who has previously received one or more of the other agents, provided that the subject ultimately receives a modified immune cell of this disclosure and an agent associated with induction of immunogenic cell death (ICD) in amounts effective to treat the disease or disorder, such as a tumor or cancer.

Agents for Secondary Therapies

Also contemplated are secondary therapies comprising one or more of: an antibody or an antigen binding fragment thereof specific for an antigen expressed by a targeted diseased cell or tissue; a chemotherapeutic agent; surgery; radiation therapy treatment; a cytokine; an RNA interference therapy, or any combination thereof. In some embodiments, the methods further comprise administering a secondary therapy, such as any described herein.

Exemplary monoclonal antibodies useful in cancer therapies are known in the art and include, for example, monoclonal antibodies described in Galluzzi et al., *Oncotarget* 5(24):12472-12508, 2014.

In certain embodiments, a secondary therapy comprises a radiation treatment (e.g., a radiation treatment that may or may not be one associated with inducing ICD) or a surgery. In certain embodiments, a combination therapy method comprises administering a modified human immune cell and an ICD-induction associated agent, and further administering a radiation treatment (e.g., a radiation treatment that may or may not be one associated with inducing ICD) or a surgery. Radiation therapy is well-known in the art and includes X-ray therapies, such as gamma-irradiation, and radiopharmaceutical therapies. Surgeries and surgical techniques appropriate to treating a given cancer or non-inflamed solid tumor in a subject are well-known to those of ordinary skill in the art.

In certain embodiments, a secondary therapy comprises a chemotherapeutic agent (which chemotherapeutic agent may or may not be associated with inducing ICD). In certain embodiments, a combination therapy method comprises administering a modified human immune cell and an ICD-induction associated agent, and further administering a chemotherapeutic agent (which chemotherapeutic agent may or may not be associated with inducing ICD). In some embodiments, a chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor. Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors.

Cytokines can be used and in some contexts are increasingly used to manipulate host immune response towards anticancer activity. See, e.g., Floros & Tarhini, *Semin. Oncol.* 42(4):539-548, 2015. Cytokines useful for promoting immune anticancer or antitumor response include, for example, IFN-α, IL-2, IL-3, IL-4, IL-10, IL-12, IL-13, IL-15, IL-16, IL-17, IL-18, IL-21, IL-24, and GM-CSF, singly or in any combination.

Another cancer therapy (e.g., secondary therapy) or treatment approach involves reducing expression of oncogenes and other genes needed for growth, maintenance, proliferation, and immune evasion by cancer cells. RNA interference, and in particular the use of microRNAs (miRNAs) small inhibitory RNAs (siRNAs) provides an approach for knocking down expression of cancer genes. See, e.g., Larsson et al., *Cancer Treat. Rev.* 16(55):128-135, 2017. Techniques for making and using RNA for cancer therapy or treatment are known to those having ordinary skill in the art.

In any of the embodiments disclosed herein, any of the therapeutic agents (e.g., a modified immune cell, an ICD-induction-associated agent, an inhibitor of an immune suppression component, an agonist of a stimulatory immune checkpoint molecule, an antitumor lymphocyte, a chemotherapeutic agent, a radiation therapy, a surgery, a cytokine, or an inhibitory RNA) may be administered once or more than once to the subject over the course of a treatment, and, in combinations, may be administered to the subject in any order (e.g., simultaneously, concurrently, or in any sequence) or any combination. An appropriate dose, suitable duration, and frequency of administration of the compositions will be determined by such factors as a condition of the patient; size, type, spread, growth, and severity of the tumor or cancer; particular form of the active ingredient; and the method of administration.

Kits

Also provided herein are kits that comprise: (i) one or more of (a) modified immune cell comprising a heterologous polynucleotide that encodes a binding protein that specifically binds to an antigen expressed by or associated with the disease or condition; (b) an agent associated with induction of immunogenic cell death (ICD); (c) an agent that specifically binds to and/or is an inhibitor of an immune suppression component; and (d) an agonist of an immune stimulatory molecule; and (ii) instructions for performing a method according the present disclosure.

Uses

Compositions of the present disclosure are useful in treating diseases or conditions. "Treat" or "treatment" or "ameliorate" in some contexts refers to medical management of a disease, disorder, or condition of a subject (e.g., a human or non-human mammal, such as a primate, horse, cat, dog, goat, mouse, or rat). In general, an appropriate dose or treatment regimen comprising a host cell expressing a binding protein of the present disclosure, and optionally an adjuvant, is administered in an amount sufficient to elicit a therapeutic or prophylactic benefit. Therapeutic or prophylactic/preventive benefit includes improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; prolonged survival; or any combination thereof.

Presently disclosed methods are based, in part, on the use of modified immune cells of the instant disclosure in conjunction with an agent that is associated with induction of ICD, which methods can further comprise use of an agonist of a stimulatory immune checkpoint molecule, use of an agent that specifically binds to and/or is an inhibitor of an immune suppression component, or both. Accordingly, it will be appreciated that a method can involve administration of one agent (modified immune cell; agent associated with induction of ICD; agonist of a stimulatory immune checkpoint molecule; agent that specifically binds to and/or is an inhibitor of an immune suppression component) to a subject that is also receiving or has previously received one or more other agent, provided that the subject ultimately receives at least both of a modified immune cell and an agent associated with induction of ICD.

For example, a method may comprise administering to a subject an effective amount of a modified immune cell of this disclosure, provided that the subject has previously been administered an agent associated with induction of ICD. As another example, a method may comprise administering to a subject an effective amount of an agent associated with induction of ICD, provided that the subject has previously been administered an agent associated with induction of modified immune cell of this disclosure.

In certain aspects, the instant disclosure provides methods for treating a disease or condition in a subject, wherein the methods comprise administering to the subject: (a) an effective amount of a modified immune cell comprising a heterologous polynucleotide that encodes a binding protein that specifically binds to an antigen expressed by or associated with the disease or condition; and (b) an effective amount of an agent associated with induction of immunogenic cell death (ICD), thereby treating the disease or condition.

In other aspects, methods are provided for treating a disease or condition in a subject, wherein the methods comprise administering to the subject an effective amount of a modified immune cell comprising a heterologous polynucleotide that encodes a binding protein that specifically binds to an antigen expressed by or associated with the disease or condition, wherein the subject, prior to administering the modified immune cell, has been administered an agent associated with induction of immunogenic cell death (ICD), thereby treating the disease or condition.

In yet other aspects, the present disclosure provides methods for treating a disease or condition in a subject, wherein the methods comprise administering to the subject an effective amount of an agent associated with induction of immunogenic cell death (ICD), wherein the subject, prior to administering the agent associated with induction of ICD, has been administered a modified immune cell comprising a heterologous polynucleotide that encodes a binding protein that specifically binds to an antigen expressed by or associated with the disease or condition, thereby treating the disease or condition.

In still other aspects, methods are provided for treating a disease or disorder in a subject, wherein the methods comprise administering to the subject an effective amount of an agent that specifically binds to and/or is an inhibitor of an immune suppression component, wherein the subject, prior to administering the agent that specifically binds to and/or is an inhibitor of an immune suppression component, has been administered: (i) a modified immune cell comprising a heterologous polynucleotide that encodes a binding protein that specifically binds to an antigen expressed by or associated with the disease or condition; and/or (ii) an agent associated with induction of ICD, wherein the subject was optionally previously administered an agonist of a stimulatory immune checkpoint molecule, thereby treating the disease or condition.

In yet further aspects, methods are provided herein for treating a disease or disorder in a subject, wherein the methods comprise administering to the subject an effective amount of a modified immune cell comprising a heterologous polynucleotide that encodes a binding protein that specifically binds to an antigen expressed by or associated with the disease or condition, wherein the subject, prior to administering the modified immune cell, has been administered: (i) an effective amount of an agent that specifically binds to and/or is an inhibitor of an immune suppression component; and/or (ii) an agent associated with induction of ICD, thereby treating the disease or condition, wherein the subject was optionally previously administered an agonist of a stimulatory immune checkpoint molecule, thereby treating the disease or condition.

In still further aspects, methods are provided herein for treating a disease or disorder in a subject, wherein the methods comprise administering to the subject an effective amount of an agent associated with induction of ICD, wherein the subject, prior to administering the agent associated with induction of ICD, been administered: (i) an agent that specifically binds to and/or is an inhibitor of an immune suppression component; and/or (ii) a modified immune cell comprising a heterologous polynucleotide that encodes a binding protein that specifically binds to an antigen expressed by or associated with the disease or condition, wherein the subject was optionally previously administered an agonist of a stimulatory immune checkpoint molecule, thereby treating the disease or condition.

Also provided herein are methods of treating a disease or disorder in a subject, wherein the methods comprise administering to the subject an effective amount of an agonist of a stimulatory immune checkpoint molecule, wherein the subject, prior to administering the agonist of a stimulatory immune checkpoint molecule, been administered: (i) a modified immune cell comprising a heterologous polynucleotide that encodes a binding protein that specifically binds to an antigen expressed by or associated with the disease or condition; and/or (ii) an agent associated with induction of ICD, thereby treating the disease or condition, wherein the subject was optionally previously administered an agent that specifically binds to and/or is an inhibitor of an immune suppression component, thereby treating the disease or condition.

In certain aspects, methods are provided herein for treating a disease or disorder in a subject, wherein the methods comprise administering to the subject an effective amount of a modified immune cell comprising a heterologous polynucleotide that encodes a binding protein that specifically binds to an antigen expressed by or associated with the disease or condition, wherein the subject, prior to administering the modified immune cell, has been administered: (i) an agonist of a stimulatory immune checkpoint molecule; and/or (ii) an agent associated with induction of ICD, and wherein the subject was optionally previously administered an agent that specifically binds to and/or is an inhibitor of the immune suppression component, thereby treating the disease or condition.

In certain other aspects, methods are provided for treating a disease or disorder in a subject, wherein the methods comprise administering to the subject an effective amount of an agent associated with induction of ICD, wherein the subject, prior to administering the agent associated with induction of ICD, been administered: (i) an agonist of a stimulatory immune checkpoint molecule; and/or (ii) a modified immune cell comprising a heterologous polynucleotide that encodes a binding protein that specifically binds to an antigen expressed by or associated with the disease or condition, and wherein the subject was optionally previously administered an agent that specifically binds to and/or is an inhibitor of the immune suppression component, thereby treating the disease or condition.

Following any of the treatment methods described herein (i.e., following administration of: (i) the modified immune cell and the agent associated with induction of ICD; (ii) the modified immune cell, the agent associated with induction of ICD, and the agent that specifically binds to and/or is an inhibitor of an immune suppression component;
(iii) the modified immune cell, the agent associated with induction of ICD, and the agonist of a stimulatory immune checkpoint molecule; or (iv) the modified immune cell, the agent associated with induction of ICD, the agonist of a stimulatory immune checkpoint molecule, and the agent that specifically binds to and/or is an inhibitor of an immune suppression component), the subject can achieve an immune response against the disease or disorder that is elevated as compared to the immune response achieved by a reference subject that is not administered the agent associated with induction of ICD.

In some embodiments, a reference subject can mean a comparator subject (i.e., of the same or a similar species, gender, size, age, and disease state) that was administered an identical therapy to a tested subject with the exception of the agent associated with induction of ICD.

In certain embodiments, an elevated immune response comprises: (i) an increased amount of immune cell localization to, and/or immune cell activity at, a site of the disease or disorder (e.g., a tumor or a site of an infection); (ii) an increase in proliferation of immune cells in the subject (e.g., an increase in the number of proliferating immune cells, the rate of proliferation of the immune cells, or both); (iii) an increased amount of activated immune cells in the subject; (iv) an increased expression level in the subject, optionally in a sample of diseased tissue from the subject, of a gene associated with (a) a cytokine-cytokine receptor interaction, (b) a chemokine signaling pathway, (c) a cell adhesion molecule, or (d) any combination of (a)-(c); (v) a reduction in the amount, growth, rate of growth, or spread, of diseased cells and/or tissue; or (vi) any combination of (i)-(iv).

In further embodiments, an elevated immune response comprises an increased expression level of one or more of: Ccl12; Ccl17; Ccl2; Ccl7; Ccl9; Ccr2; Ccr8; CD40; CD401g; Csf1; Csβr; Cxcl10; Cxcr2; Eda2r; Fas; IL21r; IL2rb; IL17r; Tnfrsf25; Tnfsrf9; Tnfsf8; Xcl1; Gng7; CD226; CD80; CD8a; Cldn2; H2-M2; Pdcd1lg2; Sele; Selp; or any combination thereof.

In some embodiments, a "therapeutically effective amount" or "effective amount" of a modified immune cell, an agent associated with induction of ICD, an agonist of an immune stimulatory agent, or an agent that specifically binds to and/or is an inhibitor of an immune suppression component of this disclosure refers to an amount of binding proteins or host cells sufficient to result in a therapeutic effect, including improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; or prolonged survival in a statistically significant manner. When referring to an individual active ingredient or a cell expressing a single active ingredient, administered alone, a therapeutically effective amount can refer to the effects of that ingredient or cell expressing that ingredient alone. When referring to a combination, a therapeutically effective amount can refer to the combined amounts of active ingredients or combined adjunctive active ingredient with a cell expressing an active ingredient that results in a therapeutic effect, whether administered serially or simultaneously. A combination may also be a cell expressing more than one active ingredient, such as two different binding proteins (e.g., CARs) that each specifically bind to a target (e.g., each binding to the same or to a different disease-associated antigen) or a modified immune cell, an agent associated with induction of ICD, and another relevant therapeutic.

In some embodiments, a modified immune cell is administered to a subject at a dose comprising up to about $3.3 \times 10^5$ cells/kg. In some embodiments, a modified immune cell is administered to a subject at a dose comprising at least about $3.3 \times 10^5$ cells/kg.

In some embodiments, a modified immune cell is administered to a subject at a dose comprising up to about $1 \times 10^6$ cells/kg. In some embodiments, a modified immune cell is administered to a subject at a dose comprising least about $1 \times 10^6$ cells/kg.

In some embodiments, a modified immune cell is administered to a subject at a dose comprising up to about $3.3 \times 10^6$ cells/kg. In some embodiments, a modified immune cell is administered to a subject at a dose comprising at least about $3.3 \times 10^6$ cells/kg.

In some embodiments, a modified immune cell is administered to a subject at a dose comprising up to about $1 \times 10^7$ cells/kg. In some embodiments, a modified immune cell is administered to a subject at a dose comprising at least about $1 \times 10^7$ cells/kg.

In certain embodiments, a modified immune cell is administered to a subject at a dose comprising up to about $5 \times 10^4$ cells/kg, $5 \times 10^5$ cells/kg, $5 \times 10^6$ cells/kg, or up to about $5 \times 10^7$ cells/kg. In certain embodiments, a modified immune cell is administered to a subject at a dose comprising at least about $5 \times 10^4$ cells/kg, $5 \times 10^5$ cells/kg, $5 \times 10^6$ cells/kg, or up to about $5 \times 10^7$ cells/kg.

In certain embodiments, an agent associated with induction of ICD comprises oxaliplatin. In certain embodiments, a single dose of oxaliplatin comprises about 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 mg/m$^2$, or more. In particular embodiments, a single dose of oxaliplatin comprises about 50, 55, 60, 65, 70, 75, 80, 85, 90, 95, or 100 mg/m$^2$. In further embodiments, a single dose of oxaliplatin comprises about 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 mg/kg, or more.

In certain embodiments, an agent associated with induction of ICD comprises cyclophosphamide. In some embodiments, a single dose of cyclophosphamide comprises about 10, 20, 30, 40, 50, 60, 70, 80, 90, 100, 120, 130, 140, 150, 160, 170, 180, 190, 200 mg/kg cyclophosphamide, or more. In some embodiments, a subject is administered about 50, 100, 200, 300, 400, 500, 600, 700, 800, 900, 1000, 1500, 2000, 2500, 3000, 3500, 4000, 4500, 5000 mg/m$^2$ cyclophosphamide (or of a pharmaceutical composition comprising cyclophosphamide) per day, or more. In particular embodiments, In certain embodiments, an agent associated with induction of ICD comprises oxaliplatin and cyclophosphamide, wherein the oxaliplatin and the cyclophosphamide are each present in any amount and/or in any ratio to one another. In some embodiments, a single dose of an agent associated with induction of ICD comprises about 50 to about 100 mg/m$^2$ of oxaliplatin and about 200 to about 1000 mg/m$^2$ cyclophosphamide. In further embodiments, the single dose comprises about 300 mg/m$^2$ cyclophosphamide.

In certain embodiments, an agent that specifically binds to and/or is an inhibitor of an immune suppression component comprises an antibody or antigen binding fragment thereof that specifically binds to PD-L1, which, in any of the herein disclosed embodiments, is, comprises, or is derived from BMS-936559, durvalumab (MEDI4736), atezolizumab (RG7446), avelumab (MSB0010718C), MPDL3280A, or any combination thereof. In certain embodiments, an anti-PD-L1 antibody or antigen-binding fragment thereof is administered at a dose of about 1, 2, 3, 4, 5, 6, 7, 8, 9, 10, 11, 12, 13, 14, 15, 16, 17, 18, 19, 20, 25, 30, 35, 40, 45, 50, or more mg/kg. In certain embodiments, a single dose of an agent that specifically binds to and/or is an inhibitor of an immune suppression component (e.g., an anti-PD-L1 antibody or antigen-binding fragment thereof, or a pharmaceutical composition comprising the same) comprises about 100, 200, 300, 400, 500, 600, 700, 800, 900, 1000, 1100, 1200, 1300, 1400, 1500, 1600, 1700, 1800, 1900, 2000 milligrams, or more of the agent (or of a composition comprising the agent).

Dosing of any of the agents described herein (e.g., modified immune cell, agent associated with induction of ICD; agent that specifically binds to and/or is an inhibitor of an immune suppression component; agent that is an agonist of an immune stimulatory component), may be performed using any route of delivery, and over any period of time. In certain embodiments, delivery of an agent is performed intravenously. In certain embodiments, a single dose of the agent may be delivered intravenously over the course of about 5, 10, 15, 20, 25, 30, 60, 75, 90, 120, 180, 240 minutes, or more. Doses may be delivered about 1, 2, 3, 4, 5, 6, 7, 8, 9, 10, or more times per day. In some embodiments, a single dose is administered once per day. In some embodiments, a single daily dose is administered about once per week, once per every two, three, four, five, six, seven, eight weeks, or more.

In some embodiments, any two or more agents (i.e., two or more of a modified immune cell; an agent associated with induction of ICD; an agonist of a stimulatory immune checkpoint molecule; an agent that specifically binds to and/or is an inhibitor of an immune suppression component; and/or an agent that is an agonist of an immune stimulatory component) are administered simultaneously. In some embodiments, any two or more of the agents are administered contemporaneously. In some embodiments, any two or more of the agents are administered in a sequence and/or intermittently, in any order and with any amount of time between administrations.

Administrations of any single agent or of any two or more of the herein described agents may be performed at any appropriate interval, such as on a daily or weekly basis, or about 2, 3, 4, 5, 6, 7, 8, 9, 10, or more weeks apart. In certain embodiments, a subject is administered the agent associated with induction of ICD and the modified immune cell multiple times (e.g., 2, 3, 4, 5, 6, 7, 8, 9, 10, or more times). In certain embodiments, the subject is administered the agent associated with induction of ICD and the modified immune cell together at intervals of about one week, about two weeks, about three weeks, about four weeks, about five weeks, or about six weeks. In further embodiments, the subject receiving the agent associated with induction of ICD and the modified immune cell has not previously received either the agent or the modified immune cell. In yet further embodiments, the agent associated with induction of ICD and the modified immune cell are administered 2, 3, 4, 5, 6, 7, 8, 9, 10, or more times (e.g., two or more weekly, bi-weekly, or tri-weekly doses).

In certain embodiments, a modified immune cell is administered to a subject simultaneously with an agent that is associated with induction of ICD. In certain embodiments, a modified immune cell is administered to a subject after the subject has been administered an agent that is associated with induction of ICD. In certain embodiments, an agent that is associated with induction of ICD is administered to a subject after the subject has been administered a modified immune cell. In certain embodiments, an agent that is associated with induction of ICD and a modified immune cell are administered to the subject in a sequence (i.e., in any sequence and for any number of iterations). In any of the methods disclosed herein, an agent that specifically binds to and/or is an inhibitor of an immune suppression component, and/or an agent that is an agonist of an immune stimulatory molecule, is administered prior to, following, or intermittently between (e.g., once, twice, three times, or more between) either or both of administration of a modified immune cell and administration of an agent that is associated with induction of ICD.

In certain embodiments, a method comprises administering the agent associated with induction of ICD and the modified immune cell in conjunction with an agent that specifically binds to and/or is an inhibitor of an immune suppression component such that the an agent that specifically binds to and/or is an inhibitor of an immune suppression component is administered 1, 2, 3, 4, 5, 6, 7, 8, 9, or 10 times per day, and/or is administered 1, 2, 3, 4, 5, 6, 7, 8, 9, or 10 times per week. In some embodiments, a modified immune cell is administered about 12, 24, 36, 48, 60, 72, 84, or 96 hours following administration of an agent that is associated with induction of ICD.

In any of the presently disclosed embodiments, the subject has not received any of the modified immune cell, the agent associated with inducement of ICD, the agonist of an immune stimulatory molecule, and the agent that specifically binds to and/or is an inhibitor of an immune suppression component prior to a presently disclosed therapeutic regimen.

Alternatively, in some embodiments, the subject has (or has not) received any of the agents (modified immune cell, the agent associated with inducement of ICD, the agonist of an immune stimulatory molecule, and the agent that specifically binds to and/or is an inhibitor of an immune suppression component) for 1, 2, 3, 4, 5, 6, 7, 8, 9, 10, 11, 12, 13, 14, 21, or 28 days prior to commencing a therapy of the instant disclosure.

In particular embodiments, the agent associated with induction of ICD comprises oxaliplatin and cyclophosphamide and the agent that specifically binds to and/or is an inhibitor of an immune suppression component comprises an anti PD-L1 antibody. In further embodiments, a method comprises administering oxaliplatin and cyclophosphamide about once per week, an anti-PD-L1 antibody about twice per week, and the modified immune cell (alone or in combination with a lymphodepleting chemotherapy such as cyclophosphamide) about every three weeks.

In still further embodiments, a method comprises administering the modified immune cell with cyclophosphamide for 2 or more triweekly intervals, oxaliplatin and cyclophosphamide once per week for 3 or more weeks, beginning the same week as the modified immune cell and cyclophosphamide, and an anti-PD-L1 antibody twice per week for 2 or more weeks, beginning the same week as the modified immune cell and cyclophosphamide.

In some embodiments, a method further comprises administering to the subject a cytokine (e.g., IL-2, IL-15, IL-21) is administered sequentially, provided that the subject was administered the modified immune cell at least three or four times before cytokine administration. In certain embodiments, the cytokine is administered concurrently with the modified immune cell.

In certain embodiments, the subject being treated has received or is further receiving immunosuppressive therapy, such as calcineurin inhibitors, corticosteroids, microtubule inhibitors, low dose of a mycophenolic acid prodrug, or any combination thereof. In yet further embodiments, the subject being treated has received a non-myeloablative or a myeloablative hematopoietic cell transplant, wherein the treatment may be administered at least two to at least three months after the non-myeloablative hematopoietic cell transplant.

In any of the herein described embodiments, a disease or condition can be or comprise a hyperproliferative disease. In some contexts, as used herein, "hyperproliferative disease" refers to excessive growth or proliferation as compared to a normal or undiseased cell. Exemplary hyperproliferative disorders include tumors, cancers, neoplastic tissue, carcinoma, sarcoma, gliomas, leukemias, lymphomas, myelomas, malignant cells, pre-malignant cells, as well as non-neoplastic or non-malignant hyperproliferative disorders (e.g., adenoma, fibroma, lipoma, leiomyoma, hemangioma, fibrosis, restenosis, as well as autoimmune diseases such as rheumatoid arthritis, osteoarthritis, psoriasis, inflammatory bowel disease, or the like).

Furthermore, in some contexts, "cancer" may refer to any accelerated proliferation of cells, including solid tumors, ascites tumors, blood or lymph or other malignancies; connective tissue malignancies; metastatic disease; minimal residual disease following transplantation of organs or stem cells; multi-drug resistant cancers, primary or secondary malignancies, angiogenesis related to malignancy, or other forms of cancer.

In certain embodiments, the cancer comprises a cancer of the head or neck, melanoma, pancreatic cancer, cholangiocarcinoma, hepatocellular cancer, breast cancer, gastric cancer, non-small-cell lung cancer, prostate cancer, esophageal cancer, mesothelioma, small-cell lung cancer, colorectal cancer, glioblastoma, or any combination thereof.

In further embodiments, the cancer comprises Askin's tumor, sarcoma botryoides, chondrosarcoma, Ewing's sarcoma, PNET, malignant hemangioendothelioma, malignant schwannoma, osteosarcoma, alveolar soft part sarcoma, angiosarcoma, cystosarcoma phyllodes, dermatofibrosarcoma protuberans (DFSP), desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, undifferentiated pleomorphic sarcoma, malignant peripheral nerve sheath tumor (MPNST), neurofibrosarcoma, rhabdomyosarcoma, synovial sarcoma, undifferentiated pleomorphic sarcoma, squamous cell carcinoma, basal cell carcinoma, adenocarcinoma, linitis plastic, vipoma, cholangiocarcinoma, hepatocellular carcinoma, adenoid cystic carcinoma, renal cell carcinoma, Grawitz tumor, ependymoma, astrocytoma, oligodendroglioma, brainstem glioma, optice nerve glioma, a mixed glioma, Hodgkin's lymphoma, a B-cell lymphoma, non-Hodgkin's lymphoma (NHL), Burkitt's lymphoma, small lymphocytic lymphoma (SLL), diffuse large B-cell lymphoma, follicular lymphoma, immunoblastic large cell lymphoma, precursor B-lymphoblastic lymphoma, and mantle cell lymphoma, Waldenstrom's macroglobulinemia, CD37+ dendritic cell lymphoma, lymphoplasmacytic lymphoma, splenic marginal zone lymphoma, extranodal marginal zone B-cell lymphoma of mucosa-associated (MALT) lymphoid tissue, nodal marginal zone B-cell lymphoma, mediastinal (thymic) large B-cell lymphoma, intravascular large B-cell lymphoma, primary effusion lymphoma, adult T-cell lymphoma, extranodal NK/T-cell lymphoma, nasal type, enteropathy-associated T-cell lymphoma, hepatosplenic T-cell lymphoma, blastic NK cell lymphoma, Sezary syndrome, angioimmunoblastic T cell lymphoma, anaplastic large cell lymphoma, or any combination thereof.

In certain embodiments, cancer comprises a solid tumor, which may, in embodiments, comprise a sarcoma, a carcinoma, or both. Exemplary solid tumors treatable according to the presently disclosed methods include chondrosarcoma; fibrosarcoma (fibroblastic sarcoma); Dermatofibrosarcoma protuberans (DFSP); osteosarcoma; rhabdomyosarcoma; Ewing's sarcoma; a gastrointestinal stromal tumor; Leiomyosarcoma; angiosarcoma (vascular sarcoma); Kaposi's sarcoma; liposarcoma; pleomorphic sarcoma; or synovial sarcoma.

In further embodiments, the solid tumor is selected from a lung carcinoma (e.g., Adenocarcinoma, Squamous Cell Carcinoma (Epidermoid Carcinoma); Squamous cell carcinoma; Adenocarcinoma; Adenosquamous carcinoma; anaplastic carcinoma; Large cell carcinoma; Small cell carcinoma; a breast carcinoma (e.g., Ductal Carcinoma in situ (non-invasive), Lobular carcinoma in situ (non-invasive), Invasive Ductal Carcinoma, Invasive lobular carcinoma, Non-invasive Carcinoma); a liver carcinoma (e.g., Hepatocellular Carcinoma, Cholangiocarcinomas or Bile Duct Cancer); Large-cell undifferentiated carcinoma, Bronchioalveolar carcinoma); an ovarian carcinoma (e.g., Surface epithelial-stromal tumor (Adenocarcinoma) or ovarian epithelial carcinoma (which includes serous tumor, endometrioid tumor and mucinous cystadenocarcinoma), Epidermoid (Squamous cell carcinoma), Embryonal carcinoma and choriocarcinoma (germ cell tumors)); a kidney carcinoma (e.g., Renal adenocarcinoma, hypernephroma, Transitional cell carcinoma (renal pelvis), Squamous cell carcinoma, Bellini duct carcinoma, Clear cell adenocarcinoma, Transitional cell carcinoma, Carcinoid tumor of the renal pelvis); an adrenal carcinoma (e.g., Adrenocortical carcinoma), a carcinoma of the testis (e.g., Germ cell carcinoma (Seminoma, Choriocarcinoma, Embryonal carciroma, Teratocarcinoma), Serous carcinoma); Gastric carcinoma (e.g., Adenocarcinoma); an intestinal carcinoma (e.g., Adenocarcinoma of the duodenum); a colorectal carcinoma; or a skin carcinoma (e.g., Basal cell carcinoma, Squamous cell carcinoma).

In certain embodiments, the solid tumor is: an ovarian carcinoma; an ovarian epithelial carcinoma; a cervical adenocarcinoma or small cell carcinoma; a pancreatic carcinoma; a colorectal carcinoma (e.g., an adenocarcinoma or squamous cell carcinoma); a lung carcinoma; a breast ductal carcinoma; or an adenocarcinoma of the prostate.

In some embodiments, disease-associated antigens of this disclosure include tumor-associated antigens, such as, for example, ROR1, EGFR, EGFRvIII, EGP-2, EGP-40, GD2, GD3, HPV E6, HPV E7, Her2, L1-CAM, Lewis A, Lewis Y, MUC1, MUC16, PSCA, PSMA, CD19, CD20, CD22, CD56, CD23, CD24, CD30, CD33, CD37, CD44v7/8, CD38, CD56, CD123, CA125, c-MET, FcRH5, WT1, folate receptor α, VEGF-α, VEGFR1, VEGFR2, IL-13Ra2, IL-11Ra, MAGE-A1, PSA, ephrin A2, ephrin B2, an NKG2D, NY-ESO-1, TAG-72, mesothelin, NY-ESO, 5T4, BCMA, FAP, Carbonic anhydrase 9, ERBB2, BRAFV600E, MAGE-A3, MAGE-A4, SSX-2, PRAIVIE, HA-1, and CEA. In particular embodiments, the tumor-associated antigen is ROR1. In further embodiments, the disease or condition comprises triple-negative breast cancer, mantle cell lymphoma, acute lymphocytic leukemia, non-small-cell lung cancer, or any combination thereof. Subjects that can be treated by the present invention are, in general, human and other primate subjects, such as monkeys and apes for veterinary medicine purposes. In any of the aforementioned embodiments, the subject may be a human subject. The subjects can be male or female and can be any suitable age, including infant, juvenile, adolescent, adult, and geriatric subjects. one or more compositions, e.g., comprising modified cells, agents or combinations thereof according to the present disclosure, may be administered in a manner appropriate to the disease, condition, or disorder to be treated as determined by persons skilled in the medical art. In any of the above embodiments, a cell comprising a binding protein as described herein is administered intravenously, intraperitoneally, intratumorally, into the bone marrow, into a lymph node, or into the cerebrospinal fluid so as to encounter the tagged cells or tagged immunotherapy cells to be ablated. An appropriate dose, suitable duration, and frequency of administration of the compositions will be determined by such factors as a condition of the patient; size, type, and severity of the disease, condition, or disorder; the undesired type or level or activity of the tagged immunotherapy cells, the particular form of the active ingredient; and the method of administration.

As used herein, the term "adoptive immune therapy" or "adoptive immunotherapy" in some contexts can refer to administration of naturally occurring or genetically engineered, disease antigen-specific immune cells (e.g., T cells). Adoptive cellular immunotherapy may be autologous (immune cells are from the recipient), allogeneic (immune cells are from a donor of the same species) or syngeneic (immune cells are from a donor genetically identical to the recipient).

In any of the above embodiments, methods of the present disclosure comprise administering an effective amount of a modified immune cell (which may be autologous, allogeneic or syngeneic, and e.g., expressing a binding protein of the present disclosure) comprising a desired polynucleotide as described herein that is stably integrated into the chromosome of the cell. For example, such a cellular composition may be generated ex vivo using autologous, allogeneic or syngeneic immune system cells (e.g., T cells, antigen-presenting cells, natural killer cells) in order to administer a desired, binding protein-expressing T-cell composition to a subject as an adoptive immunotherapy. In certain embodiments, the host cell is a hematopoietic progenitor cell or a human immune cell. In certain embodiments, the immune system cell is a $CD4^+$ T cell, a $CD8^+$ T cell, a $CD4^-$ $CD8^-$ double negative T cell, a γδ T cell, a natural killer cell, a dendritic cell, or any combination thereof. In certain embodiments, the immune system cell is a naïve T cell, a central memory T cell, an effector memory T cell, or any combination thereof. In particular embodiments, the cell comprises a $CD4^+$ T cell, a $CD8^+$ T cell, or both.

An effective amount, e.g., a therapeutically n effective amount of cells in a composition is at least one cell (for example, one binding protein modified $CD8^+$ T cell subpopulation; one binding protein modified $CD4^+$ T cell subpopulation) or is more typically greater than $10^2$ cells, for example, up to $10^6$, up to $10^7$, up to $10^8$ cells, up to $10^9$ cells, or more than $10^{10}$ cells. In certain embodiments, the cells are administered in a range from about $10^4$ to about $10^{10}$ cells/m², preferably in a range of about $10^5$ to about $10^9$ cells/m².

In some embodiments, a modified immune cell is administered to a subject at a dose comprising up to about $3.3 \times 10^5$ cells/kg. In some embodiments, a modified immune cell is administered to a subject at a dose comprising at least about $3.3 \times 10^5$ cells/kg.

In some embodiments, a modified immune cell is administered to a subject at a dose comprising up to about $1 \times 10^6$ cells/kg. In some embodiments, a modified immune cell is administered to a subject at a dose comprising least about $1 \times 10^6$ cells/kg. In some embodiments, a modified immune cell is administered to a subject at a dose comprising up to about $3.3 \times 10^6$ cells/kg. In some embodiments, a modified immune cell is administered to a subject at a dose comprising at least about $3.3 \times 10^6$ cells/kg. In some embodiments, a modified immune cell is administered to a subject at a dose comprising up to about $1 \times 10^7$ cells/kg. In some embodiments, a modified immune cell is administered to a subject at a dose comprising at least about $1 \times 10^7$ cells/kg. In certain embodiments, a modified immune cell is administered to a subject at a dose comprising up to about $5 \times 10^4$ cells/kg, $5 \times 10^5$ cells/kg, $5 \times 10^6$ cells/kg, or up to about $5 \times 10^7$ cells/kg. In certain embodiments, a modified immune cell is administered to a subject at a dose comprising at least about $5 \times 10^4$ cells/kg, $5 \times 10^5$ cells/kg, $5 \times 10^6$ cells/kg, or up to about $5 \times 10^7$ cells/kg.

The number of cells will depend upon the ultimate use for which the composition is intended as well the type of cells included therein. For example, cells modified to contain a binding protein specific for a particular antigen will comprise a cell population containing at least 30%, 35%, 40%, 45%, 50%, 55%, 60%, 65%, 70%, 75%, 80%, 85%, 90%, 95% or more of such cells. For uses provided herein, cells are generally in a volume of a liter or less, 500 mls or less, 250 mls or less, or 100 mls or less. In embodiments, the density of the desired cells is typically greater than $10^4$ cells/ml and generally is greater than $10^7$ cells/ml, generally $10^8$ cells/ml or greater. The cells may be administered as a single infusion or in multiple infusions over a range of time. A clinically relevant number of immune cells can be apportioned into multiple infusions that cumulatively equal or exceed $10^6$, $10^7$, $10^8$, $10^9$, $10^{10}$, or $10^{11}$ cells.

Unit doses are also provided herein which comprise a therapeutically effective amount of the host cells (e.g., modified immune cells comprising a polynucleotide of the present disclosure). In certain embodiments, a unit dose comprises (i) a composition comprising at least about 30%, at least about 40%, at least about 50%, at least about 60%, at least about 70%, at least about 80%, at least about 85%, at least about 90%, or at least about 95% modified $CD4^+$ T cells, combined with (ii) a composition comprising at least about 30%, at least about 40%, at least about 50%, at least about 60%, at least about 70%, at least about 80%, at least about 85%, at least about 90%, or at least about 95% modified $CD8^+$ T cells, in about a 1:1 ratio, wherein the unit dose contains a reduced amount or substantially no naïve T cells (i.e., has less than about 50%, less than about 40%, less than about 30%, less than about 20%, less than about 10%, less than about 5%, or less then about 1% the population of naïve T cells present in a unit dose as compared to a subject sample having a comparable number of PBMCs).

In some embodiments, a unit dose comprises (i) a composition comprising at least about 50% modified $CD4^+$ T cells, combined with (ii) a composition comprising at least about 50% modified $CD8^+$ T cells, in about a 1:1 ratio, wherein the unit dose contains a reduced amount or substantially no naïve T cells. In further embodiments, a unit dose comprises (i) a composition comprising at least about 60% modified $CD4^+$ T cells, combined with (ii) a composition comprising at least about 60% modified $CD8^+$ T cells, in about a 1:1 ratio, wherein the unit dose contains a reduced amount or substantially no naïve T cells. In still further embodiments, a unit dose comprises (i) a composition comprising at least about 70% modified $CD4^+$ T cells, combined with (ii) a composition comprising at least about 70% modified $CD8^+$ T cells, in about a 1:1 ratio, wherein the unit dose contains a reduced amount or substantially no naïve T cells. In some embodiments, a unit dose comprises (i) a composition comprising at least about 80% modified CD4⁺ T cells, combined with (ii) a composition comprising at least about 80% modified CD8⁺ T cells, in about a 1:1 ratio, wherein the unit dose contains a reduced amount or substantially no naïve T cells. In some embodiments, a unit dose comprises (i) a composition comprising at least about 85% modified CD4⁺ T cells, combined with (ii) a composition comprising at least about 85% modified CD8+ T cells, in about a 1:1 ratio, wherein the unit dose contains a reduced amount or substantially no naïve T cells. In some embodiments, a unit dose comprises (i) a composition comprising at least about 90% modified CD4⁺ T cells, combined with (ii) a composition comprising at least about 90% modified CD8⁺ T cells, in about a 1:1 ratio, wherein the unit dose contains a reduced amount or substantially no naïve T cells.

In any of the embodiments described herein, a unit dose comprises equal, or approximately equal numbers of modified CD45RA⁻ CD3⁺ CD8⁺ and modified CD45RA− CD3⁺ CD4⁺ $T_M$ cells.

Also contemplated are pharmaceutical compositions that comprise modified cells as disclosed herein and a pharmaceutically acceptable carrier, diluents, or excipient. In some contexts, the term "pharmaceutically acceptable excipient or carrier" or "physiologically acceptable excipient or carrier" can refer to biologically compatible vehicles, e.g., physiological saline, which are described in greater detail herein, that are suitable for administration to a human or other non-human mammalian subject and generally recognized as safe or not causing a serious adverse event. Suitable excipients include water, saline, dextrose, glycerol, or the like and combinations thereof. In embodiments, compositions comprising binding proteins or host cells as disclosed herein further comprise a suitable infusion media. Suitable infusion media can be any isotonic medium formulation, typically normal saline, Normosol R (Abbott) or Plasma-Lyte A (Baxter), 5% dextrose in water, Ringer's lactate can be utilized. An infusion medium can be supplemented with human serum albumin or other human serum components.

In some contexts, an effective amount of a therapeutic or pharmaceutical composition refers to an amount sufficient, at dosages and for periods of time needed, to achieve the desired clinical results or beneficial treatment, as described herein. An effective amount may be delivered in one or more administrations. If the administration is to a subject already known or confirmed to have a disease or disease-state, the term "therapeutic amount" may be used in reference to treatment, whereas "prophylactically effective amount" may be used to describe administrating an effective amount to a subject that is susceptible or at risk of developing a disease or disease-state (e.g., recurrence) as a preventative course.

Pharmaceutical compositions may be administered in a manner appropriate to the disease or condition to be treated (or prevented) as determined by persons skilled in the medical art. An appropriate dose and a suitable duration and frequency of administration of the compositions will be determined by such factors as the health condition of the patient, size of the patient (i.e., weight, mass, or body area), the type and severity of the patient's condition, the undesired type or level or activity of the tagged immunotherapy cells, the particular form of the active ingredient, and the method of administration. In general, an appropriate dose and treatment regimen provide the composition(s) in an amount sufficient to provide therapeutic and/or prophylactic benefit (such as described herein, including an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with disease or disorder. Prophylactic benefit of the immunogenic compositions administered according to the methods described herein can be determined by performing pre-clinical (including in vitro and in vivo animal studies) and clinical studies and analyzing data obtained therefrom by appropriate statistical, biological, and clinical methods and techniques, all of which can readily be practiced by a person skilled in the art.

As used herein, administration of a composition or therapy in some aspects can refer to delivering the same to a subject, regardless of the route or mode of delivery. Administration may be effected continuously or intermittently, and parenterally. Administration may be for treating a subject already confirmed as having a recognized condition, disease or disease state, or for treating a subject susceptible to or at risk of developing such a condition, disease or disease state. Co-administration with an adjunctive therapy may include simultaneous and/or sequential delivery of multiple agents in any order and on any dosing schedule (e.g., binding protein-expressing recombinant (i.e., engineered) host cells with one or more cytokines; immunosuppressive therapy such as calcineurin inhibitors, corticosteroids, microtubule inhibitors, low dose of a mycophenolic acid prodrug, or any combination thereof).

In certain embodiments, a plurality of doses of a recombinant host cell as described herein is administered to the subject, which may be administered at intervals between administrations of about two to about four weeks.

In still further embodiments, the subject being treated is further receiving immunosuppressive therapy, such as calcineurin inhibitors, corticosteroids, microtubule inhibitors, low dose of a mycophenolic acid prodrug, or any combination thereof. In yet further embodiments, the subject being treated has received a non-myeloablative or a myeloablative hematopoietic cell transplant, wherein the treatment may be administered at least two to at least three months after the non-myeloablative hematopoietic cell transplant.

In some aspects, the level of a CTL immune response may be determined by any one of numerous immunological methods described herein and routinely practiced in the art. The level of a CTL immune response may be determined prior to and following administration of any one of the herein described binding proteins expressed by, for example, a T cell. Cytotoxicity assays for determining CTL activity may be performed using any one of several techniques and methods routinely practiced in the art (see, e.g., Henkart et al., "Cytotoxic T-Lymphocytes" in *Fundamental Immunology*, Paul (ed.) (2003 Lippincott Williams & Wilkins, Philadelphia, PA), pages 1127-50, and references cited therein).

Antigen-specific T cell responses are typically determined by comparisons of observed T cell responses according to any of the herein described T cell functional parameters (e.g., proliferation, cytokine release, CTL activity, altered cell surface marker phenotype, etc.) that may be made between T cells that are exposed to a cognate antigen in an appropriate context (e.g., the antigen used to prime or activate the T cells, when presented by immunocompatible antigen-presenting cells) and T cells from the same source population that are exposed instead to a structurally distinct or irrelevant control antigen. A response to the cognate antigen that is greater, with statistical significance, than the response to the control antigen signifies antigen-specificity.

In some aspects, a biological sample may be obtained from a subject for determining the presence and level of an immune response to a cell or other agents as described herein. A "biological sample" as used herein may be a blood sample (from which serum or plasma may be prepared), biopsy specimen, body fluids (e.g., lung lavage, ascites, mucosal washings, synovial fluid), bone marrow, lymph nodes, tissue explant, organ culture, or any other tissue or cell preparation from the subject or a biological source. Biological samples may also be obtained from the subject prior to receiving any immunogenic composition, which biological sample is useful as a control for establishing baseline (i.e., pre-immunization) data.

The pharmaceutical compositions described herein may be presented in unit-dose or multi-dose containers, such as sealed ampoules or vials. Such containers may be frozen to preserve the stability of the formulation until. In certain embodiments, a unit dose comprises a recombinant host cell as described herein at a dose of about $10^7$ cells/m$^2$ to about $10^{11}$ cells/m$^2$. The development of suitable dosing and treatment regimens for using the particular compositions described herein in a variety of treatment regimens, including e.g., parenteral or intravenous administration or formulation.

If the subject composition is administered parenterally, the composition may also include sterile aqueous or oleaginous solution or suspension. Suitable non-toxic parenterally acceptable diluents or solvents include water, Ringer's solution, isotonic salt solution, 1,3-butanediol, ethanol, propylene glycol or polythethylene glycols in mixtures with water. Aqueous solutions or suspensions may further comprise one or more buffering agents, such as sodium acetate, sodium citrate, sodium borate or sodium tartrate. Of course, any material used in preparing any dosage unit formulation should be pharmaceutically pure and substantially non-toxic in the amounts employed. In addition, the active compounds may be incorporated into sustained-release preparation and formulations. Dosage unit form, as used herein, refers to physically discrete units suited as unitary dosages for the subject to be treated; each unit may contain a predetermined quantity of recombinant cells or active compound calculated to produce the desired therapeutic effect in association with an appropriate pharmaceutical carrier.

In general, an appropriate dosage and treatment regimen provides the active molecules or cells in an amount sufficient to provide therapeutic or prophylactic benefit. Such a response can be monitored by establishing an improved clinical outcome (e.g., more frequent remissions, complete or partial, or longer disease-free survival) in treated subjects as compared to non-treated subjects. Increases in preexisting immune responses to a tumor protein generally correlate with an improved clinical outcome. Such immune responses may generally be evaluated using standard proliferation, cytotoxicity or cytokine assays, which are routine in the art and may be performed using samples obtained from a subject before and after treatment.

Methods according to this disclosure may further include administering one or more additional agents to treat the disease or disorder in a combination therapy (such as any described above). For example, in certain embodiments, a combination therapy comprises a modified host cell (e.g., expressing a binding protein) and an agent associated with induction of ICD (e.g., together, or in a sequence, or administering one to a subject who has previously received the other) with (concurrently, simultaneously, or sequentially) an agent that specifically binds to and/or is an inhibitor of an immune suppression component; e.g., provided that the subject has not previously received the agent that specifically binds to and/or is an inhibitor of an immune suppression component as part of the method. In some embodiments, a combination therapy comprises administering a modified host cell and an agent associated with induction of ICD with an agonist of a stimulatory immune checkpoint agent; e.g., provided that the subject has not previously received the agonist of a stimulatory immune checkpoint agent as part of the method. In further embodiments, a combination therapy comprises administering modified host cell and an agent associated with induction of ICD with a secondary therapy, such as chemotherapeutic agent, a radiation therapy, a surgery, an antibody, or any combination thereof. In some aspects, the combination therapy can include a modified host cell, an agent associated with induction of ICD, and any of the agents described herein.

In certain embodiments, a combination therapy comprises a modified immune cell of the present disclosure and an agent associated with induction of ICD (e.g., together, or in a sequence, or administering one to a subject who has previously received the other) and a secondary therapy comprising one or more of: an antibody or antigen binding-fragment thereof that is specific for a disease-associated antigen (e.g., cancer or tumor-associated antigen or antigen expressed by a non-inflamed solid tumor), a radiation treatment, a surgery, a chemotherapeutic agent, a cytokine, RNAi, or any combination thereof.

In certain embodiments, a combination therapy method comprises administering a modified immune cell and an agent associated with induction of ICD (e.g., together, or in a sequence, or administering one to a subject who has previously received the other) and further administering a radiation treatment or a surgery. Radiation therapy is well-known in the art and includes X-ray therapies, such as gamma-irradiation, and radiopharmaceutical therapies. Surgeries and surgical techniques appropriate to treating a given disease or disorder (e.g., cancer, tumor or non-inflamed solid tumor) in a subject are well-known to those of ordinary skill in the art.

In certain embodiments, a combination therapy method comprises administering a modified immune cell and an agent associated with induction of ICD (e.g., together, or in a sequence, or administering one to a subject who has previously received the other) and further administering a chemotherapeutic agent. A chemotherapeutic agent may or may not be associated with induction of ICD and includes, but is not limited to any described herein.

EXAMPLES

Example 1

Generation of an Animal Model of ROR1-Expressing NSCLC

Figure 2A:
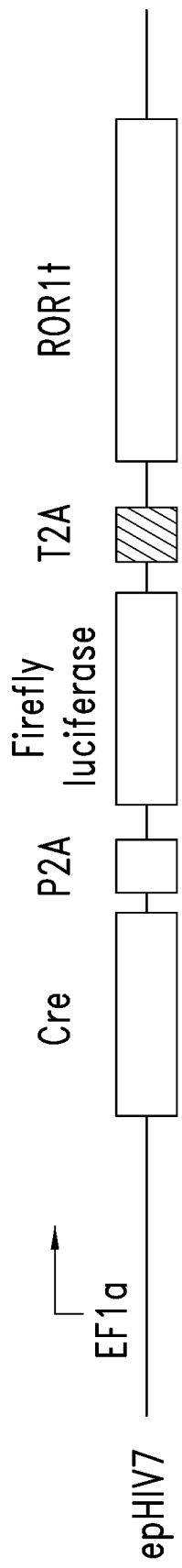
FIG. 2A shows the design of a lentiviral construct that co-expresses Cre recombinase, firefly luciferase, and human ROR1 ("Cre-p-ffluc-t-hROR1").
Figure 2B:
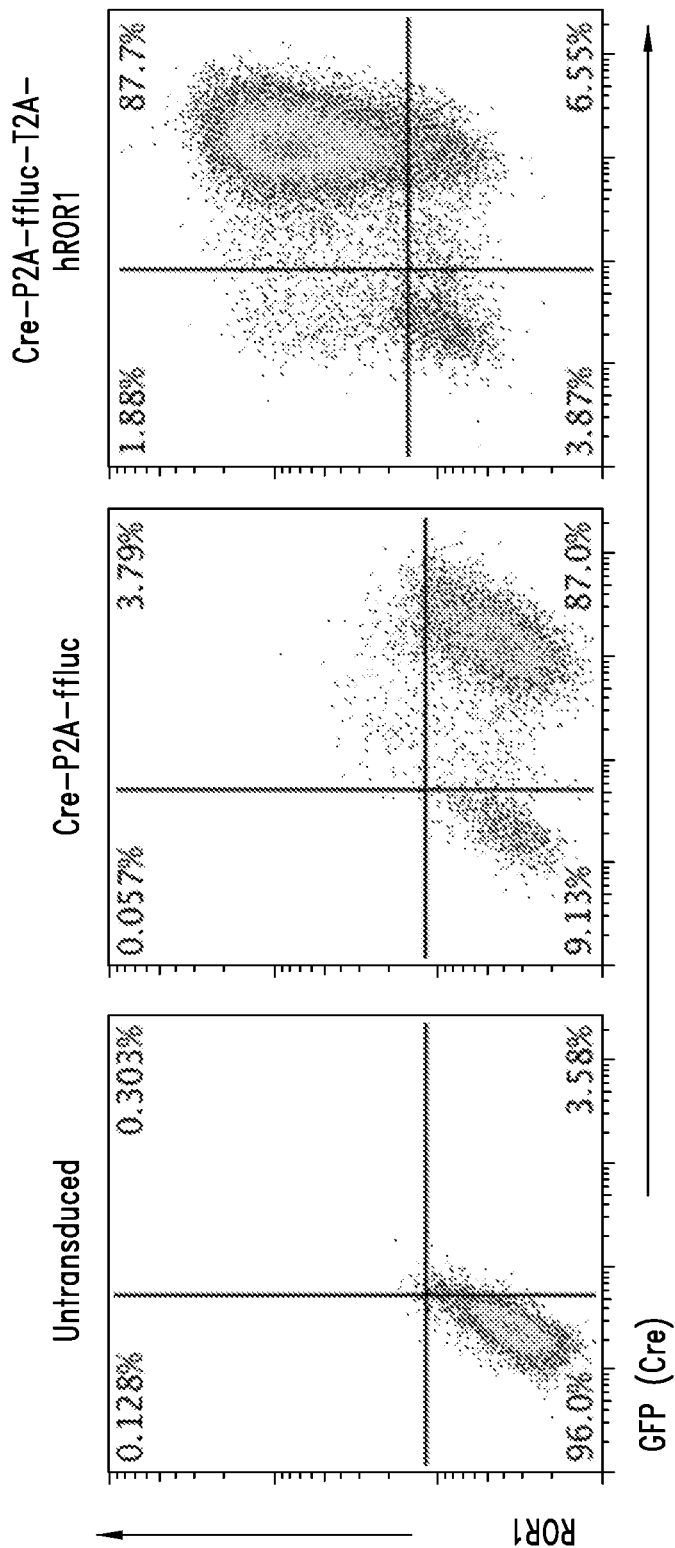
FIG. 2B provides flow cytometry data showing expression of the lentiviral construct in 3TZ Green-Go reporter cells (L-R): untransduced; Cre-P2A-ffluc; Cre-P2A-ffluc-t-hROR1.
Figure 2C:
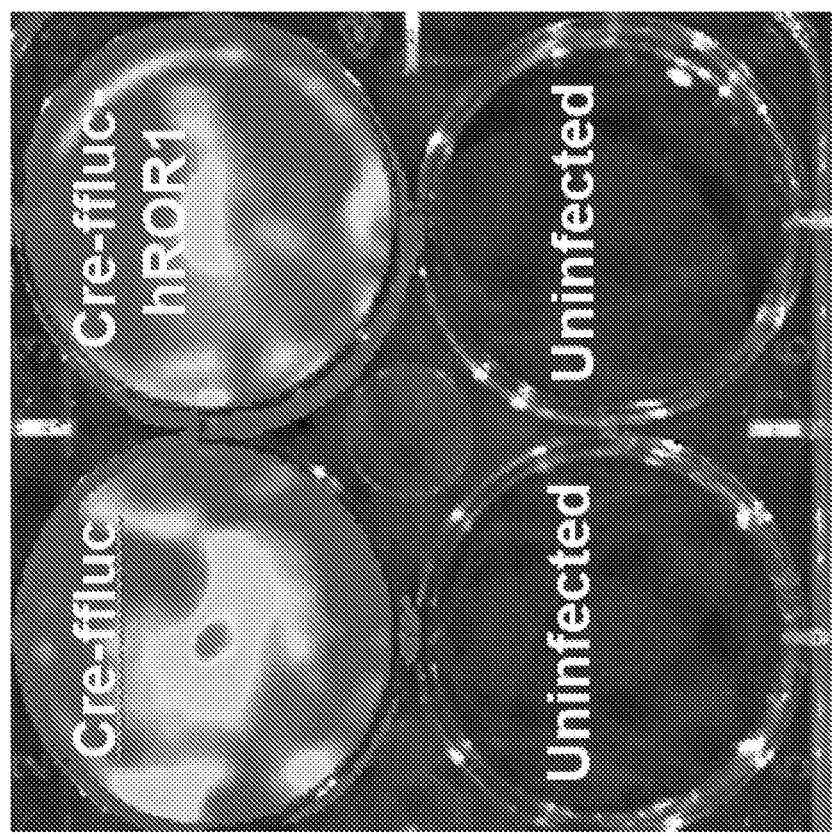
FIG. 2C shows bioluminescence imaging (BLI) of firefly luciferase expression in cells.

An in vivo xenograft tumor model in which the tumor expresses ROR1 was developed using the KP mouse model of lung adenocarcinoma (Jackson et al., *Cancer Res.* 65(22): 10280 (2005)). Generally speaking, KP mice carry foxed alleles of p53 and an oncogenic Kras-G12D mutant allele preceded by a lox-stop-lox cassette. At baseline, these mice are phenotypically normal, expressing wild-type levels of p53 and Kras. Upon intratracheal delivery of a Cre-expressing lentivirus, the virus integrates randomly into lung epithelia, where it initiates deletion of p53 and activation of the oncogenic Kras-G12D mutant allele, resulting in transformation. (FIG. 1). The lentivirus was engineered to coexpress Cre recombinase, firefly luciferase (ffluc), and hROR1, linked by P2A and T2A ribosomal skip elements, under control of the EF1α promoter (FIG. 2A). Co-expression of Cre and hROR1 by lentiviral infection of 3TZ GreenGo reporter cells, which express a floxed "stop" element in front of the GFP gene. ROR1 and GFP expression by was detected flow cytometry in the vast majority of infected 3TZ cells (FIG. 2B), and ffluc expression was confirmed by bioluminescent imaging (BLI) (FIG. 2C).

Figure 3A:
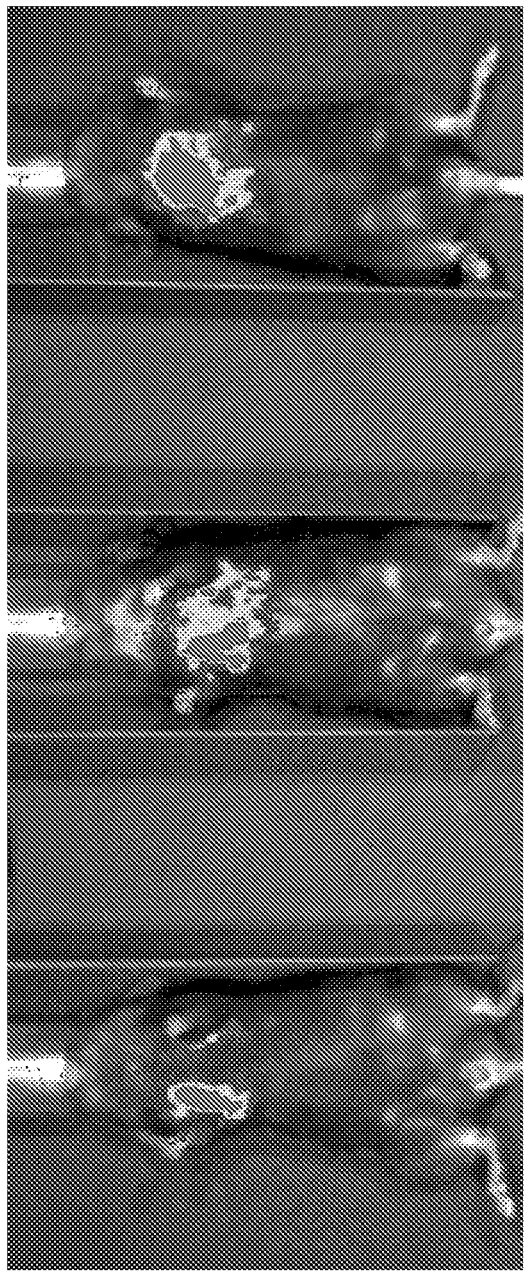
FIGS. 3A-3E show the induction of tumors in KP mice infected with the Cre-p-ffluc-t-hROR1 lentivirus. (A) Representative BLI taken 13 weeks after mice were administered lentivirus at the indicated titer. (B) Quantitated BLI data from a dosage experiment wherein mice were administered the lentivirus at the indicated doses (uninfected mice=control). (C) Representative Magnetic Resonance Imaging (MM) of a mouse from each infection group 13 weeks p.i. (D) Average tumor volume from each infection group. (E) Mean percent survival of the infection groups.
Figure 3B:
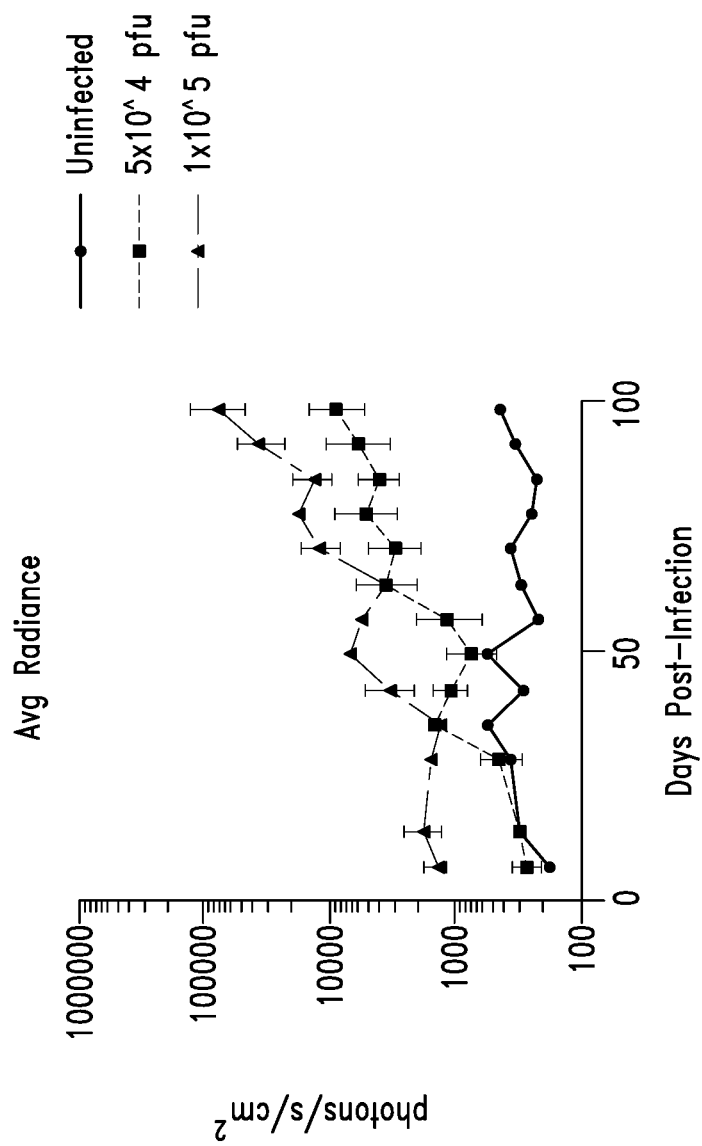

Lentivirus doses and their ability to induce lung tumors in KP mice were assessed. Cre-P2A-ffluc-T2A-ROR1 lentivirus was administered intratracheally at two dose levels ($1 \times 10^5$ pfu and $5 \times 10^4$ pfu) and tumor development was monitored by BLI (FIG. 3A; representative data) and magnetic resonance imaging (MRI). Tumor burden was quantified by acquiring serial 1 mm images spanning the entire lung and summing the tumor area across all images. Both doses of lentivirus resulted in a roughly two-log increase in BLI in the lungs of infected mice with similar kinetics, with the higher dose providing higher radiance at all time points (FIG. 3B).

Figure 3C:
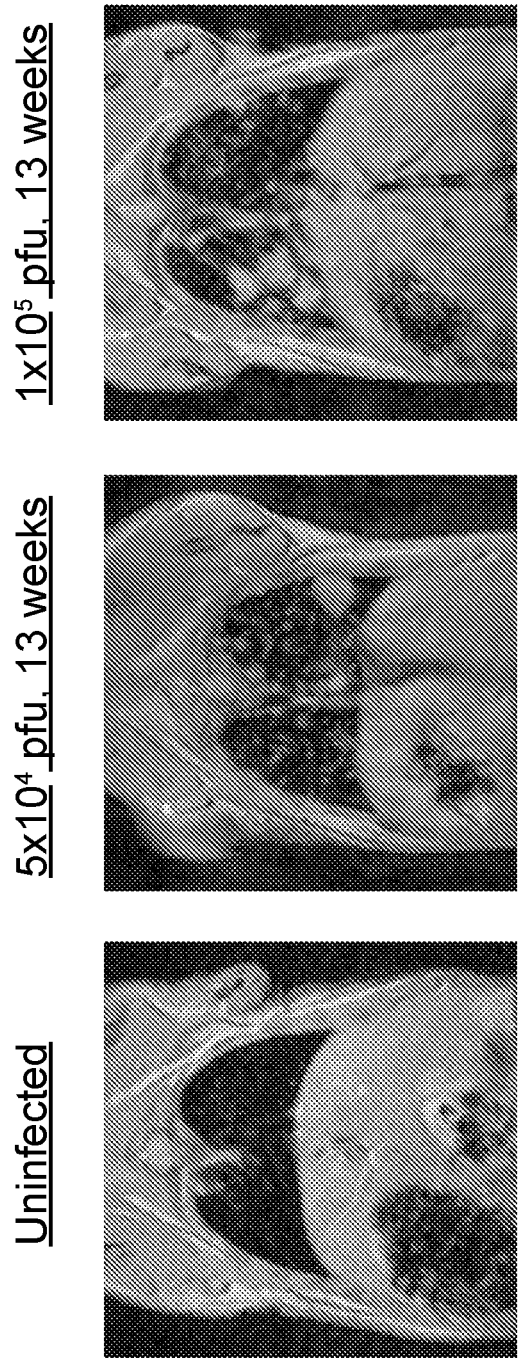
Figure 3D:
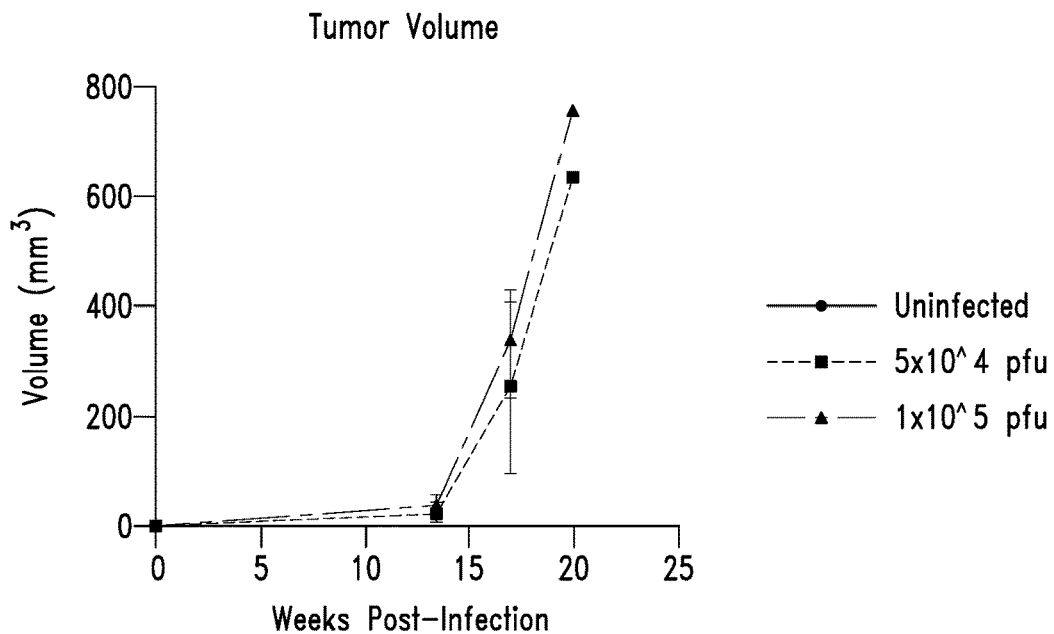
Figure 3E:
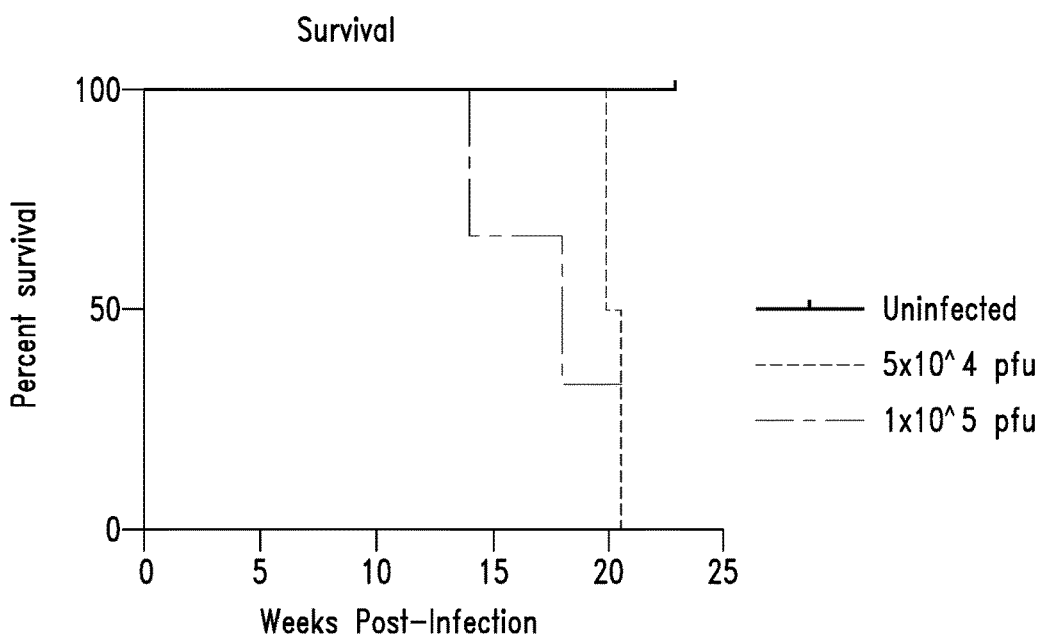

By 10-13 weeks post-infection (p.i.), tumor nodules could be detected in the lungs of infected mice by MRI (FIG. 3C). Mice infected with the higher lentivirus dose had slightly larger tumors (FIG. 3D) and decreased survival, although all mice died of tumor progression by ~20 weeks p.i. (FIG. 3E). The $1 \times 10^5$ pfu dose of lentivirus gave consistent tumor induction and growth and was selected for future experiments.

Figure 4:
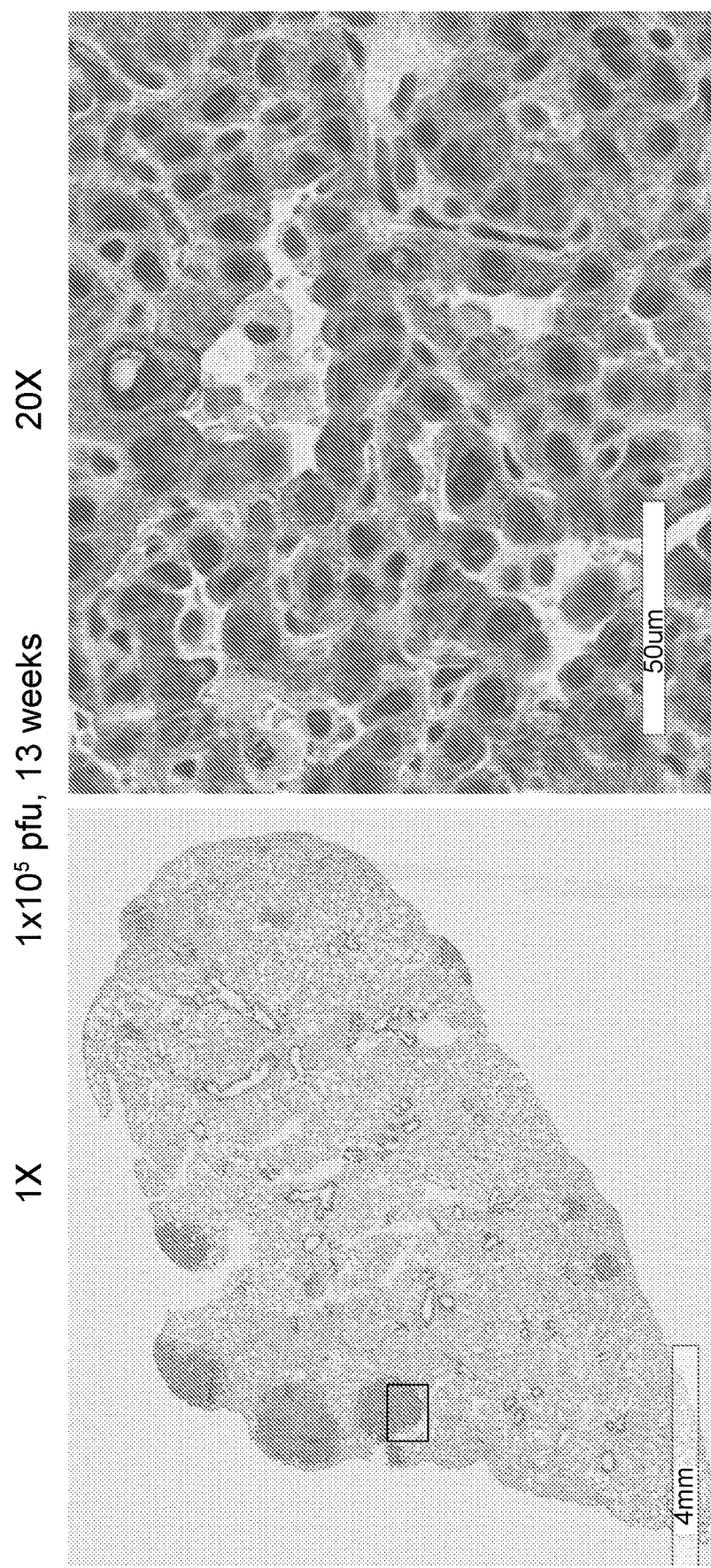
FIG. 4 shows IHC staining for hROR1 in tumors harvested from KP-hROR1 mice 13 weeks p.i. Left: 1× magnification. Right: 20× magnification.

In general, ROR1-targeted CAR T therapy may be applicable in contexts in which tumor or other target cells or tissues express the antigen targeted. To confirm expression of ROR1 in this model, lungs were harvested from KP-hROR1 mice 13 weeks p.i. and analyzed for hROR1 expression by immunohistochemistry. As shown in FIG. 4, tumors that developed in KP-hROR1 mice were observed to highly and uniformly express ROR1.

Example 2

Figure 5A:
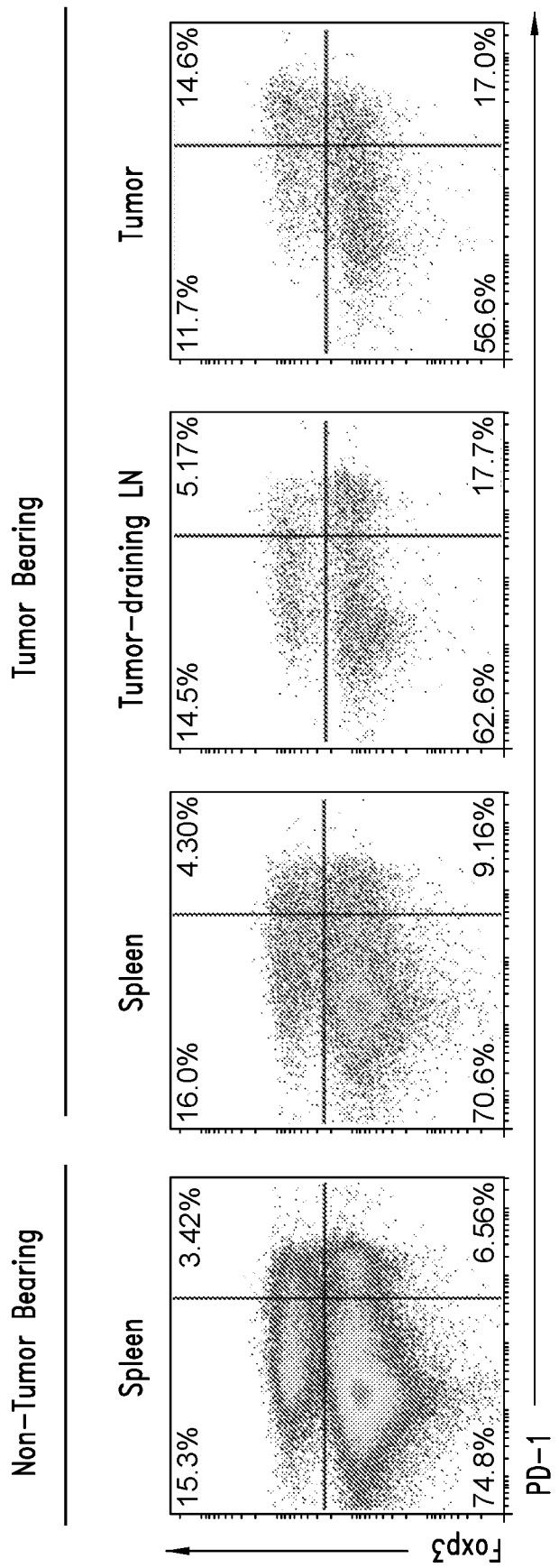
FIGS. 5A-5E provide data characterizing Treg cells in tissue samples from non-tumor-bearing (spleen only) and tumor-bearing KP (spleen, tumor-draining mediastinal lymph node (mLN), and lung tumor) mice. (A) Flow cytometry data showing Treg cell counts in indicated tissues, stained for Foxp3 and PD-1. (B) Quantification of $CD4^+$ $Foxp3^+$ Treg cell frequency as a percentage of live cells. (C) Proliferation of Treg cells as measured by expression of the proliferation marker Ki-67. (D) Quantification of PD-1 expression by Treg cells as represented by MFI of tagged anti-PD-1 binding. (E) Ratio of $CD8^+$ T cells:Treg cells.
Figure 5B:
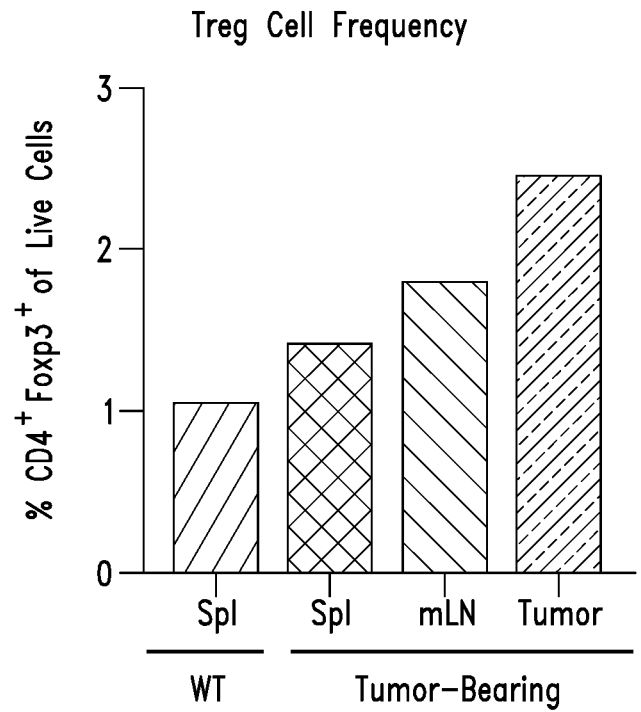
Figure 5C:
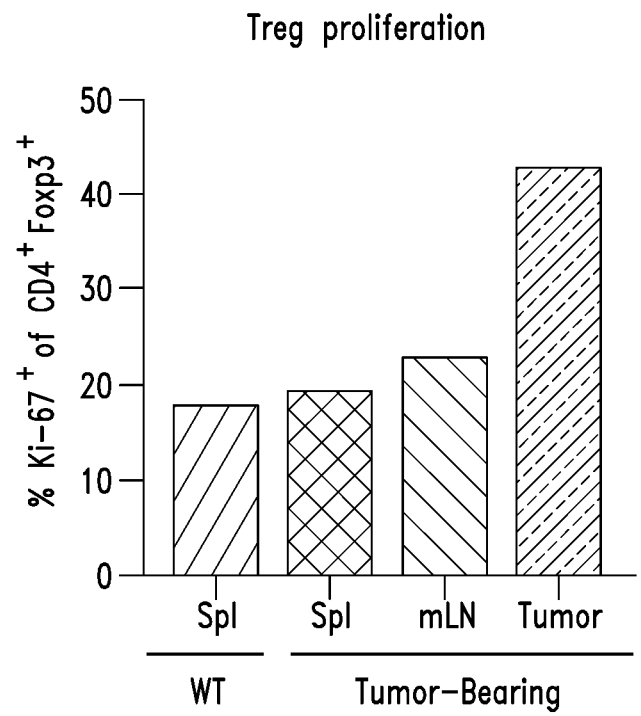
Figure 5D:
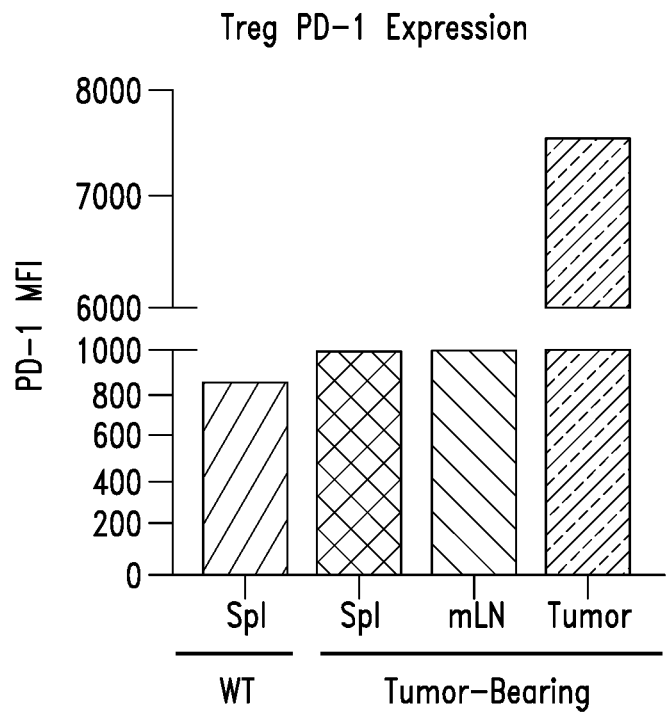
Figure 5E:
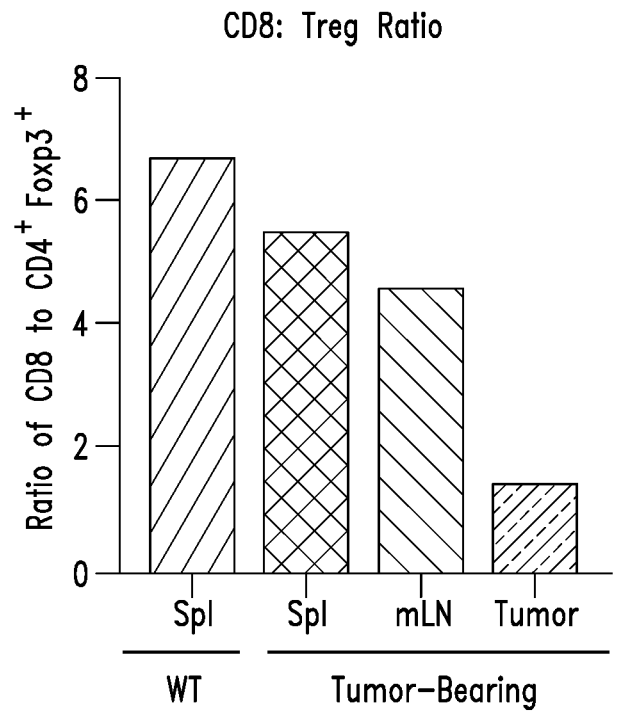

Characterization of the Tumor Microenvironment in KP-HROR1 Mice $CD4^+$ $Foxp3^+$ regulatory T cells (Treg) and myeloid-derived suppressor cells (MDSCs) have been observed to infiltrate the tumor microenvironment (TME) in both induced KP and human lung adenocarcinomas and suppress host immunity. To assess impact on immunosuppressive TME of hROR1 expression induction in KP lung tumors, samples were examined from spleen, lung-draining mediastinal lymph nodes (mLN), and lung tumors for various immune cells 22 weeks p.i. in KP-hROR1. Tregs were observed to be selectively increased in frequency in the tumor relative to spleen and mLN (FIGS. 5A and 5B), with the Treg to CD8 T cell ratio highest in the tumor (FIG. 5E). Tumor Tregs also showed enhanced proliferation, as marked by Ki-67 expression, compared to splenic or mLN Tregs (FIG. 5C). PD-1 expression was also enhanced in tumor Tregs as compared to splenic or mLN Tregs (FIG. 5D).

Figure 6A:
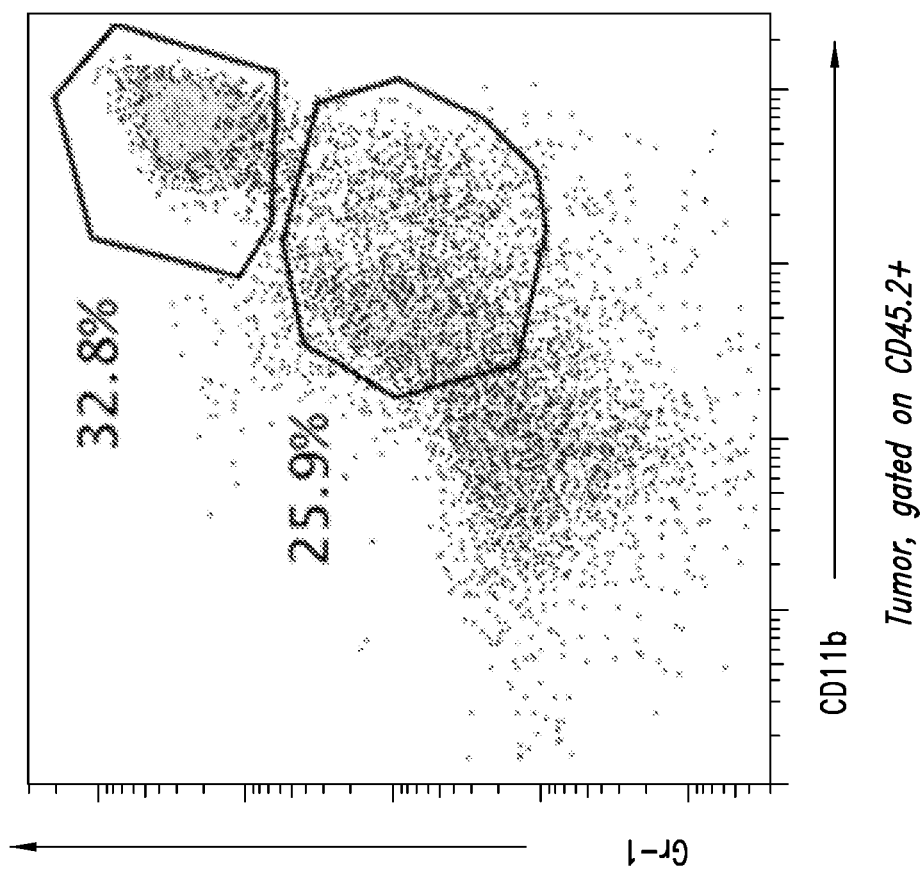
FIGS. 6A-6F provide data characterizing myeloid-derived suppressor cells (MDSCs) in tissue samples from non-tumor-bearing (spleen only) and tumor-bearing KP (spleen, tumor-draining mediastinal lymph node (mLN), and lung tumor) mice. (A) Representative flow cytometry data showing MDSC cell count in a tumor. (B) Frequency of $CD11b^+$ MDSCs with intermediate ("int") Gr-1 expression ("Monocytic" MDSCs) among live cells. (C) Frequency of $CD11b^+$ MDSCs with high ("hi") Gr-1 expression ("Granulocytic" MDSCs) among live cells. (D) Histogram showing PD-L1 expression by granulocytic (dashed line) and monocytic (solid line) MDSCs. (E) Quantification of PD-L1 expression on monocytic MDSCs. (F) Quantification of PD-L1 expression on granulocytic MDSCs.
Figure 6B:
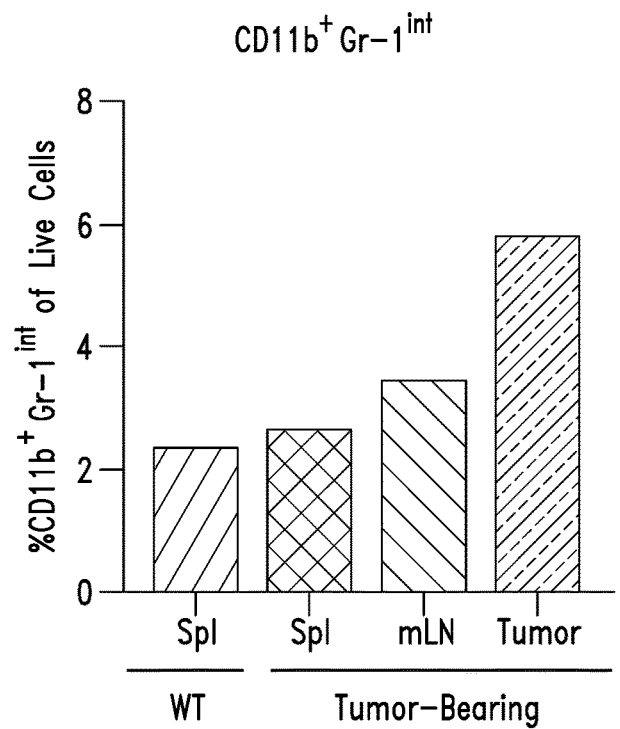
Figure 6C:
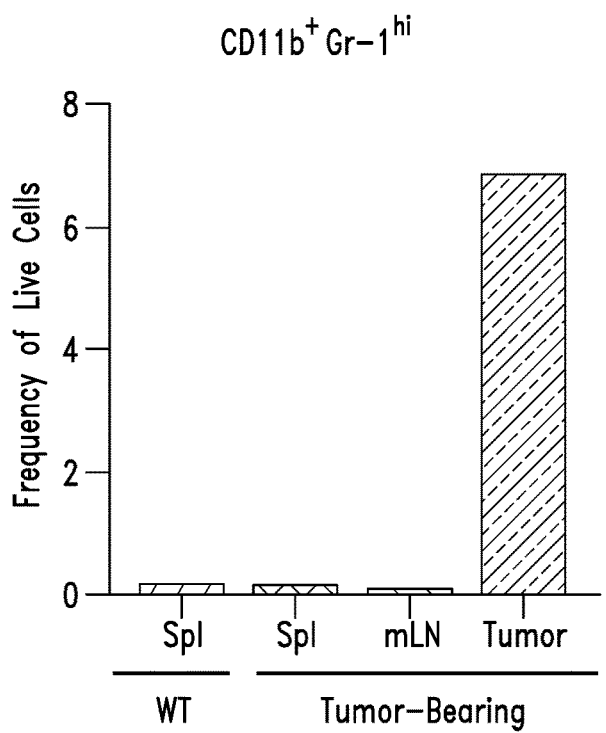
Figure 6D:
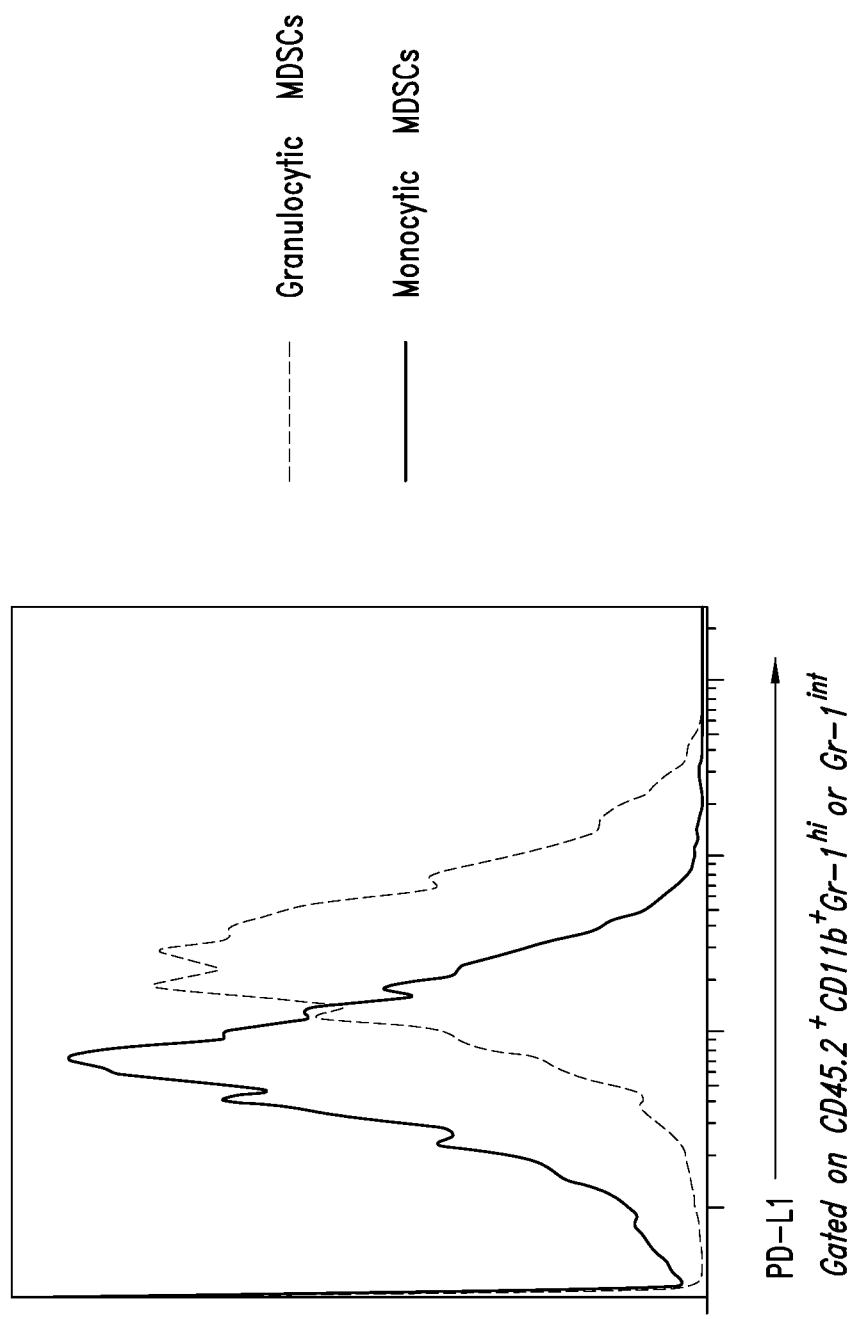
Figure 6E:
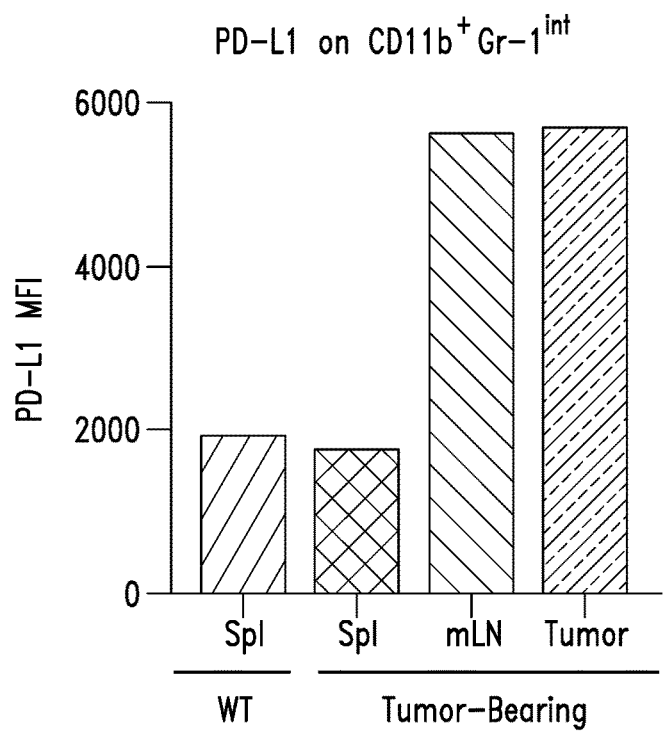
Figure 6F:
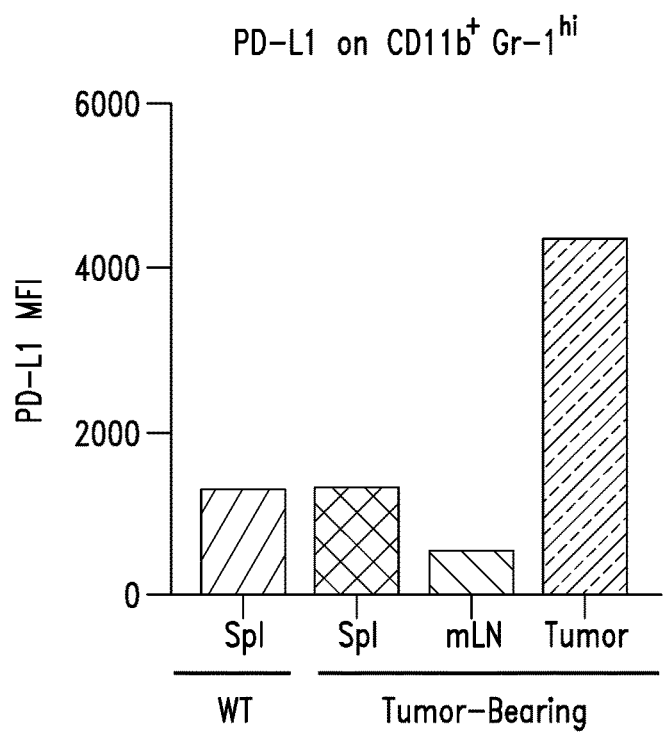

$CD11b^+$ MDSCs with high Gr-1 expression ($CD11b^+$ MDSCs; e.g., "monocytic" MDSCs) were also selectively increased in frequency at the tumor (FIGS. 6A and 6C), and the MDSCs expressed higher levels of PD-L1 in lung tumors relative to spleen (FIG. 6F). Results from $CD11b^+$ MDSCs with intermediate Gr-1 expression ($CD11b^+$ $Gr-1^{int}$ MDSCs; e.g., "granulocytic" MDSCs) were different from the MDSCs with high Gr-1 expression (FIGS. 6B, 6D, and 6E). The results were consistent with a conclusion that the TME in KP-hROR1 mice had similar immunosuppressive cell phenotypes and/or features as those in human lung cancer.

Example 3

Development and Testing of Murine Anti-ROR1 Car T Cells

Figure 7A:
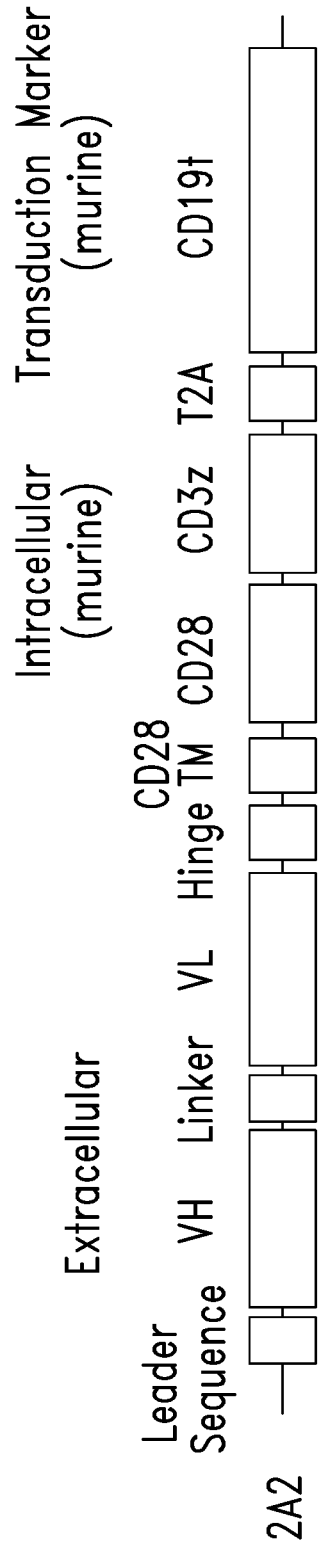
FIGS. 7A-7C show the design and testing of a murine chimeric antigen receptor (CAR) specific for human ROR1 (hROR1). (A) Schematic diagram of coding construct for CAR with an anti-hROR1 binding domain derived from 2A2 antibody and murine 4-1BB and CD3ζ domains; the construct also includes a truncated CD19 transduction marker sequence downstream of a T2A ribosomal skip element. (B, C) Data from in vitro killing assays in which 4T1 mammary carcinoma cells expressing human (triangles) or murine ROR1 (squares), or without ROR1 expression (circle) were incubated with control tCD19 T cells (B) or 2A2-41BBz CAR T cells (C) at the indicated effector:target ratios.
Figure 7B:
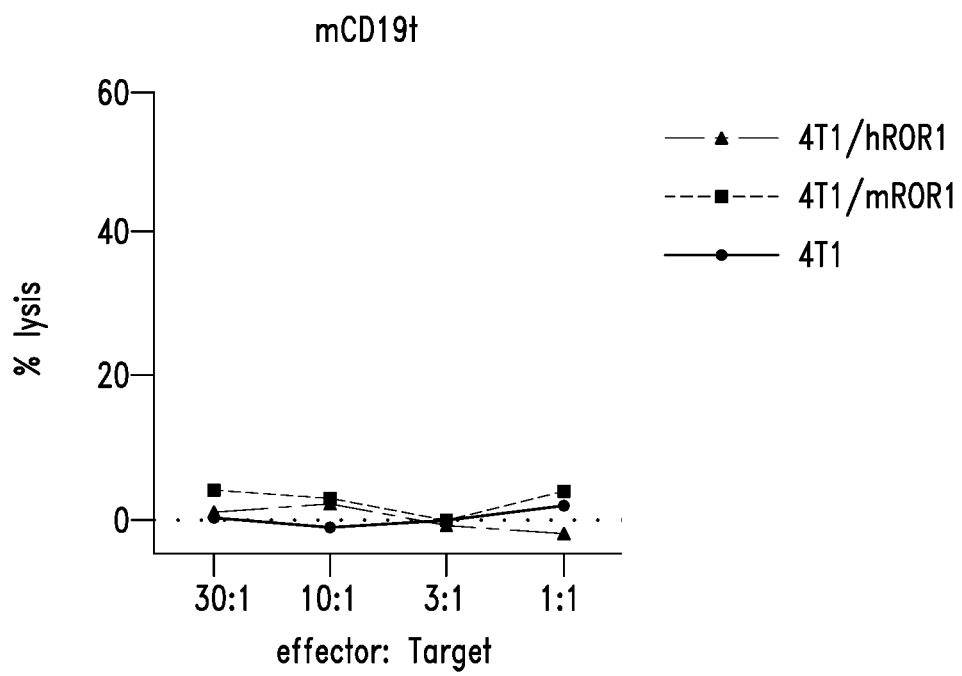
Figure 7C:
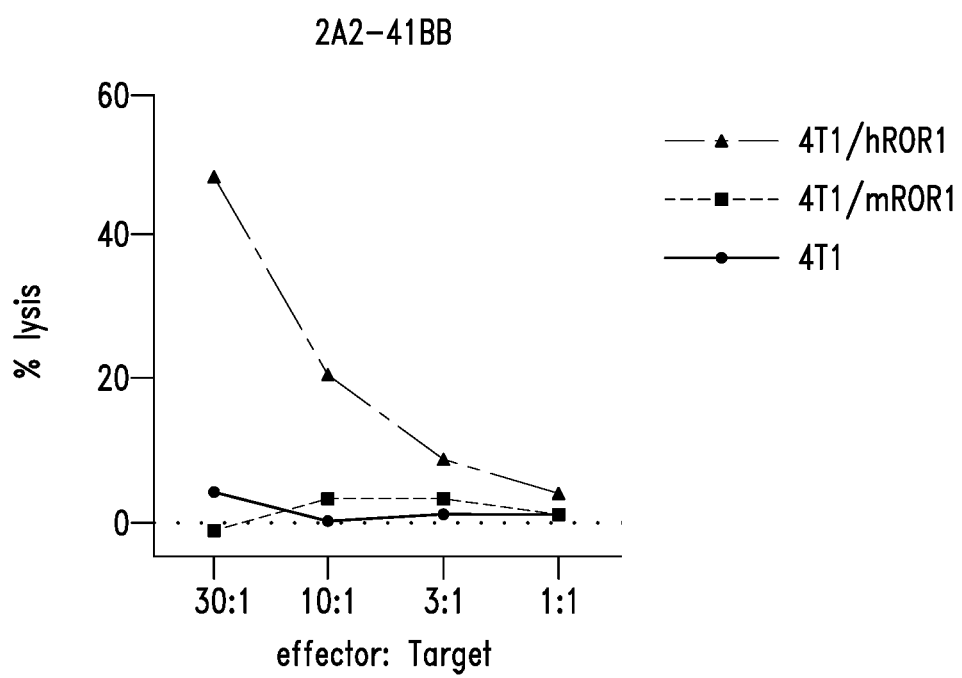

An exemplary ROR1-specific CAR was prepared for use in the KP-hROR1 mouse model. Briefly, a constructed and validated hROR1-specific CAR comprised of an extracellular scFv derived from the 2A2 antibody linked to human CD3ζ and 4-1BB signaling domains was modified to replace the 4-1BB and CD3ζ domains with murine sequences. The CAR coding construct further included a truncated murine CD19 (tCD19) transduction marker in the downstream of a P2A ribosomal skip element to allow in vivo tracking (FIG. 7A). Murine $CD8^+$ T cells were transduced to express the CARs, and cells expressing the transduction marker were incubated with $hROR1^+$, mROR+, or ROR1-negative 4T1 mammary carcinoma cells in vitro at various effector:target ratios. T cells expressing the CAR construct, but not unmodified T cells, lysed $hROR1^+$ target cells, but not $mROR1^+$ or ROR1-negative target cells. See FIGS. 7B and 7C. Thus, the murine CAR T cells were observed to specifically recognize and kill target cells that express human, but not murine, ROR1.

Figure 8A:
FIG. 8A shows a diagram of an experimental treatment scheme in which KP mice were infected with the Cre-ffluc-hROR1 lentivirus and thereafter received treatment with a combination of cyclophosphamide and 1:1 $CD8^+/CD4^+$ 2A2-41BBz CAR T cells at weeks 11, 14, and 17 p.i.
Figure 8B:
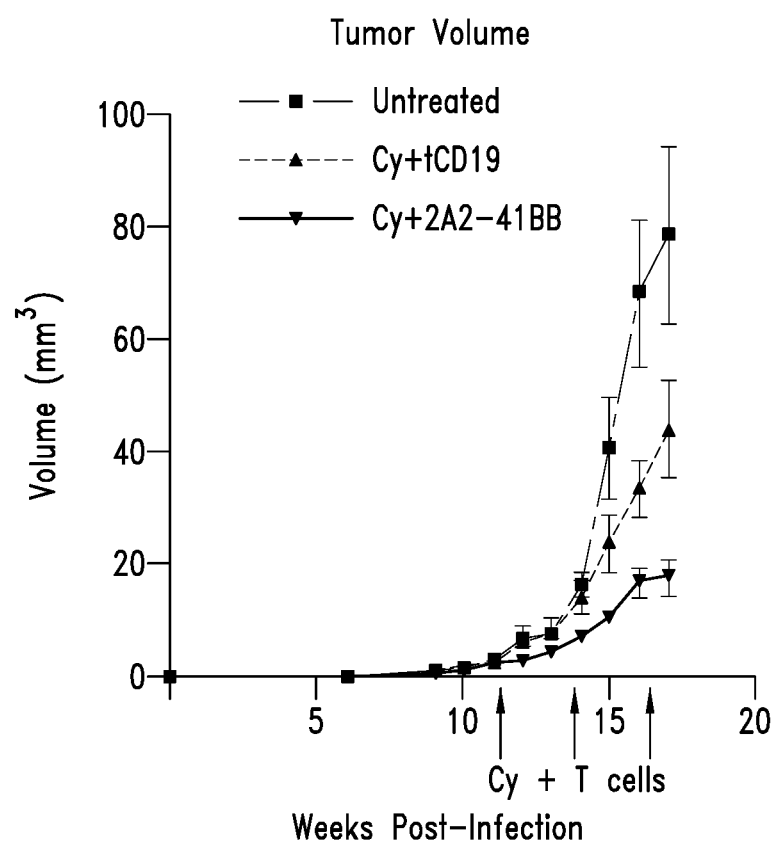
FIG. 8B shows average tumor volumes from mice that received treatment according to the schedule shown in FIG. 8A.
Figure 8C:
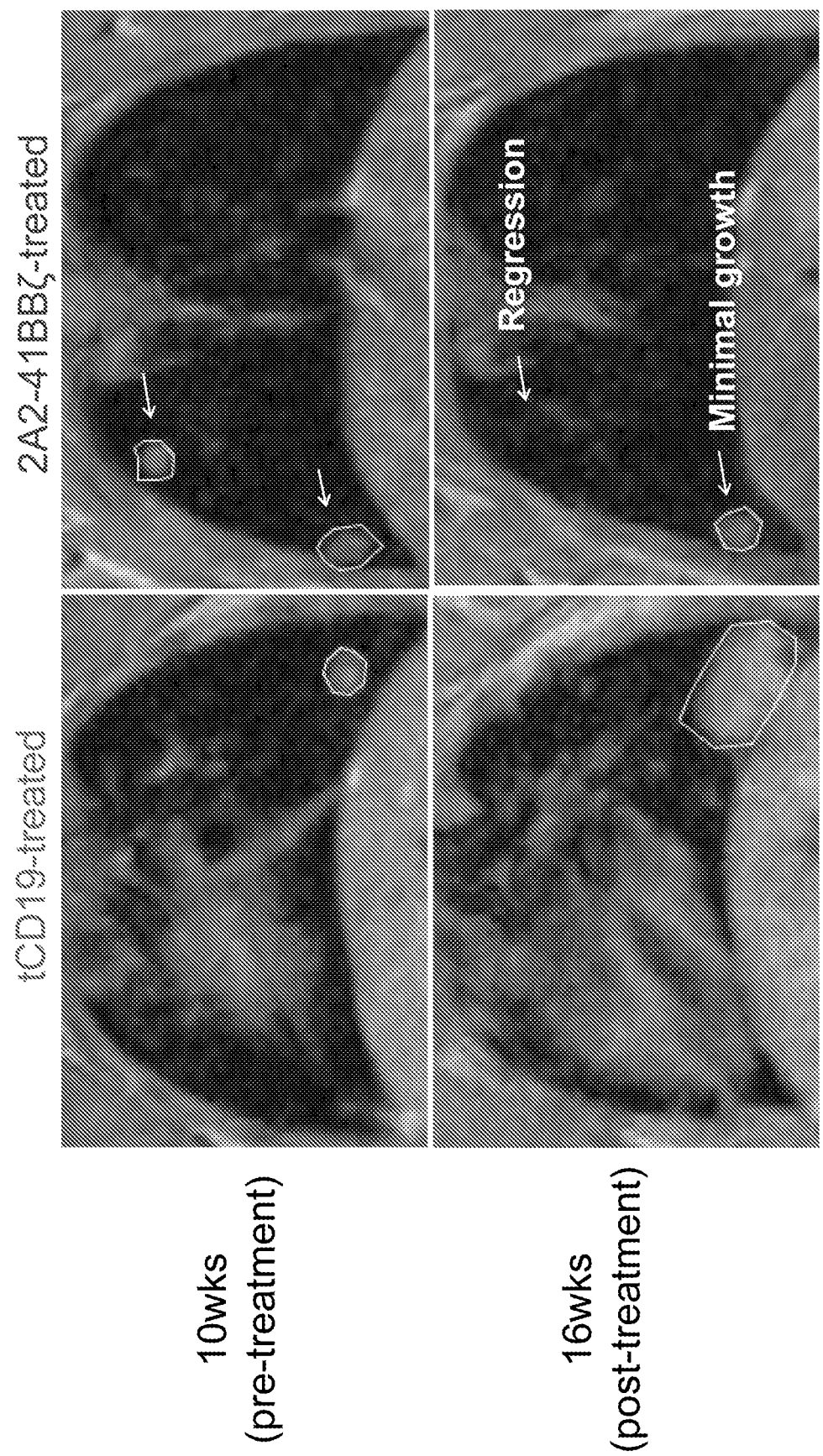
FIG. 8C shows representative MRI scans from tCD19-treated and 2A2-41BBz CAR T-treated mice, comparing tumor size pre-treatment (10 weeks p.i) and post-treatment (16 weeks p.i). Tumors are encircled.

The antitumor activity of anti-ROR1 CAR T cells was assessed in vivo by infecting KP mice with Cre-ffluc-hROR1 lentivirus and monitoring tumor growth by MM. When tumor nodules reached ≥1 $mm^3$ in all mice, the mice were administered 100 mg/kg cyclophosphamide (Cy) for lymphodepletion and $6 \times 10^6$ 2A2-41BK CAR T cells (CD8:CD4 of 1:1) or an equal number of control T cells modified only with the tCD19 marker were adoptively transferred (FIG. 8A). Adoptively transferred T cells were derived from congenic B6.SJL mice and could be identified within $CD45.2^+$ KP recipient mice as $CD45.1^+$. Mice continued to receive Cy and control tCD19 or 2A2 CAR T cells every 3 weeks. Notably, 2A2 CAR T cells significantly reduced tumor growth compared to control mice (FIG. 8B). Further, MM scans from control tCD19-treated and 2A2 CAR-treated mice pre-treatment (10 weeks post-infection) and post-treatment (16 weeks post-infection) showed that while all tumor nodules grew steadily in control mice, tumors in 2A2 CAR T cell-treated mice either regressed or showed minimal growth in the first 6 weeks of T cell treatment (FIG. 8C).

Figure 9A:
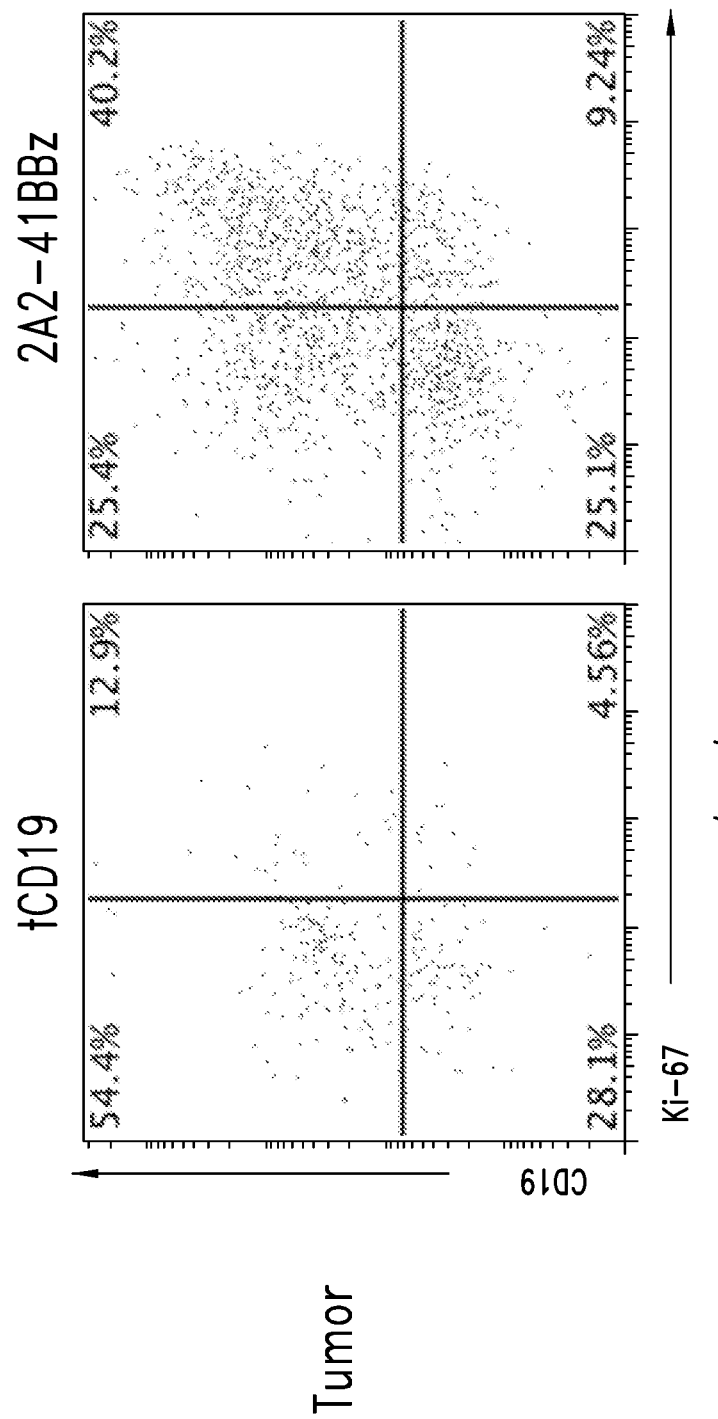
FIGS. 9A-9E show in vivo characterization of the control (tCD19) and 2A2-41BBz CAR T cells administered according to the treatment schedule shown in FIG. 8A. Spleen and tumor samples were harvested at 22 weeks p.i. and cell phenotypes were analyzed by flow cytometry. (A) Proliferation of the administered CAR T cells in representative tumor samples. (B) PD-1 expression profiles of CART cells in representative tumor samples. (C) Frequency, (D) proliferation, and (E) PD-1 expression of $CD8^+$ CART cells were also measured.
Figure 9B:
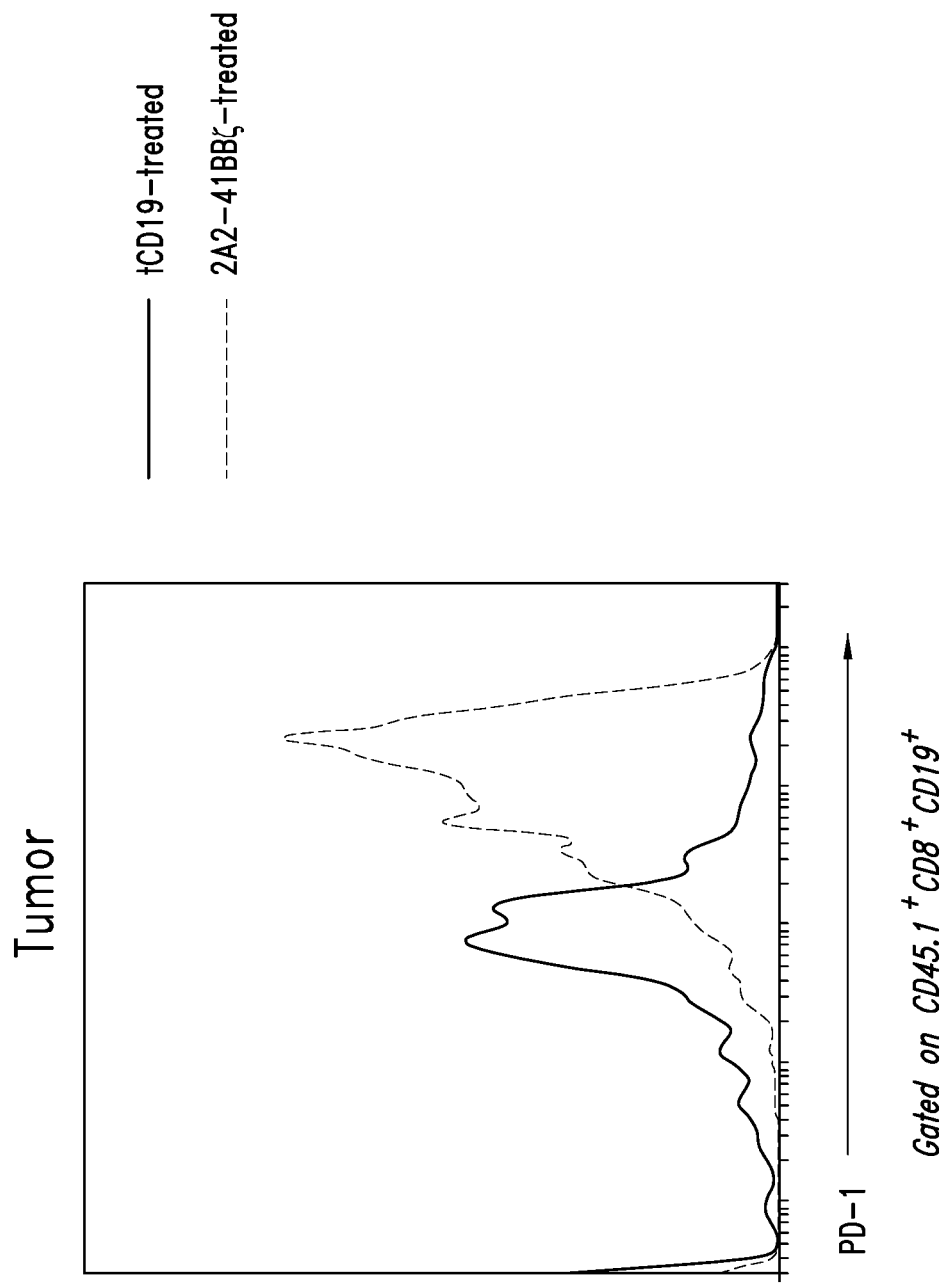
Figure 9C:
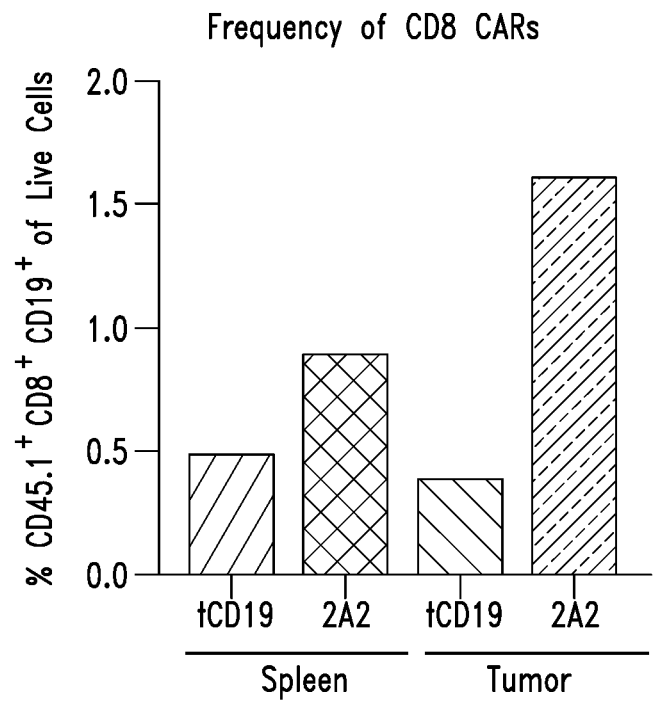
Figure 9D:
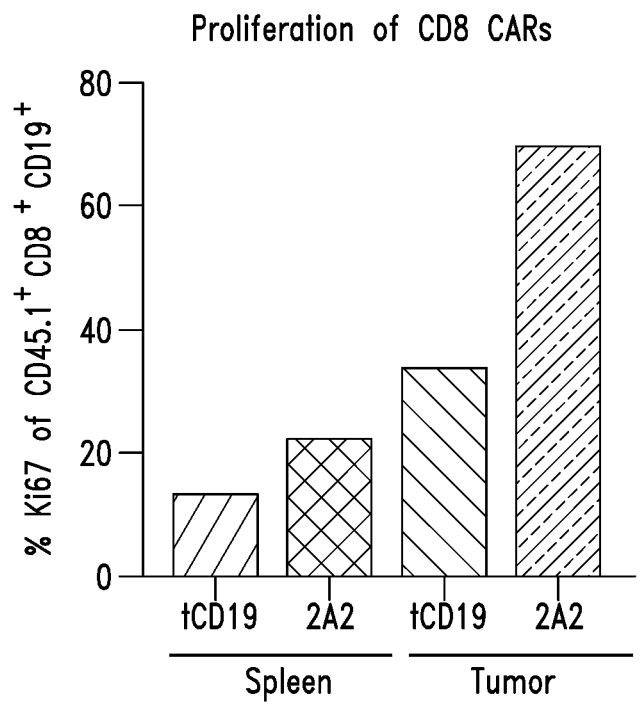
Figure 9E:
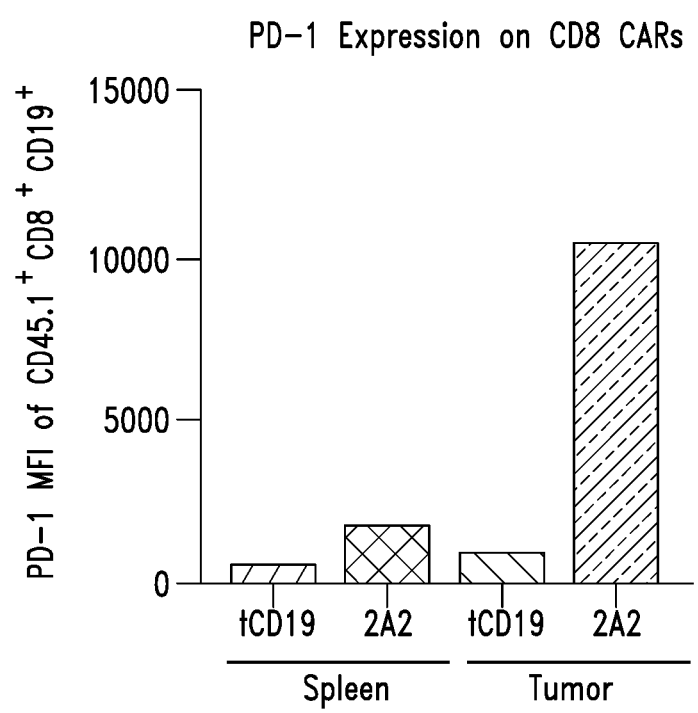
Figure 10A:
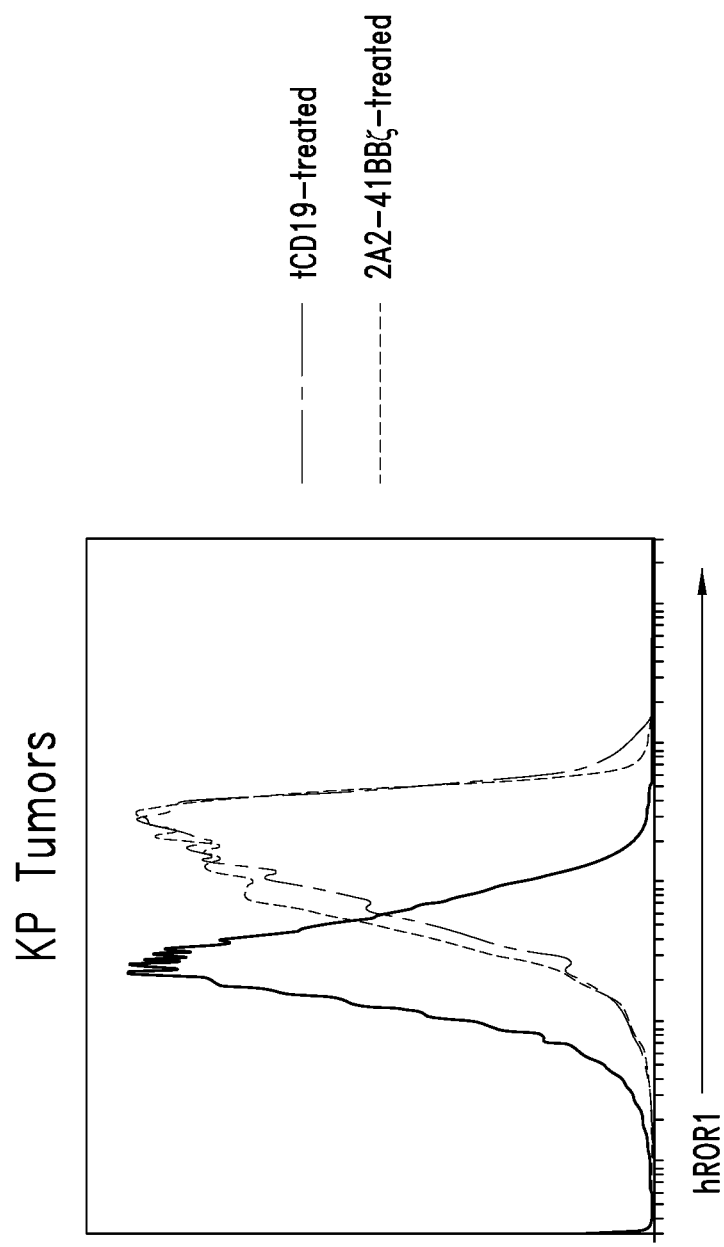
FIG. 10A shows expression of hROR1 in KP tumors that were untreated (solid line) or that received T cells expressing control tCD19 or 2A2-41BBz CAR T cells as indicated in the figure key.
Figure 10B:
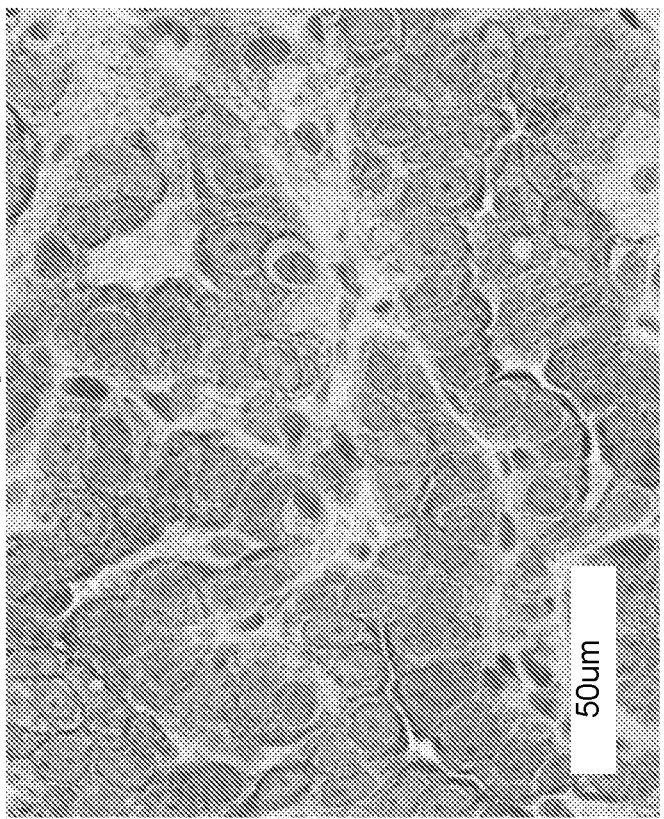
FIG. 10B shows IHC staining for hROR1 in KP tumors from the two treatment groups, at 40× magnification.
Figure 10B:
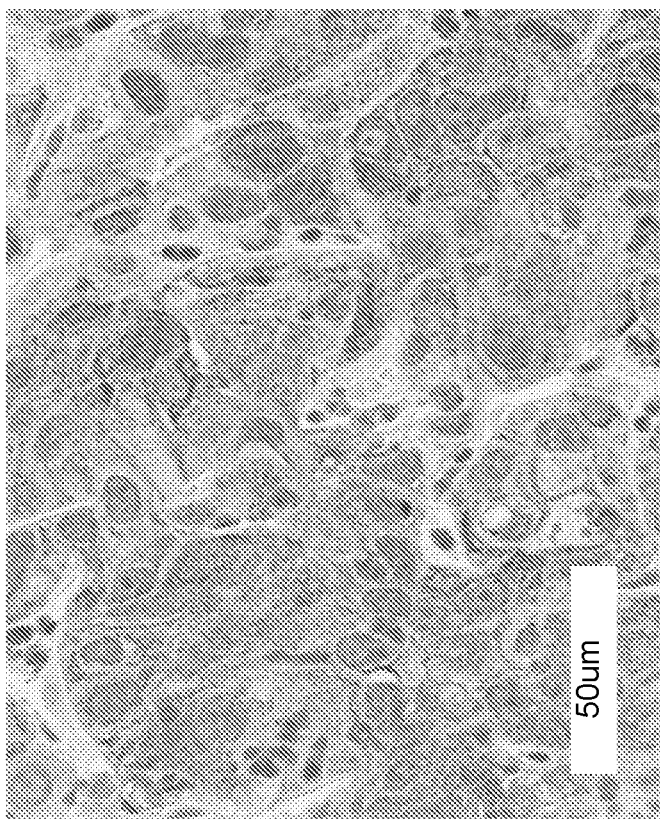

Tumors were then harvested from tCD19 control or 2A2 CAR-T treated mice 22 weeks post-infection (4 cell infusions), and CAR T cell phenotype was analyzed by flow cytometry. 2A2 CAR T cells were present at 5-fold higher frequency in the tumor compared to control T cells (FIG. 9C), proliferated strongly based on Ki67 expression (FIGS. 9A and 9D), and were uniformly PD-$1^{hi}$ by 22 weeks p.i. (FIGS. 9B and 9E). ROR1 expression on tCD19- and 2A2 CAR-treated tumors was measured by flow cytometry (FIG. 10A) and IHC (FIG. 10B). Tumors in both control and 2A2 CAR T cell-treated groups maintained similar levels of hROR1 expression, consistent with a finding that there had not been any outgrowth of antigen-loss variants.

Figure 11A:
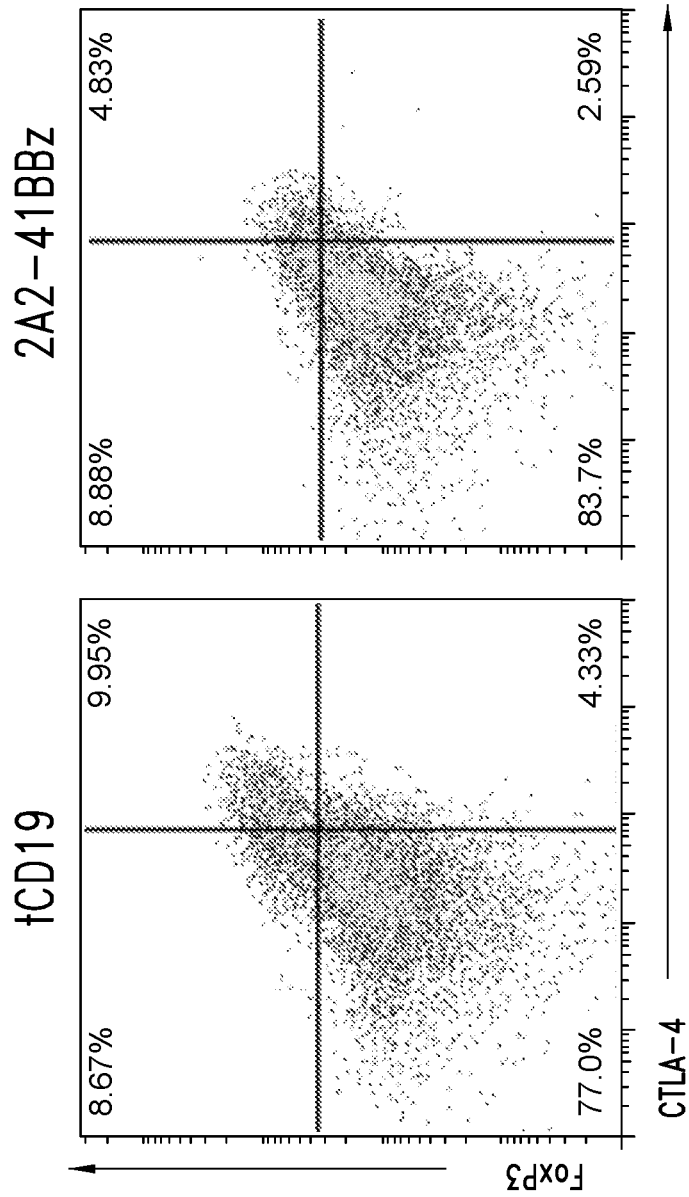
FIGS. 11A-11D show characterization of the tumor microenvironment of KP-hROR1 mice that received tCD19 or 2A2-41BBz CAR T cells. (A) Data from a flow cytometry experiment showing Treg populations in tumors from the two CAR T cell-receiving groups. (B) Frequency of Tregs (as a percentage of live cells) in spleen and tumor samples from each group. (C) Ratio of $CD8^+$ T cells to endogenous Tregs in spleen and tumor samples from each group. (D) Frequency of monocytic and granulocytic tumor MDSCs as a percentage of live cells.
Figure 11B:
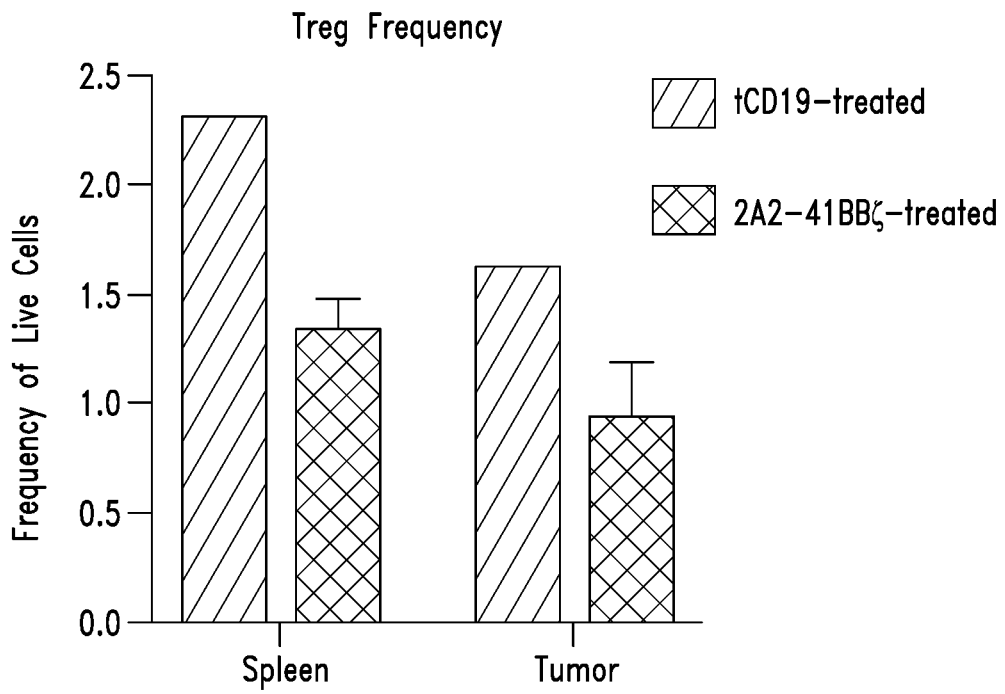
Figure 11C:
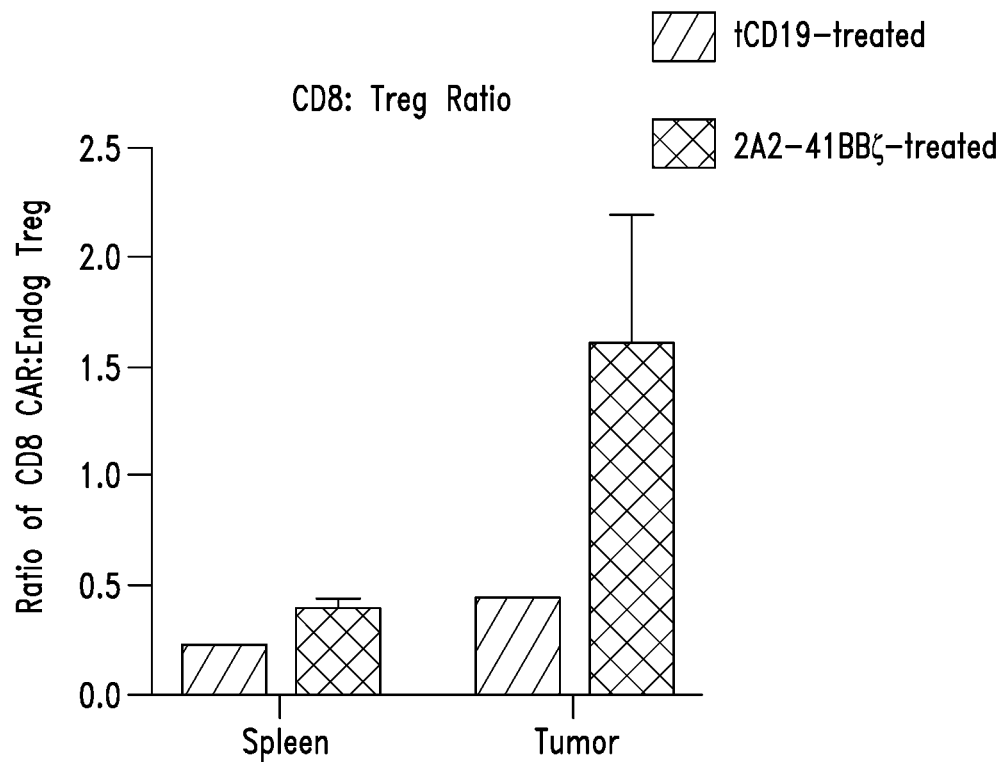
Figure 11D:
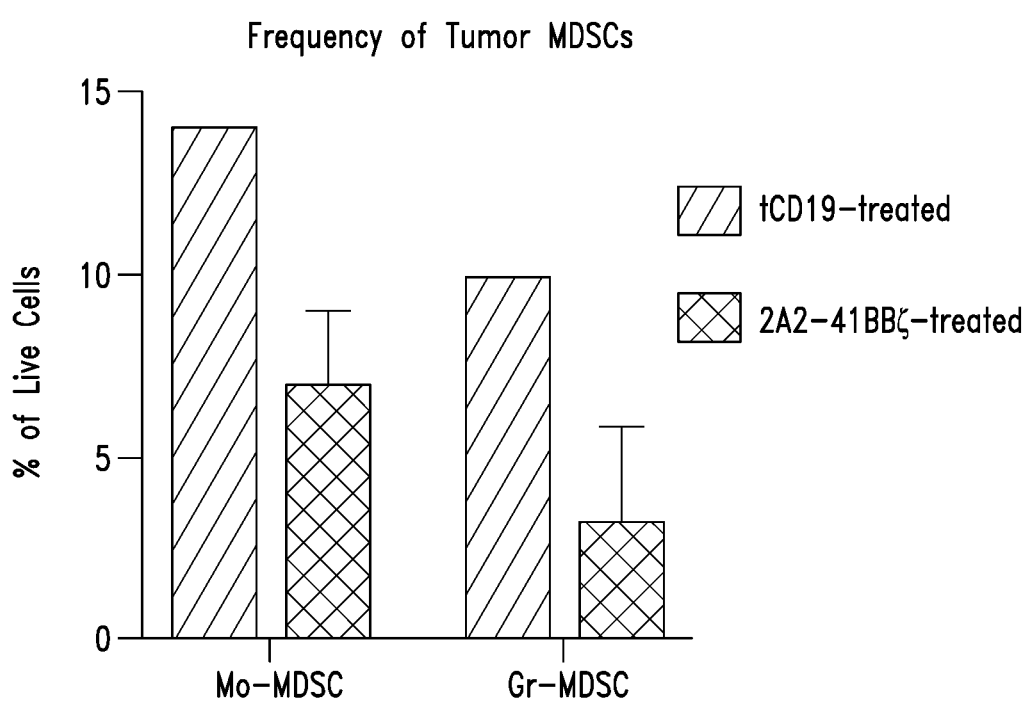

The immunosuppressive environment of tumors in 2A2 anti-ROR1 CAR T cell-treated mice was also analyzed. These tumors demonstrated a decline in suppressive Treg cells (FIGS. 11A-11C) and MDSCs (FIG. 11D), as compared to non-CAR T cell-treated mice.

Figure 12A:
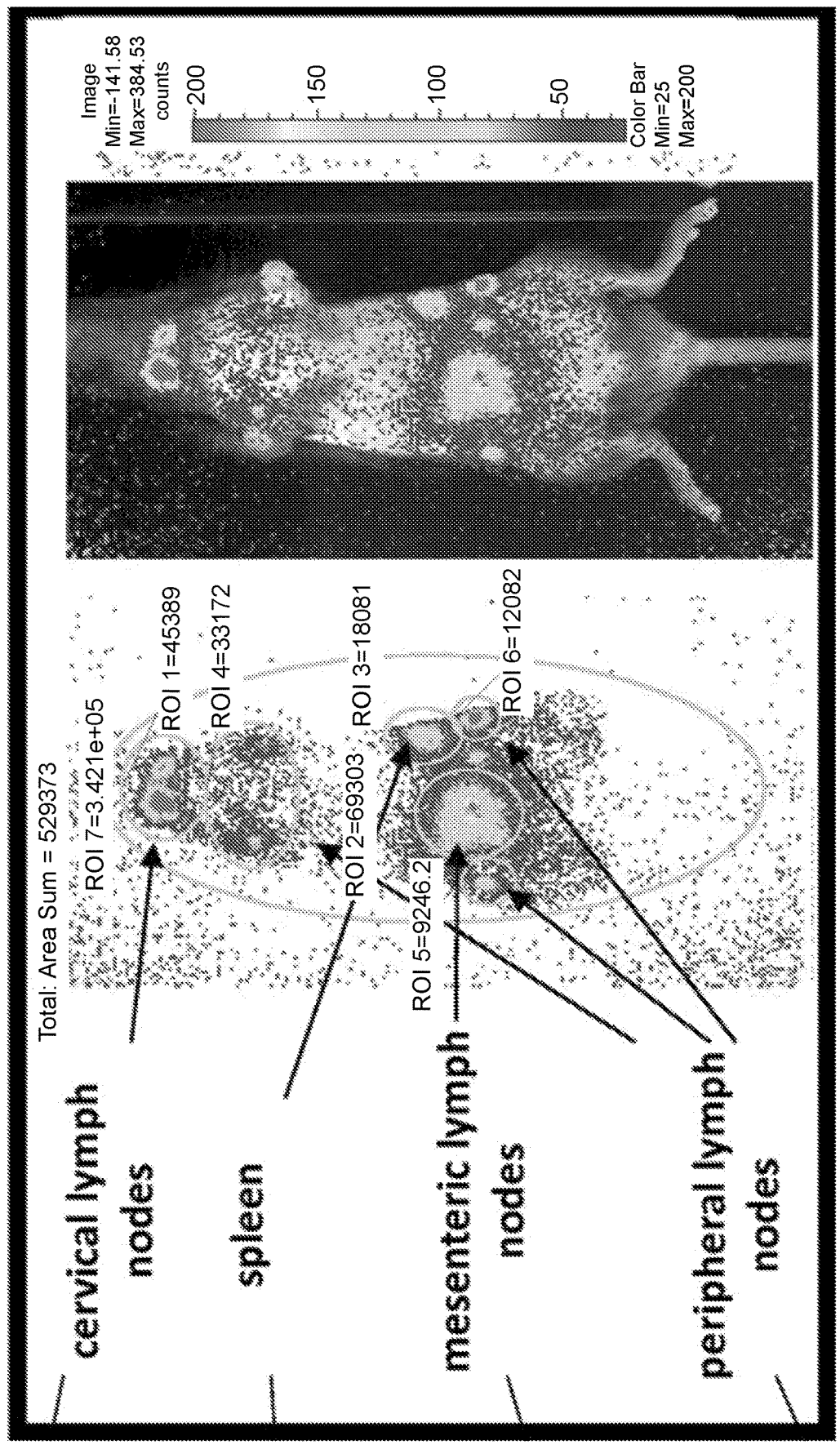
FIGS. 12A-12C show representative BLI showing localization of introduced T cells in mice. (A) Example showing localization of Gaussia luciferase-labeled T cells in a mouse. (left-to-right): fluorescence image with localization sites indicated; BLI image overlaid with mouse; brightness scale for luminescence interpretation. (B) BLI of mice that were injected with luciferase-labeled tCD19 control cells. Tissue sites of localization are described below the images. (C) BLI of mice that were injected with luciferase-labeled 2A2-41BBz CAR T cells; tissue sites of localization are described below the images.
Figure 12B:
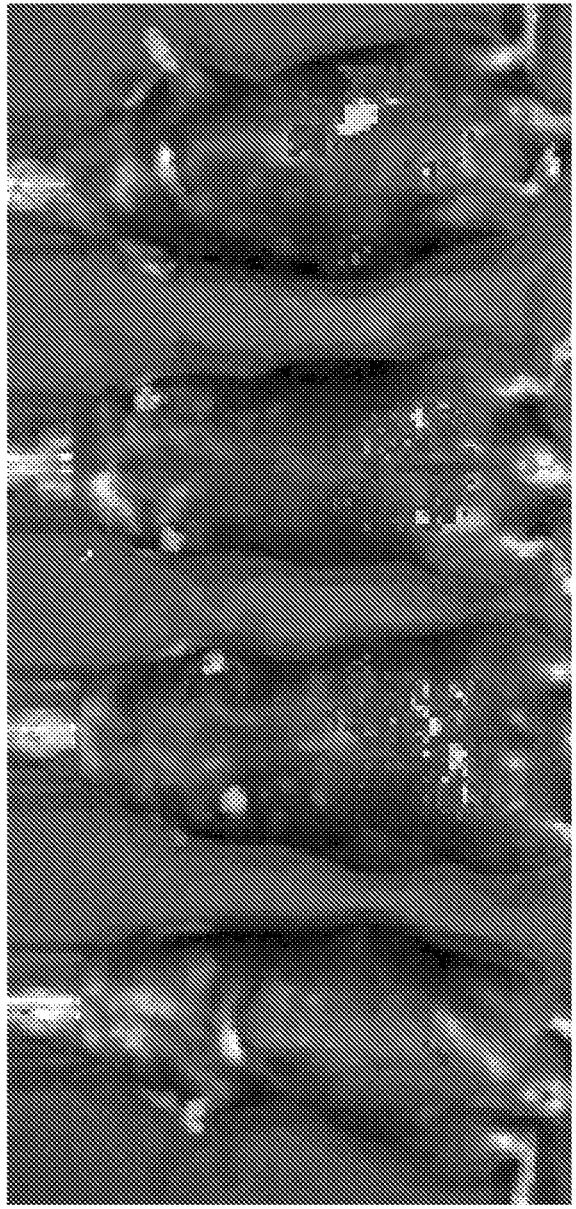
Figure 12C:
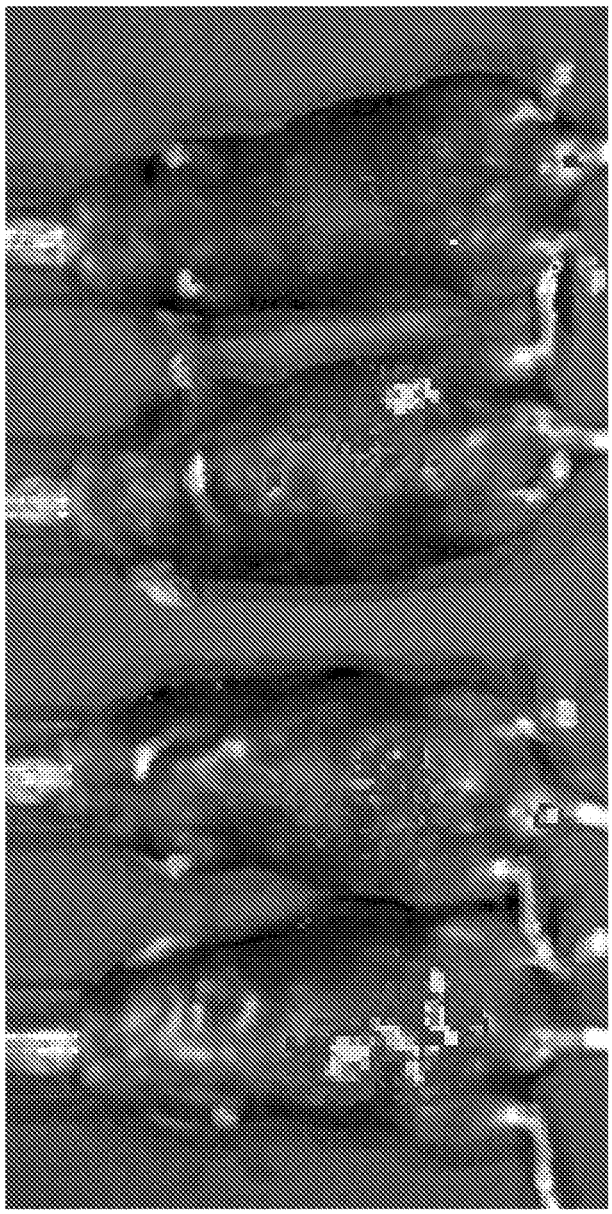

To analyze in vivo localization of the T cells following transfer, tCD19 control and 2A2 anti-ROR1 CAR T cells were transduced with *Gaussia* luciferase (illustrative BLI shown in FIG. 12A). Mice were imaged 1 week after transfer after receiving the 4th dose of T cells. BLI imaging showed that the majority of donor T cells migrate to spleen and lymph nodes, rather than to the lung (FIGS. 12B and 12C). The result was consistent with the interpretation that the majority of CAR T cells transferred did not recognize or effectively recognize, target or reduce tumor in the lung and/or were unable to effectively traffic to the lung.

Example 4

PD-1 Blockade does not Enhance Anti-Tumor Efficacy of Anti-ROR1 Car T Cells

Figure 13A:
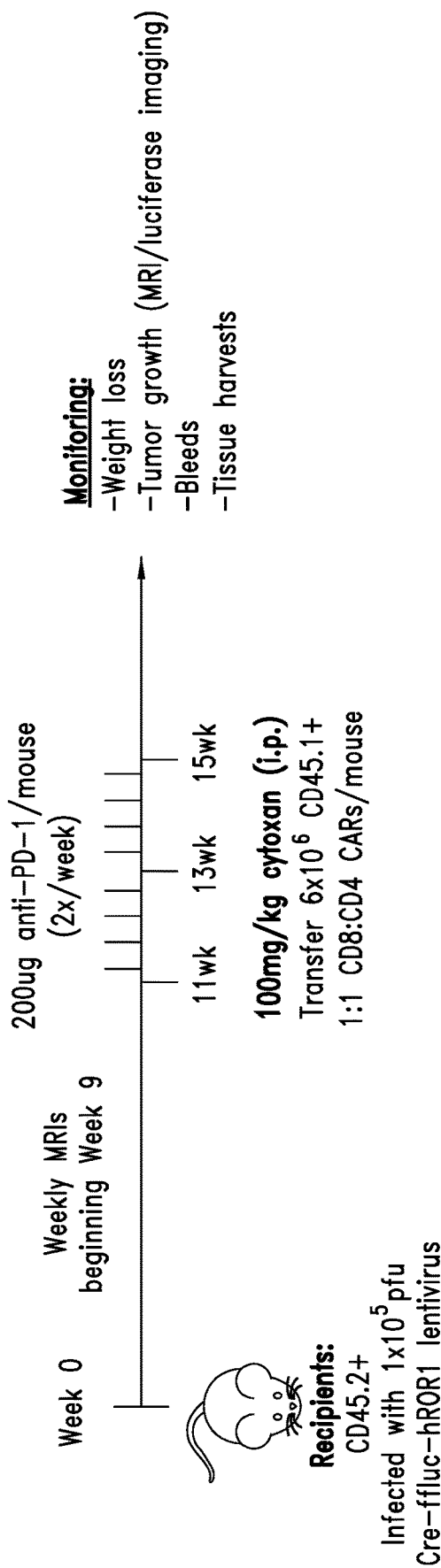
FIG. 13A shows a diagram of an experimental treatment scheme in which KP mice were infected with the Cre-ffluc-hROR1 lentivirus and subsequently treated with a combination of cyclophosphamide and 1:1 $CD8^+/CD4^+$ 2A2-41BBz CART cells at weeks 11, 13, and 15 p.i., with 200m anti-PD-1/murine antibody administered 2×/week during the treatment period. Mice were imaged and monitored as indicated (weekly weighings, MRI/luciferase imaging, bleeds, and tissues harvests beginning at Week 9 p.i.).

As anti-ROR1 CAR T cells can up-regulate PD-1, and also that suppressive cells in the tumor microenvironment express PD-L1, whether PD-1 blockade could enhance the efficacy of anti-ROR1 CAR T cells was assessed. Briefly, KP mice were infected with Cre-ffluc-hROR1 lentivirus and tumor growth was monitored by MM. When tumor nodules reached $\geq 1$ mm$^3$ in all mice, cyclophosphamide (Cy) was administered (100 mg/kg cyclophosphamide) for lymphodepletion and the mice received transfer of $6 \times 10^6$ 2 A2-41BK CART cells (CD8:CD4 of 1:1) or of an equal number of control T cells modified only with the tCD19 marker (FIG. 13A). Adoptively transferred T cells were derived from congenic B6.SJL mice and could be identified within CD45.2$^+$ KP recipient mice as CD45.1$^+$. Mice continued to receive Cy and control tCD19 or 2A2 CAR T cells every 3 weeks. A subset of mice were treated with 200 ug anti-PD-1 blocking antibody intraperitoneally twice a week beginning at the time of T cell transfer and continuing throughout the course of the study.

Figure 13B:
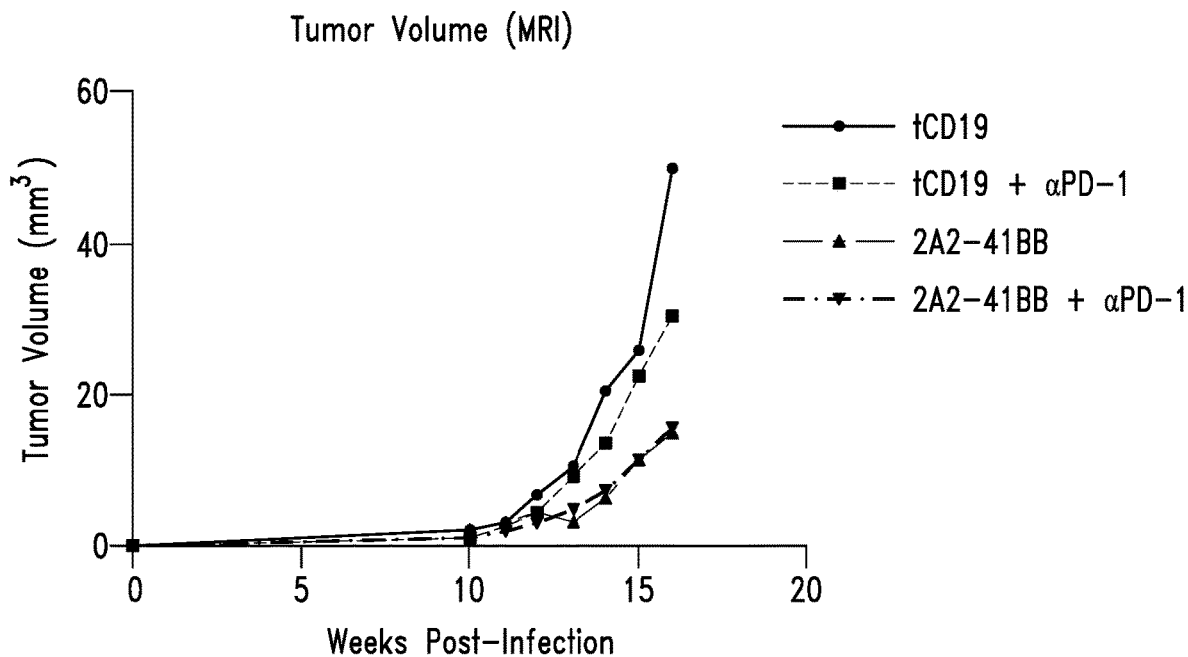
FIG. 13B shows average tumor volumes calculated from MRI z-stacks of mice that received tCD19 T cells, tCD19 T+anti-PD-1, 2A2-41BBz CAR T, or 2A2-41BBz CAR T+anti-PD-1 (as indicated in the figure key) according to the treatment scheme shown in FIG. 13A.
Figure 13C:
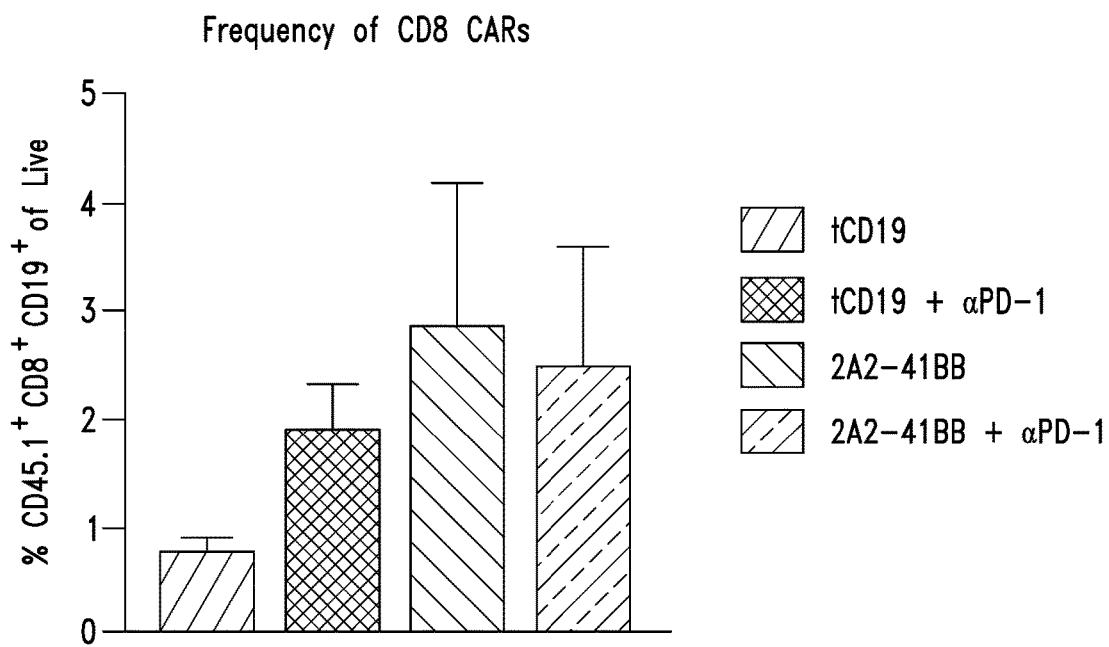
FIG. 13C shows the frequency of transduced $CD45.1^+CD8^+$ cells (expressing the transduction marker or the CAR transduction marker) in live cells of mice from the indicated treatment groups.
Figure 13D:
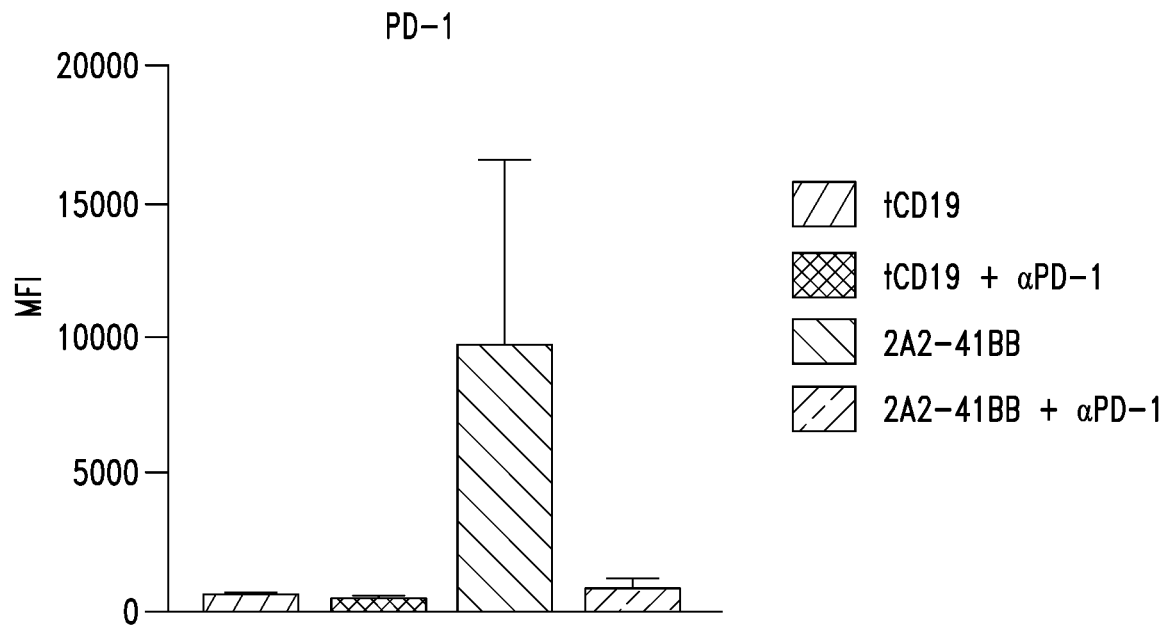
FIG. 13D shows PD-1 expression (MFI) in transduced cells.
Figure 13E:
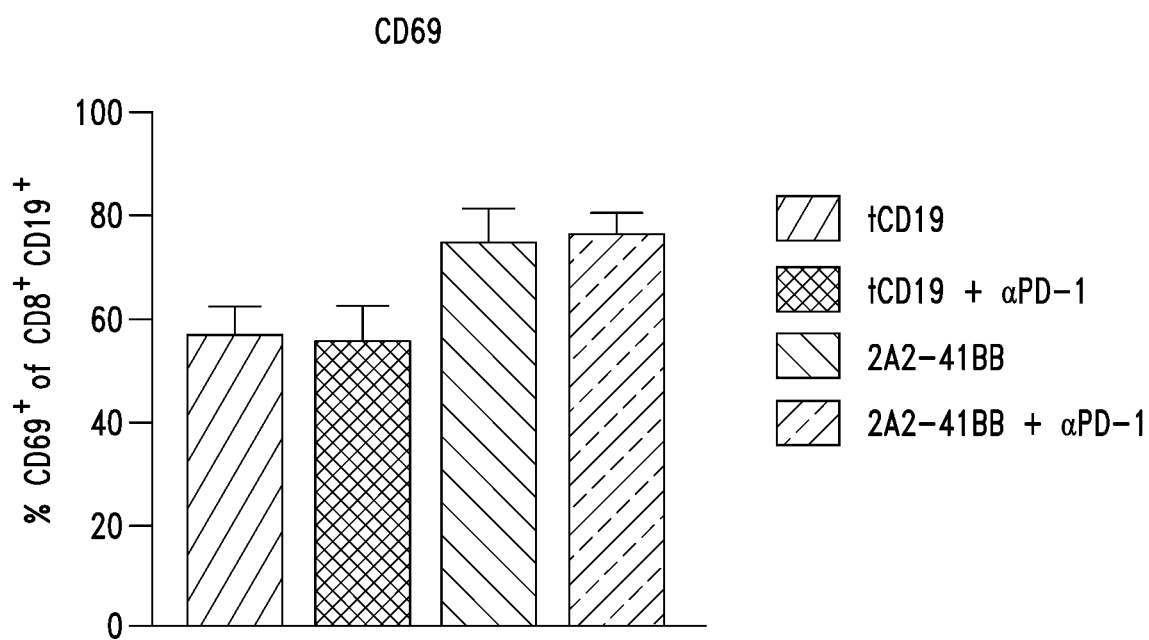
FIG. 13E shows the percentage of activated cells (CD69 assay) within each cell group.

PD-1 blockade was observed not to improve tumor control by anti-ROR1 CAR T cells, as quantitated by MM z-stack scans (FIG. 13B). Moreover, the frequency of anti-ROR1 CAR T cells was not observed to be improved within the tumor (FIG. 13C). PD-1 staining was reduced on CAR T cells from anti-PD-1 treated mice, indicating that the antibody was active in vivo (FIG. 13D). However, anti-ROR1 CAR T cells did not exhibit signs of greater activation with anti-PD-1 treatment and showed similar levels of the activation marker CD69 in the tumor as CAR T cells in the absence of anti-PD-1 treatment (FIG. 13E).

Example 5

Immunogenic Chemotherapy Enhances Anti-ROR1 CAR T Anti-Tumor Activity

Immunogenic cell death (ICD) has been reported to improve priming and trafficking of antigen-specific T cells to the tumor. Whether chemotherapy regimens known to induce ICD could enhance CAR T cell infiltration of ROR1$^+$ lung tumors was assessed with a combination treatment experiment (FIG. 14A). Briefly, KP mice were infected with Cre-ffluc-hROR1 lentivirus and tumor growth was monitored by MRI. When tumor nodules reached $\geq 1$ mm$^3$ in all mice, the mice were pre-treated with 2.5 mg/kg oxaliplatin and 50 mg/kg cyclophosphamide (Cytoxan) once per week for a total of 3 weeks (week 12, 13, 14). At weeks 12 and 15, mice were administered 100 mg/kg cyclophosphamide (Cy) for lymphodepletion and $6 \times 10^6$ 2 A2-41BK CAR T cells (CD8:CD4 of 1:1) or an equal number of control T cells modified only with the tCD19 marker. Mice also received 200 µg anti-PD-L1 (αPD-L1) checkpoint antibody twice a week beginning at the time of T cell transfer and continuing throughout the course of the study. Weight loss, blood samples, and IHC were also monitored throughout the course of the study.

Figure 14B:
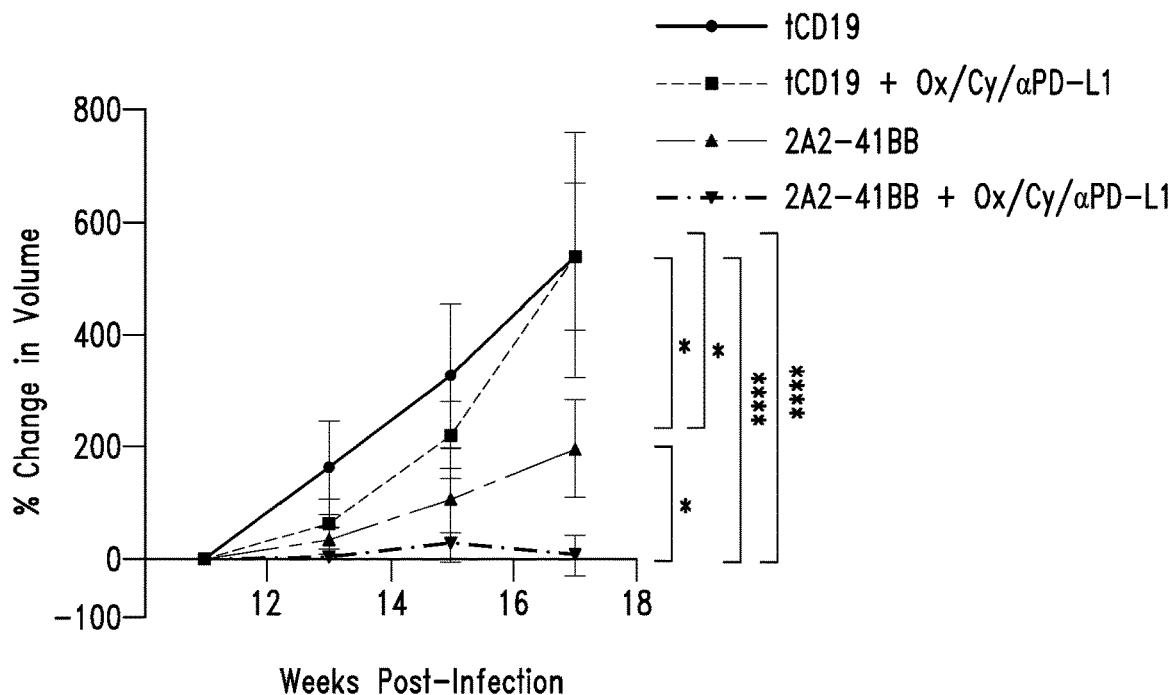
FIGS. 14A-14T show the effects of adding oxaliplatin+cyclophosphamide to an anti-ROR1-CAR T+PD-L1 blockade immunotherapy regimen. (A) diagram of an experimental treatment scheme in which KP mice were infected with the Cre-ffluc-hROR1 lentivirus and pre-treated with a combination of oxaliplatin+cyclophosphamide (1×/week at weeks 12, 13, and 14 p.i.), followed by lymphodepletion with cyclophosphamide and transfer of 1:1 $CD8^+/CD4^+$ 2A2-41BBz CAR T cells at weeks 12 and 15 p.i. 200 µg anti-PD-L1/murine antibody was administered 2×/week concurrent with T cell transfer and continued throughout the course of the study. Mice were imaged and monitored as indicated (weekly weighings, MRI/luciferase imaging, bleeds, and tissues harvests beginning Week 9 p.i.). Treatment groups and sample sizes were as indicated. (B)-(F) and (L-P) Percent change in volume of individual tumor nodules in KP mice receiving the indicated treatments. Tumor nodules were counted and scored for regression. (G, Q) Representative MM scans from the indicated treatment groups at weeks 11 (post-infection, pre-treatment) and 17 (post-infection, post-treatment). (H, R, T) Representative IHC images of CD3 staining of KP lung tumors following 5 weeks of T cell treatment as indicated. Darker staining=increased infiltration by $CD3^+$ T lymphocytes. (I, S) Quantification of CD3 staining in individual tumors by HALO imaging software. (J) Percentage of tumors having intratumoral CD3 staining in individual mice from each treatment group. (K) Fraction of tumors from each treatment group having >15% $CD3^+$ infiltration.
Figure 14C:
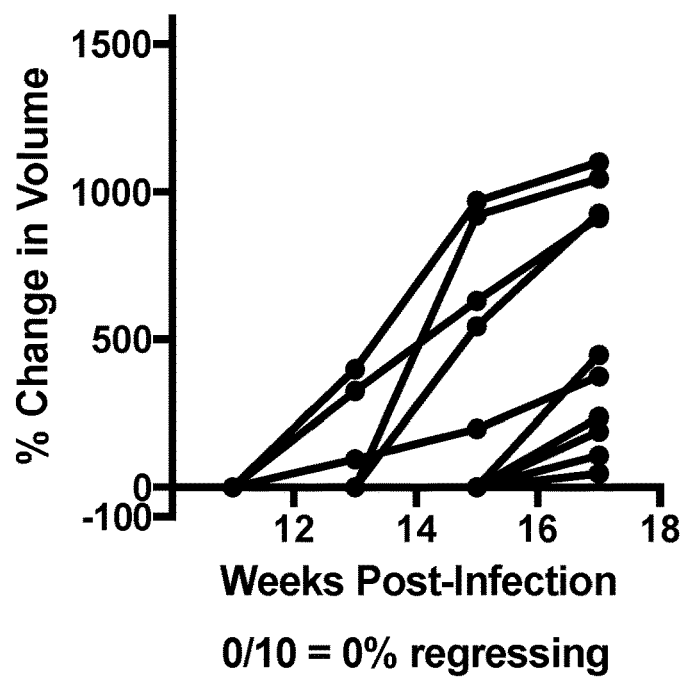
Figure 14D:
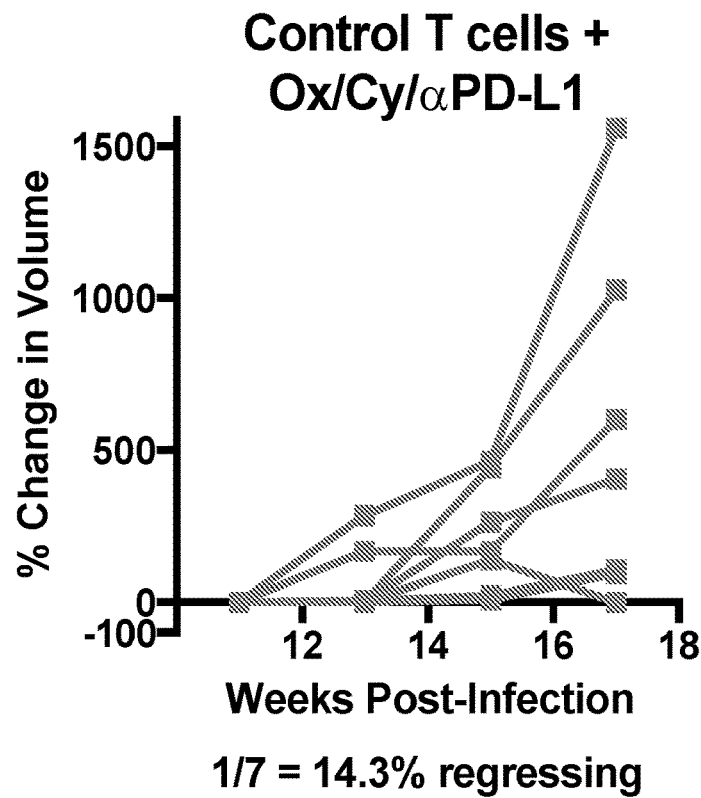
Figure 14E:
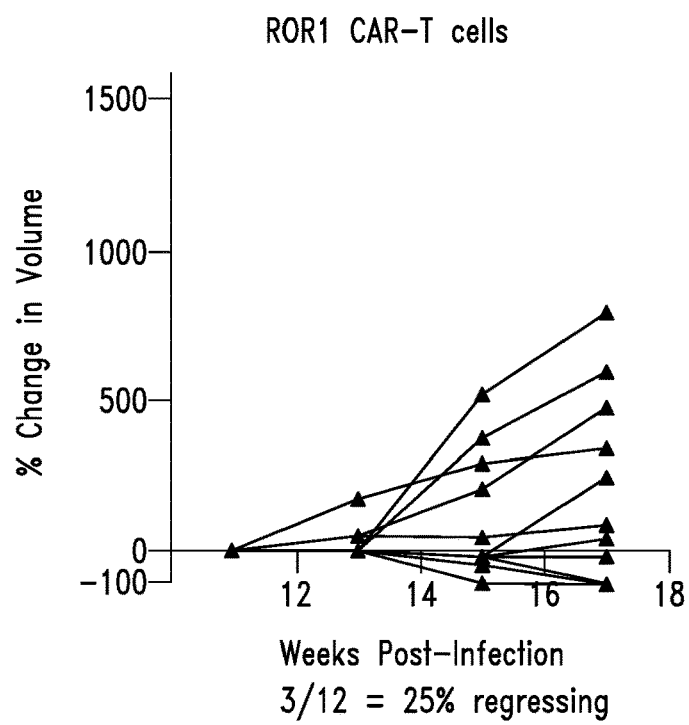
Figure 14F:
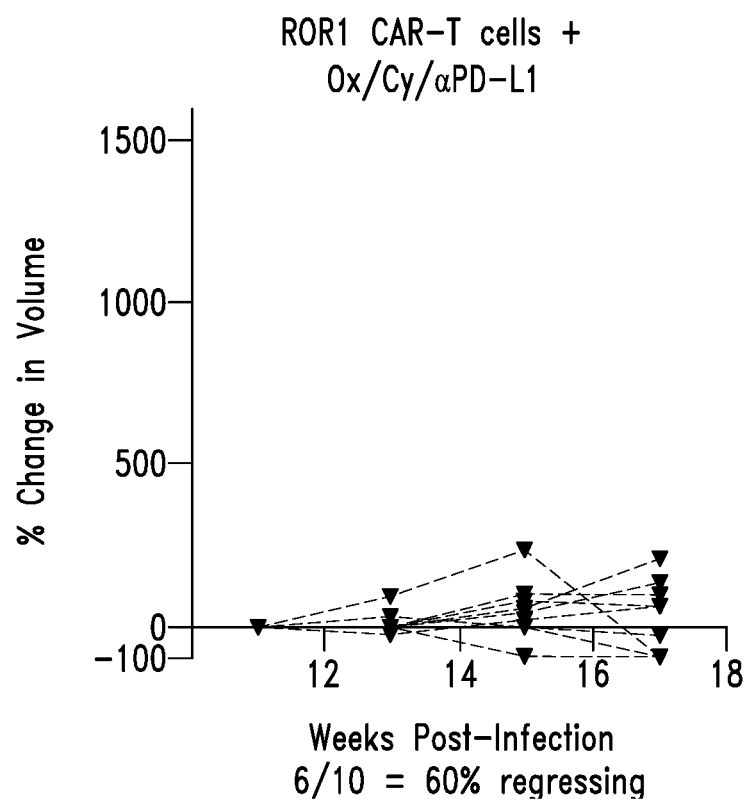
Figure 14G:
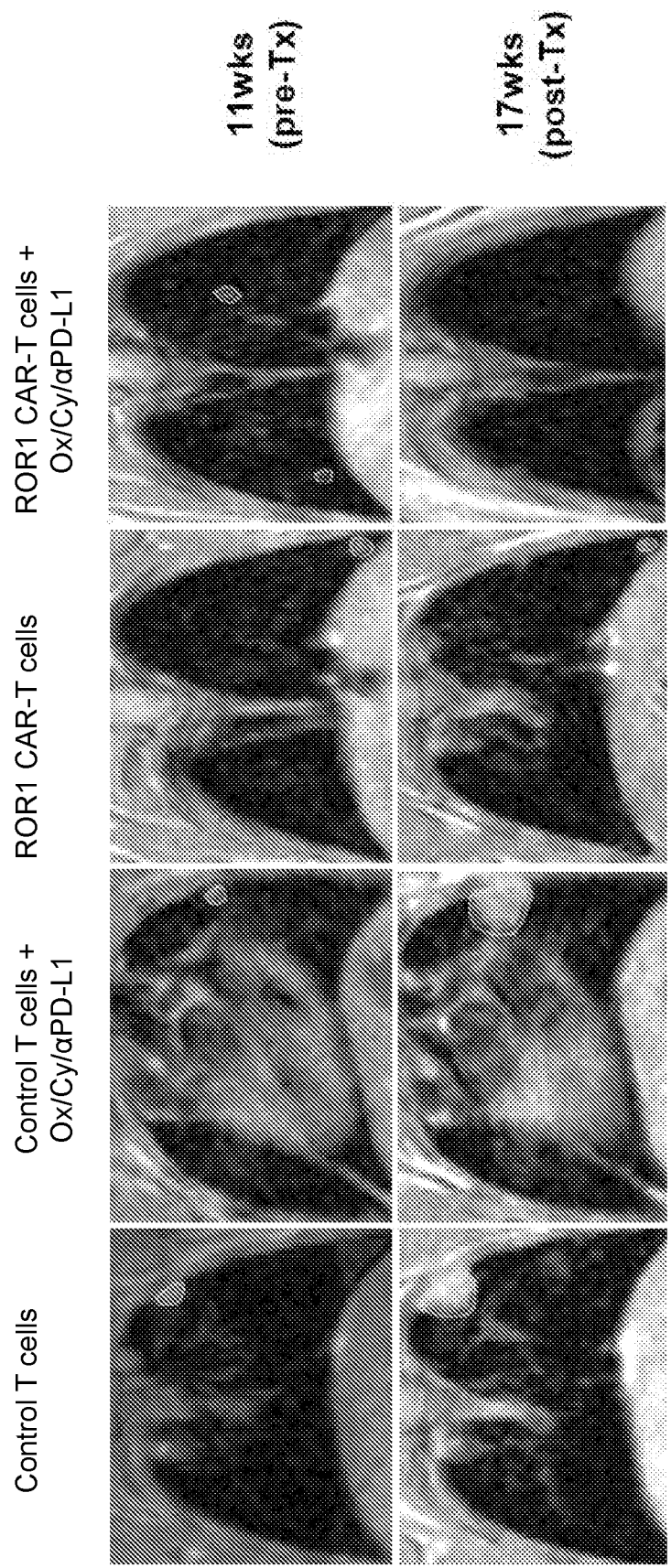
Figure 14H:
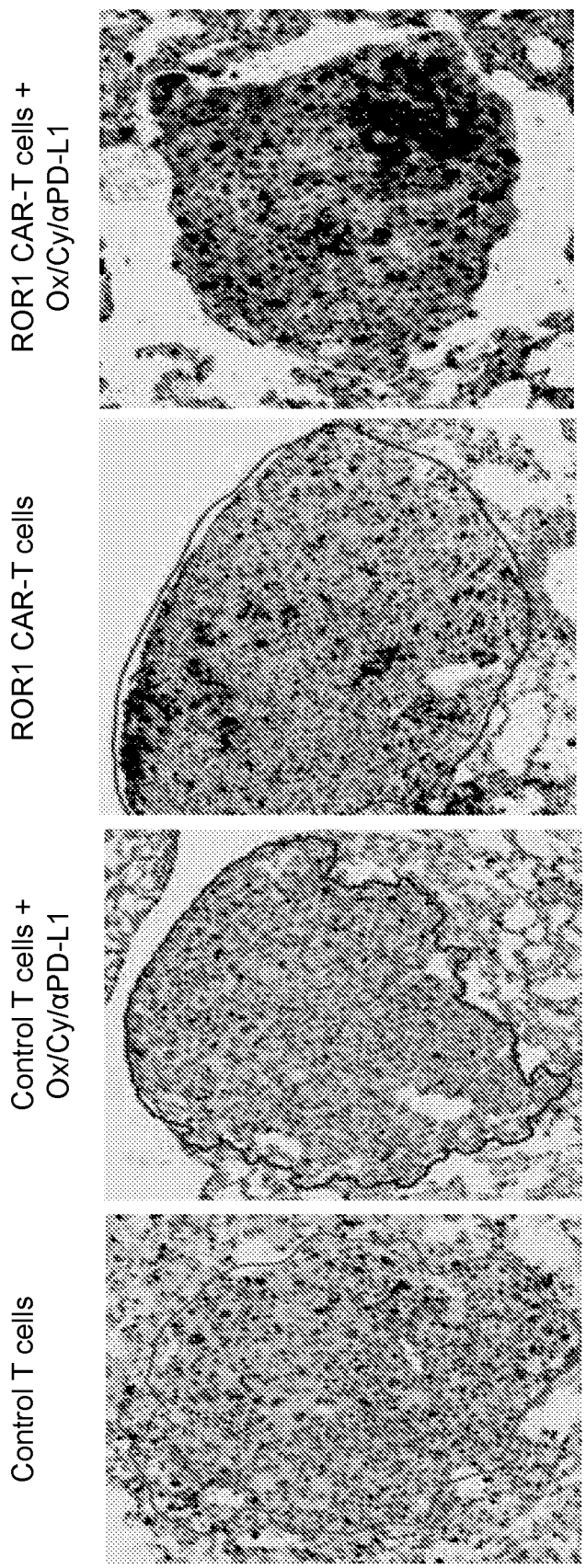
Figure 14I:
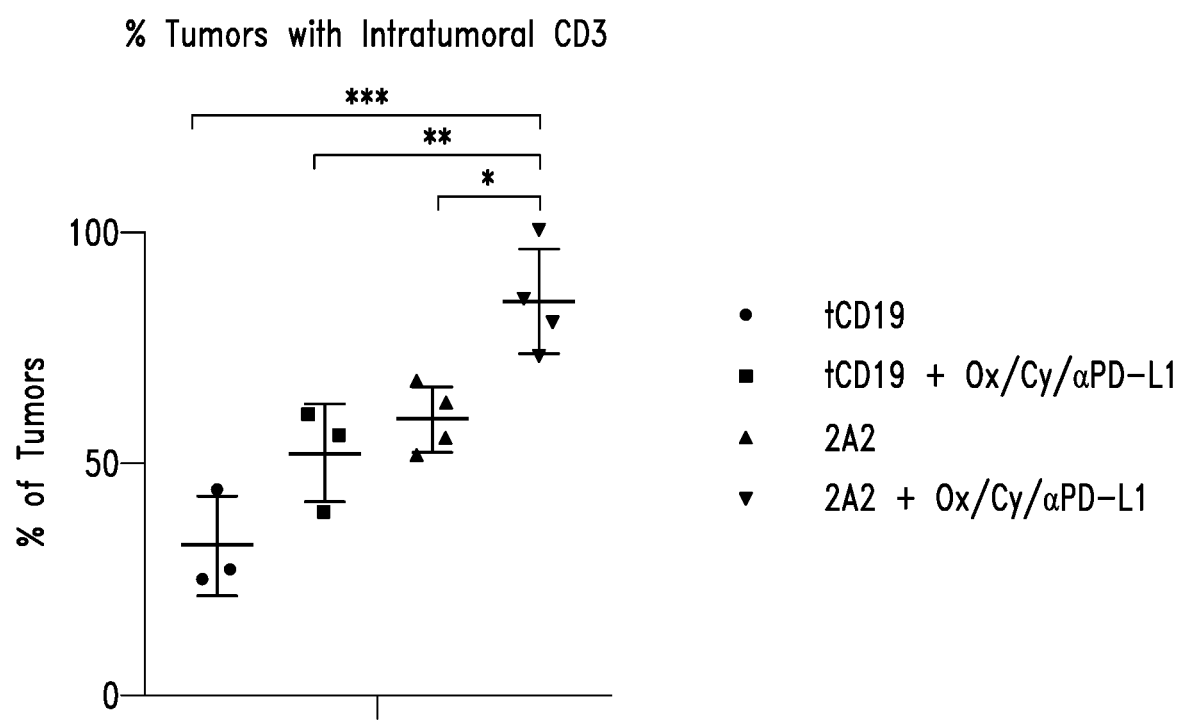
Figure 14J:
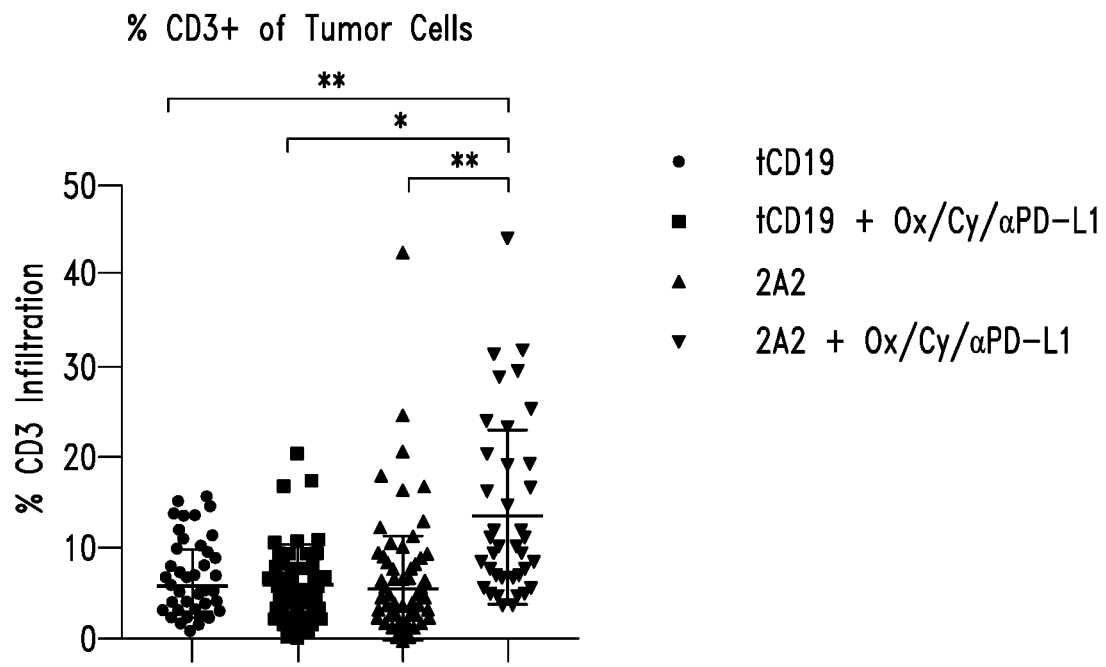
Figure 14K:
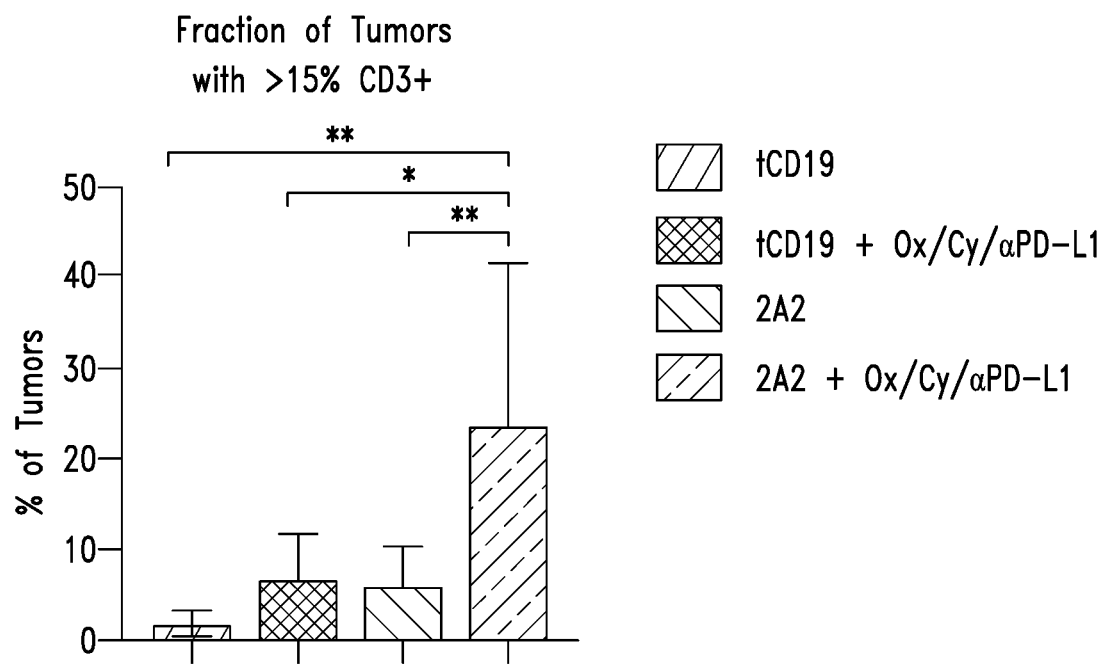
Figure 14L:
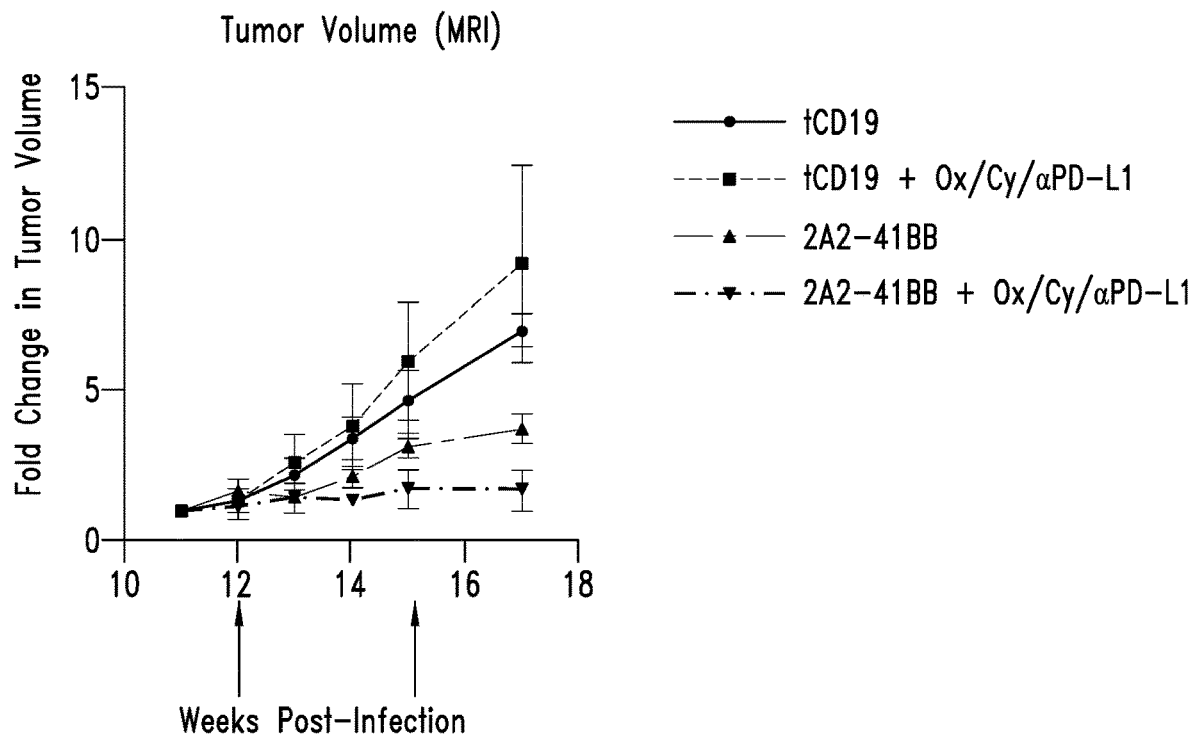
Figure 14M:
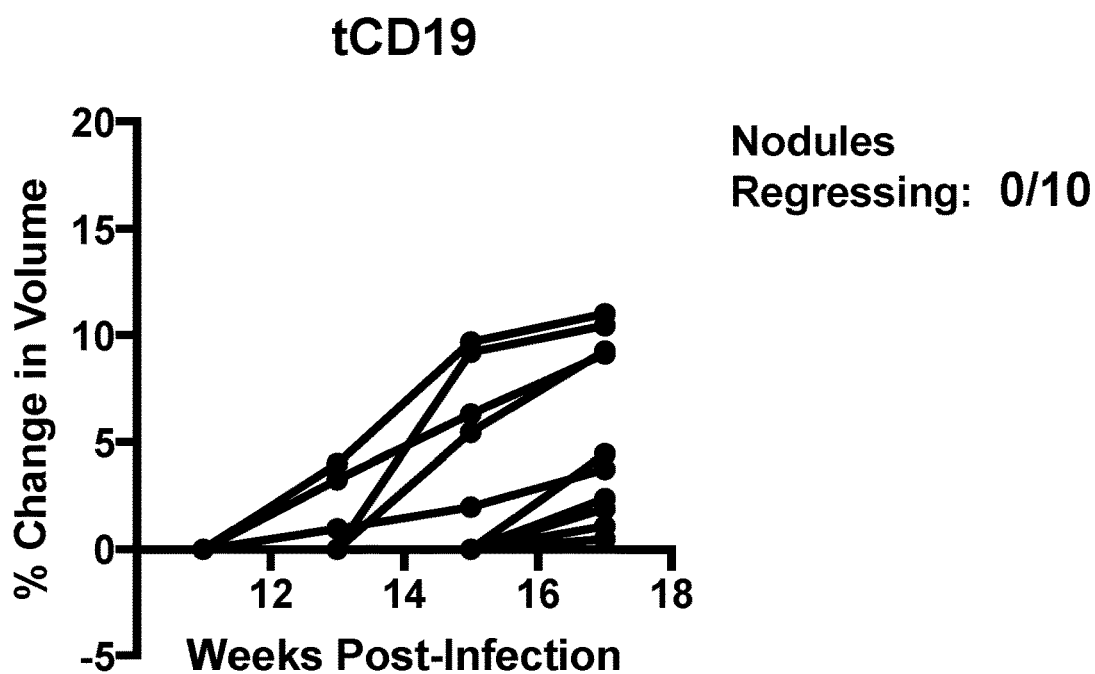
Figure 14N:
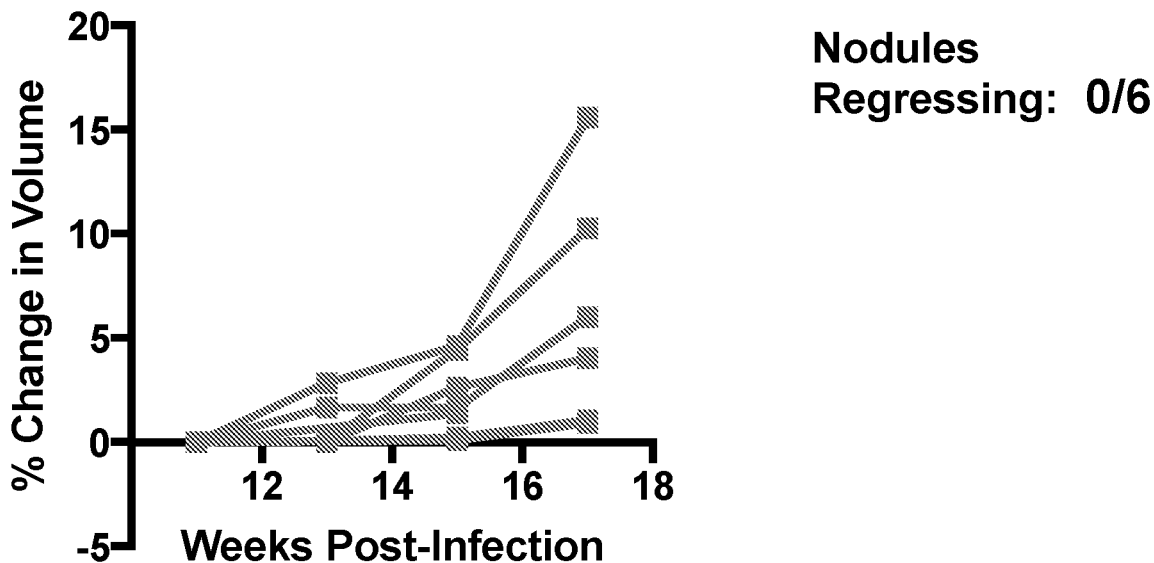
Figure 14O:
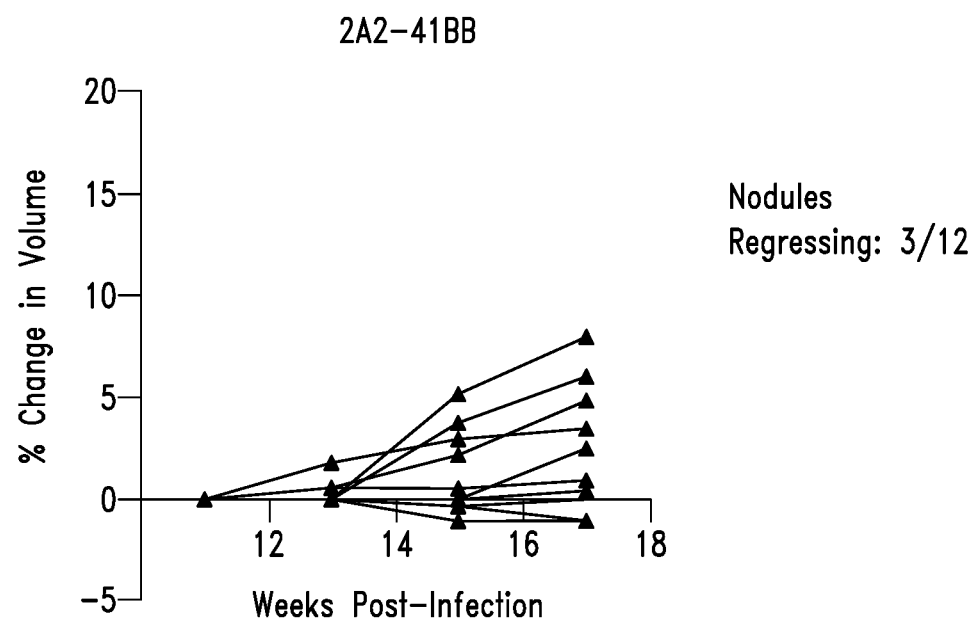
Figure 14P:
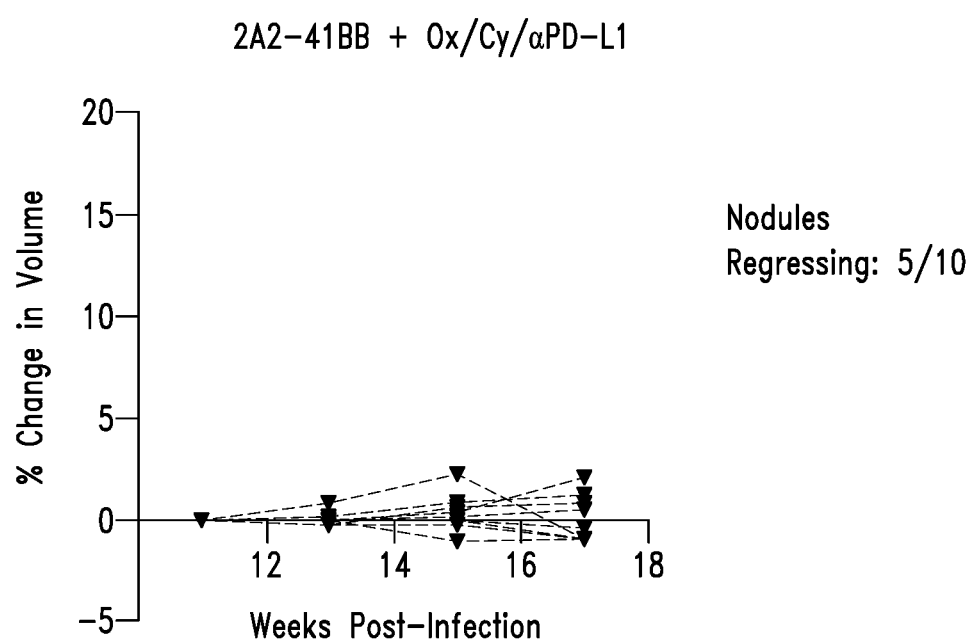
Figure 14Q:
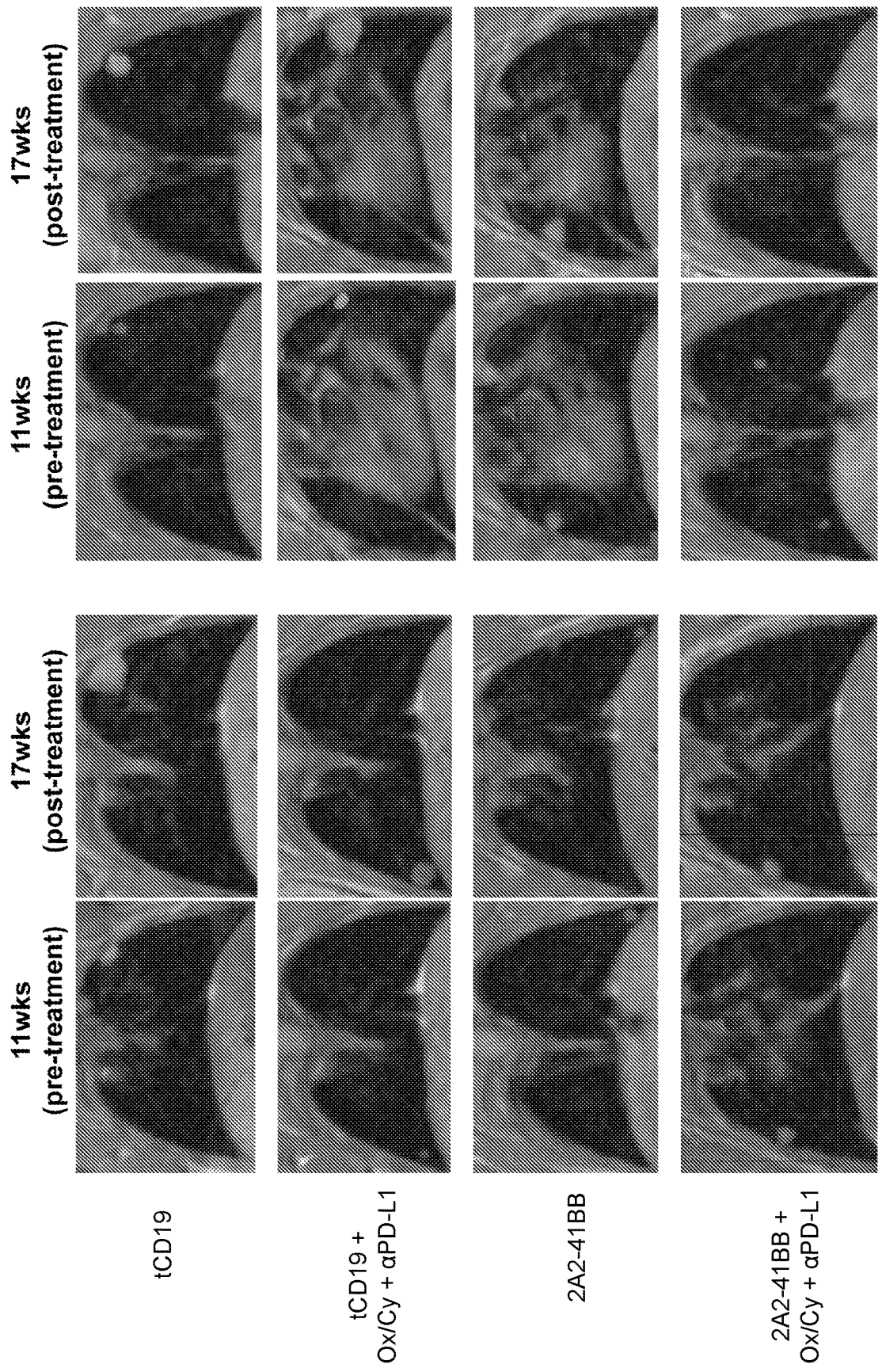

As shown in FIGS. 14B and 14L, combination therapy with oxaliplatin, cyclophosphamide, and anti-PD-L1 surprisingly and synergistically improves tumor control by anti-ROR1 CAR T cells. Tumor volumes quantified by MRI are summarized for each treatment group in the top panel (n=3-4 per group). Growth patterns of individual tumor nodules are summarized for each treatment group in FIGS. 14C-14F and 14M-14P. Whereas nearly all tumor nodules in tCD19 control and tCD19 control+Ox/Cy/αPD-L1-treated mice progressed steadily (1/7 regressing in the group that received combination treatment), a fraction of nodules (3/12) regressed in mice treated with anti-ROR1 CAR T cells only. By comparison, anti-ROR1 CAR T cell combination therapy with Ox/Cy/αPD-L1 increases the proportion of regressing nodules (6/10 vs 3/12). Representative MRI scans are provided in FIGS. 14G and 14Q and show steady tumor progression in tCD19 control and tCD19+Ox/Cy/αPD-L1 treated mice, slower or minimal growth in anti-ROR1 CAR-treated mice, and regression in anti-ROR1 CAR+Ox/Cy/αPD-L1 treated mice.

Figure 14R:
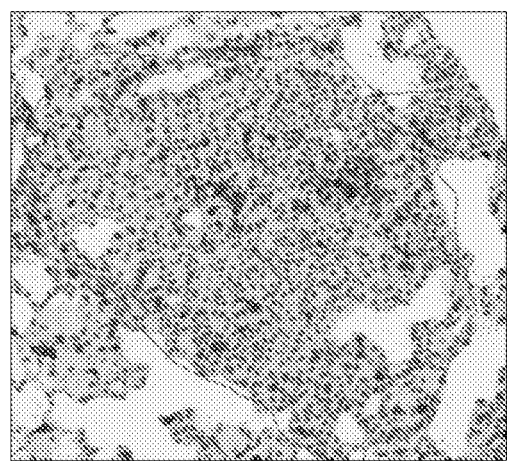
Figure 14R:
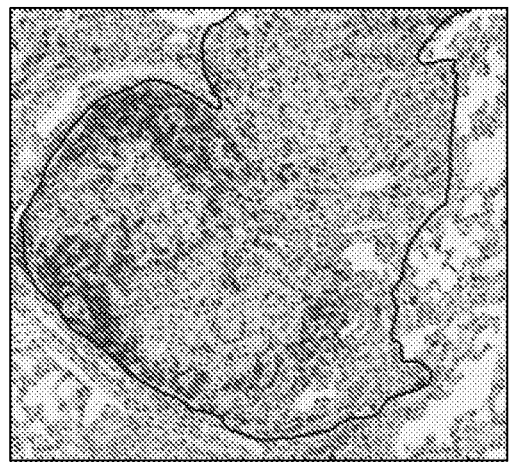
Figure 14R:
Figure 14S:
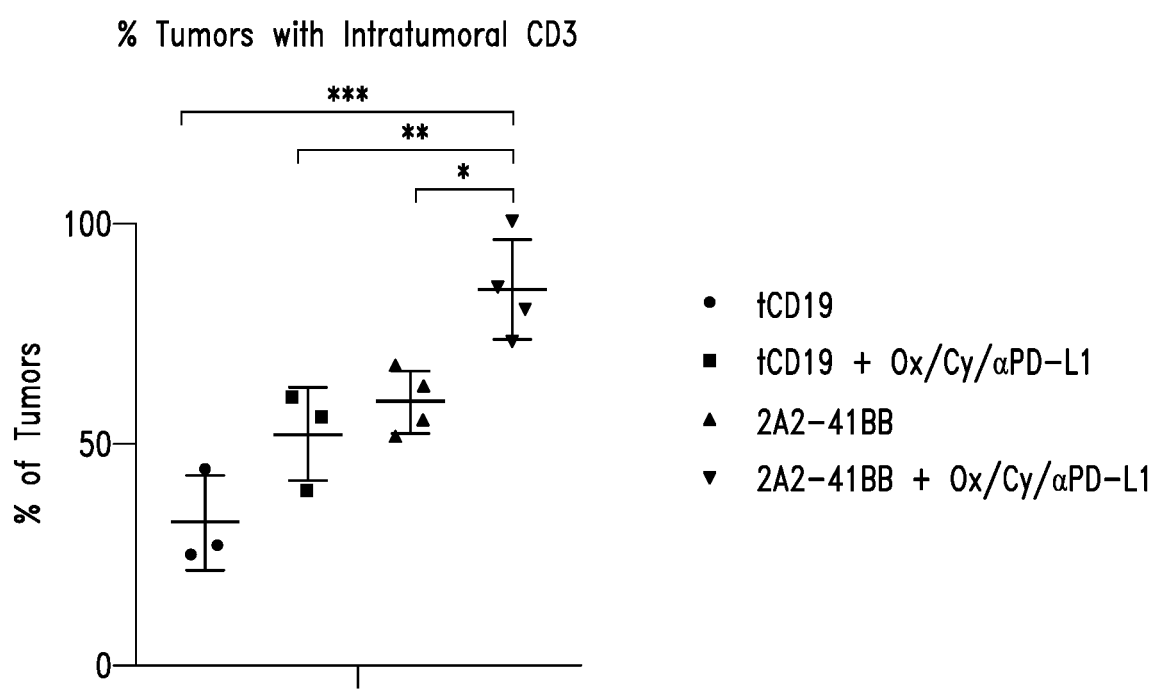
Figure 14T:
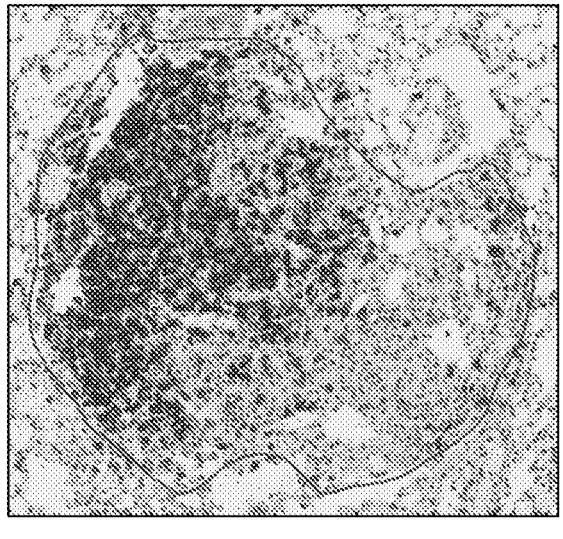
Figure 14T:

To further characterize CAR T cell activity in the CAR+Ox/Cy/αPD-L1 treated mice, tumors from this group were harvested at 17 weeks p.i. and IHC staining for CD3 was performed. Tumors were scored independently by a pathologist for localization of T cells around tumors. Tumors were scored as having primarily stromal infiltrate, peripheral infiltrate, or intratumor infiltrate. Representative data are shown in FIGS. 14H 14R, and 14T. The % of CD3$^+$ cells/total number of cells in each tumor was quantified. Combination therapy of anti-ROR1 CAR T cells with Ox/Cy/αPD-L1 significantly improved the fraction of tumor nodules in each mouse with intratumoral T cell infiltrate (FIGS. 14I and 14S).

The IHC tumor nodule samples were quantified for CD3 expression. The fraction of CD3$^+$ cells of total nucleated cells was calculated for using HALO imaging software each tumor nodule in each mouse. The level of CD3 infiltration for all tumor nodules each of the various treatment groups is summarized in FIG. 14J, with CAR+Ox/Cy/αPD-L1-treated mice showing the highest level of T cell infiltration. A substantially larger fraction of tumors showed a level of at least 15% CD3$^+$ T cells in CAR+Ox/Cy/αPDL1 treated mice (FIG. 14K).

Figure 15A:
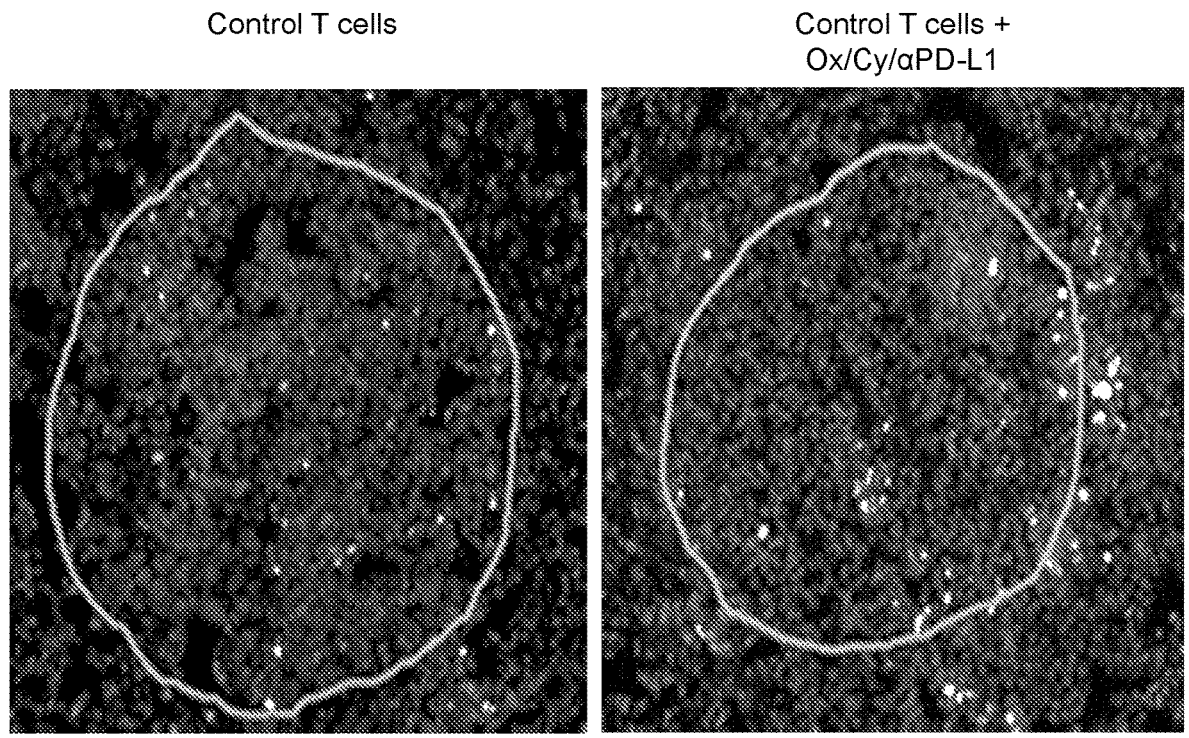
FIGS. 15A-15D show multiplex immunohistochemistry (IHC) of lung tumors from treated mice and quantification of the same. (A, B) Representative multiplex IHC of lung tumors 5 weeks post-treatment (as indicated) showing CD8a, Foxp3, control or CAR T ($GFP^+$) cells, and DAPI. (C) Quantification (HALO imaging software) of GFP staining (CAR T cells) as a percentage of nucleated cells in tumor samples (individual tumors) from mice administered anti-ROR1 CAR T cells with (downward triangles) or without (upward triangles) oxaliplatin+cyclophosphamide (Ox/Cy) and anti-PD-L1 antibody. (D) Quantification of $CD8^+$ T cells as a percentage of nucleated cells in tumor samples (individual tumors) from the indicated treatment groups.
Figure 15B:
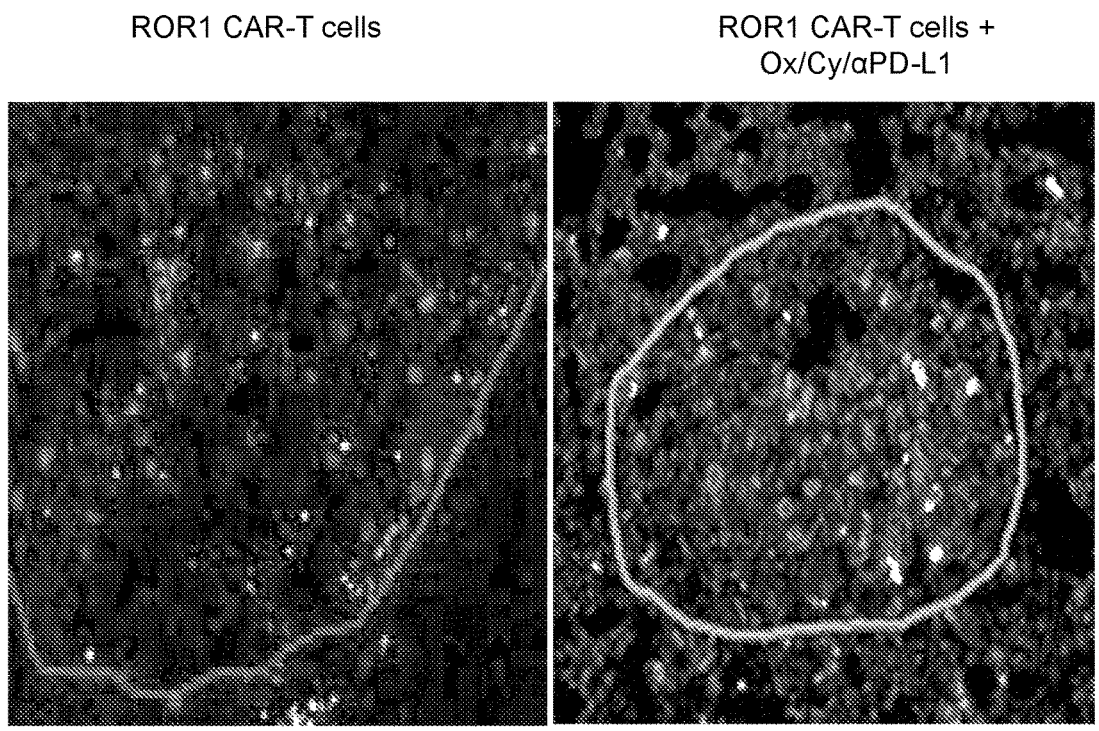
Figure 15C:
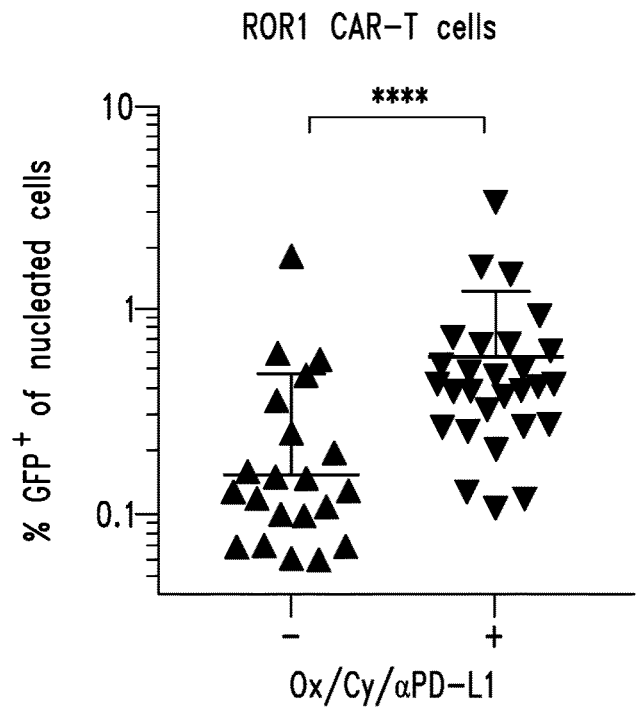
Figure 15D:
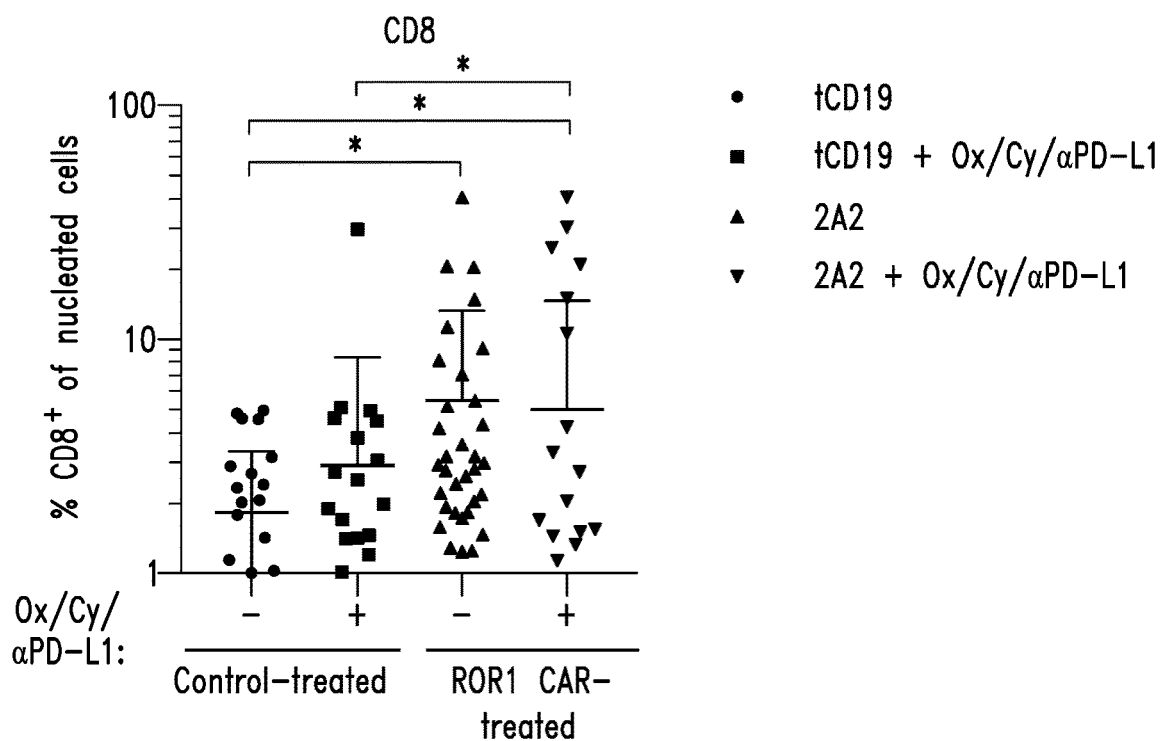

Multiplex IHC was also performed, staining for CD8a, Foxp3 or showing control T cells or CAR T cells (GFP), and DAPI. As shown in FIGS. 15A, 15B, and 15D, tumors from anti-ROR1 CAR+Ox/Cy/αPD-L1-treated mice had increased levels of CD8a, Foxp3, and overall T cells as compared to mice that received control T cells (either group). HALO quantification showed that tumors from anti-ROR1 CAR+Ox/Cy/αPD-L1-treated mice had higher levels T cells as compared to tumors from mice that received anti-ROR1 CAR T cells alone (FIG. 15C).

Example 6

Functional Characterization of CAR T Cells in Combination Therapy

Figure 16A:
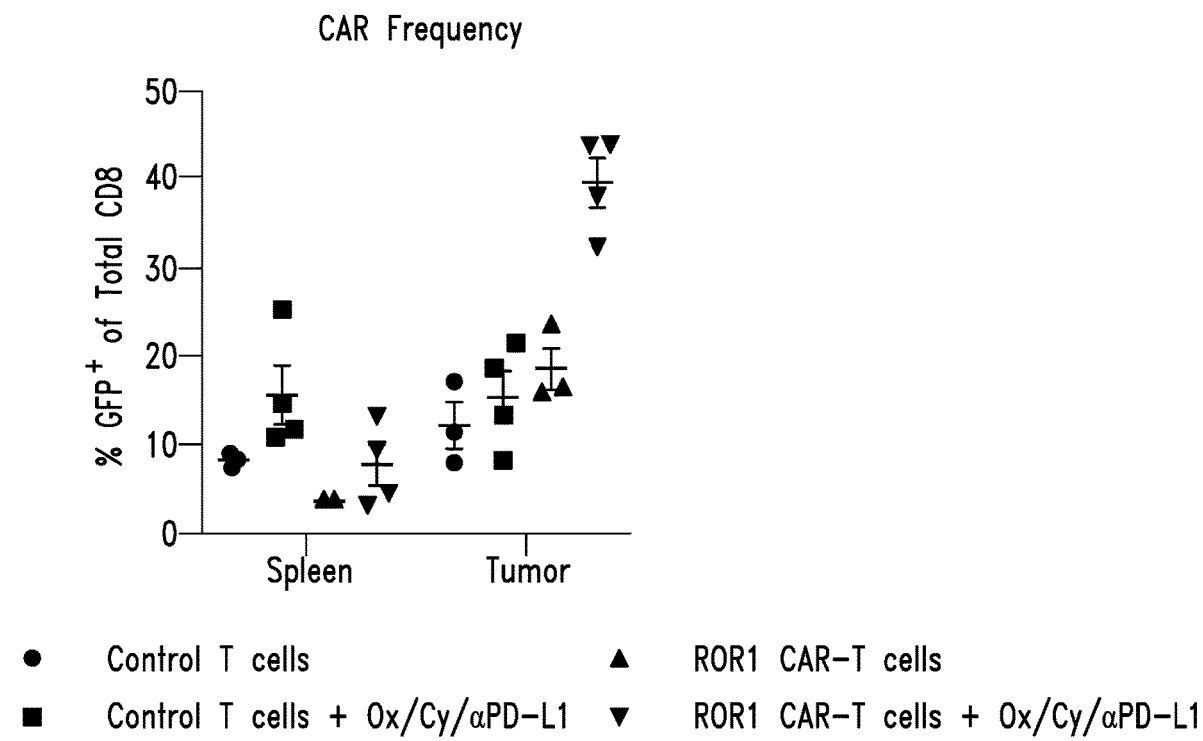
FIGS. 16A-16E show flow cytometric analysis of $CD45.1^+CD8^+GFP^+$ control or anti-ROR1 CAR-T cells in samples from the indicated treatment groups 5 weeks post-T cell treatment. (A) Frequency of CAR T cells as a percentage of total $CD8^+$ T cells in spleen or tumor samples from the indicated treatment groups. (B) PD-1 expression. (C) Ki-67 expression. (D) CD25 expression. (E) 1B11 expression.
Figure 16B:
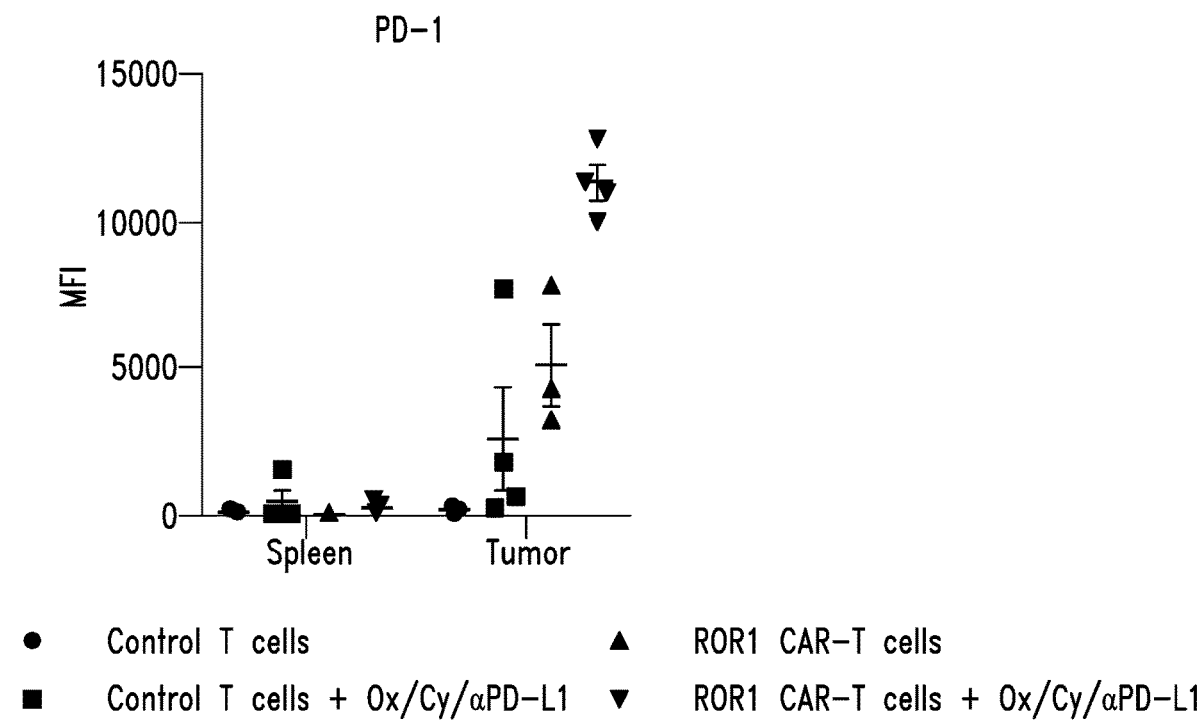
Figure 16C:
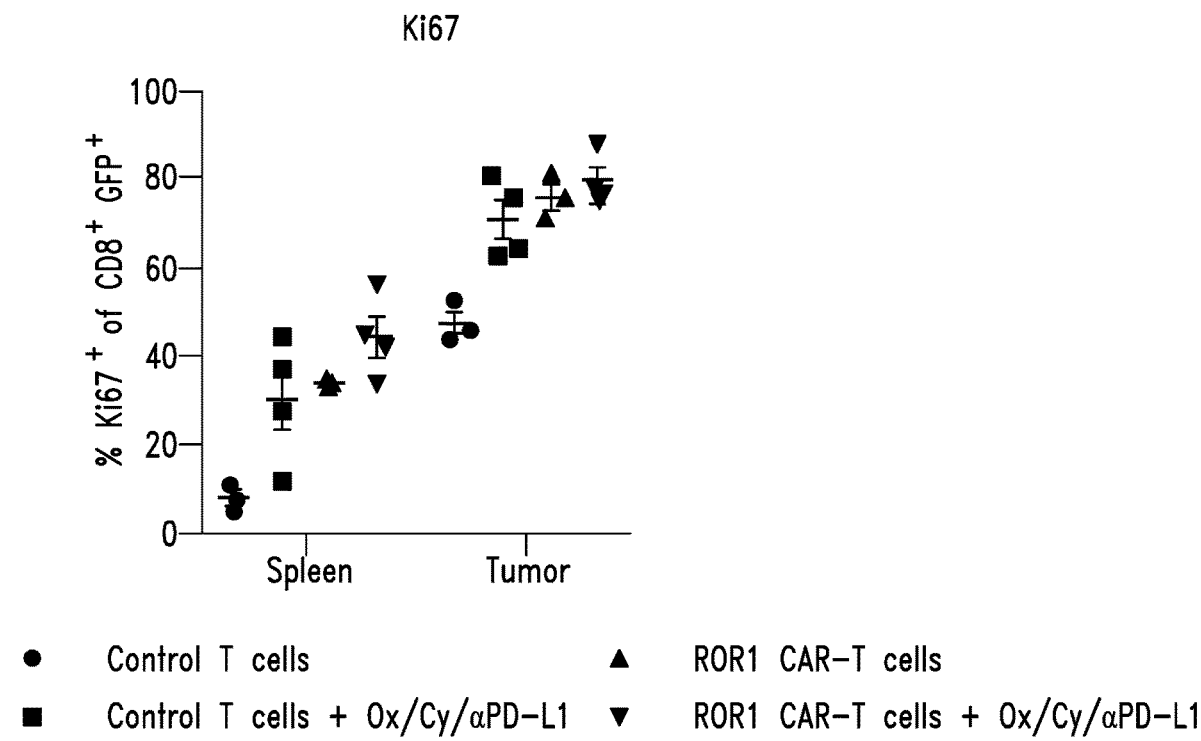
Figure 16D:
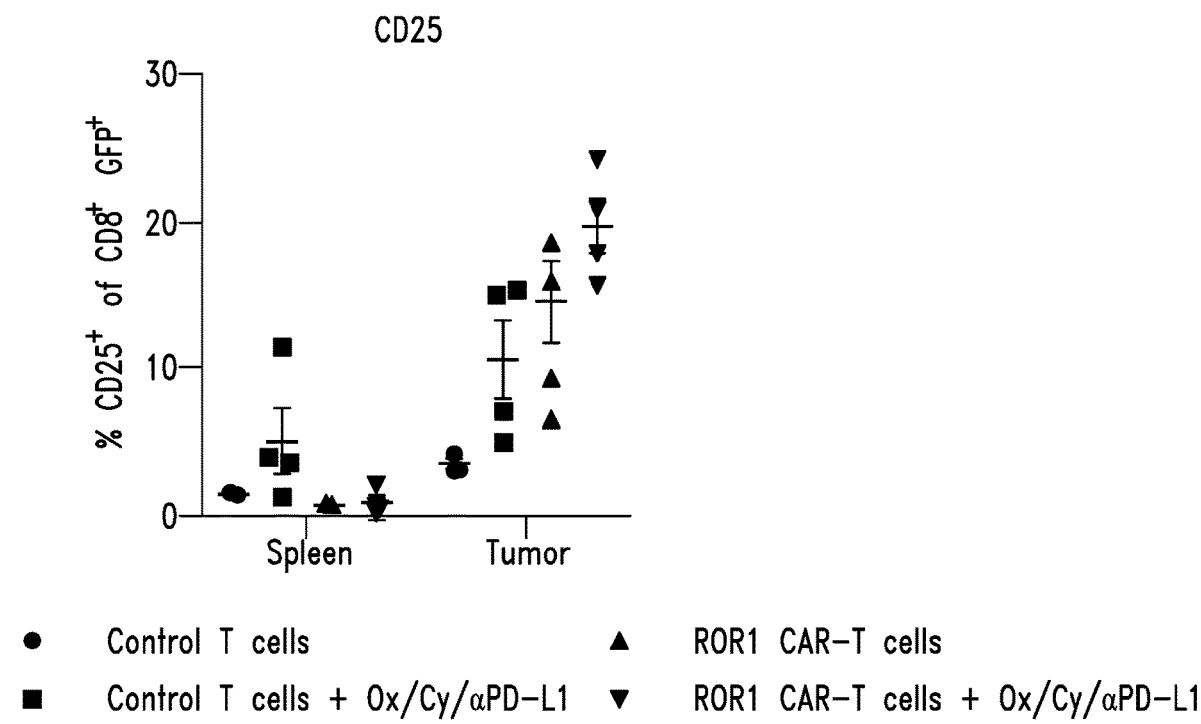
Figure 16E:
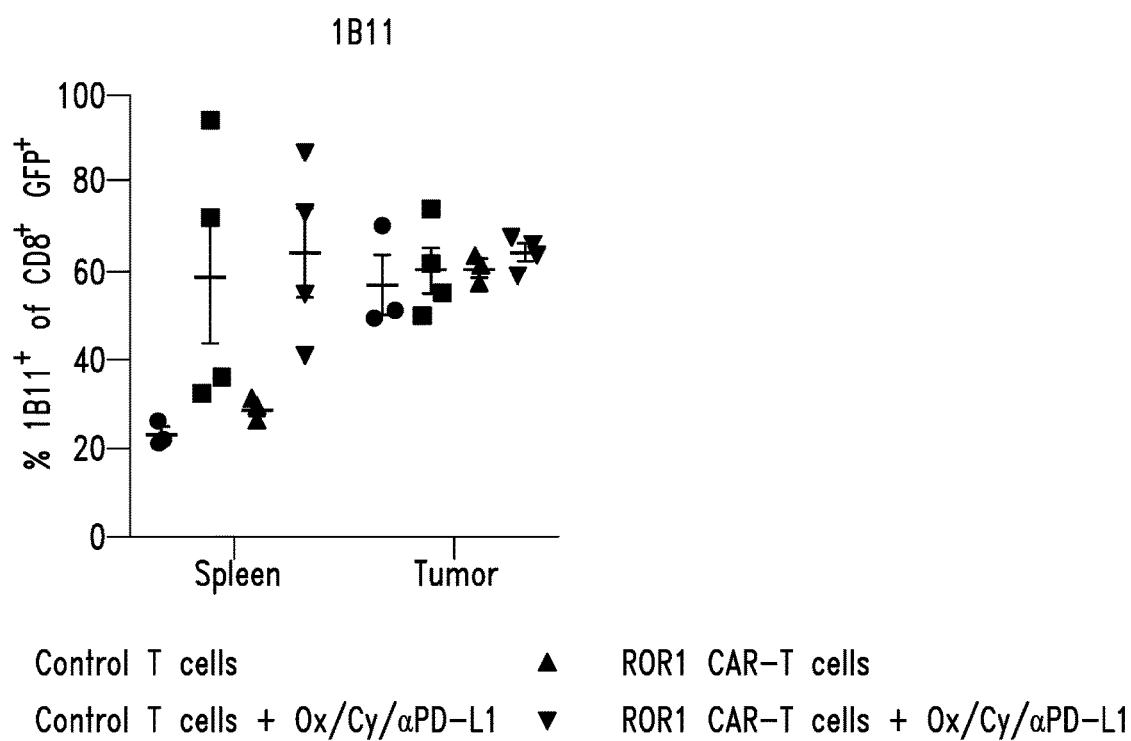

The effect of Ox/Cy/αPD-L1 on anti-ROR1 CAR T cells was investigated. Flow cytometry analysis of CD45.1$^+$ CD8$^+$ GFP$^+$ control or anti-ROR1 CAR T cells in tumors 5 weeks post-T cell treatment was performed. As shown in FIG. 16A, combination with Ox/Cy/αPD-L1 resulted in an increased frequency of anti-ROR1 CAR T cells in tumors compared to treatment with anti-ROR1 CAR T cells alone. The combination therapy also resulted in increased expression of PD-1 by anti-ROR1 CAR T cells (FIG. 16B), of Ki-67 (by control and anti-ROR1 CAR T cells; FIG. 16C), and of CD25 (of all T cells in tumor; FIG. 16D). 1B11 expression was observed to be higher for all T cells in tumor samples, but expression was not observed to be affected by Ox/Cy/αPD-L1 (FIG. 16E).

Example 7

Effect of ICD Therapy on Gene Expression

Figures 17A, 17B:
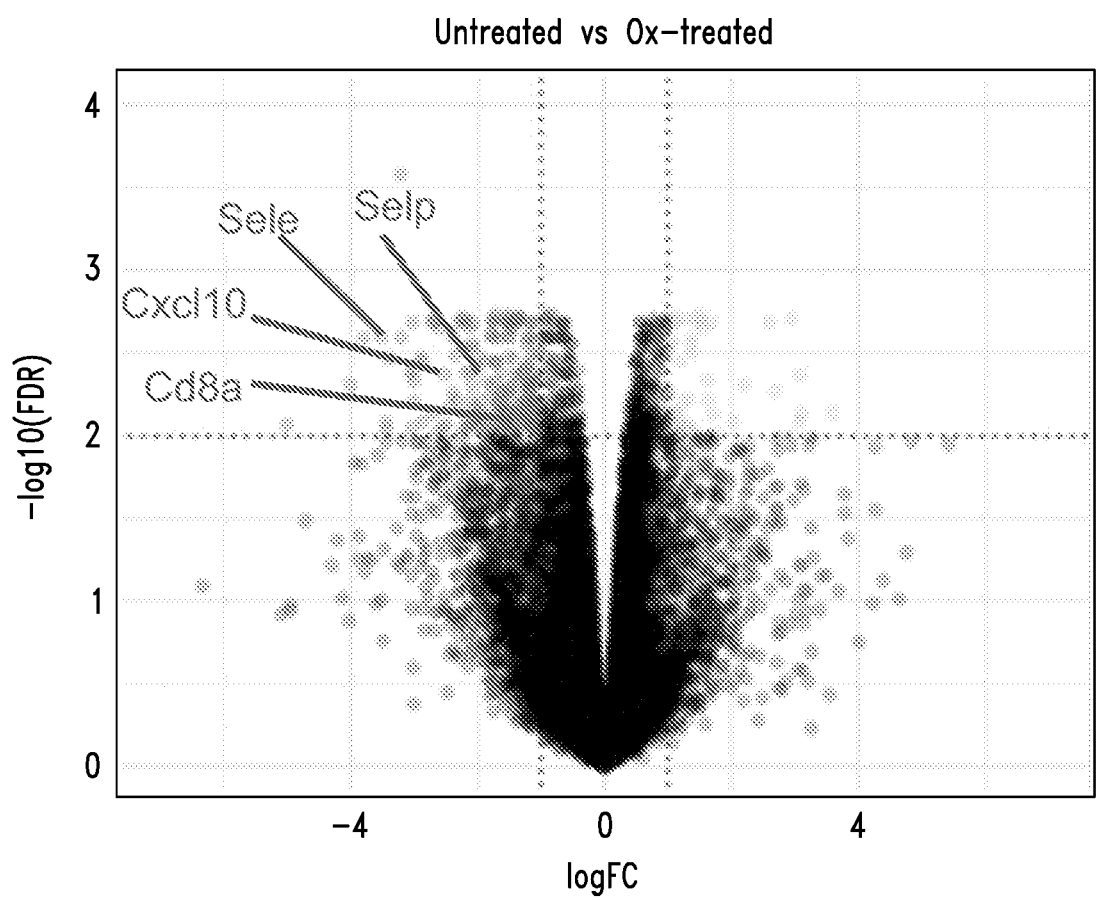
FIGS. 17A-17D show results of gene expression analysis upon treatment with oxaliplatin and cyclophosphamide in KP tumors. (A) Volcano plot showing genes differentially expressed between tumors excised from KP mice that were left untreated or were treated with Ox/Cy in vivo. The upper left corner of the plot represents genes that were up-regulated in Ox/Cy-treated tumors by more than 2-fold and with a false discovery rate <1%. The upper right corner of the plot represents genes that were down-regulated in Ox/Cy-treated tumors by more than 2-fold and with a false discovery rate of <1%. (B) Results of STRING database pathway analysis of the 253 genes upregulated in Ox/Cy-treated KP tumors. (C, D) Log 2 counts per million (CPM) of genes included in the enriched pathways described in (B).
Figure 17C:
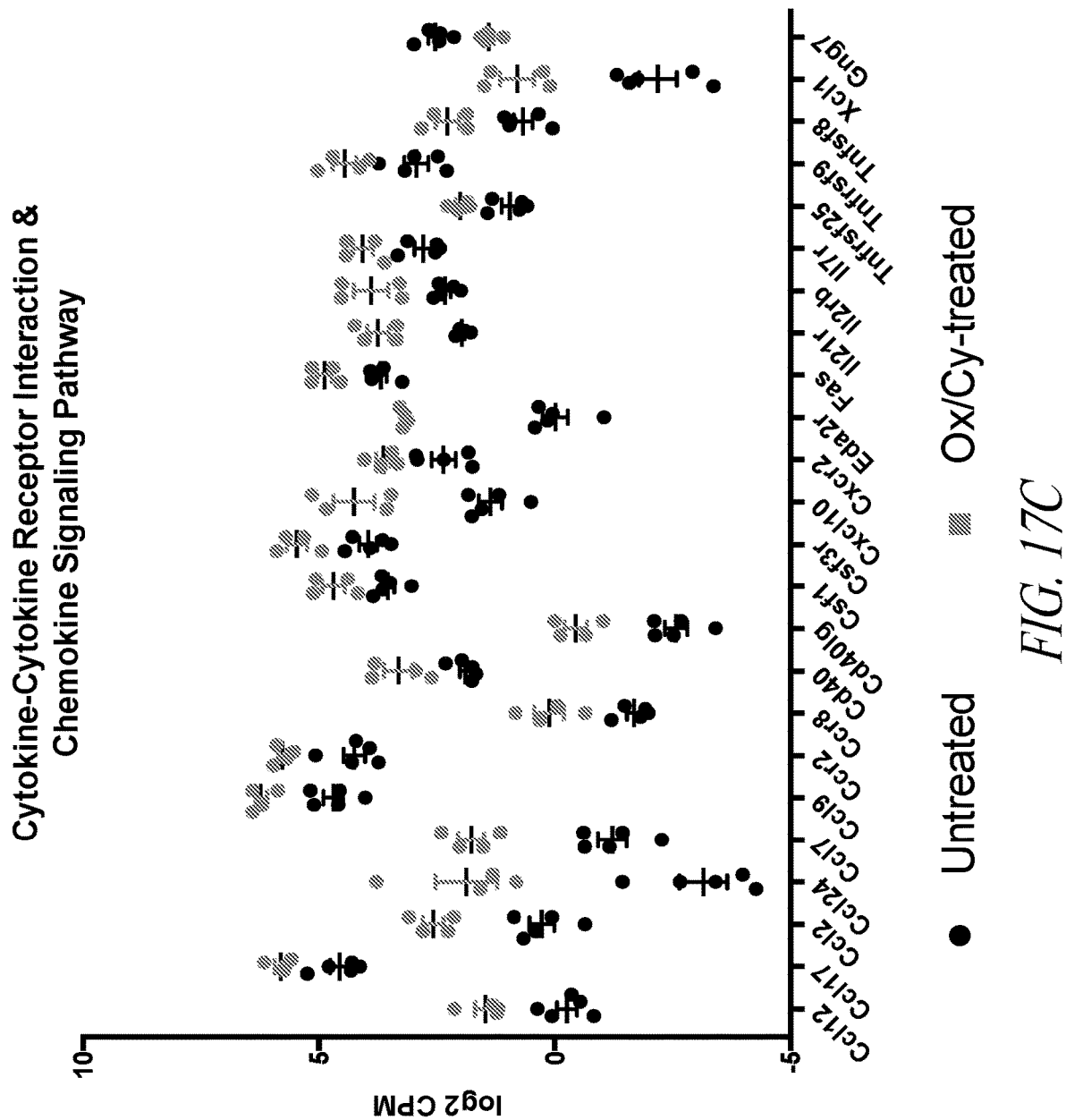
Figure 17D:
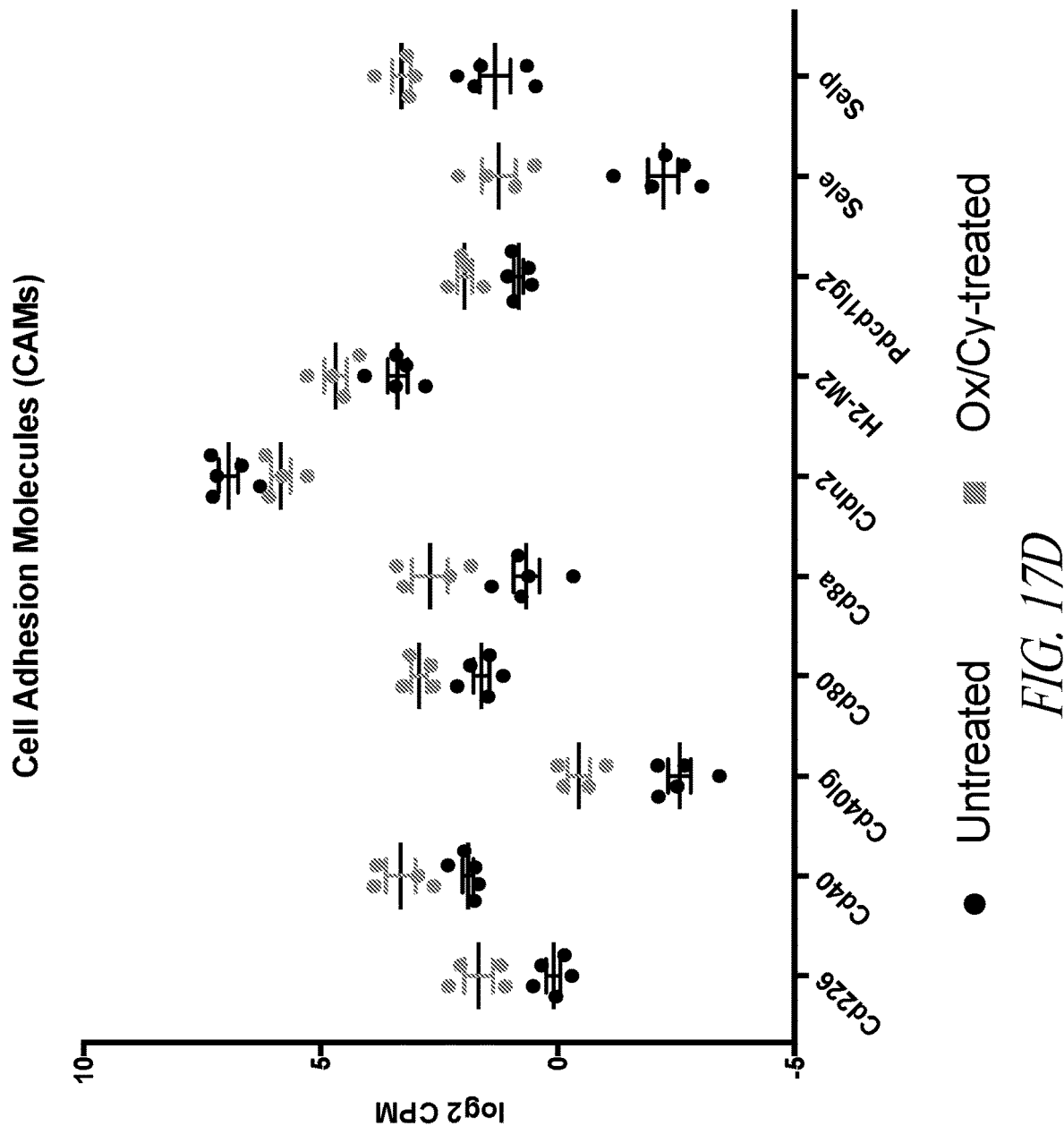

High-throughput RNA sequencing was performed on KP mouse tumor samples. The volcano plot in FIG. 16A shows genes that were observed to be differentially expressed between tumors excised from KP mice that did or did not receive Ox/Cy in vivo. 253 genes were observed to be upregulated more than 2-fold in Ox/Cy-treated KP mouse tumors (upper left hand-corner of FIG. 17A, with representative genes identified). The upregulated genes were interrogated against the STRING database, and exemplary functional pathways summarized in FIG. 17B were identified. Without wishing to be bound by theory, these pathways (cytokine-cytokine receptor interaction; chemokine signaling pathway; and cell adhesion molecules) in some contexts can be associated with T cell trafficking. Expression (Log 2 counts per million) levels of selected genes within the three exemplary pathways were compared in tumors from untreated KP mice and mice that received Ox/Cy. As shown in FIGS. 17C and 17D, nearly all genes had increased expression in tumors from Ox/Cy-treated mice.

The results were consistent with an observation that treatment with agents that induce immunogenic cell death induces expression of genes that may be associated with T cell trafficking in tumors and can improve CAR T cell therapy in a synergistic manner.

Example 8

ICD+CAR T Cell Therapy in a Human TNBC Patient

A single-center study was conducted to evaluate the safety and anti-tumor activity of adoptively-transferred autologous CAR T cells targeting ROR1 in patients with advanced ROR1$^+$ chronic lymphocytic leukemia (CLL), mantle cell lymphoma (MCL), or acute lymphoblastic leukemia (ALL), and in patients with ROR1$^+$ non-small cell lung cancer (NSCLC) or triple negative breast cancer (TNBC; not expressing the genes for estrogen receptor (ER), progesterone receptor (PR), and HER2/Neu). Briefly, patients who met selection criteria received cytoreductive chemotherapy (cyclophosphamide with fludarabine or with oxaliplatin) approximately 36 to 96 hours prior to infusion with autologous T cells (1:1 CD4$^+$:CD8$^+$) transduced with a lentiviral vector encoding a ROR1-specific CAR that includes a scFv from antibody R12, a spacer domain, and 4-1BB and CD3ζ signaling domains, as described in PCT Publication No. WO 2014/031687. T cells were administered at various initial doses and dose-escalation or de-escalation was performed dependent on patient response and efficacy. Persistence of CAR T cells in the blood, cytokine levels, measures of immunogenicity and multi-parametric flow cytometry were evaluated at multiple time points. Imaging assessments by RECIST 1.1 was performed at day 28-90, then at 6 and 12 months, and every 6 months, as clinically indicated.

Figure 18:
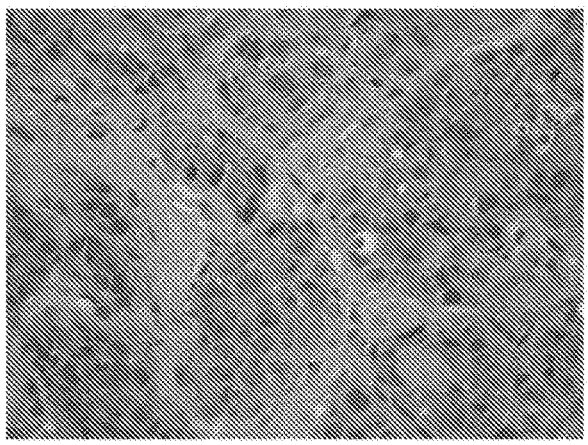
FIG. 18 shows hematoxylin and eosin stain (H&E) of a pre-treatment tumor biopsy from a human patient showing isotype control at 10× (left) and membranous ROR1 expression at 40× (right).
Figure 18:
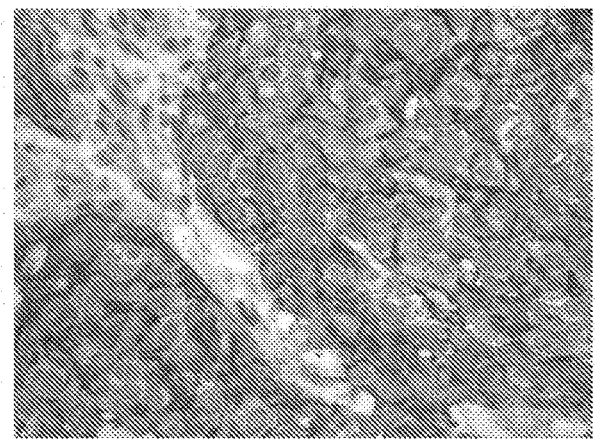
Figure 19A:
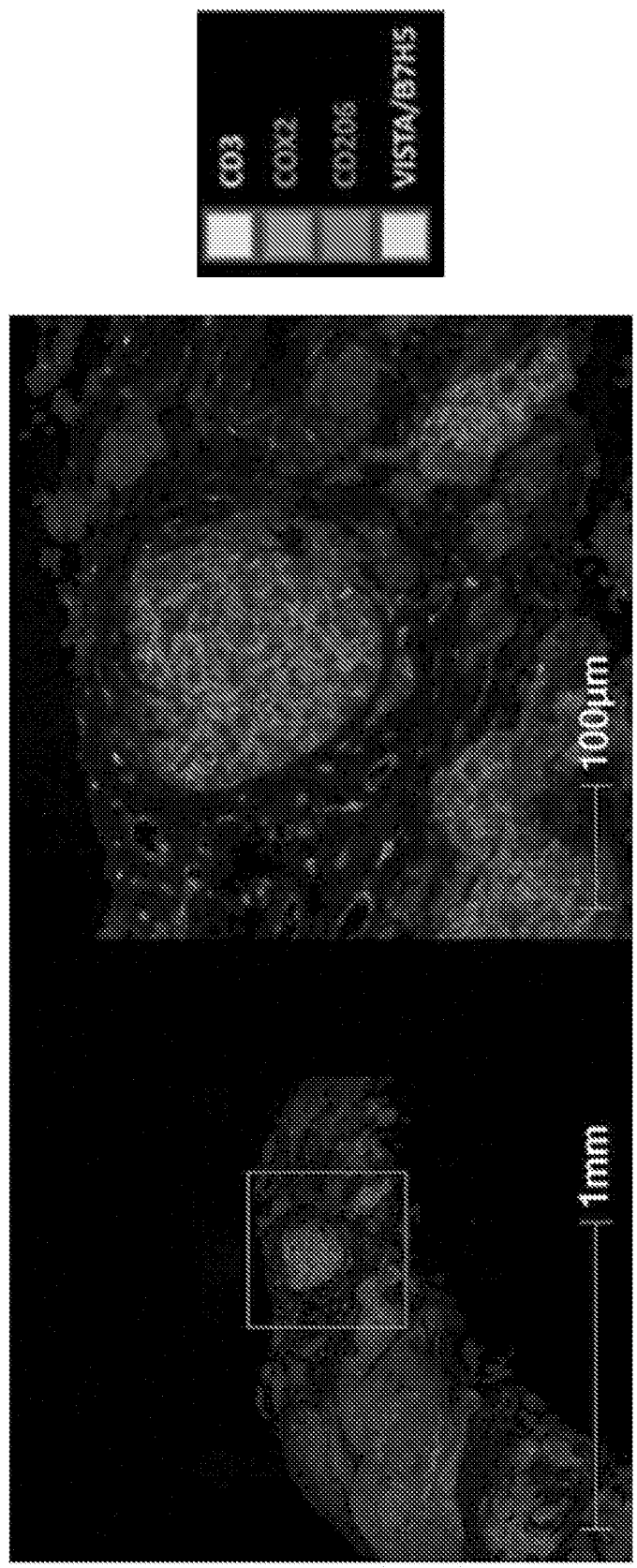
FIGS. 19A and 19B show multiplex immunohistochemistry (IHC) staining of a human TNBC patient tumor biopsy pre-treatment (A) and post-treatment (B) with Ox/Cy and an anti-ROR1 CAR-T cell product. At left of each figure is the sample at low magnification. The right photograph of each figure is high magnification of the sample. The biopsy samples were stained with primary antibodies specific for CD3, COX2, CD206, VISTA/B7-H5, and CD163 (see key in each figure). Nuclear staining (DAPI) served as a counter-stain. Imaging was performed using the Vectra 3.0 platform.
Figure 19B:
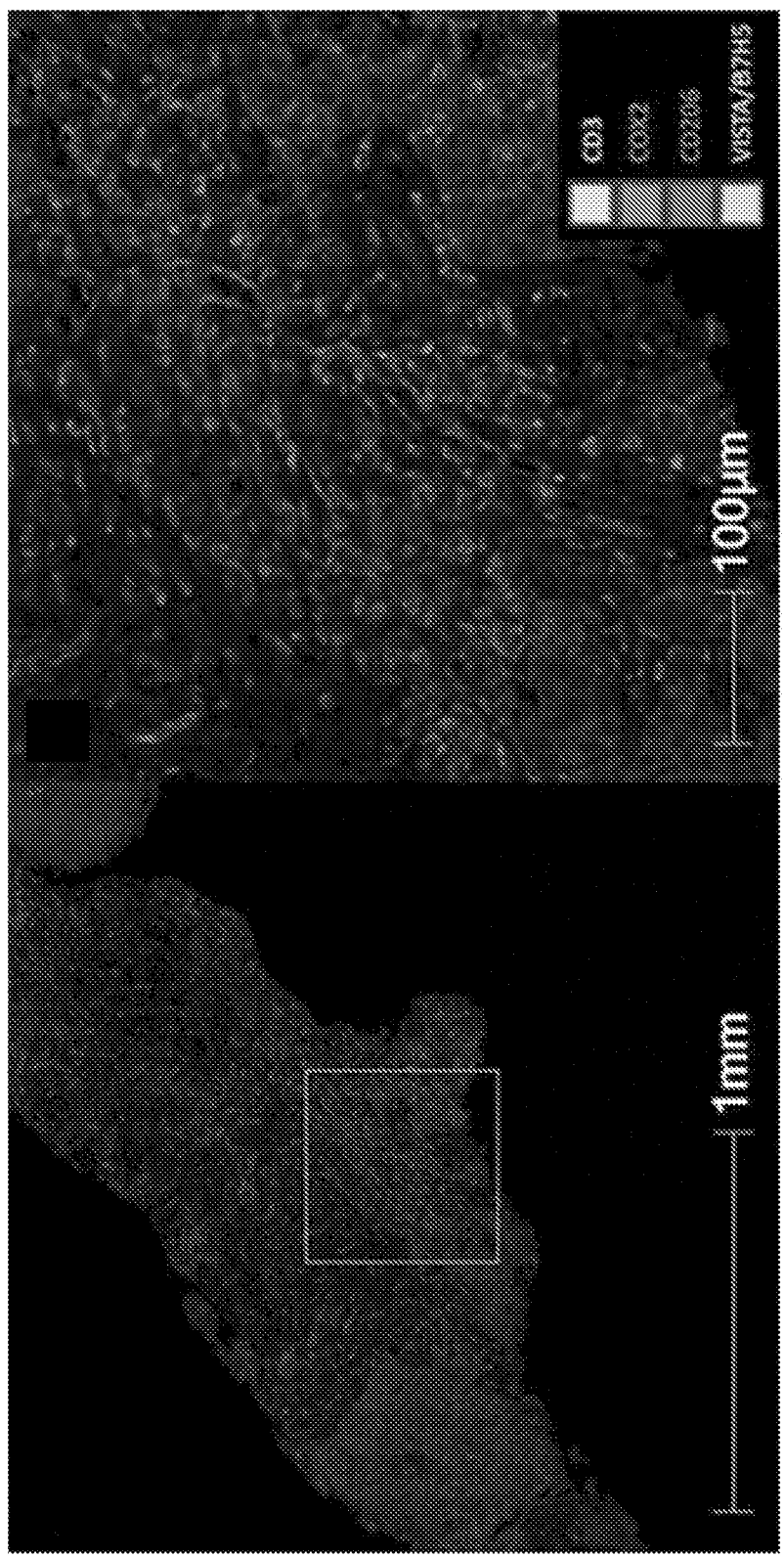
Figure 19C:
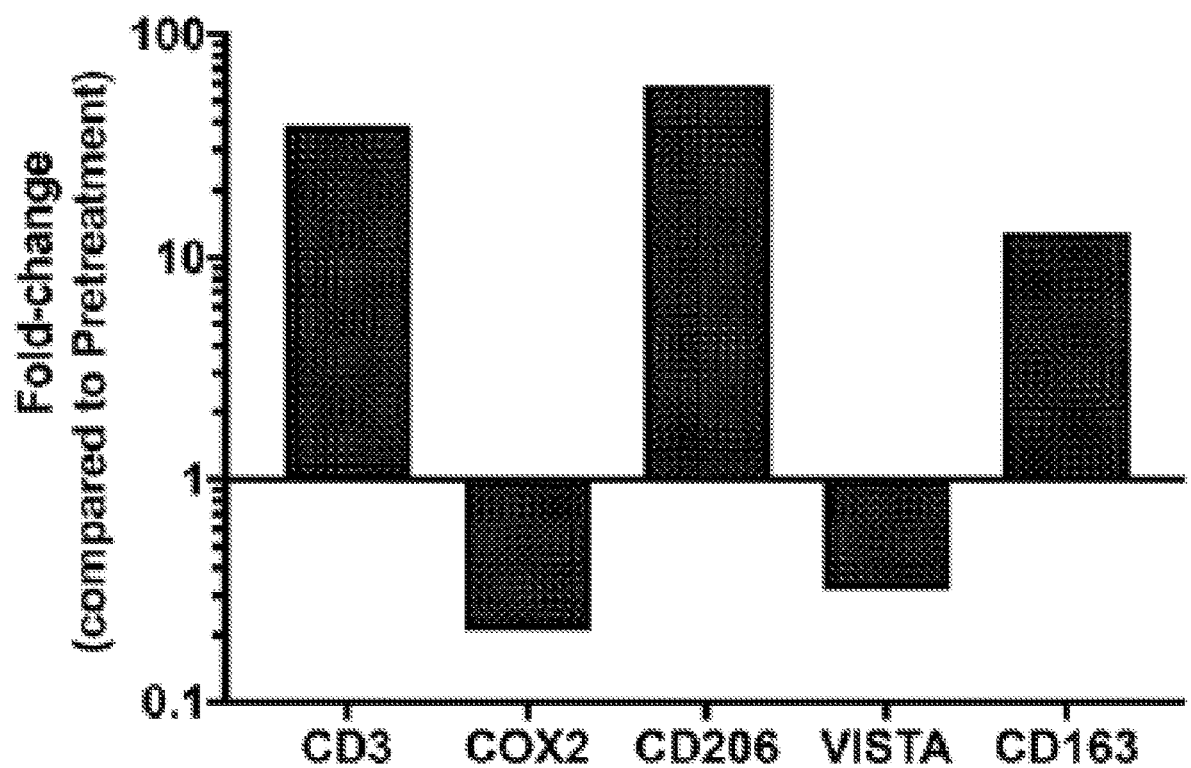
FIG. 19C shows HALO-based quantification depicting log 10 fold-change of cell densities across the entire sample.

Seven (7) patients (4 TNBC, 3 NSCLC) were enrolled and received treatment. All 29 TNBC tumors and 11 of 20 NSCLC tumors screened had >20% ROR1 expression as determined by IHC. Exemplary ROR1 IHC for one TNBC patient that received Ox/Cy is shown in FIG. 18. Post-treatment tumor biopsy was performed in this patient; as shown in FIGS. 19A-19C, CD3$^+$ T cells and macrophages were observed to be present in the tumor following therapy with the anti-ROR1 CAR T cells.

The results were consistent with an observation that that treatment with ICD-inducing chemotherapy was associated with the presence of CAR T cells in a solid tumor (TNBC) in a human patient.

The various embodiments described above can be combined to provide further embodiments. All of the U.S. patents, U.S. patent application publications, U.S. patent applications, foreign patents, foreign patent applications and non-patent publications referred to in this specification and/or in U.S. Provisional Patent Application No. 62/555,034, and/or are listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for treating a solid tumor in a subject, the method comprising administering to the subject:
   (a) an effective amount of a T cell comprising a heterologous polynucleotide that encodes a chimeric antigen receptor (CAR) that specifically binds to a ROR1 cell-surface antigen expressed by tumor cells of the solid tumor; and
   (b) an effective amount of an antibody or antigen-binding fragment thereof that specifically binds to and is an inhibitor of PD-1 or PD-L1,
   wherein prior to administering (a) and (b), the subject has been administered (c) oxaliplatin, or an active metabolite or derivative thereof, and (d) cyclophosphamide,
   wherein the T cell is a CD4+ T cell, a CD8+ T cell, a stem cell memory T cell, or any combination thereof.

2. A method for treating a solid tumor in a subject, the method comprising administering to the subject an effective amount of an antibody or antigen-binding fragment thereof that specifically binds to and is an inhibitor of PD-1 or PD-L1,
   wherein prior to administering the effective amount of the antibody or antigen-binding fragment, the subject has been administered (1) a T cell comprising a heterologous polynucleotide that encodes a chimeric antigen receptor (CAR) that specifically binds to a ROR1 cell-surface antigen expressed by tumor cells of the solid tumor, (2) oxaliplatin or an active metabolite or derivative thereof, and (3) cyclophosphamide,
   wherein the T cell is a CD4+ T cell, a CD8+ T cell, a stem cell memory T cell, or any combination thereof.

3. A method for treating a solid tumor in a subject, the method comprising administering to the subject an effective amount of a T cell comprising a heterologous polynucleotide that encodes a chimeric antigen receptor (CAR) that specifically binds to a ROR1 cell-surface antigen expressed by tumor cells of the solid tumor, wherein the subject, prior to administering the effective amount of the T cell, has been administered (1) an antibody or antigen-binding fragment that specifically binds to and is an inhibitor of PD-1 or PD-L1, (2) oxaliplatin or an active metabolite or derivative thereof, and (3) cyclophosphamide, and wherein the T cell comprises a CD4+ T cell, a CD8+ T cell, a stem cell memory T cell, or any combination thereof.

4. A method of treating a solid tumor in a subject, the method comprising administering to the subject (1) an effective amount of oxaliplatin or an active metabolite or derivative thereof, (2) an effective amount of a T cell comprising a heterologous polynucleotide that encodes a chimeric antigen receptor (CAR) that specifically binds to a ROR1 cell-surface antigen expressed by tumor cells of the solid tumor, and (3) an effective amount of an antibody or antigen-binding fragment that specifically binds to and/or is an inhibitor of PD-1 or PD-L1, wherein the subject has previously been administered cyclophosphamide, and wherein the T cell comprises a CD4+ T cell, a CD8+ T cell, a stem cell memory T cell, or any combination thereof.

5. A method of treating a solid tumor in a subject, the method comprising administering to the subject (1) an effective amount of cyclophosphamide, (2) an effective amount of oxaliplatin or an active metabolite or derivative thereof, (3) an effective amount of a T cell comprising a heterologous polynucleotide that encodes a chimeric antigen receptor (CAR) that specifically binds to a ROR1 cell-surface antigen expressed by tumor cells of the solid tumor, and (4) an effective amount of an antibody or antigen-binding fragment that specifically binds to and is an inhibitor of PD-1 or PD-L1, wherein (1) and (2) are administered prior to (3) and (4), and wherein the T cell is a CD4+ T cell, a CD8+ T cell, a stem cell memory T cell, or any combination thereof.

6. The method of claim 1, wherein prior to administering (a) and (b), the subject has further been administered (e) fludarabine.

7. The method of claim 2, wherein prior to administering the effective amount of the antibody or antigen-binding fragment, the subject has further been administered (4) fludarabine.

8. The method of claim 3, wherein prior to administering the effective amount of the T cell, the subject has further been administered (4) fludarabine.

9. The method of claim 4, wherein the subject has previously further been administered fludarabine.

10. The method of claim 1, whereupon following administration of the T cell and the antibody or antigen binding fragment, the subject achieves an immune response against the solid tumor that is elevated as compared to the immune response achieved by a reference subject that is not administered the oxaliplatin, or the active metabolite or derivative thereof, and the cyclophosphamide.

11. The method of claim 1, further comprising administering to the subject a CTLA4-specific antibody or antigen-binding fragment thereof.

12. The method of claim 11, wherein the CTLA4 specific antibody or antigen-binding fragment thereof comprises ipilimumab, tremelimumab, or any combination thereof.

13. The method of claim 1, wherein the antibody that specifically binds to and is an inhibitor of PD-1 or PD-L1 comprises pidilizumab, nivolumab, pembrolizumab, MEDI0680, BMS-936559, durvalumab, atezolizumab, avelumab, or any combination thereof.

14. The method of claim 11, wherein the CTLA4 specific antibody or antigen-binding fragment thereof is administered to the subject concurrently, simultaneously, or sequentially with: (i) the T cell; (ii) the antibody or antigen binding fragment; or (iii) both.

15. The method of claim 10, wherein the elevated immune response comprises:

(1) an increased amount of immune cell localization to, and/or immune cell activity at, a site of the solid tumor;
  (2) an increase in proliferation of immune cells in the subject;
  (3) an increased amount of activated immune cells in the subject;
  (4) an increased expression level in the subject, optionally in a sample of solid tumor tissue from the subject, of a gene associated with (a) a cytokine-cytokine receptor interaction, (b) a chemokine signaling pathway, (c) a cell adhesion molecule, or (d) any combination of (a)-(c);
  (5) a reduction in the amount, growth, rate of growth, or spread, of solid tumor cells and/or tissue; or
  (6) any combination of (1)-(5).

16. The method of claim 1, wherein the CAR of the T cell comprises a transmembrane component disposed between an extracellular component comprising a binding domain and an intracellular component comprising an effector domain, wherein the transmembrane component of the CAR is from CD28 and the intracellular component effector domain comprises a 4-1BB signaling domain and a CD3ζ domain.

17. The method of claim 1, wherein the T cell comprises a CD4+ T cell and a CD8+ T cell.

18. The method of claim 17, wherein the subject is administered a unit dose comprising about a 1:1 ratio of CAR-encoding CD4+ T cells and CAR-encoding CD8+ T cells.

19. A kit, comprising:

(i) any one or more of (a)-(d):
    (a) a T cell comprising a heterologous polynucleotide that encodes a chimeric antigen receptor (CAR) that specifically binds to a ROR1 cell-surface antigen expressed by or associated with a solid tumor;
    (b) an antibody or antigen-binding fragment thereof that specifically binds to and is an inhibitor of PD-1 or PD-L1;
    (c) oxaliplatin, or an active metabolite or derivative thereof; and
    (d) cyclophosphamide, and
  (ii) instructions for performing a method according to claim 1.

20. The method of claim 5, wherein, the method comprises administering an effective amount of fludarabine with the effective amount of cyclophosphamide.

21. The method of claim 1, wherein, prior to administering the antibody or antigen-binding fragment or the T cell, the subject has been administered:

(i) a single dose of oxaliplatin comprising about 10 mg/m$^2$, or more;

(ii) a single dose of oxaliplatin comprising about 50 to about 100 mg/m²;
(iii) a single dose of oxaliplatin comprising about 85 mg/m²;
(iv) about 50 to about 100 mg/m² of oxaliplatin and about 200 to about 1000 mg/m² of cyclophosphamide;
(v) 300 mg/m² of cyclophosphamide;
(vi) a single dose of cyclophosphamide comprising about 50 to about 4400 mg/m² cyclophosphamide; or
(vii) a single dose of cyclophosphamide comprising about 300 mg/m² cyclophosphamide.

22. The method of claim 1, wherein the solid tumor is a sarcoma or a carcinoma.

23. The method of claim 1, wherein:
(1) the solid tumor is selected from: chondrosarcoma; sarcoma botryoides; fibrosarcoma; Dermatofibrosarcoma protuberans; osteosarcoma; alveolar soft part sarcoma; cystosarcoma phyllodes; rhabdomyosarcoma; Ewing's sarcoma; Askin's tumor; epitheloid sarcoma; extraskeletal chondrosarcoma; a gastrointestinal stromal tumor; Leiomyosarcoma; hemangiosarcoma; angiosarcoma; Kaposi's sarcoma; liposarcoma; lymphangiosarcoma; lymphosaroma; undifferentiated pleomorphic sarcoma; neurofibrosarcoma; rhabdomysarcoma; synovial sarcoma; or synovial sarcoma; or
(2) the solid tumor is selected from a lung carcinoma; Squamous Cell Carcinoma; Adenocarcinoma; Adenosquamous carcinoma; anaplastic carcinoma; Large cell carcinoma; Small cell carcinoma; a breast carcinoma; a liver carcinoma; an ovarian carcinoma; a kidney carcinoma; an adrenal carcinoma; a carcinoma of the testis; Gastric carcinoma; an intestinal carcinoma; a colorectal carcinoma; or a skin carcinoma; an adenocarcinoma; linitis plastica; adenoid cystic carcinoma; Grawitz tumor; and/or
(3) the solid tumor is an ovarian carcinoma, an ovarian epithelial carcinoma, a cervical adenocarcinoma or small cell carcinoma, a pancreatic carcinoma, a colorectal carcinoma, a lung carcinoma, a breast ductal carcinoma, or an adenocarcinoma of the prostate.

24. The method of claim 1, wherein the solid tumor comprises breast cancer including triple-negative breast cancer, non-small-cell lung cancer, gastric cancer, prostate cancer, esophageal cancer, mesothelioma, small cell lung cancer, colorectal cancer, glioblastoma, melanoma, PNET, malignant hemagioendothelioma, malignant schwannoma, desmoid tumor, desmoplastic small round cell tumor, gastrointestinal stromal tumor, hemangiopericytoma, peripheral nerve sheath tumor, vipoma; astrocytoma, oligodendroglioma, brainstem glioma, optic nerve glioma, mixed glioma, or any combination thereof.

25. The method of claim 1, wherein the solid tumor is breast cancer.

26. The method of claim 1, wherein the solid tumor is triple-negative breast cancer, a breast carcinoma, or a breast ductal carcinoma.

27. The method of claim 1, wherein the solid tumor is lung cancer.

28. The method of claim 1, wherein the solid tumor is non-small-cell lung cancer, small cell lung cancer, or a lung carcinoma.

29. The method of claim 1, wherein the CAR comprises an antigen-binding domain comprising a scFv, a single chain Fab, a ligand, or a synthetic polypeptide that specifically binds to the ROR1 cell-surface antigen.

30. The method of claim 1, wherein the method comprises administering (b) after administering (a).

31. The method of claim 23, wherein:
(1) the lung carcinoma is an Adenocarcinoma;
(2) the breast carcinoma is selected from a Ductal Carcinoma in situ; a Lobular carcinoma in situ; an Invasive Ductal Carcinoma; an Invasive lobular carcinoma; and a Non-invasive Carcinoma;
(3) the liver carcinoma is selected from a Hepatocellular Carcinoma; a Cholangiocarcinoma; a Bile Duct Cancer; a Large-cell undifferentiated carcinoma; and a Bronchioalveolar carcinoma;
(4) the ovarian carcinoma is selected from a Surface epithelial-stromal tumor; an ovarian epithelial carcinoma; a Squamous cell carcinoma; an Embryonal carcinoma; and a choriocarcinoma;
(5) the kidney carcinoma is selected from a Renal adenocarcinoma; a hypernephroma; a Transitional cell carcinoma; a Squamous cell carcinoma; a Bellini duct carcinoma; a Clear cell adenocarcinoma; a Transitional cell carcinoma; and a Carcinoid tumor of the renal pelvis;
(6) the adrenal carcinoma is an Adrenocortical carcinoma;
(7) the carcinoma of the testis is selected from a Germ cell carcinoma; a Seminoma; a Choriocarcinoma; an Embryonal carcinoma; a Teratocarcinoma; and a Serous carcinoma;
(8) the Gastric carcinoma is an Adenocarcinoma;
(9) the intestinal carcinoma is an Adenocarcinoma of the duodenum;
(10) the skin carcinoma is selected from a Basal cell carcinoma and a Squamous cell carcinoma; and/or
(11) the colorectal carcinoma is selected from an adenocarcinoma and a squamous cell carcinoma.

32. The method of claim 1, wherein the CAR comprises a heavy chain variable domain (VH) and a light chain variable domain (VL), wherein the VH and VL comprise complementarity determining region (CDR) H1, CDRH2, CDRH3 and CDRL1, CDRL2, and CDRL3 amino acid sequences of (1) SEQ ID NO: 6-8 and 2-4, respectively; or (2) SEQ ID NO: 15-17 and 11-13, respectively.

33. The method of claim 5, further comprising, prior to administering (3), administering to the subject a lymphodepleting chemotherapy in an amount effective to cause lymphodepletion in the subject.

34. A method for treating a ROR1+ solid tumor in a subject, the method comprising administering to the subject:
an effective amount of cyclophosphamide;
an effective amount of oxaliplatin, or an active metabolite or derivative thereof;
an effective amount of a T cell comprising a heterologous polynucleotide that encodes a chimeric antigen receptor (CAR), wherein the CAR comprises a single chain variable fragment (scFv) or a single chain fragment antigen-binding (scFab) specific for the ROR1, an extracellular hinge, a transmembrane component, and an intracellular component effector domain comprising a 4-1BB costimulatory domain and a CD32 domain, and wherein the T cell comprises a CD8+ T cell and a CD4+ T cell; and
an effective amount of an antibody or antigen binding fragment that specifically binds to and is an inhibitor of PD-1 or PD-L1.

35. The method of claim 34, wherein the CAR comprises a scFv comprising the CDRH1, CDRH2, CDRH3, CDRL1, CDRL2, and CDRL3 amino acid sequences of SEQ ID NO: 6-8 and 2-4, respectively.

36. The method of claim 34, wherein the scFv comprises the amino acid sequence of SEQ ID NO: 1 and the amino acid sequence of SEQ ID NO: 5.

37. The method of claim 34, wherein:
the effective amount of cyclophosphamide and the effective amount of oxaliplatin are administered to the subject simultaneously or contemporaneously, and wherein the effective amount of cyclophosphamide is a first dose of cyclophosphamide; and
the method further comprises administering to the subject a second dose of cyclophosphamide, in an amount effective to cause lymphodepletion in the subject, prior to administering the effective amount of the T cell.

38. The method of claim 37, comprising:
administering the effective amount of the T cell contemporaneously with cyclophosphamide for 2 or more triweekly intervals;
administering oxaliplatin and cyclophosphamide once per week for 3 or more weeks, beginning the same week as the modified T cell; and
administering the antibody that specifically binds to and is an inhibitor of PD-1 or PD-L1 twice per week for 2 or more weeks, beginning the same week as the modified T cell.

39. The method of claim 37, wherein:
administering an effective amount of cyclophosphamide and oxaliplatin comprises administering the cyclophosphamide and oxaliplatin about once per week for 3, 4, 5, 6, 7, 8, 9, 10, or more weeks;
administering an effective amount of the T cell comprises two administrations of the T cell following an amount of cyclophosphamide effective to cause lymphodepletion in the subject, the two administrations being three weeks apart and comprising a first administration and a second administration, the first administration occurring during the same week as a first administration of the effective amount of a combination of cyclophosphamide and oxaliplatin, and wherein each of the two administrations of the T cell comprises the CD8+ T cell and the CD4+ T cell in about a 1:1 ratio; and
administering the effective amount of an antibody that specifically binds to and is an inhibitor of PD-1 or PD-L1 comprises administering the antibody that specifically binds to and is an inhibitor of PD-1 or PD-L1 twice per week for 2 or more weeks, beginning the same week as the first administration of the T cell.

40. The method of claim 34, wherein the subject has ROR1+ lung cancer.

41. The method of claim 40, wherein the ROR1+ lung cancer is a non-small cell lung cancer.

42. The method of claim 34, wherein the subject has ROR1+ breast cancer.

43. The method of claim 42, wherein the ROR1+ breast cancer is triple negative breast cancer.

44. The method of claim 1, wherein the antibody that specifically binds to and is an inhibitor of PD-1 or PD-L1 specifically binds to PD-L1 and is an inhibitor of PD-L1.

45. The method of claim 34, wherein the antibody that specifically binds to and is an inhibitor of PD-1 or PD-L1 specifically binds to PD-L1 and is an inhibitor of PD-L1.

46. The method of claim 1, wherein the CAR comprises an antigen-binding domain comprising a scFv that specifically binds to the ROR1 cell-surface antigen.

47. The method of claim 34, wherein the CAR comprises an antigen-binding domain comprising a scFv specific for the ROR1.

* * * * *

UNITED STATES PATENT AND TRADEMARK OFFICE
CERTIFICATE OF CORRECTION

| | | |
|---|---|---|
| PATENT NO. | : 12,350,312 B2 | Page 1 of 1 |
| APPLICATION NO. | : 16/645092 | |
| DATED | : July 8, 2025 | |
| INVENTOR(S) | : Shivani Srivastava et al. | |

It is certified that error appears in the above-identified patent and that said Letters Patent is hereby corrected as shown below:

In the Claims

Column 72, Claim 16, Line 38:
"CD35" should read: -- CD3ζ --.

Column 74, Claim 34, Line 58:
"CD32" should read: -- CD3ζ --.

Signed and Sealed this
Fourth Day of November, 2025

John A. Squires
*Director of the United States Patent and Trademark Office*

SEQUENCE LISTING

```
<160> NUMBER OF SEQ ID NOS: 24

<210> SEQ ID NO 1
<211> LENGTH: 112
<212> TYPE: PRT
<213> ORGANISM: Artificial Sequence
<220> FEATURE:
<223> OTHER INFORMATION: Synthetic R12 light chain variable domain
      sequence

<400> SEQUENCE: 1

Glu Leu Val Leu Thr Gln Ser Pro Ser Val Ser Ala Ala Leu Gly Ser
1               5                   10                  15

Pro Ala Lys Ile Thr Cys Thr Leu Ser Ser Ala His Lys Thr Asp Thr
            20                  25                  30
```

```
Ile Asp Trp Tyr Gln Gln Leu Gln Gly Glu Ala Pro Arg Tyr Leu Met
        35                  40                  45

Gln Val Gln Ser Asp Gly Ser Tyr Thr Lys Arg Pro Gly Val Pro Asp
 50                  55                  60

Arg Phe Ser Gly Ser Ser Ser Gly Ala Asp Arg Tyr Leu Ile Ile Pro
 65                  70                  75                  80

Ser Val Gln Ala Asp Asp Glu Ala Asp Tyr Tyr Cys Gly Ala Asp Tyr
                 85                  90                  95

Ile Gly Gly Tyr Val Phe Gly Gly Thr Gln Leu Thr Val Thr Gly
            100                 105                 110

<210> SEQ ID NO 2
<211> LENGTH: 12
<212> TYPE: PRT
<213> ORGANISM: Artificial Sequence
<220> FEATURE:
<223> OTHER INFORMATION: Synthetic R12 LCDR1 sequence

<400> SEQUENCE: 2

Thr Leu Ser Ser Ala His Lys Thr Asp Thr Ile Asp
 1               5                  10

<210> SEQ ID NO 3
<211> LENGTH: 7
<212> TYPE: PRT
<213> ORGANISM: Artificial Sequence
<220> FEATURE:
<223> OTHER INFORMATION: Synthetic R12 LCDR2 sequence

<400> SEQUENCE: 3

Gly Ser Tyr Thr Lys Arg Pro
 1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic R12 LCDR3 sequence

<400> SEQUENCE: 4

Gly Ala Asp Tyr Ile Gly Gly Tyr Val
 1               5

<210> SEQ ID NO 5
<211> LENGTH: 121
<212> TYPE: PRT
<213> ORGANISM: Artificial Sequence
<220> FEATURE:
<223> OTHER INFORMATION: Synthetic R12 heavy chain variable domain
      sequence

<400> SEQUENCE: 5

Gln Glu Gln Leu Val Glu Ser Gly Gly Arg Leu Val Thr Pro Gly Gly
 1               5                  10                  15

Ser Leu Thr Leu Ser Cys Lys Ala Ser Gly Phe Asp Phe Ser Ala Tyr
             20                  25                  30

Tyr Met Ser Trp Val Arg Gln Ala Pro Gly Lys Gly Leu Glu Trp Ile
         35                  40                  45

Ala Thr Ile Tyr Pro Ser Ser Gly Lys Thr Tyr Tyr Ala Thr Trp Val
     50                  55                  60

Asn Gly Arg Phe Thr Ile Ser Ser Asp Asn Ala Gln Asn Thr Val Asp
```

```
                65                  70                  75                  80
Leu Gln Met Asn Ser Leu Thr Ala Ala Asp Arg Ala Thr Tyr Phe Cys
                    85                  90                  95

Ala Arg Asp Ser Tyr Ala Asp Asp Gly Ala Leu Phe Asn Ile Trp Gly
                100                 105                 110

Pro Gly Thr Leu Val Thr Ile Ser Ser
            115                 120

<210> SEQ ID NO 6
<211> LENGTH: 5
<212> TYPE: PRT
<213> ORGANISM: Artificial Sequence
<220> FEATURE:
<223> OTHER INFORMATION: Synthetic R12 HCDR1 sequence

<400> SEQUENCE: 6

Ala Tyr Tyr Met Ser
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic R12 HCDR2 sequence

<400> SEQUENCE: 7

Thr Ile Tyr Pro Ser Ser Gly Lys Thr Tyr Tyr Ala Thr Trp Val Asn
1               5                   10                  15

Gly

<210> SEQ ID NO 8
<211> LENGTH: 12
<212> TYPE: PRT
<213> ORGANISM: Artificial Sequence
<220> FEATURE:
<223> OTHER INFORMATION: Synthetic R12 HCDR3 sequence

<400> SEQUENCE: 8

Asp Ser Tyr Ala Asp Asp Gly Ala Leu Phe Asn Ile
1               5                   10

<210> SEQ ID NO 9
<211> LENGTH: 248
<212> TYPE: PRT
<213> ORGANISM: Artificial Sequence
<220> FEATURE:
<223> OTHER INFORMATION: Synthetic R12 scFv sequence

<400> SEQUENCE: 9

Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
                20                  25                  30

Tyr Met Ser Trp Val Arg Gln Ala Pro Gly Lys Gly Leu Glu Trp Ile
            35                  40                  45

Ala Thr Ile Tyr Pro Ser Ser Gly Lys Thr Tyr Tyr Ala Thr Trp Val
        50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
                85                  90                  95
```

```
Ala Arg Asp Ser Tyr Ala Asp Gly Ala Leu Phe Asn Ile Trp Gly
            100                 105                 110

Pro Gly Thr Leu Val Thr Ile Ser Ser Gly Gly Gly Gly Ser Gly
            115                 120                 125

Gly Gly Ser Gly Gly Gly Ser Glu Leu Val Leu Thr Gln Ser Pro
            130                 135                 140

Ser Val Ser Ala Ala Leu Gly Ser Pro Ala Lys Ile Thr Cys Thr Leu
145                 150                 155                 160

Ser Ser Ala His Lys Thr Asp Thr Ile Asp Trp Tyr Gln Gln Leu Gln
                    165                 170                 175

Gly Glu Ala Pro Arg Tyr Leu Met Gln Val Gln Ser Asp Gly Ser Tyr
                    180                 185                 190

Thr Lys Arg Pro Gly Val Pro Asp Arg Phe Ser Gly Ser Ser Ser Gly
                    195                 200                 205

Ala Asp Arg Tyr Leu Ile Ile Pro Ser Val Gln Ala Asp Asp Glu Ala
                    210                 215                 220

Asp Tyr Tyr Cys Gly Ala Asp Tyr Ile Gly Gly Tyr Val Phe Gly Gly
225                 230                 235                 240

Gly Thr Gln Leu Thr Val Thr Gly
                    245

<210> SEQ ID NO 10
<211> LENGTH: 107
<212> TYPE: PRT
<213> ORGANISM: Artificial Sequence
<220> FEATURE:
<223> OTHER INFORMATION: Synthetic 2A2 light chain variable domain
      sequence

<400> SEQUENCE: 10

Asp Ile Val Met Thr Gln Ser Gln Lys Ile Met Ser Thr Thr Val Gly
1               5                   10                  15

Asp Arg Val Ser Ile Thr Cys Lys Ala Ser Gln Asn Val Asp Ala Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Asp Ile Tyr Pro Tyr
                85                  90                  95

Thr Phe Gly Gly Gly Thr Lys Leu Glu Ile Lys
                100                 105

<210> SEQ ID NO 11
<211> LENGTH: 11
<212> TYPE: PRT
<213> ORGANISM: Artificial Sequence
<220> FEATURE:
<223> OTHER INFORMATION: Synthetic 2A2 LCDR1 sequence

<400> SEQUENCE: 11

Lys Ala Ser Gln Asn Val Asp Ala Ala Val Ala
1               5                   10

<210> SEQ ID NO 12
<211> LENGTH: 7
```

```
<212> TYPE: PRT
<213> ORGANISM: Artificial Sequence
<220> FEATURE:
<223> OTHER INFORMATION: Synthetic 2A2 LCDR2 sequence

<400> SEQUENCE: 12

Ser Ala Ser Asn Arg Tyr Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic 2A2 LCDR3 sequence

<400> SEQUENCE: 13

Gln Gln Tyr Asp Ile Tyr Pro Tyr Thr
1               5

<210> SEQ ID NO 14
<211> LENGTH: 118
<212> TYPE: PRT
<213> ORGANISM: Artificial Sequence
<220> FEATURE:
<223> OTHER INFORMATION: Synthetic 2A2 heavy chain variable domain
      sequence

<400> SEQUENCE: 14

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ser Asp Tyr
                20                  25                  30

Glu Met His Trp Val Ile Gln Thr Pro Val His Gly Leu Glu Trp Ile
            35                  40                  45

Gly Ala Ile Asp Pro Glu Thr Gly Gly Thr Ala Tyr Asn Gln Lys Phe
        50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Gly Tyr Tyr Asp Tyr Asp Ser Phe Thr Tyr Trp Gly Gln Gly Thr
            100                 105                 110

Leu Val Thr Val Ser Ala
        115

<210> SEQ ID NO 15
<211> LENGTH: 5
<212> TYPE: PRT
<213> ORGANISM: Artificial Sequence
<220> FEATURE:
<223> OTHER INFORMATION: Synthetic 2A2 HCDR1 sequence

<400> SEQUENCE: 15

Asp Tyr Glu Met His
1               5

<210> SEQ ID NO 16
<211> LENGTH: 17
<212> TYPE: PRT
<213> ORGANISM: Artificial Sequence
<220> FEATURE:
<223> OTHER INFORMATION: Synthetic 2A2 HCDR2 sequence
```

```
<400> SEQUENCE: 16

Ala Ile Asp Pro Glu Thr Gly Gly Thr Ala Tyr Asn Gln Lys Phe Lys
1               5                   10                  15

Gly

<210> SEQ ID NO 17
<211> LENGTH: 9
<212> TYPE: PRT
<213> ORGANISM: Artificial Sequence
<220> FEATURE:
<223> OTHER INFORMATION: Synthetic 2A2 HCDR3 sequence

<400> SEQUENCE: 17

Tyr Tyr Asp Tyr Asp Ser Phe Thr Tyr
1               5

<210> SEQ ID NO 18
<211> LENGTH: 15
<212> TYPE: PRT
<213> ORGANISM: Artificial Sequence
<220> FEATURE:
<223> OTHER INFORMATION: Synthetic (Gly4Ser)3 linker sequence

<400> SEQUENCE: 18

Gly Gly Gly Gly Ser Gly Gly Gly Gly Ser Gly Gly Gly Gly Ser
1               5                   10                  15

<210> SEQ ID NO 19
<211> LENGTH: 10
<212> TYPE: PRT
<213> ORGANISM: Artificial Sequence
<220> FEATURE:
<223> OTHER INFORMATION: Synthetic (Gly4Ser)2 linker sequence

<400> SEQUENCE: 19

Gly Gly Gly Gly Ser Gly Gly Gly Gly Ser
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Synthetic (Gly3Ser)2 linker sequence

<400> SEQUENCE: 20

Gly Gly Gly Ser Gly Gly Gly Ser
1               5

<210> SEQ ID NO 21
<211> LENGTH: 11
<212> TYPE: PRT
<213> ORGANISM: Artificial Sequence
<220> FEATURE:
<223> OTHER INFORMATION: Synthetic (Gly3Ser)2Gly2Ser linker sequence

<400> SEQUENCE: 21

Gly Gly Gly Ser Gly Gly Gly Ser Gly Gly Ser
1               5                   10

<210> SEQ ID NO 22
<211> LENGTH: 28
<212> TYPE: PRT
<213> ORGANISM: Artificial Sequence
<220> FEATURE:
<223> OTHER INFORMATION: Synthetic CD28tm sequence
```

```
<400> SEQUENCE: 22

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 23
<211> LENGTH: 42
<212> TYPE: PRT
<213> ORGANISM: Artificial Sequence
<220> FEATURE:
<223> OTHER INFORMATION: Synthetic 4-1BB sequence

<400> SEQUENCE: 23

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 24
<211> LENGTH: 112
<212> TYPE: PRT
<213> ORGANISM: Artificial Sequence
<220> FEATURE:
<223> OTHER INFORMATION: Synthetic CD3zeta sequence

<400> SEQUENCE: 24

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```